US010767162B2

(12) United States Patent
Li et al.

(10) Patent No.: US 10,767,162 B2
(45) Date of Patent: Sep. 8, 2020

(54) METHODS FOR DIFFERENTIATION

(71) Applicant: PRESIDENT AND FELLOWS OF HARVARD COLLEGE, Cambridge, MA (US)

(72) Inventors: Victor Chun Li, Boston, MA (US); Marc W. Kirschner, Newton, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/222,184

(22) Filed: Dec. 17, 2018

(65) Prior Publication Data

US 2019/0106677 A1 Apr. 11, 2019

Related U.S. Application Data

(63) Continuation of application No. 15/317,205, filed as application No. PCT/US2015/034849 on Jun. 9, 2015, now abandoned.

(60) Provisional application No. 62/010,244, filed on Jun. 10, 2014.

(51) Int. Cl.

*C12N 15/00* (2006.01)
*C12N 5/02* (2006.01)
*C12N 5/00* (2006.01)
*C12N 5/0793* (2010.01)
*C12N 5/0735* (2010.01)

(52) U.S. Cl.

CPC ......... *C12N 5/0619* (2013.01); *C12N 5/0606* (2013.01); *C12N 2501/405* (2013.01); *C12N 2501/60* (2013.01); *C12N 2501/606* (2013.01); *C12N 2501/727* (2013.01); *C12N 2506/02* (2013.01)

(58) Field of Classification Search

CPC .................................................... C12N 5/0619
USPC .......................................................... 435/377
See application file for complete search history.

(56) References Cited

U.S. PATENT DOCUMENTS

2006/0084655 A1 4/2006 Moon et al.

OTHER PUBLICATIONS

Aziz et al., "Regulating a master regulator: establishing tissue-specific gene expression in skeletal muscle." Epigenetics 5(8):691-695 (2010).

Bhattacharyya et al., "The voyage of stem cell toward terminal differentiation: a brief overview." Acta Biochim Eliophys Sin 44(6):463-475 (2012).

Burdon et al., "Signalling, cell cycle and pluripotency in embryonic stem cells", Trends in Cell Biology 12 (9):432-438 (2002).

Chetty et al., "A simple tool to improve pluripotent stem cell differentiation." Nature Methods 10(6):553-556 (2013).

Conklin et al., "The RB family is required for the self-renewal and survival of human embryonic stem cells." Nature Communications 3(1244):1-12 (2012).

Dinsmore et al., "Embryonic stem cells differentiated in vitro as a novel source of cells for transplantation." Cell Transplantation 5(2):131-143 (1996).

Calderisi et al., "Cell cycle regulation and neural differentiation", Oncogene 22:5208-5219 (2003).

Hong et al., "TAZ, a transcriptional modulator of mesenchymal stem cell differentiation." Science 309 (5737)1074-1078 (2005).

Jirmanova et al., "Differential contributions of ERK and PI3-kinase to the regulation of cyclin D1 expression and to be control of the G1/S transition in mouse embryonic stem cells", Oncogene 21:5515-5528 (2002).

Laflamme et al., "Cardiomyocytes derived from human embryonic stem cells in pro-survival factors enhance function of infarcted rat hearts." Nature Biotechnology 25(9):1015-1024 (2007).

Ling et al., "Lysine methyltransferase G9a methylates the transcription factor MyoD and regulates skeletal muscle differentiation." PNAS 109(3):841-846 (2012).

Neganova et al., "Expression and functional analysis of G1 to S regulatory components reveals an important role for CDK2 in cell cycle regulation in human embryonic stem cells", Oncogene 28:20-30 (2009).

Ruiz et al., "A High Proliferation Rate Is Required for Cell Reprogramming and Maintenance of Human Embryonic Stem Cell Identity", Current Biology 21(1):45-52 (2011).

Takayanagi et al., "Induction and activation of the transcription factor NFATc1 (NFAT2) integrate RANKL signaling in terminal differentiation of osteoclasts." Developmental Cell 3(6):889-901 (2002).

Viswanathan et al., "Supplementation-Dependent Differences in the Rates of Embryonic Stem Cell Self-Renewal, Differentiation, and Apoptosis", Biotechnology and Bioengineering 84(5):505-517 (2003).

Zhou et al., "Generation of induced pluripotent stem cells using recombinant proteins." Cell Stem Cell 4(5):381-384 (2009).

*Primary Examiner* — Valarie E Bertoglio
(74) *Attorney, Agent, or Firm* — Nixon Peabody LLP; David S. Resnick; Nicole D. Kling

(57) ABSTRACT

Described herein are methods relating to the differentiation of stem cells to more differentiated phenotypes, e.g. to terminally differentiated cell types and/or precursors thereof. In some embodiments, the methods relate to contacting the stem cells with differentiation factors and halting the cell cycle, thereby increasing the rate of differentiation.

13 Claims, 21 Drawing Sheets

Specification includes a Sequence Listing.

SEQUENCE LISTING

```
<160> NUMBER OF SEQ ID NOS: 178

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

gtgttcctac ccccaatgtg t                                              21


<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

gttgaagtcg caggagacaa c                                              21


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

acagacgctc tgcaaaggtt t                                              21


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

ggactggtag gagtagggat g                                              21


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 5
taccagtgtc taccagccaa t 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tgcacgagta tgaggaggtc t 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gcaggacctt ctttcgcgta t 21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
aaggggaatc ggatggggtt 20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ttttccgaag aaccatccga tt 22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
atggcattgt gagacatccc c 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
aagcatttca aaaccgacgg a 21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
cctcaaatcc acagatgacc aga 23

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ccaagagcga gttggcact 19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cgggccatag aagctgtgg 19

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gataagaaca gcaacgagta ccg 23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtcactggtc aactccaaca cc 22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
catcgacttc agcccctacc 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ggctcacgta accgtagtcg 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tctccgcgtt cttatcccac 20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
aggagttgct acggaaacca c 21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ccccagttta caagctcgct 20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ctcggttcca ttcgggaaag g 21

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ccctgaagtc gaggagctg 19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ctgctgcacc tctaagcga 19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
tcaacctgcc aaacaaaagc 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gctggatctg ttctcgcatc 20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tccgagggtt tgtatcacga g 21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cctcctggca taatgtgagg c 21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ccaaggaaca aaccgtcaaa 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
aagcgggtct gcagagtgta 20

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
agattccagg tcgtggtgtc ta 22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
acagggagta gcatgttcca ga 22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
ggtcctcaca ccaaagtagt gc 22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cggaggatct cattcttgct ta 22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ataatctcct tcaccccagc tc 22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gggcagggct tctatgtcta gt 22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
atttgttggc tgcatgatct tt 22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cggtatgact tttcctgatc ca 22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
aggcagaaaa aggacaatca ca 22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
cttccggatg tagtccacag ag 22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
aagcgaaaac caaactgcat aa 22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ccaagaacca ctcaaaggac tg 22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tcccatttgt gaataagcca tt 22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tccttcatgc ctttcttaca gc 22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ctcccaatag cccttctcac tt 22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
agcaagagaa tggctgactc ac 22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
acagatgcac gtcctcgata ct 22

<210> SEQ ID NO 48

<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cttctccatc agacacctcc ag 22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 49 tctcccctt ttctttgttg tt 22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
acgcacacat ccacatacag tc 22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cttgcttcca ctctgctctg tt 22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
acggcaagac caagacagat aa 22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cagaatagcc ttgaccttgt gg 22

<210> SEQ ID NO 54
<211> LENGTH: 22

<212> TYPE: DNA
<213> ORGANISM: Artificial Sequence
<220> FEATURE:
<223> OTHER INFORMATION: Description of Artificial Sequence: Synthetic primer

<400> SEQUENCE: 54
aggaaaatgt caggcatagc aa 22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gtttgttgcc cagtaagacg ag 22

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
gctttggctt ccaagaagtt tt 22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
ccaaatcatg tgcttcttgt ga 22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tattcttgtt gagaccccag ga 22

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
atggcatact gtggacctc 19

<210> SEQ ID NO 60
<211> LENGTH: 20
<212> TYPE: DNA

<213> ORGANISM: Artificial Sequence
<220> FEATURE:
<223> OTHER INFORMATION: Description of Artificial Sequence: Synthetic primer

<400> SEQUENCE: 60
agcagcttgg caaactgttc 20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
cagcagatgc aagaactctc c 21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ggatactcca ctggtgctga g 21

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ctctaatgtc ctcccttgtt gcc 23

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tgcagattgt ctttggctac tt 22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
acaacgcaga gctaagcaag at 22

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
gtacttgtag ttggggtggt cct 23

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
aaaagacaaa taccgggtgg tg 22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
tgattttcct ctccttggct ct 22

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
catccgacct ggtgccatc 19

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
atttcccagc taaacatgcc c 21

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
tggggtcttc atcaacggtc 20

<210> SEQ ID NO 72
<211> LENGTH: 21
<212> TYPE: DNA
<213> ORGANISM: Artificial Sequence
<220> FEATURE:

<223> OTHER INFORMATION: Description of Artificial Sequence: Synthetic primer

<400> SEQUENCE: 72
atcggcacag aatcttggag a 21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
caccaccaac cctaaccaga g 21

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
aggctgtaat agttctccac ctg 23

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gcaggctcaa gaaagtgaat ga 22

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
taggcgctca atgtactgga t 21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
agagggctct cctttgtatc c 21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
ctgctttccg acgatctgtg g 21

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
ctgcagcagc agagggcgca cca 23

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gaagaacggc ttcgaaagga cagttgg 27

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
gaaagggaga acaccgaaaa ca 22

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
gtggcccata ttgctctgga 20

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
accccagtac cgaggatgaa t 21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
aactccagac gagcttagtg a 21

<210> SEQ ID NO 85
<211> LENGTH: 2379
<212> TYPE: DNA
<213> ORGANISM: Homo sapiens

<400> SEQUENCE: 85
gacccccgag ctgtgctgct cgcggccgcc accgccgggc cccggccgtc cctggctccc 60
ctcctgcctc gagaagggca gggcttctca gaggcttggc gggaaaaaga acggagggag 120
ggatcgcgct gagtataaaa gccggttttc ggggctttat ctaactcgct gtagtaattc 180
cagcgagagg cagagggagc gagcgggcgg ccggctaggg tggaagagcc gggcgagcag 240
agctgcgctg cgggcgtcct gggaagggag atccggagcg aataggggc ttcgcctctg 300 gcccagccct cccgctgatc ccccagccag cggtccgcaa cccttgccgc atccacgaaa 360
ctttgcccat agcagcgggc gggcactttg cactggaact tacaacaccc gagcaaggac 420
gcgactctcc cgacgcgggg aggctattct gcccatttgg ggacacttcc ccgccgctgc 480
caggacccgc ttctctgaaa ggctctcctt gcagctgctt agacgctgga ttttttcgg 540 gtagtggaaa accagcagcc tcccgcgacg atgcccctca acgttagctt caccaacagg 600
aactatgacc tcgactacga ctcggtgcag ccgtatttct actgcgacga ggaggagaac 660
ttctaccagc agcagcagca gagcgagctg cagcccccgg cgcccagcga ggatatctgg 720
aagaaattcg agctgctgcc caccccgccc ctgtccccta gccgccgctc cgggctctgc 780
tcgccctcct acgttgcggt cacacccttc tcccttcggg gagacaacga cggcggtggc 840
gggagcttct ccacggccga ccagctggag atggtgaccg agctgctggg aggagacatg 900
gtgaaccaga gtttcatctg cgacccggac gacgagacct tcatcaaaaa catcatcatc 960
caggactgta tgtggagcgg cttctcggcc gccgccaagc tcgtctcaga gaagctggcc 1020
tcctaccagg ctgcgcgcaa agacagcggc agcccgaacc ccgcccgcgg ccacagcgtc 1080
tgctccacct ccagcttgta cctgcaggat ctgagcgccg ccgcctcaga gtgcatcgac 1140
ccctcggtgg tcttccccta ccctctcaac gacagcagct cgcccaagtc ctgcgcctcg 1200
caagactcca gcgccttctc tccgtcctcg gattctctgc tctcctcgac ggagtcctcc 1260
ccgcagggca gccccgagcc cctggtgctc catgaggaga caccgcccac caccagcagc 1320
gactctgagg aggaacaaga agatgaggaa gaaatcgatg ttgtttctgt ggaaaagagg 1380
caggctcctg gcaaaaggtc agagtctgga tcaccttctg ctggaggcca cagcaaacct 1440
cctcacagcc cactggtcct caagaggtgc cacgtctcca cacatcagca caactacgca 1500
gcgcctccct ccactcggaa ggactatcct gctgccaaga gggtcaagtt ggacagtgtc 1560
agagtcctga gacagatcag caacaaccga aaatgcacca gccccaggtc ctcggacacc 1620
gaggagaatg tcaagaggcg aacacacaac gtcttggagc gccagaggag gaacgagcta 1680
aaacggagct tttttgccct gcgtgaccag atcccggagt tggaaaacaa tgaaaaggcc 1740
cccaaggtag ttatccttaa aaaagccaca gcatacatcc tgtccgtcca agcagaggag 1800
caaaagctca tttctgaaga ggacttgttg cggaaacgac gagaacagtt gaaacacaaa 1860
cttgaacagc tacggaactc ttgtgcgtaa ggaaaagtaa ggaaaacgat tccttctaac 1920
agaaatgtcc tgagcaatca cctatgaact tgtttcaaat gcatgatcaa atgcaacctc 1980

```
acaaccttgg ctgagtcttg agactgaaag atttagccat aatgtaaact gcctcaaatt   2040

ggactttggg cataaaagaa ctttttttatg cttaccatct ttttttttttc tttaacagat   2100

ttgtatttaa gaattgtttt taaaaaattt taagatttac acaatgtttc tctgtaaata   2160

ttgccattaa atgtaaataa ctttaataaa acgtttatag cagttacaca gaatttcaat   2220

cctagtatat agtacctagt attataggta ctataaaccc taattttttt tatttaagta   2280

cattttgctt tttaaagttg attttttttct attgttttta gaaaaaataa aataactggc   2340

aaatatatca ttgagccaaa tcttaaaaaa aaaaaaaaa                          2379
```

```
<210> SEQ ID NO 86
<211> LENGTH: 454
<212> TYPE: PRT
<213> ORGANISM: Homo sapiens

<400> SEQUENCE: 86

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300
```

```
Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450
```

<210> SEQ ID NO 87
<211> LENGTH: 1000
<212> TYPE: DNA
<213> ORGANISM: Homo sapiens

<400> SEQUENCE: 87

```
actctcattc cacgttctta actgttccat tttccgtatc tgcttcgggc ttccacctca      60

ttttttcgc tttgcccatt ctgtttcagc cagtcgccaa gaatcatgaa agtcgccagt     120

ggcagcaccg ccaccgccgc cgcgggcccc agctgcgcgc tgaaggccgg caagacagcg     180

agcggtgcgg gcgaggtggt gcgctgtctg tctgagcaga gcgtggccat ctcgcgctgc     240

gccgggggcg ccggggcgcg cctgcctgcc ctgctggacg agcagcaggt aaacgtgctg     300

ctctacgaca tgaacggctg ttactcacgc ctcaaggagc tggtgcccac cctgccccag     360

aaccgcaagg tgagcaaggt ggagattctc cagcacgtca tcgactacat cagggacctt     420

cagttggagc tgaactcgga atccgaagtt ggaacccccg ggggccgagg gctgccggtc     480

cgggctccgc tcagcaccct caacggcgag atcagcgccc tgacggccga ggcggcatgc     540

gttcctgcgg acgatcgcat cttgtgtcgc tgaagcgcct cccccaggga ccggcggacc     600

ccagccatcc agggggcaag aggaattacg tgctctgtgg gtctccccca acgcgcctcg     660

ccggatctga gggagaacaa gaccgatcgg cggccactgc gcccttaact gcatccagcc     720

tggggctgag gctgaggcac tggcgaggag agggcgctcc tctctgcaca cctactagtc     780

accagagact ttagggggtg ggattccact cgtgtgtttc tattttttga aaagcagaca     840

ttttaaaaaa tggtcacgtt tggtgcttct cagatttctg aggaaattgc tttgtattgt     900

atattacaat gatcaccgac tgaaaatatt gttttacaat agttctgtgg ggctgttttt     960

ttgttattaa acaaataatt tagatggtgg taaaaaaaaa                          1000
```

<210> SEQ ID NO 88
<211> LENGTH: 155
<212> TYPE: PRT
<213> ORGANISM: Homo sapiens

<400> SEQUENCE: 88

```
Met Lys Val Ala Ser Gly Ser Thr Ala Thr Ala Ala Ala Gly Pro Ser
1               5                   10                  15

Cys Ala Leu Lys Ala Gly Lys Thr Ala Ser Gly Ala Gly Glu Val Val
            20                  25                  30

Arg Cys Leu Ser Glu Gln Ser Val Ala Ile Ser Arg Cys Ala Gly Gly
        35                  40                  45

Ala Gly Ala Arg Leu Pro Ala Leu Leu Asp Glu Gln Gln Val Asn Val
    50                  55                  60

Leu Leu Tyr Asp Met Asn Gly Cys Tyr Ser Arg Leu Lys Glu Leu Val
65                  70                  75                  80

Pro Thr Leu Pro Gln Asn Arg Lys Val Ser Lys Val Glu Ile Leu Gln
                85                  90                  95

His Val Ile Asp Tyr Ile Arg Asp Leu Gln Leu Glu Leu Asn Ser Glu
            100                 105                 110

Ser Glu Val Gly Thr Pro Gly Gly Arg Gly Leu Pro Val Arg Ala Pro
        115                 120                 125

Leu Ser Thr Leu Asn Gly Glu Ile Ser Ala Leu Thr Ala Glu Ala Ala
    130                 135                 140

Cys Val Pro Ala Asp Asp Arg Ile Leu Cys Arg
145                 150                 155
```

<210> SEQ ID NO 89
<211> LENGTH: 4772
<212> TYPE: DNA
<213> ORGANISM: Homo sapiens

<400> SEQUENCE: 89

```
gctcagttgc cgggcggggg agggcgcgtc cggtttttct caggggacgt tgaaattatt      60

tttgtaacgg gagtcgggag aggacggggc gtgccccgac gtgcgcgcgc gtcgtcctcc     120

ccggcgctcc tccacagctc gctggctccc gccgcggaaa ggcgtcatgc cgcccaaaac     180

cccccgaaaa acggccgcca ccgccgccgc tgccgccgcg gaacccccgg caccgccgcc     240

gccgccccct cctgaggagg acccagagca ggacagcggc ccggaggacc tgcctctcgt     300

caggcttgag tttgaagaaa cagaagaacc tgattttact gcattatgtc agaaattaaa     360

gataccagat catgtcagag agagagcttg gttaacttgg gagaaagttt catctgtgga     420

tggagtattg ggaggttata ttcaaaagaa aaaggaactg tggggaatct gtatctttat     480

tgcagcagtt gacctagatg agatgtcgtt cacttttact gagctacaga aaaacataga     540

aatcagtgtc cataaattct ttaacttact aaaagaaatt gataccagta ccaaagttga     600

taatgctatg tcaagactgt tgaagaagta tgatgtattg tttgcactct tcagcaaatt     660

ggaaaggaca tgtgaactta tatatttgac acaacccagc agttcgatat ctactgaaat     720

aaattctgca ttggtgctaa aagtttcttg gatcacattt ttattagcta aaggggaagt     780

attacaaatg gaagatgatc tggtgatttc atttcagtta atgctatgtg tccttgacta     840

ttttattaaa ctctcacctc ccatgttgct caaagaacca tataaaacag ctgttatacc     900

cattaatggt tcacctcgaa cacccaggcg aggtcagaac aggagtgcac ggatagcaaa     960

acaactagaa aatgatacaa gaattattga agttctctgt aaagaacatg aatgtaatat    1020

agatgaggtg aaaaatgttt atttcaaaaa ttttatacct tttatgaatt ctcttggact    1080

tgtaacatct aatggacttc cagaggttga aaatctttct aaacgatacg aagaaattta    1140

tcttaaaaat aaagatctag atgcaagatt atttttggat catgataaaa ctcttcagac    1200
```

-continued

```
tgattctata gacagttttg aaacacagag aacaccacga aaaagtaacc ttgatgaaga   1260
ggtgaatgta attcctccac acactccagt taggactgtt atgaacacta tccaacaatt   1320
aatgatgatt ttaaattcag caagtgatca accttcagaa aatctgattt cctattttaa   1380
caactgcaca gtgaatccaa aagaaagtat actgaaaaga gtgaaggata taggatacat   1440
ctttaaagag aaatttgcta aagctgtggg acagggttgt gtcgaaattg gatcacagcg   1500
atacaaactt ggagttcgct tgtattaccg agtaatggaa tccatgctta aatcagaaga   1560
agaacgatta tccattcaaa attttagcaa acttctgaat gacaacattt ttcatatgtc   1620
tttattggcg tgcgctcttg aggttgtaat ggccacatat agcagaagta catctcagaa   1680
tcttgattct ggaacagatt tgtctttccc atggattctg aatgtgctta atttaaaagc   1740
ctttgatttt tacaaagtga tcgaaagttt tatcaaagca gaaggcaact tgacaagaga   1800
aatgataaaa catttagaac gatgtgaaca tcgaatcatg gaatcccttg catggctctc   1860
agattcacct ttatttgatc ttattaaaca atcaaaggac cgagaaggac caactgatca   1920
ccttgaatct gcttgtcctc ttaatcttcc tctccagaat aatcacactg cagcagatat   1980
gtatcttttct cctgtaagat ctccaaagaa aaaaggttca actacgcgtg taaattctac  2040
tgcaaatgca gagacacaag caacctcagc cttccagacc cagaagccat tgaaatctac   2100
ctctctttca ctgttttata aaaaagtgta tcggctagcc tatctccggc taaatacact   2160
ttgtgaacgc cttctgtctg agcacccaga attagaacat atcatctgga cccttttcca   2220
gcacaccctg cagaatgagt atgaactcat gagagacagg catttggacc aaattatgat   2280
gtgttccatg tatggcatat gcaaagtgaa gaatatagac cttaaattca aaatcattgt   2340
aacagcatac aaggatcttc ctcatgctgt tcaggagaca ttcaaacgtg ttttgatcaa   2400
agaagaggag tatgattcta ttatagtatt ctataactcg gtcttcatgc agagactgaa   2460
aacaaatatt ttgcagtatg cttccaccag gcccccctacc ttgtcaccaa tacctcacat  2520
tcctcgaagc ccttacaagt ttcctagttc acccttacgg attcctggag ggaacatcta   2580
tatttcaccc ctgaagagtc catataaaat ttcagaaggt ctgccaacac caacaaaaat   2640
gactccaaga tcaagaatct tagtatcaat tggtgaatca ttcgggactt ctgagaagtt   2700
ccagaaaata aatcagatgg tatgtaacag cgaccgtgtg ctcaaaagaa gtgctgaagg   2760
aagcaaccct cctaaaccac tgaaaaaact acgctttgat attgaaggat cagatgaagc   2820
agatggaagt aaacatctcc caggagagtc caaatttcag cagaaactgg cagaaatgac   2880
ttctactcga acacgaatgc aaaagcagaa aatgaatgat agcatggata cctcaaacaa   2940
ggaagagaaa tgaggatctc aggaccttgg tggacactgt gtacacctct ggattcattg   3000
tctctcacag atgtgactgt ataactttcc caggttctgt ttatggccac atttaatatc   3060
ttcagctctt tttgtggata taaaatgtgc agatgcaatt gtttgggtga ttcctaagcc   3120
acttgaaatg ttagtcattg ttatttatac aagattgaaa atcttgtgta aatcctgcca   3180
tttaaaaagt tgtagcagat tgtttcctct tccaaagtaa aattgctgtg ctttatggat   3240
agtaagaatg gccctagagt gggagtcctg ataacccagg cctgtctgac tactttgcct   3300
tcttttgtag catataggtg atgtttgctc ttgtttttat taatttatat gtatattttt   3360
ttaatttaac atgaacaccc ttagaaaatg tgtcctatct atcttccaaa tgcaatttga   3420
ttgactgccc attcaccaaa attatcctga actcttctgc aaaaatggat attattagaa   3480
attagaaaaa aattactaat tttacacatt agattttatt ttactattgg aatctgatat   3540
actgtgtgct tgttttataa aattttgctt ttaattaaat aaaagctgga agcaaagtat   3600
```

```
aaccatatga tactatcata ctactgaaac agatttcata cctcagaatg taaaagaact   3660
tactgattat tttcttcatc caacttatgt ttttaaatga ggattattga tagtactctt   3720
ggtttttata ccattcagat cactgaattt ataaagtacc catctagtac ttgaaaaagt   3780
aaagtgttct gccagatctt aggtatagag gaccctaaca cagtatatcc caagtgcact   3840
ttctaatgtt tctgggtcct gaagaattaa gatacaaatt aattttactc cataaacaga   3900
ctgttaatta taggagcctt aatttttttt tcatagagat ttgtctaatt gcatctcaaa   3960
attattctgc cctccttaat ttgggaaggt ttgtgttttc tctggaatgg tacatgtctt   4020
ccatgtatct tttgaactgg caattgtcta tttatctttt attttttaa gtcagtatgg   4080
tctaacactg gcatgttcaa agccacatta tttctagtcc aaaattacaa gtaatcaagg   4140
gtcattatgg gttaggcatt aatgtttcta tctgattttg tgcaaaagct tcaaattaaa   4200
acagctgcat tagaaaaaga ggcgcttctc ccctccccta cacctaaagg tgtatttaaa   4260
ctatcttgtg tgattaactt atttagagat gctgtaactt aaaatagggg atatttaagg   4320
tagcttcagc tagcttttag gaaaatcact ttgtctaact cagaattatt tttaaaaaga   4380
aatctggtct tgttagaaaa caaaatttta ttttgtgctc atttaagttt caaacttact   4440
attttgacag ttattttgat aacaatgaca ctagaaaact tgactccatt tcatcattgt   4500
ttctgcatga atatcataca aatcagttag tttttaggtc aagggcttac tatttctggg   4560
tcttttgcta ctaagttcac attagaatta gtgccagaat tttaggaact tcagagatcg   4620
tgtattgaga tttcttaaat aatgcttcag atattattgc tttattgctt ttttgtattg   4680
gttaaaactg tacatttaaa attgctatgt tactattttc tacaattaat agtttgtcta   4740
ttttaaaata aattagttgt taagagtctt aa                                4772
```

<210> SEQ ID NO 90
<211> LENGTH: 928
<212> TYPE: PRT
<213> ORGANISM: Homo sapiens

<400> SEQUENCE: 90

```
Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160
```

```
Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
    290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
        355                 360                 365

Ile Pro Pro His Thr Pro Val Arg Thr Val Met Asn Thr Ile Gln Gln
    370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
            420                 425                 430

Ala Val Gly Gln Gly Cys Val Glu Ile Gly Ser Gln Arg Tyr Lys Leu
        435                 440                 445

Gly Val Arg Leu Tyr Tyr Arg Val Met Glu Ser Met Leu Lys Ser Glu
    450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
    530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
```

```
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
    610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
        675                 680                 685

Gln Asn Glu Tyr Glu Leu Met Arg Asp Arg His Leu Asp Gln Ile Met
    690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
    770                 775                 780

Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
        915                 920                 925


<210> SEQ ID NO 91
<211> LENGTH: 1267
<212> TYPE: DNA
<213> ORGANISM: Homo sapiens

<400> SEQUENCE: 91

cgagggctgc ttccggctgg tgcccccggg ggagacccaa cctggggcga cttcaggggt      60

gccacattcg ctaagtgctc ggagttaata gcacctcctc cgagcactcg ctcacggcgt     120

ccccttgcct ggaaagatac cgcggtccct ccagaggatt tgagggacag ggtcggaggg     180
```

```
ggctcttccg ccagcaccgg aggaagaaag aggaggggct ggctggtcac cagagggtgg    240
ggcggaccgc gtgcgctcgg cggctgcgga gagggggaga gcaggcagcg ggcggcgggg    300
agcagcatgg agccggcggc ggggagcagc atggagcctt cggctgactg gctggccacg    360
gccgcggccc ggggtcgggt agaggaggtg cgggcgctgc tggaggcggg ggcgctgccc    420
aacgcaccga atagttacgg tcggaggccg atccaggtca tgatgatggg cagcgcccga    480
gtggcggagc tgctgctgct ccacggcgcg gagcccaact gcgccgaccc cgccactctc    540
acccgacccg tgcacgacgc tgcccgggag ggcttcctgg acacgctggt ggtgctgcac    600
cgggccgggg cgcggctgga cgtgcgcgat gcctggggcc gtctgcccgt ggacctggct    660
gaggagctgg gccatcgcga tgtcgcacgg tacctgcgcg cggctgcggg gggcaccaga    720
ggcagtaacc atgcccgcat agatgccgcg gaaggtccct cagacatccc cgattgaaag    780
aaccagagag gctctgagaa acctcgggaa acttagatca tcagtcaccg aaggtcctac    840
agggccacaa ctgcccccgc cacaacccac cccgctttcg tagttttcat ttagaaaata    900
gagcttttaa aaatgtcctg ccttttaacg tagatatatg ccttccccca ctaccgtaaa    960
tgtccattta tatcattttt tatatattct tataaaaatg taaaaaagaa aaacaccgct   1020
tctgcctttt cactgtgttg gagttttctg gagtgagcac tcacgcccta agcgcacatt   1080
catgtgggca tttcttgcga gcctcgcagc ctccggaagc tgtcgacttc atgacaagca   1140
ttttgtgaac tagggaagct caggggggtt actggcttct cttgagtcac actgctagca   1200
aatggcagaa ccaaagctca aataaaaata aaataatttt cattcattca ctcaaaaaaa   1260
aaaaaaa                                                             1267
```

```
<210> SEQ ID NO 92
<211> LENGTH: 156
<212> TYPE: PRT
<213> ORGANISM: Homo sapiens

<400> SEQUENCE: 92

Met Glu Pro Ala Ala Gly Ser Ser Met Glu Pro Ser Ala Asp Trp Leu
1               5                   10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Ala Gly Gly Thr Arg Gly Ser Asn His Ala Arg
    130                 135                 140

Ile Asp Ala Ala Glu Gly Pro Ser Asp Ile Pro Asp
145                 150                 155


<210> SEQ ID NO 93
<211> LENGTH: 3878
```

<212> TYPE: DNA
<213> ORGANISM: Homo sapiens

<400> SEQUENCE: 93

```
ggctccccac tctgccagag cgaggcgggg cagtgaggac tccgcgacgc gtccgcaccc     60
tgcggccaga gcggctttga gctcggctgc gtccgcgcta ggcgcttttt cccagaagca    120
atccaggcgc gcccgctggt tcttgagcgc caggaaaagc ccggagctaa cgaccggccg    180
ctcggccact gcacggggcc ccaagccgca gaaggacgac gggagggtaa tgaagctgag    240
cccaggtctc ctaggaagga gagagtgcgc cggagcagcg tgggaaagaa gggaagagtg    300
tcgttaagtt tacggccaac ggtggattat ccgggccgct gcgcgtctgg gggctgcgga    360
atgcgcgagg agaacaaggg catgcccagt gggggcggca gcgatgaggg tctggccagc    420
gccgcggcgc ggggactagt ggagaaggtg cgacagctcc tggaagccgg cgcggatccc    480
aacggagtca accgtttcgg gaggcgcgcg atccaggtca tgatgatggg cagcgcccgc    540
gtggcggagc tgctgctgct ccacggcgcg gagcccaact gcgcagaccc tgccactctc    600
acccgaccgg tgcatgatgc tgcccgggag ggcttcctgg acacgctggt ggtgctgcac    660
cgggccgggg cgcggctgga cgtgcgcgat gcctggggtc gtctgcccgt ggacttggcc    720
gaggagcggg gccaccgcga cgttgcaggg tacctgcgca cagccacggg ggactgacgc    780
caggttcccc agccgcccac aacgacttta ttttcttacc caatttccca cccccaccca    840
cctaattcga tgaaggctgc caacggggag cggcggaaag cctgtaagcc tgcaagcctg    900
tctgagactc acaggaagga ggagccgacc gggaataacc ttccatacat ttttttcttt    960
gtcttatctg gccctcgaca ctcaccatga agcgaaacac agagaagcgg atttccaggg   1020
atatttagga gtgtgtgaca ttccaggggt cgtttgcttt tcagggtttt ctgagggaaa   1080
gtgcatatga aatccttgac tggacctggt ggctacgaat cttccgatgg atgaatctcc   1140
cactccagcg ctgagtggga gaaggcagtg attagcactt gggtgacggc agtcgatgcg   1200
ttcactccaa tgtctgctga ggagttatgg tgaacccaca acttaggccc tagcggcaga   1260
aaggaaaacc tgaagactga ggacaaagtg gaggagggcc gaggtgggct tcagtaagtc   1320
cccggcggcg ctttagtttg agcgcatggc aagtcacatg cgtaaacgac actctctgga   1380
agccctggag accctcgccc aactccacca gatagcagag ggtaagagaa ggatgtgcaa   1440
gcgacgacag atgctaaaat ccctggatca cgacgctgca gagcaccttt gcacaggatg   1500
ctggcctttg ctcttactac actgaggaga gattcccgcg ggttccgcag gcagactaca   1560
caggatgagg tggtggagtg gagtgagagc aattgtaacg gttaactgta acgttttctt   1620
tcacacacac acacacacac acacacacac atgctaggat gcggaaatcc ccttatgact   1680
tgctactttt tgattttgtg atattttgta ctttttagtt gttcagcaac tgtcttattt   1740
aatggggaga ttttaagtaa cataactagt ggctctcagt taaaatgtga ggaagaacta   1800
cagctcttaa atgtagcaat ggcactgttg caaactcagt gcaaacgcct agattgcttt   1860
cttcttaacc tatttatttc tttgttaaat ttttctgatt gtttccttta tagagtgtct   1920
cagggtgcag aggtcagact aagaaatatt ccaaatgtct tttagaagat agatgcactt   1980
atgcagtaaa ttatcttggg atagttccca aaagattgct gaaaaagtag attgagtata   2040
aaaacttgaa aatatatgat ggctcgtggg atgtcctact atcactgaac aaactaaagg   2100
tgcactgctt tgggatttaa tttccagggt tgcttgatca ttatatcatt ggaacaactg   2160
atacttcact actttaataa agaattaaca gagattgaac tccaagaggt gggtaatttg   2220
```

```
gtttaaaaat acatgttcat gggtttacca ctaactcctg agaaatgtta aaggttcaca   2280

ggggttccct tctctcaatg tttgtaataa ttgctcataa gcaataccag caattcataa   2340

aaactgctta cttatgccat agaaaattaa acacaaagtg tatacatgta ttatgcttct   2400

aaatgctcat tctaccagat acacatttaa aagagaaaaa aggaacagaa acaagtcatt   2460

tgagagtgga gacttataag aaggagtaca tttgagttga atacacaaat ctttacttct   2520

ctaccaattc ctattcccaa aatgaacata ttactgggga aagttagttg agaatcagag   2580

catatgttat tggggaaagg atatgtttat tgacacataa tctgtaccag gtatgcatta   2640

aaatatattt gttaatttaa tatttaaacc tgagagatag gtattgtttc ccagatgagg   2700

acaatgaggc aaagaaatat caagtaactt gccaaaggtt acaagatatt cattccatgg   2760

atgcacaaag aagtgcatct agttccacag ctgattatgg ttgtcttgct tttcttccca   2820

ttgcaccagc ttgtcctcca aaatcatgaa tgatacacat gaagataact tttttaaaa    2880

aaaagcagaa atacacaatg atctcccttg taagctccta aggtggcttt tctttctcta   2940

acttctagta aatataaacg gtttgtttga aaactatttt aaaatgtcaa caatatggag   3000

aataaccccc cccaacacac ctataaaaac ccaaattttt ggaacaaaga taatggaacc   3060

tccattttca aactgaagca cagggacaga aaatatattt ctagttatca cttaagcact   3120

caatcattag aggctacaag aataatattt ttaaagttac agtattttac aattattaga   3180

aaacattcta tataaaagaa gtcagttgat actttaaaat ctcccatttg gtttataaaa   3240

tcccttaatt tgacctctat atcttaaatt ccaagatgtt taaatttgct agttgcatta   3300

tactgggtca tgaaaaatta tcccttgaaa tagatatgaa acatgttact tcatttctgg   3360

tttaaataac ttgtggaatc tttcctaatg acaacctgat attaagggaa actaaagaaa   3420

atgttattgt ggatcccaca gtactatatt acactgtttt ttttgtttgt tttgttagtt   3480

ttttttattt aaagcaaacc tcaaacatta ttgggtatca attaccacct ggttgtattg   3540

aaatagtaac ttatcaatgc catgtaaaaa ttaattccat tttcgaagcc acctggcaga   3600

caggtttagc tgtttcatca gcagcctaat atatactgtt aaatttgtta aggatttcac   3660

tttgaaggat acatgcaaaa catatagtta ctattttcat gagtcctgct tctagctcca   3720

ttgtggaata cagaaaatta aatatacctg ttaagttcgt atctaaacct aagacattac   3780

caaggtttgt acaaattcta ctacctgaca tttattccaa gaagatctgg aaagttaaat   3840

aaatttataa atttaataac aaaaaaaaaa aaaaaaaa                           3878
```

<210> SEQ ID NO 94
<211> LENGTH: 138
<212> TYPE: PRT
<213> ORGANISM: Homo sapiens

<400> SEQUENCE: 94

```
Met Arg Glu Glu Asn Lys Gly Met Pro Ser Gly Gly Gly Ser Asp Glu
1               5                   10                  15

Gly Leu Ala Ser Ala Ala Ala Arg Gly Leu Val Glu Lys Val Arg Gln
            20                  25                  30

Leu Leu Glu Ala Gly Ala Asp Pro Asn Gly Val Asn Arg Phe Gly Arg
        35                  40                  45

Arg Ala Ile Gln Val Met Met Met Gly Ser Ala Arg Val Ala Glu Leu
    50                  55                  60

Leu Leu Leu His Gly Ala Glu Pro Asn Cys Ala Asp Pro Ala Thr Leu
65                  70                  75                  80
```

```
Thr Arg Pro Val His Asp Ala Ala Arg Glu Gly Phe Leu Asp Thr Leu
                85                  90                  95

Val Val Leu His Arg Ala Gly Ala Arg Leu Asp Val Arg Asp Ala Trp
            100                 105                 110

Gly Arg Leu Pro Val Asp Leu Ala Glu Glu Arg Gly His Arg Asp Val
        115                 120                 125

Ala Gly Tyr Leu Arg Thr Ala Thr Gly Asp
    130                 135


<210> SEQ ID NO 95
<211> LENGTH: 2104
<212> TYPE: DNA
<213> ORGANISM: Homo sapiens

<400> SEQUENCE: 95

ctctgccgag cctccttaaa actctgccgt taaaatgggg gcgggttttt caactcaaaa     60

agcgctcaat ttttttcttt tcaaaaaaag ctgatgaggt cggaaaaaag ggagaagaaa    120

ccggcaccct ctctgagagg caacagaagc agcaattgtt tcagcgaaaa aagcagcaag    180

ggagggagtg aaggaaaaaa gcaaaaaagg gggcgacacg caagtgcctg taggggtgaa    240

aggagcaggg accggcgatc taggggggga tcagctacaa aagaaactgt cactgggagc    300

ggtgcggcca aggaggaagc agtgctgcca ggctctgctc cagggcacag ctggctggcg    360

gctgccctgt ccgcagcaaa ggggcacagg ccggggaccg cgagaggtgg caaagtggca    420

ccgggcgccg aggctgctga gcgctcgccg agacggcgac cggactggct gccccggaac    480

tgcggcgact ctccctactc agaacttggc ctacgtttcc caggactctc cccatctcca    540

gaggccccca caaaaccggg aaaggaagga aaggacagcg gcggcagcag ctcaatgagt    600

gcctacagca gaaagcctga acgagctcgg tcgtaggcgg gaagttcccg ggggggctgc    660

ccagtgcagc cgcaatgctg ccgcgagctg ccccagcagt ccgggctccg tagacgcttt    720

ccgcatcact ctccttcctc gggctgccgg gagtcccggg acctggcggg gccggcatga    780

cgggcttctc gggggcccgc cgcacgcccg gcagcctccg gagacgcgcg ccgagcccgg    840

ctcccacggc ctctgaggct cggcggggct gcggctgcct ggcgggcggg ctccggagct    900

ttcctgagcg gcattagccc acggcttggc ccggacgcga ccaaaggctc ttctggagaa    960

gcccagagca ctgggcaatc gttacgacct gtaacttgag ggccaccgaa ctgctactcc   1020

cgttcgcctt tggcgatcat cttttaaccc tccggagcac gtcagcatcc agccaccgcg   1080

gcgctctccc agcagcggag gacccaggac tatcccttcg gcgagacgga tggaaaccga   1140

gccccctgga ggacctgccc ctgcagttct gcctcacacg gctcaagtca ccaccgtgaa   1200

caagggaccc taaagaatgg ccgagccttg ggggaacgag ttggcgtccg cagctgccag   1260

gggggaccta gagcaactta ctagtttgtt gcaaaataat gtaaacgtca atgcacaaaa   1320

tggatttgga aggactgcgc tgcaggttat gaaacttgga aatcccgaga ttgccaggag   1380

actgctactt agaggtgcta atcccgattt gaaagaccga actggtttcg ctgtcattca   1440

tgatgcggcc agagcaggtt tcctggacac tttacagact ttgctggagt ttcaagctga   1500

tgttaacatc gaggataatg aagggaacct gcccttgcac ttggctgcca aagaaggcca   1560

cctccgggtg gtggagttcc tggtgaagca cacggccagc aatgtggggc atcggaacca   1620

taagggggac accgcctgtg atttggccag gctctatggg aggaatgagg ttgttagcct   1680

gatgcaggca aacggggctg gggagccac aaatcttcaa taaacgtggg gagggctccc   1740

ccacgttgcc tctactttat caattaactg agtagctctc ctgactttta atgtcatttg   1800
```

```
ttaaaataca gttctgtcat atgttaagca gctaaatttt ctgaaactgc ataagtgaaa   1860

atcttacaac aggcttatga atatatttaa gcaacatctt tttaacctgc aaaatctgtt   1920

ctaacatgta attgcagata actttgactt tcttctgaat attttatctt tccttggctt   1980

ttcccttgct tccccttttg ccaatctcaa cacccaagtt gaagactttg tttttaaaat   2040

ggtttgtcct gatgcttttg tctaattaaa acactttcaa aacaggaaaa aaaaaaaaaa   2100

aaaa                                                                2104
```

<210> SEQ ID NO 96
<211> LENGTH: 168
<212> TYPE: PRT
<213> ORGANISM: Homo sapiens

<400> SEQUENCE: 96

```
Met Ala Glu Pro Trp Gly Asn Glu Leu Ala Ser Ala Ala Ala Arg Gly
1               5                   10                  15

Asp Leu Glu Gln Leu Thr Ser Leu Leu Gln Asn Asn Val Asn Val Asn
            20                  25                  30

Ala Gln Asn Gly Phe Gly Arg Thr Ala Leu Gln Val Met Lys Leu Gly
        35                  40                  45

Asn Pro Glu Ile Ala Arg Arg Leu Leu Leu Arg Gly Ala Asn Pro Asp
    50                  55                  60

Leu Lys Asp Arg Thr Gly Phe Ala Val Ile His Asp Ala Ala Arg Ala
65                  70                  75                  80

Gly Phe Leu Asp Thr Leu Gln Thr Leu Leu Glu Phe Gln Ala Asp Val
                85                  90                  95

Asn Ile Glu Asp Asn Glu Gly Asn Leu Pro Leu His Leu Ala Ala Lys
            100                 105                 110

Glu Gly His Leu Arg Val Val Glu Phe Leu Val Lys His Thr Ala Ser
        115                 120                 125

Asn Val Gly His Arg Asn His Lys Gly Asp Thr Ala Cys Asp Leu Ala
    130                 135                 140

Arg Leu Tyr Gly Arg Asn Glu Val Val Ser Leu Met Gln Ala Asn Gly
145                 150                 155                 160

Ala Gly Gly Ala Thr Asn Leu Gln
                165
```

<210> SEQ ID NO 97
<211> LENGTH: 1416
<212> TYPE: DNA
<213> ORGANISM: Homo sapiens

<400> SEQUENCE: 97

```
ggagggaggg tgagttaggg ggagacccgg cccccaaggg gcgggcgccg ggcagggccc     60

cgcgggcggc cgagggttgg gcccggctcc cagcccctcg ccgtcctccg gctgacaggg    120

ggaggagccc gccgggaggg ccggggtctc gggctgggga gccgggacgg gagagcagcg    180

cagccgggtg caccgcggcc gcgccccggg agggctgttc gggccagcgc ccgccggctg    240

ctccgcgctg acagcgccgg gctggggcgg ggcggggggc tttgcaggcc gccagtgtcg    300

acatgctgct ggaggaggtt cgcgccggcg accggctgag tggggcggcg gcccggggcg    360

acgtgcagga ggtgcgccgc cttctgcacc gcgagctggt gcatcccgac gccctcaacc    420

gcttcggcaa gacggcgctg caggtcatga tgtttggcag caccgccatc gccctggagc    480

tgctgaagca aggtgccagc cccaatgtcc aggacacctc cggtaccagt ccagtccatg    540
```

```
acgcagcccg cactggattc ctggacaccc tgaaggtcct agtggagcac ggggctgatg    600

tcaacgtgcc tgatggcacc ggggcacttc caatccatct ggcagttcaa gagggtcaca    660

ctgctgtggt cagctttctg gcagctgaat ctgatctcca tcgcagggac gccaggggtc    720

tcacaccctt ggagctggca ctgcagagag ggctcagga cctcgtggac atcctgcagg    780

gccacatggt ggccccgctg tgatctgggg tcaccctctc cagcaagaga accccgtggg    840

gttatgtatc agaagagagg ggaagaaaca ctttctcttc ttgtttctcc tgcccactgc    900

tgcagtaggg gaggagcaca gtttgtggct tataggtgtt ggttttgggg gtgtgagtgt    960

ttgggggacg tttctcattt gtttttctca ctccttttgg tgtgttggac agagaagggc   1020

tcctgcaggc cacagccacc taaacggttc agtttcttct gcgcctcagg ctgctggggc   1080

ctcagacgag acccaagggc agagcattta agagtgaagt catgacctcc agggagccta   1140

gaagctggtg gccttggccg gctgtgctca gagacctgaa gtgtgcacgt tgcttcaggc   1200

atggggggtg gggggagcgt cccaaatcaa taagaaggta gaatgagtta tgagttattc   1260

atattctgtt ggaagcttgt tttccagtct cttgtacagc gttttaaaag aaatggattc   1320

tatttattat gctttattgg aaaaaatgtt gtaataattt aatgttttta cccattaaat   1380

taagacttgt gcatgatcaa aaaaaaaaaa aaaaaa                             1416
```

<210> SEQ ID NO 98
<211> LENGTH: 166
<212> TYPE: PRT
<213> ORGANISM: Homo sapiens

<400> SEQUENCE: 98

```
Met Leu Leu Glu Glu Val Arg Ala Gly Asp Arg Leu Ser Gly Ala Ala
1               5                   10                  15

Ala Arg Gly Asp Val Gln Glu Val Arg Arg Leu Leu His Arg Glu Leu
            20                  25                  30

Val His Pro Asp Ala Leu Asn Arg Phe Gly Lys Thr Ala Leu Gln Val
        35                  40                  45

Met Met Phe Gly Ser Thr Ala Ile Ala Leu Glu Leu Leu Lys Gln Gly
    50                  55                  60

Ala Ser Pro Asn Val Gln Asp Thr Ser Gly Thr Ser Pro Val His Asp
65                  70                  75                  80

Ala Ala Arg Thr Gly Phe Leu Asp Thr Leu Lys Val Leu Val Glu His
                85                  90                  95

Gly Ala Asp Val Asn Val Pro Asp Gly Thr Gly Ala Leu Pro Ile His
            100                 105                 110

Leu Ala Val Gln Glu Gly His Thr Ala Val Val Ser Phe Leu Ala Ala
        115                 120                 125

Glu Ser Asp Leu His Arg Arg Asp Ala Arg Gly Leu Thr Pro Leu Glu
    130                 135                 140

Leu Ala Leu Gln Arg Gly Ala Gln Asp Leu Val Asp Ile Leu Gln Gly
145                 150                 155                 160

His Met Val Ala Pro Leu
                165
```

<210> SEQ ID NO 99
<211> LENGTH: 2535
<212> TYPE: DNA
<213> ORGANISM: Homo sapiens

<400> SEQUENCE: 99

```
ttaaggccgc gctcgccagc ctcggcgggg cggctcccgc cgccgcaacc aatggatctc     60
ctcctctgtt taaatagact cgccgtgtca atcattttct tcttcgtcag cctcccttcc    120
accgccatat tgggccacta aaaaaagggg gctcgtcttt tcggggtgtt tttctccccc    180
tcccctgtcc ccgcttgctc acggctctgc gactccgacg ccggcaaggt ttggagagcg    240
gctgggttcg cgggacccgc gggcttgcac ccgcccagac tcggacgggc tttgccaccc    300
tctccgcttg cctggtcccc tctcctctcc gccctcccgc tcgccagtcc atttgatcag    360
cggagactcg gcggccgggc cggggcttcc ccgcagcccc tgcgcgctcc tagagctcgg    420
gccgtggctc gtcggggtct gtgtcttttg gctccgaggg cagtcgctgg gcttccgaga    480
ggggttcggg ctgcgtaggg gcgctttgtt ttgttcggtt ttgttttttt gagagtgcga    540
gagaggcggt cgtgcagacc cgggagaaag atgtcaaacg tgcgagtgtc taacgggagc    600
cctagcctgg agcggatgga cgccaggcag gcggagcacc ccaagccctc ggcctgcagg    660
aacctcttcg gcccggtgga ccacgaagag ttaacccggg acttggagaa gcactgcaga    720
gacatggaag aggcgagcca gcgcaagtgg aatttcgatt ttcagaatca caaaccccta    780
gagggcaagt acgagtggca agaggtggag aagggcagct tgcccgagtt ctactacaga    840
cccccgcggc cccccaaagg tgcctgcaag gtgccggcgc aggagagcca ggatgtcagc    900
gggagccgcc cggcggcgcc tttaattggg gctccggcta actctgagga cacgcatttg    960
gtggacccaa agactgatcc gtcggacagc cagacggggt tagcggagca atgcgcagga   1020
ataaggaagc gacctgcaac cgacgattct tctactcaaa acaaaagagc caacagaaca   1080
gaagaaaatg tttcagacgg ttccccaaat gccggttctg tggagcagac gcccaagaag   1140
cctggcctca gaagacgtca aacgtaaaca gctcgaatta agaatatgtt tccttgttta   1200
tcagatacat cactgcttga tgaagcaagg aagatataca tgaaaatttt aaaaatacat   1260
atcgctgact tcatggaatg gacatcctgt ataagcactg aaaaacaaca acacaataac   1320
actaaaattt taggcactct taaatgatct gcctctaaaa gcgttggatg tagcattatg   1380
caattaggtt tttccttatt tgcttcattg tactacctgt gtatatagtt tttacctttt   1440
atgtagcaca taaactttgg ggaagggagg gcagggtggg gctgaggaac tgacgtggag   1500
cggggtatga agagcttgct ttgatttaca gcaagtagat aaatatttga cttgcatgaa   1560
gagaagcaat tttggggaag ggtttgaatt gttttcttta aagatgtaat gtccctttca   1620
gagacagctg atacttcatt taaaaaaatc acaaaaattt gaacactggc taaagataat   1680
tgctatttat ttttacaaga agtttattct catttgggag atctggtgat ctcccaagct   1740
atctaaagtt tgttagatag ctgcatgtgg ctttttttaaa aaagcaacag aaacctatcc   1800
tcactgccct ccccagtctc tcttaaagtt ggaatttacc agttaattac tcagcagaat   1860
ggtgatcact ccaggtagtt tggggcaaaa atccgaggtg cttgggagtt ttgaatgtta   1920
agaattgacc atctgctttt attaaatttg ttgacaaaat tttctcattt tcttttcact   1980
tcgggctgtg taaacacagt caaaataatt ctaaatccct cgatattttt aaagatctgt   2040
aagtaacttc acattaaaaa atgaaatatt ttttaattta aagcttactc tgtccattta   2100
tccacaggaa agtgttattt ttcaaggaag gttcatgtag agaaaagcac acttgtagga   2160
taagtgaaat ggatactaca tctttaaaca gtatttcatt gcctgtgtat ggaaaaacca   2220
tttgaagtgt acctgtgtac ataactctgt aaaaacactg aaaaattata ctaacttatt   2280
tatgttaaaa gatttttttt aatctagaca atatacaagc caaagtggca tgttttgtgc   2340
```

```
atttgtaaat gctgtgttgg gtagaatagg ttttcccctc ttttgttaaa taatatggct   2400

atgcttaaaa ggttgcatac tgagccaagt ataatttttt gtaatgtgtg aaaaagatgc   2460

caattattgt tacacattaa gtaatcaata aagaaaactt ccatagctat tcattgagtc   2520

aaaaaaaaaa aaaaa                                                    2535


<210> SEQ ID NO 100
<211> LENGTH: 198
<212> TYPE: PRT
<213> ORGANISM: Homo sapiens

<400> SEQUENCE: 100

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195


<210> SEQ ID NO 101
<211> LENGTH: 1943
<212> TYPE: DNA
<213> ORGANISM: Homo sapiens

<400> SEQUENCE: 101

agtgcgctgt gctcgagggg tgccggccag gcctgagcga gcgagctagc cagcaggcat     60

cgagggggcg cggctgccgt ccggacgaga caggcgaacc cgacgcagaa gagtccacca    120

ccggacagcc aggtagccgc cgcgtccctc gcacacgcag agtcgggcgg cgcggggtct    180

cccttgcgcc cggcctccgc cctctcctcc tctcctttcc ccttcttctc gctgtcctct    240

cctctctcgc tgcccgcgtt tgcgcagccc cgggccatgt ccgacgcgtc cctccgcagc    300

acatccacga tggagcgtct tgtcgcccgt gggaccttcc cagtactagt gcgcaccagc    360

gcctgccgca gcctcttcgg gccggtggac cacgaggagc tgagccgcga gctgcaggcc    420

cgcctggccg agctgaacgc cgaggaccag aaccgctggg attacgactt ccagcaggac    480
```

```
atgccgctgc ggggccctgg acgcctgcag tggaccgaag tggacagcga ctcggtgccc    540
gcgttctacc gcgagacggt gcaggtgggg cgctgccgcc tgctgctggc gccgcggccc    600
gtcgcggtcg cggtggctgt cagcccgccc ctcgagccgg ccgctgagtc cctcgacggc    660
ctcgaggagg cgccggagca gctgcctagt gtcccggtcc cggcccccggc gtccaccccg    720
cccccagtcc cggtcctggc tccagccccg gccccggctc cggctccggt cgcggctccg    780
gtcgcggctc cggtcgcggt cgcggtcctg gccccggccc cggcccccggc tccggctccg   840
gctccggccc cggctccagt cgcggccccg gccccagccc cggccccggc cccggccccg    900
gcccccgccc cggccccggc cccggacgcg gcgcctcaag agagcgccga gcagggcgcg    960
aaccaggggc agcgcggcca ggagcctctc gctgaccagc tgcactcggg gatttcggga   1020
cgtcccgcgg ccggcaccgc ggccgccagc gccaacggcg cggcgatcaa gaagctgtcc   1080
gggcctctga tctccgattt cttcgccaag cgcaagagat cagcgcctga gaagtcgtcg   1140
ggcgatgtcc ccgcgccgtg tccctctcca agcgccgccc ctggcgtggg ctcggtggag   1200
cagaccccgc gcaagaggct gcggtgagcc aatttagagc ccaaagagcc ccgagggaac   1260
ctgccggggc agcggacgtt ggaagggcgc tgggcctcgg ctgggaccgt tcatgtagca   1320
gcaaccggcg gcggctgccg cagagcagcg ttcggttttg tttttaaatt ttgaaaactg   1380
tgcaatgtat taataacgtc tttttatatc taaatgtatt ctgcacgaga aggtacactg   1440
gtcccaaggt gtaaagcttt aagagtcatt tatataaaat gtttaatctc tgctgaaact   1500
cagtgcaaaa aaaagaaaaa agaaaaaaaa aaggaaaaaa taaaaaaacc atgtatattt   1560
gtacaaaaag tttttaaagt tatactaact tatattttct atttatgtcc aggcgtggac   1620
cgctctgcca cgcactagct cggttattgg ttatgccaaa ggcactctcc atctcccaca   1680
tctggttatt gacaagtgta actttatttt catcgcggac tctggggaag gggtcactc    1740
acaagctgta gctgccatac atgcccatct agcttgcagt ctcttcgcgc tttcgctgtc   1800
tctcttatta tgactgtgtt tatctgaaac ttgaagacaa gtctgttaaa atggttcctg   1860
agccgtctgt accactgccc cggcccctcg tccgccgggt tctaaataaa gaggccgaaa   1920
aatgctgcaa aaaaaaaaaa aaa                                            1943
```

<210> SEQ ID NO 102
<211> LENGTH: 316
<212> TYPE: PRT
<213> ORGANISM: Homo sapiens

<400> SEQUENCE: 102

```
Met Ser Asp Ala Ser Leu Arg Ser Thr Ser Thr Met Glu Arg Leu Val
1               5                   10                  15

Ala Arg Gly Thr Phe Pro Val Leu Val Arg Thr Ser Ala Cys Arg Ser
            20                  25                  30

Leu Phe Gly Pro Val Asp His Glu Glu Leu Ser Arg Glu Leu Gln Ala
        35                  40                  45

Arg Leu Ala Glu Leu Asn Ala Glu Asp Gln Asn Arg Trp Asp Tyr Asp
    50                  55                  60

Phe Gln Gln Asp Met Pro Leu Arg Gly Pro Gly Arg Leu Gln Trp Thr
65                  70                  75                  80

Glu Val Asp Ser Asp Ser Val Pro Ala Phe Tyr Arg Glu Thr Val Gln
                85                  90                  95

Val Gly Arg Cys Arg Leu Leu Leu Ala Pro Arg Pro Val Ala Val Ala
            100                 105                 110
```

```
Val Ala Val Ser Pro Pro Leu Glu Pro Ala Ala Glu Ser Leu Asp Gly
        115                 120                 125

Leu Glu Glu Ala Pro Glu Gln Leu Pro Ser Val Pro Val Pro Ala Pro
    130                 135                 140

Ala Ser Thr Pro Pro Pro Val Pro Val Leu Ala Pro Ala Pro Ala Pro
145                 150                 155                 160

Ala Pro Ala Pro Val Ala Ala Pro Val Ala Ala Pro Val Ala Val Ala
                165                 170                 175

Val Leu Ala Pro Ala Pro Ala Pro Ala Pro Ala Pro Ala Pro Ala Pro
            180                 185                 190

Ala Pro Val Ala Ala Pro Ala Pro Ala Pro Ala Pro Ala Pro Ala Pro
        195                 200                 205

Ala Pro Ala Pro Ala Pro Ala Pro Asp Ala Ala Pro Gln Glu Ser Ala
    210                 215                 220

Glu Gln Gly Ala Asn Gln Gly Gln Arg Gly Gln Glu Pro Leu Ala Asp
225                 230                 235                 240

Gln Leu His Ser Gly Ile Ser Gly Arg Pro Ala Ala Gly Thr Ala Ala
                245                 250                 255

Ala Ser Ala Asn Gly Ala Ala Ile Lys Lys Leu Ser Gly Pro Leu Ile
            260                 265                 270

Ser Asp Phe Phe Ala Lys Arg Lys Arg Ser Ala Pro Glu Lys Ser Ser
        275                 280                 285

Gly Asp Val Pro Ala Pro Cys Pro Ser Pro Ser Ala Ala Pro Gly Val
    290                 295                 300

Gly Ser Val Glu Gln Thr Pro Arg Lys Arg Leu Arg
305                 310                 315


<210> SEQ ID NO 103
<211> LENGTH: 2175
<212> TYPE: DNA
<213> ORGANISM: Homo sapiens

<400> SEQUENCE: 103

gttgtatatc agggccgcgc tgagctgcgc cagctgaggt gtgagcagct gccgaagtca      60

gttccttgtg gagccggagc tgggcgcgga ttcgccgagg caccgaggca ctcagaggag     120

gcgccatgtc agaaccggct ggggatgtcc gtcagaaccc atgcggcagc aaggcctgcc     180

gccgcctctt cggcccagtg gacagcgagc agctgagccg cgactgtgat gcgctaatgg     240

cgggctgcat ccaggaggcc cgtgagcgat ggaacttcga ctttgtcacc gagacaccac     300

tggagggtga cttcgcctgg gagcgtgtgc ggggccttgg cctgcccaag ctctaccttc     360

ccacggggcc ccggcgaggc cgggatgagt tgggaggagg caggcggcct ggcacctcac     420

ctgctctgct gcaggggaca gcagaggaag accatgtgga cctgtcactg tcttgtaccc     480

ttgtgcctcg ctcaggggag caggctgaag ggtccccagg tggacctgga gactctcagg     540

gtcgaaaacg gcggcagacc agcatgacag atttctacca ctccaaacgc cggctgatct     600

tctccaagag gaagccctaa tccgcccaca ggaagcctgc agtcctggaa gcgcgagggc     660

ctcaaaggcc cgctctacat cttctgcctt agtctcagtt tgtgtgtctt aattattatt     720

tgtgttttaa tttaaacacc tcctcatgta cataccctgg ccgccccctg ccccccagcc     780

tctggcatta gaattattta aacaaaaact aggcggttga atgagaggtt cctaagagtg     840

ctgggcattt ttattttatg aaatactatt taaagcctcc tcatcccgtg ttctcctttt     900

cctctctccc ggaggttggg tgggccggct tcatgccagc tacttcctcc tccccacttg     960
```

```
tccgctgggt ggtaccctct ggaggggtgt ggctccttcc catcgctgtc acaggcggtt   1020

atgaaattca cccccttcc tggacactca gacctgaatt ctttttcatt tgagaagtaa   1080

acagatggca ctttgaaggg gcctcaccga gtgggggcat catcaaaaac tttggagtcc   1140

cctcacctcc tctaaggttg ggcagggtga ccctgaagtg agcacagcct agggctgagc   1200

tggggacctg gtaccctcct ggctcttgat accccctct gtcttgtgaa ggcaggggga   1260

aggtggggtc ctggagcaga ccaccccgcc tgccctcatg gcccctctga cctgcactgg   1320

ggagcccgtc tcagtgttga gccttttccc tctttggctc ccctgtacct tttgaggagc   1380

cccagctacc cttcttctcc agctgggctc tgcaattccc ctctgctgct gtccctcccc   1440

cttgtccttt cccttcagta ccctctcagc tccaggtggc tctgaggtgc ctgtcccacc   1500

cccaccccca gctcaatgga ctggaagggg aagggacaca caagaagaag ggcaccctag   1560

ttctacctca ggcagctcaa gcagcgaccg cccccctcctc tagctgtggg ggtgagggtc   1620

ccatgtggtg gcacaggccc ccttgagtgg ggttatctct gtgttagggg tatatgatgg   1680

gggagtagat ctttctagga gggagacact ggcccctcaa atcgtccagc gaccttcctc   1740

atccacccca tccctcccca gttcattgca ctttgattag cagcggaaca aggagtcaga   1800

cattttaaga tggtggcagt agaggctatg gacagggcat gccacgtggg ctcatatggg   1860

gctgggagta gttgtctttc ctggcactaa cgttgagccc ctggaggcac tgaagtgctt   1920

agtgtacttg gagtattggg gtctgacccc aaacaccttc cagctcctgt aacatactgg   1980

cctggactgt tttctctcgg ctccccatgt gtcctggttc ccgtttctcc acctagactg   2040

taaacctctc gagggcaggg accacaccct gtactgttct gtgtctttca cagctcctcc   2100

cacaatgctg aatatacagc aggtgctcaa taaatgattc ttagtgactt tacttgtaaa   2160

aaaaaaaaaa aaaaa                                                    2175
```

```
<210> SEQ ID NO 104
<211> LENGTH: 164
<212> TYPE: PRT
<213> ORGANISM: Homo sapiens

<400> SEQUENCE: 104

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160
```

Lys Arg Lys Pro

<210> SEQ ID NO 105
<211> LENGTH: 3808
<212> TYPE: DNA
<213> ORGANISM: Homo sapiens

<400> SEQUENCE: 105
cttcctggac tggggatccc ggctaaatat agctgtttct gtcttacaac acaggctcca 60
gtatataaat caggcaaatt ccccatttga gcatgaacct ctgaaaactg ccggcatctg 120
aggtttcctc caaggccctc tgaagtgcag cccataatga aggtcttggc ggcagtacac 180
agcccagggg gagccgttcc ccaacaacct ggacaagcta tgtggcccca acgtgacgga 240
cttcccgccc ttccacgcca acggcacgga gaaggccaag ctggtggagc tgtaccgcat 300
agtcgtgtac cttggcacct ccctgggcaa catcacccgg gaccagaaga tcctcaaccc 360
cagtgccctc agcctccaca gcaagctcaa cgccaccgcc gacatcctgc gaggcctcct 420
tagcaacgtg ctgtgccgcc tgtgcagcaa gtaccacgtg ggccatgtgg acgtgaccta 480
cggccctgac acctcgggta aggatgtctt ccagaagaag aagctgggct gtcaactcct 540
ggggaagtat aagcagatca tcgccgtgtt ggcccaggcc ttctagcagg aggtcttgaa 600
gtgtgctgtg aaccgaggga tctcaggagt tgggtccaga tgtgggggcc tgtccaaggg 660
tggctggggc ccagggcatc gctaaaccca aatgggggct gctggcagac cccgagggtg 720
cctggccagt ccactccact ctgggctggg ctgtgatgaa gctgagcaga gtggaaactt 780
ccatagggag ggagctagaa gaaggtgccc cttcctctgg gagattgtgg actggggagc 840
gtgggctgga cttctgcctc tacttgtccc tttggcccct tgctcacttt gtgcagtgaa 900
caaactacac aagtcatcta caagagccct gaccacaggg tgagacagca gggcccaggg 960
gagtggacca gcccccagca aattatcacc atctgtgcct ttgctgcccc ttaggttggg 1020
acttaggtgg gccagagggg ctaggatccc aaaggactcc ttgtccccta gaagtttgat 1080
gagtggaaga tagagagggg cctctgggat ggaaggctgt cttcttttga ggatgatcag 1140
agaacttggg cataggaaca atctggcaga agtttccaga aggaggtcac ttggcattca 1200
ggctcttggg gaggcagaga agccaccttc aggcctggga aggaagacac tgggaggagg 1260
agaggcctgg aaagctttgg taggttcttc gttctcttcc ccgtgatctt ccctgcagcc 1320
tgggatggcc agggtctgat ggctggacct gcagcagggg tttgtggagg tgggtagggc 1380
aggggcaggt tgctaagtca ggtgcagagg ttctgaggga cccaggctct tcctctgggt 1440
aaaggtctgt aagaaggggc tggggtagct cagagtagca gctcacatct gaggccctgg 1500
gaggccttgt gaggtcacac agaggtactt gagggggact ggaggccgtc tctggtcccc 1560
agggcaaggg aacagcagaa cttagggtca gggtctcagg gaaccctgag ctccaagcgt 1620
gctgtgcgtc tgacctggca tgatttctat ttattatgat atcctattta tattaactta 1680
ttggtgcttt cagtggccaa gttaattccc ctttccctgg tccctactca acaaaatatg 1740
atgatggctc ccgacacaag cgccagggcc agggcttagc agggcctggt ctggaagtcg 1800
acaatgttac aagtggaata agccttacgg gtgaagctca gagaagggtc ggatctgaga 1860
gaatggggag gcctgagtgg gagtgggggg ccttgctcca ccccccccca tcccctactg 1920
tgacttgctt tagggtgtca gggtccaggc tgcaggggct gggccaattt gtggagaggc 1980
cgggtgcctt tctgtcttga ttccaggggg ctggttcaca ctgttcttgg gcgccccagc 2040

```
attgtgttgt gaggcgcact gttcctggca gatattgtgc cccctggagc agtgggcaag   2100
acagtccttg tggcccaccc tgtccttgtt tctgtgtccc catgctgcct ctgaaatagc   2160
gccctggaac aaccctgccc ctgcacccag catgctccga cacagcaggg aagctcctcc   2220
tgtggcccgg acacccatag acggtgcggg gggcctggct gggccagacc ccaggaaggt   2280
ggggtagact ggggggatca gctgcccatt gctcccaaga ggaggagagg gaggctgcag   2340
atgcctggga ctcagaccag gaagctgtgg gccctcctgc tccacccccca tcccactccc   2400
acccatgtct gggctcccag gcagggaacc cgatctcttc ctttgtgctg gggccaggcg   2460
agtggagaaa cgccctccag tctgagagca ggggagggaa ggaggcagca gagttggggc   2520
agctgctcag agcagtgttc tggcttcttc tcaaaccctg agcgggctgc cggcctccaa   2580
gttcctccga caagatgatg gtactaatta tggtactttt cactcacttt gcacctttcc   2640
ctgtcgctct ctaagcactt tacctggatg gcgcgtgggc agtgtgcagg caggtcctga   2700
ggcctggggt tggggtggag ggtgcggccc ggagttgtcc atctgtccat cccaacagca   2760
agacgaggat gtggctgttg agatgtgggc cacactcacc cttgtccagg atgcagggac   2820
tgccttctcc ttcctgcttc atccggctta gcttggggct ggctgcattc ccccaggatg   2880
ggcttcgaga aagacaaact tgtctggaaa ccagagttgc tgattccacc cggggggccc   2940
ggctgactcg cccatcacct catctccctg tggacttggg agctctgtgc caggcccacc   3000
ttgcggccct ggctctgagt cgctctccca cccagcctgg acttggcccc atgggaccca   3060
tcctcagtgc tccctccaga tcccgtccgg cagcttggcg tccaccctgc acagcatcac   3120
tgaatcacag agcctttgcg tgaaacagct ctgccaggcc gggagctggg tttctcttcc   3180
ctttttatct gctggtgtgg accacacctg ggcctggccg gaggaagaga gagtttacca   3240
agagagatgt ctccgggccc ttatttatta tttaaacatt tttttaaaaa gcactgctag   3300
tttacttgtc tctcctcccc atcgtcccca tcgtcctcct tgtccctgac ttggggcact   3360
tccaccctga cccagccagt ccagctctgc cttgccggct ctccagagta gacatagtgt   3420
gtggggttgg agctctggca cccggggagg tagcatttcc ctgcagatgg tacagatgtt   3480
cctgccttag agtcatctct agttccccac ctcaatcccg gcatccagcc ttcagtcccg   3540
cccacgtgct agctccgtgg gcccaccgtg cggccttaga ggtttccctc cttcctttcc   3600
actgaaaagc acatggcctt gggtgacaaa ttcctctttg atgaatgtac cctgtgggga   3660
tgtttcatac tgacagatta tttttattta ttcaatgtca tatttaaaat atttattttt   3720
tataccaaat gaatactttt ttttttaaga aaaaaaagag aaatgaataa agaatctact   3780
cttggctggc aaaaaaaaaa aaaaaaaa                                      3808
```

<210> SEQ ID NO 106
<211> LENGTH: 88
<212> TYPE: PRT
<213> ORGANISM: Homo sapiens

<400> SEQUENCE: 106

```
Met Lys Val Leu Ala Ala Val His Ser Pro Gly Gly Ala Val Pro Gln
1               5                   10                  15

Gln Pro Gly Gln Ala Met Trp Pro Gln Arg Asp Gly Leu Pro Ala Leu
            20                  25                  30

Pro Arg Gln Arg His Gly Glu Gly Gln Ala Gly Gly Ala Val Pro His
        35                  40                  45

Ser Arg Val Pro Trp His Leu Pro Gly Gln His His Pro Gly Pro Glu
    50                  55                  60
```

```
Asp Pro Gln Pro Gln Cys Pro Gln Pro Pro Gln Gln Ala Gln Arg His
65                  70                  75                  80

Arg Arg His Pro Ala Arg Pro Pro
                85


<210> SEQ ID NO 107
<211> LENGTH: 2747
<212> TYPE: DNA
<213> ORGANISM: Homo sapiens

<400> SEQUENCE: 107

gtcggaggga gggagggagg gagagaaaga aagagagaaa aagaaggaaa gggagaggga     60

gacggctgga gcccgaggac gagcgcggag ccgcggaccg agcggggggc gggagacagg    120

aaggagggag gcgagcagag ggaaggggaa gaggtcgggg agcgagggcg ggagcggtcg    180

cggtcgcgat cgagcaagca agcgggcgag aggacgccct cccctggcct ccagtgcgcc    240

gcttccctcg ccgccgcccc gccagcatgc ccggcgtggc ccgcctgccg ctgctgctcg    300

ggctgctgct gctcccgcgt cccggccggc cgctggactt ggccgactac acctatgacc    360

tggcggagga ggacgactcg gagcccctca actacaaaga cccctgcaag gcggctgcct    420

ttcttgggga cattgccctg gacgaagagg acctgagggc cttccaggta cagcaggctg    480

tggatctcag acggcacaca gctcgtaagt cctccatcaa agctgcagtt ccaggaaaca    540

cttctacccc cagctgccag agcaccaacg ggcagcctca gaggggagcc tgtgggagat    600

ggagaggtag atcccgtagc cggcgggcgg cgacgtcccg accagagcgt gtgtggcccg    660

atggggtcat ccccctttgtc attgggggaa acttcactgg tagccagagg gcagtcttcc    720

ggcaggccat gaggcactgg gagaagcaca cctgtgtcac cttcctggag cgcactgacg    780

aggacagcta tattgtgttc acctatcgac cttgcgggtg ctgctcctac gtgggtcgcc    840

gcggcggggg cccccaggcc atctccatcg gcaagaactg tgacaagttc ggcattgtgg    900

tccacgagct gggccacgtc gtcggcttct ggcacgaaca cactcggcca gaccgggacc    960

gccacgtttc catcgttcgt gagaacatcc agccagggca ggagtataac ttcctgaaga   1020

tggagcctca ggaggtggag tccctggggg agacctatga cttcgacagc atcatgcatt   1080

acgctcggaa cacattctcc aggggcatct tcctggatac cattgtcccc aagtatgagg   1140

tgaacggggt gaaacctccc attggccaaa ggacacggct cagcaagggg gacattgccc   1200

aagcccgcaa gctttacaag tgcccagcct gtggagagac cctgcaagac agcacaggca   1260

acttctcctc ccctgaatac cccaatggct actctgctca catgcactgc gtgtggcgca   1320

tctctgtcac acccggggag aagatcatcc tgaacttcac gtccctggac ctgtaccgca   1380

gccgcctgtg ctggtacgac tatgtggagg tccgagatgg cttctggagg aaggcgcccc   1440

tccgaggccg cttctgcggg tccaaactcc ctgagcctat cgtctccact gacagccgcc   1500

tctgggttga attccgcagc agcagcaatt gggttggaaa gggcttcttt gcagtctacg   1560

aagccatctg cgggggtgat gtgaaaaagg actatggcca cattcaatcg cccaactacc   1620

cagacgatta ccggcccagc aaagtctgca tctggcggat ccaggtgtct gagggcttcc   1680

acgtgggcct cacattccag tcctttgaga ttgagcgcca cgacagctgt gcctacgact   1740

atctggaggt gcgcgacggg cacagtgaga gcagcaccct catcgggcgc tactgtggct   1800

atgagaagcc tgatgacatc aagagcacgt ccagccgcct ctggctcaag ttcgtctctg   1860

acgggtccat taacaaagcg ggctttgccg tcaacttttt caaagaggtg gacgagtgct   1920
```

```
ctcggcccaa ccgcgggggc tgtgagcagc ggtgcctcaa caccctgggc agctacaagt   1980

gcagctgtga ccccgggtac gagctggccc cagacaagcg ccgctgtgag gctgcttgtg   2040

gcggattcct caccaagctc aacggctcca tcaccagccc gggctggccc aaggagtacc   2100

cccccaacaa gaactgcatc tggcagctgg tggcccccac ccagtaccgc atctccctgc   2160

agtttgactt ctttgagaca gagggcaatg atgtgtgcaa gtacgacttc gtggaggtgc   2220

gcagtggact cacagctgac tccaagctgc atggcaagtt ctgtggttct gagaagcccg   2280

aggtcatcac ctcccagtac aacaacatgc gcgtggagtt caagtccgac aacaccgtgt   2340

ccaaaaaggg cttcaaggcc cacttcttct cagaaaagag gccagctctg cagcccccctc   2400

ggggacgccc ccaccagctc aaattccgag tgcagaaaag aaaccggacc ccccagtgag   2460

gcctgccagg cctcccggac cccttgttac tcaggaacct caccttggac ggaatgggat   2520

gggggcttcg gtgcccacca accccccacc tccactctgc cattccggcc cacctccctc   2580

tggccggaca gaactggtgc tctcttctcc ccactgtgcc cgtccgcgga ccggggaccc   2640

ttccccgtgc cctacccccct cccattttga tggtgtctgt gacatttcct gttgtgaagt   2700

aaaagaggga cccctgcgtc ctgctccttt ctcttgcaga aaaaaaa                 2747
```

<210> SEQ ID NO 108
<211> LENGTH: 730
<212> TYPE: PRT
<213> ORGANISM: Homo sapiens

<400> SEQUENCE: 108

```
Met Pro Gly Val Ala Arg Leu Pro Leu Leu Leu Gly Leu Leu Leu Leu
1               5                   10                  15

Pro Arg Pro Gly Arg Pro Leu Asp Leu Ala Asp Tyr Thr Tyr Asp Leu
            20                  25                  30

Ala Glu Glu Asp Asp Ser Glu Pro Leu Asn Tyr Lys Asp Pro Cys Lys
        35                  40                  45

Ala Ala Ala Phe Leu Gly Asp Ile Ala Leu Asp Glu Glu Asp Leu Arg
    50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Arg Ala Ala Thr Ser Arg Pro Glu Arg
        115                 120                 125

Val Trp Pro Asp Gly Val Ile Pro Phe Val Ile Gly Gly Asn Phe Thr
    130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
```

```
225                 230                 235                 240

Ile Gln Pro Gly Gln Glu Tyr Asn Phe Leu Lys Met Glu Pro Gln Glu
                245                 250                 255

Val Glu Ser Leu Gly Glu Thr Tyr Asp Phe Asp Ser Ile Met His Tyr
            260                 265                 270

Ala Arg Asn Thr Phe Ser Arg Gly Ile Phe Leu Asp Thr Ile Val Pro
        275                 280                 285

Lys Tyr Glu Val Asn Gly Val Lys Pro Pro Ile Gly Gln Arg Thr Arg
    290                 295                 300

Leu Ser Lys Gly Asp Ile Ala Gln Ala Arg Lys Leu Tyr Lys Cys Pro
305                 310                 315                 320

Ala Cys Gly Glu Thr Leu Gln Asp Ser Thr Gly Asn Phe Ser Ser Pro
                325                 330                 335

Glu Tyr Pro Asn Gly Tyr Ser Ala His Met His Cys Val Trp Arg Ile
            340                 345                 350

Ser Val Thr Pro Gly Glu Lys Ile Ile Leu Asn Phe Thr Ser Leu Asp
        355                 360                 365

Leu Tyr Arg Ser Arg Leu Cys Trp Tyr Asp Tyr Val Glu Val Arg Asp
    370                 375                 380

Gly Phe Trp Arg Lys Ala Pro Leu Arg Gly Arg Phe Cys Gly Ser Lys
385                 390                 395                 400

Leu Pro Glu Pro Ile Val Ser Thr Asp Ser Arg Leu Trp Val Glu Phe
                405                 410                 415

Arg Ser Ser Ser Asn Trp Val Gly Lys Gly Phe Phe Ala Val Tyr Glu
            420                 425                 430

Ala Ile Cys Gly Gly Asp Val Lys Lys Asp Tyr Gly His Ile Gln Ser
        435                 440                 445

Pro Asn Tyr Pro Asp Asp Tyr Arg Pro Ser Lys Val Cys Ile Trp Arg
    450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Leu Glu Val Arg
                485                 490                 495

Asp Gly His Ser Glu Ser Ser Thr Leu Ile Gly Arg Tyr Cys Gly Tyr
            500                 505                 510

Glu Lys Pro Asp Asp Ile Lys Ser Thr Ser Ser Arg Leu Trp Leu Lys
        515                 520                 525

Phe Val Ser Asp Gly Ser Ile Asn Lys Ala Gly Phe Ala Val Asn Phe
    530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys Asp Pro
                565                 570                 575

Gly Tyr Glu Leu Ala Pro Asp Lys Arg Arg Cys Glu Ala Ala Cys Gly
            580                 585                 590

Gly Phe Leu Thr Lys Leu Asn Gly Ser Ile Thr Ser Pro Gly Trp Pro
        595                 600                 605

Lys Glu Tyr Pro Pro Asn Lys Asn Cys Ile Trp Gln Leu Val Ala Pro
    610                 615                 620

Thr Gln Tyr Arg Ile Ser Leu Gln Phe Asp Phe Phe Glu Thr Glu Gly
625                 630                 635                 640

Asn Asp Val Cys Lys Tyr Asp Phe Val Glu Val Arg Ser Gly Leu Thr
                645                 650                 655
```

```
Ala Asp Ser Lys Leu His Gly Lys Phe Cys Gly Ser Glu Lys Pro Glu
            660                 665                 670

Val Ile Thr Ser Gln Tyr Asn Asn Met Arg Val Glu Phe Lys Ser Asp
        675                 680                 685

Asn Thr Val Ser Lys Lys Gly Phe Lys Ala His Phe Phe Ser Glu Lys
    690                 695                 700

Arg Pro Ala Leu Gln Pro Pro Arg Gly Arg Pro His Gln Leu Lys Phe
705                 710                 715                 720

Arg Val Gln Lys Arg Asn Arg Thr Pro Gln
                725                 730


<210> SEQ ID NO 109
<211> LENGTH: 3150
<212> TYPE: DNA
<213> ORGANISM: Homo sapiens

<400> SEQUENCE: 109

ccacaaaggg cacttggccc cagggctagg agagcgaggg gagagcacag ccacccgcct     60

cggcggcccg ggactcggct cgactcgccg gagaatgcgc ccgaggacga cggggcgcca    120

gagccgcggt gctttcaact ggcgagcgcg aatgggggtg cactggagta aggcagagtg    180

atgcgggggg gcaactcgcc tggcaccgag atcgccgccg tgcccttccc tggacccggc    240

gtcgcccagg atggctgccc cgagccatgg gccgcggcgg agctagcgcg gagcgcccga    300

ccctcgaccc ccgagtcccg gagccggccc cgcgcggggc cacgcgtccc tcgggcgctg    360

gttcctaagg aggacgacag caccagcttc tcctttctcc cttcccttcc ctgccccgca    420

ctcctccccc tgctcgctgt tgttgtgtgt cagcacttgg ctggggactt cttgaacttg    480

cagggagaat aacttgcgca ccccactttg cgccggtgcc tttgccccag cggagcctgc    540

ttcgccatct ccgagcccca ccgcccctcc actcctcggc cttgcccgac actgagacgc    600

tgttcccagc gtgaaaagag agactgcgcg gccggcaccc gggagaagga ggaggcaaag    660

aaaaggaacg gacattcggt ccttgcgcca ggtcctttga ccagagtttt tccatgtgga    720

cgctctttca atggacgtgt ccccgcgtgc ttcttagacg gactgcggtc tcctaaaggt    780

cgaccatggt ggccgggacc cgctgtcttc tagcgttgct gcttccccag gtcctcctgg    840

gcggcgcggc tggcctcgtt ccggagctgg gccgcaggaa gttcgcggcg gcgtcgtcgg    900

gccgcccctc atcccagccc tctgacgagg tcctgagcga gttcgagttg cggctgctca    960

gcatgttcgg cctgaaacag agacccaccc ccagcaggga cgccgtggtg ccccccctaca   1020

tgctagacct gtatcgcagg cactcaggtc agccgggctc acccgcccca gaccaccggt   1080

tggagagggc agccagccga gccaacactg tgcgcagctt ccaccatgaa gaatctttgg   1140

aagaactacc agaaacgagt gggaaaacaa cccggagatt cttctttaat ttaagttcta   1200

tccccacgga ggagtttatc acctcagcag agcttcaggt tttccgagaa cagatgcaag   1260

atgctttagg aaacaatagc agtttccatc accgaattaa tatttatgaa atcataaaac   1320

ctgcaacagc caactcgaaa ttccccgtga ccagactttt ggacaccagg ttggtgaatc   1380

agaatgcaag caggtgggaa agttttgatg tcacccccgc tgtgatgcgg tggactgcac   1440

agggacacgc caaccatgga ttcgtggtgg aagtggccca cttggaggag aaacaaggtg   1500

tctccaagag acatgttagg ataagcaggt ctttgcacca agatgaacac agctggtcac   1560

agataaggcc attgctagta acttttggcc atgatggaaa agggcatcct ctccacaaaa   1620

gagaaaaacg tcaagccaaa cacaaacagc ggaaacgcct taagtccagc tgtaagagac   1680
```

```
acccttgta cgtggacttc agtgacgtgg ggtggaatga ctggattgtg gctcccccgg   1740

ggtatcacgc cttttactgc cacggagaat gccctttcc tctggctgat catctgaact   1800

ccactaatca tgccattgtt cagacgttgg tcaactctgt taactctaag attcctaagg   1860

catgctgtgt cccgacagaa ctcagtgcta tctcgatgct gtaccttgac gagaatgaaa   1920

aggttgtatt aaagaactat caggacatgg ttgtggaggg ttgtgggtgt cgctagtaca   1980

gcaaaattaa atacataaat atatatatat atatatattt tagaaaaaag aaaaaaacaa   2040

acaaacaaaa aaaccccacc ccagttgaca ctttaatatt tcccaatgaa gactttattt   2100

atggaatgga atggaaaaaa aaacagctat tttgaaaata tatttatatc tacgaaaaga   2160

agttgggaaa acaaatattt taatcagaga attattcctt aaagatttaa aatgtattta   2220

gttgtacatt ttatatgggt tcaaccccag cacatgaagt ataatggtca gatttatttt   2280

gtatttattt actattataa ccacttttta ggaaaaaaat agctaatttg tatttatatg   2340

taatcaaaag aagtatcggg tttgtacata attttccaaa aattgtagtt gttttcagtt   2400

gtgtgtattt aagatgaaaa gtctacatgg aaggttactc tggcaaagtg cttagcacgt   2460

ttgctttttt gcagtgctac tgttgagttc acaagttcaa gtccagaaaa aaaaagtgga   2520

taatccactc tgctgacttt caagattatt atattattca attctcagga atgttgcaga   2580

gtgattgtcc aatccatgag aatttacatc cttattaggt ggaatatttg gataagaacc   2640

agacattgct gatctattat agaaactctc ctcctgcccc ttaatttaca gaaagaataa   2700

agcaggatcc atagaaataa ttaggaaaac gatgaacctg caggaaagtg aatgatggtt   2760

tgttgttctt ctttcctaaa ttagtgatcc cttcaaaggg gctgatctgg ccaaagtatt   2820

caataaaacg taagatttct tcattattga tattgtggtc atatatattt aaaattgata   2880

tctcgtggcc ctcatcaagg gttggaaatt tatttgtgtt ttacctttac ctcatctgag   2940

agctctttat tctccaaaga acccagtttt ctaacttttt gcccaacacg cagcaaaatt   3000

atgcacatcg tgttttctgc ccaccctctg ttctctgacc tatcagcttg cttttctttc   3060

caaggttgtg tgtttgaaca catttctcca aatgttaaac ctatttcaga taataaatat   3120

caaatctctg gcatttcatt ctataaagtc                                    3150
```

<210> SEQ ID NO 110
<211> LENGTH: 396
<212> TYPE: PRT
<213> ORGANISM: Homo sapiens

<400> SEQUENCE: 110

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110
```

```
His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395
```

<210> SEQ ID NO 111
<211> LENGTH: 5734
<212> TYPE: DNA
<213> ORGANISM: Homo sapiens

<400> SEQUENCE: 111

```
agatcttgaa aacacccggg ccacacacgc cgcgacctac agctctttct cagcgttgga      60

gtggagacgg cgcccgcagc gccctgcgcg ggtgaggtcc gcgcagctgc tggggaagag     120

cccacctgtc aggctgcgct gggtcagcgc agcaagtggg gctggccgct atctcgctgc     180

acccggccgc gtcccgggct ccgtgcgccc tcgccccagc tggtttggag ttcaaccctc     240

ggctccgccg ccggctcctt gcgccttcgg agtgtcccgc agcgacgccg ggagccgacg     300

cgccgcgcgg gtacctagcc atggctgggg cgagcaggct gctctttctg tggctgggct     360

gcttctgcgt gagcctggcg cagggagaga gaccgaagcc acctttcccg gagctccgca     420

aagctgtgcc aggtgaccgc acggcaggtg gtggcccgga ctccgagctg cagccgcaag     480
```

-continued

```
acaaggtctc tgaacacatg ctgcggctct atgacaggta cagcacggtc caggcggccc    540
ggacaccggg ctccctggag ggaggctcgc agccctggcg ccctcggctc ctgcgcgaag    600
gcaacacggt tcgcagcttt cgggcggcag cagcagaaac tcttgaaaga aaaggactgt    660
atatcttcaa tctgacatcg ctaaccaagt ctgaaaacat tttgtctgcc acactgtatt    720
tctgtattgg agagctagga aacatcagcc tgagttgtcc agtgtctgga ggatgctccc    780
atcatgctca gaggaaacac attcagattg atctttctgc atggaccctc aaattcagca    840
gaaaccaaag tcaactcctt ggccatctgt cagtggatat ggccaaatct catcgagata    900
ttatgtcctg gctgtctaaa gatatcactc aactcttgag gaaggccaaa gaaaatgaag    960
agttcctcat aggatttaac attacgtcca agggacgcca gctgccaaag aggaggttac   1020
cttttccaga gccttatatc ttggtatatg ccaatgatgc cgccatttct gagccagaaa   1080
gtgtggtatc aagcttacag ggacaccgga attttcccac tggaactgtt cccaaatggg   1140
atagccacat cagagctgcc ctttccattg agcggaggaa gaagcgctct actggggtct   1200
tgctgcctct gcagaacaac gagcttcctg ggcagaata ccagtataaa aaggatgagg   1260
tgtgggagga gagaaagcct tacaagaccc ttcaggctca ggcccctgaa aagagtaaga   1320
ataaaaagaa acagagaaag gggcctcatc ggaagagcca gacgctccaa tttgatgagc   1380
agaccctgaa aaaggcaagg agaaagcagt ggattgaacc tcggaattgc gccaggagat   1440
acctcaaggt agactttgca gatattggct ggagtgaatg gattatctcc cccaagtcct   1500
ttgatgccta ttattgctct ggagcatgcc agttccccat gccaaagtct ttgaagccat   1560
caaatcatgc taccatccag agtatagtga gagctgtggg ggtcgttcct gggattcctg   1620
agccttgctg tgtaccagaa aagatgtcct cactcagtat tttattcttt gatgaaaata   1680
agaatgtagt gcttaaagta taccctaaca tgacagtaga gtcttgcgct tgcagataac   1740
ctggcaaaga actcatttga atgcttaatt caatcattag tttattttta tggacttctt   1800
cctgtttttt tttttttttt ttttgcactg ccaatgcatt ttgtttcaaa agattatttc   1860
tatagtcaga ggggaatgag caaatagact gaagattgcc accaaggaaa agaactgtat   1920
ttgtttctga atgtaactta aagcaagatt tttagtaaat atggacatct atttctcttt   1980
ttgtaatcaa acacaacaac ttatcaaact gtttttagaa ctgttagaga acacactggt   2040
ttatttttgt aatgttcttt gaaaacagaa tggagaagca gcaatagctt gtcatttatc   2100
tcatttaatg actaatggga aatagagaac aatttcgcgt tttgaattag gcttattgcc   2160
ttagaatcct gagaaagtgc taaataatca actctgatgt tttcttaagg ttcttgagac   2220
tcttgtttat ccttgttttt cctccacaag tcattgtcta agtgtaatgg aaagtttatg   2280
ctgagcgtta gtgtgtatgt atgtgcgtac atgcgccagg tgcctgtgcc ctctgtagga   2340
tggtttgctt aatatggttt tataattcag tttacacagg attctttatt tttttttaatt   2400
ttgtattttg gcaaacacca ttcagttata agaactttgc caaatatgat agaataattc   2460
aagagcatat acagagagtt accacttgac ccagctattt aattgcaaat acagttgttt   2520
tcatttcatt tcctaccaga aaaaggaatc agaaacctag tttttgaaaa cacaagtgta   2580
attcctcttt tgtacttctt tttcacaaat gcttttattt attctaaatt gaatttaaaa   2640
atccttccta aagccattaa ctctttaatt ctcctgatat gcctttactt cctatgaagt   2700
tattggtaga tgttgaggcc caaaaactgg tagaatattg aagatcttct taaatgacca   2760
atttaaccat aaccaaatat tgaatatcat tcttcagtca catctaagtc aggcactttt   2820
tcacatagat cagggctttt ggctcagtca cgaaatctac aagttagcaa agcttacaaa   2880
```

```
acattattcg tcaggtatgg gaatcaaata tagacacttg tttgtctttg ctttccattt   2940
ctatgtgtca catacatata tgtgtcctct tataacttta gtcttcaaaa ttatttcaat   3000
atccttcttc tcactatatt tatttgtgtg atggaaatgc tttcaggccg tagatcattg   3060
ttggtgttaa tctgtggtta atcctcattt tagttccgtc ttatctgata cttagaaata   3120
tctcagccat tttggaggct gtgcagtatc agaagacgtg gagtttgttc tgtctctgcc   3180
tgtagctaat tatggtggtt cagtcattta ataaatatgt tttgagcatc tattttgtga   3240
aaggcactgt gttacctgtg tgtctttagt gtcctcactg gtaaaatgaa gaggctggcc   3300
atgagctgga agggttaagt ttataattcc agctatttca cacccgtctt ccttgaagga   3360
atgatagtga tagatataaa aacactgtaa gtccctcttt taataaacta aatgaaagaa   3420
catcctatac ttcgctgttt gtaaattagt atggcattcg ctttggttta agtggtattt   3480
tattgcaaac ccattaaaag aataactcat gaaaagaagc tctttgacac cttggggtac   3540
acaaatgttg gtgtgggtgt gtgttaattc tgtgagtgag acacaccagt tctaaaaaaa   3600
atgagtgaag ttctggtgcc tgagttacca tgctttcttc tagttcttac agtagcataa   3660
aattaaagat tcaaagtgag atggaggata aaattacttt ttaatacatg ttctcaaaca   3720
tttgaaaata aaagtatatg atagaagggg gccagagtgt ggccaccatc ctgatcgtac   3780
tgtttttcaa taaagaaaac tttttcattg gtagatttgg tgaaattcta aatttaggtt   3840
tttttctaga gctgtatcaa ccaaaacttc tggcaattcc cagtatcact tcttagcctt   3900
cttatatcca aatgcctgtt tattaccttt cttaatttga atcaatgcct agttattaca   3960
gattgcaccc cacaatggcc aaaaacccac tacataataa aatttacagg tactaactag   4020
ttaagattat attttaagta gcaattgata taaaattaca acacaatgaa agaacttggg   4080
taatctctta gcaatggaaa taggttttaa ccagcagttt ttctgggtgc tttgtaacta   4140
tcattttact aatgaattga ggatgtatta tggtttaaat tggaagagtt ttattcccaa   4200
agaataaagc aagattatct ttcagtagta gagattgaag taaatgtatt aatattttaa   4260
ttaatacaga tttactaaga gtagttagaa aatttagtaa gtgcctgttt tacaaattgt   4320
taggtactag tttctgtata attcctacac agaagcttta gaaatctcct gatattaaat   4380
tattaaattg gcattcatga aaagagaagc tacaattata aactccattt gctaaatcat   4440
gcataatact ctctctctct cttcccccac aagtaatctc tctaccccat gcagtgtgca   4500
cacacacaca cacacagtca gttactgaaa aaaataattc tttttctttt ttttttttaaa   4560
tggagtttca ctcttgtcgc ccaggctgga gtgcagtggc gtgatctcgg cccactgcaa   4620
cctccacctc ccaggttcaa gcagttctcc tgcctcagcc tcctgagtag ctgggattac   4680
aggtgtccgc caccatgcct ggctaatttt tttatttgat aaaaagaatt ctttttctca   4740
ataactgttc tcttgaattc aaattaaggg actgccaaag tcaattagaa tattttaaaa   4800
atactttgtt gtaacctgtg taaataatat acaatttaca ggatttggga ttgtagaact   4860
taaactggaa gactggattc ctcagatctc aggactataa cattccagat aaatttttac   4920
attccctttg ctgtatatta actgatgatc atttatatgt taagattttt taccttaata   4980
tttctgaata aaactcttat tgcccattta atattttcat aggcaatcaa atgtgagtaa   5040
tactgctaag agtctgattt attaaaaata tttgtataat tcattcagtt tagtttttca   5100
gtttagtctt tctgctttca cttttctctg tgctaacaag taactaatgt ctgggcattg   5160
acttcttatt gaatcaaagt tgggttaggc atagctatgc acacctgatg tgtaagatta   5220
```

```
aagaagagat taaataagaa atcttgggta agttggactt ttctgtatag ctctttttc   5280

ctctgagttg tattttaatg tagtttataa gtgataaaat gatccttgtt ttctaaaagc   5340

cagtccttcc cttcagcttt ccacagtttc tgtaaatgtt taatacttgt acagtcaatg   5400

gcaattttaa atatatatat atatataata tatgtatatg gaaaaggttc aaagatgctt   5460

ttaatttatt taatgactat tgccttccta taataataat tttcatcctt aattatgata   5520

atacttttag caagaaaaat tcctttttac tacagttttt agatgcaaaa tgcagtttgg   5580

ttctttagtc aaatccactt agagggtata ttgcagtgaa actgtgaagg atacttcact   5640

accaatgtat aagctttgtt gaatttgtat cattttcttt cagtaatgaa aagctattca   5700

ttatacagta tggaaataaa aattgcttca ttga                              5734
```

<210> SEQ ID NO 112
<211> LENGTH: 472
<212> TYPE: PRT
<213> ORGANISM: Homo sapiens

<400> SEQUENCE: 112

```
Met Ala Gly Ala Ser Arg Leu Leu Phe Leu Trp Leu Gly Cys Phe Cys
1               5                   10                  15

Val Ser Leu Ala Gln Gly Glu Arg Pro Lys Pro Pro Phe Pro Glu Leu
            20                  25                  30

Arg Lys Ala Val Pro Gly Asp Arg Thr Ala Gly Gly Gly Pro Asp Ser
        35                  40                  45

Glu Leu Gln Pro Gln Asp Lys Val Ser Glu His Met Leu Arg Leu Tyr
    50                  55                  60

Asp Arg Tyr Ser Thr Val Gln Ala Ala Arg Thr Pro Gly Ser Leu Glu
65                  70                  75                  80

Gly Gly Ser Gln Pro Trp Arg Pro Arg Leu Leu Arg Glu Gly Asn Thr
                85                  90                  95

Val Arg Ser Phe Arg Ala Ala Ala Ala Glu Thr Leu Glu Arg Lys Gly
            100                 105                 110

Leu Tyr Ile Phe Asn Leu Thr Ser Leu Thr Lys Ser Glu Asn Ile Leu
        115                 120                 125

Ser Ala Thr Leu Tyr Phe Cys Ile Gly Glu Leu Gly Asn Ile Ser Leu
    130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Leu Leu Arg Lys
        195                 200                 205

Ala Lys Glu Asn Glu Glu Phe Leu Ile Gly Phe Asn Ile Thr Ser Lys
    210                 215                 220

Gly Arg Gln Leu Pro Lys Arg Arg Leu Pro Phe Pro Glu Pro Tyr Ile
225                 230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
        275                 280                 285
```

```
Arg Ser Thr Gly Val Leu Leu Pro Leu Gln Asn Asn Glu Leu Pro Gly
    290                 295                 300

Ala Glu Tyr Gln Tyr Lys Lys Asp Glu Val Trp Glu Glu Arg Lys Pro
305                 310                 315                 320

Tyr Lys Thr Leu Gln Ala Gln Ala Pro Glu Lys Ser Lys Asn Lys Lys
                325                 330                 335

Lys Gln Arg Lys Gly Pro His Arg Lys Ser Gln Thr Leu Gln Phe Asp
            340                 345                 350

Glu Gln Thr Leu Lys Lys Ala Arg Arg Lys Gln Trp Ile Glu Pro Arg
        355                 360                 365

Asn Cys Ala Arg Arg Tyr Leu Lys Val Asp Phe Ala Asp Ile Gly Trp
    370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
            420                 425                 430

Pro Glu Pro Cys Cys Val Pro Glu Lys Met Ser Ser Leu Ser Ile Leu
        435                 440                 445

Phe Phe Asp Glu Asn Lys Asn Val Val Leu Lys Val Tyr Pro Asn Met
    450                 455                 460

Thr Val Glu Ser Cys Ala Cys Arg
465                 470
```

<210> SEQ ID NO 113
<211> LENGTH: 1957
<212> TYPE: DNA
<213> ORGANISM: Homo sapiens

<400> SEQUENCE: 113

```
aagaggagga aggaagatgc gagaaggcag aggaggaggg agggagggaa ggagcgcgga      60

gcccggcccg gaagctaggt gagtgtggca tccgagctga gggacgcgag cctgagacgc     120

cgctgctgct ccggctgagt atctagcttg tctccccgat gggattcccg tccaagctat     180

ctcgagcctg cagcgccaca gtccccggcc ctcgcccagg ttcactgcaa ccgttcagag     240

gtccccagga gctgctgctg gcgagcccgc tactgcaggg acctatggag ccattccgta     300

gtgccatccc gagcaacgca ctgctgcagc ttccctgagc ctttccagca agtttgttca     360

agattggctg tcaagaatca tggactgtta ttatatgcct tgttttctgt caagacacca     420

tgattcctgg taaccgaatg ctgatggtcg ttttattatg ccaagtcctg ctaggaggcg     480

cgagccatgc tagtttgata cctgagacgg ggaagaaaaa agtcgccgag attcagggcc     540

acgcgggagg acgccgctca gggcagagcc atgagctcct gcgggacttc gaggcgacac     600

ttctgcagat gtttgggctg cgccgccgcc cgcagcctag caagagtgcc gtcattccgg     660

actacatgcg ggatctttac cggcttcagt ctggggagga ggaggaagag cagatccaca     720

gcactggtct tgagtatcct gagcgcccgg ccagccgggc caacaccgtg aggagcttcc     780

accacgaaga acatctggag aacatcccag ggaccagtga aaactctgct tttcgtttcc     840

tctttaacct cagcagcatc cctgagaacg aggtgatctc ctctgcagag cttcggctct     900

tccgggagca ggtggaccag ggccctgatt gggaaagggg cttccaccgt ataaacattt     960

atgaggttat gaagcccccca gcagaagtgg tgcctgggca cctcatcaca cgactactgg    1020
```

```
acacgagact ggtccaccac aatgtgacac ggtgggaaac ttttgatgtg agccctgcgg   1080

tccttcgctg gacccgggag aagcagccaa actatgggct agccattgag gtgactcacc   1140

tccatcagac tcggacccac cagggccagc atgtcaggat tagccgatcg ttacctcaag   1200

ggagtgggaa ttgggcccag ctccggcccc tcctggtcac ctttggccat gatggccggg   1260

gccatgcctt gacccgacgc cggagggcca agcgtagccc taagcatcac tcacagcggg   1320

ccaggaagaa gaataagaac tgccggcgcc actcgctcta tgtggacttc agcgatgtgg   1380

gctggaatga ctggattgtg gccccaccag gctaccaggc cttctactgc catggggact   1440

gcccctttcc actggctgac cacctcaact caaccaacca tgccattgtg cagaccctgg   1500

tcaattctgt caattccagt atccccaaag cctgttgtgt gcccactgaa ctgagtgcca   1560

tctccatgct gtacctggat gagtatgata aggtggtact gaaaaattat caggagatgg   1620

tagtagaggg atgtgggtgc cgctgagatc aggcagtcct tgaggataga cagatataca   1680

caccacacac acacaccaca tacaccacac acacacgttc ccatccactc acccacacac   1740

tacacagact gcttccttat agctggactt ttatttaaaa aaaaaaaaaa aaaaggaaaa   1800

aatccctaaa cattcacctt gaccttattt atgactttac gtgcaaatgt tttgaccata   1860

ttgatcatat attttgacaa aatatattta taactacgta ttaaaagaaa aaaataaaat   1920

gagtcattat tttaaaggta aaaaaaaaaa aaaaaaa                            1957
```

<210> SEQ ID NO 114
<211> LENGTH: 408
<212> TYPE: PRT
<213> ORGANISM: Homo sapiens

<400> SEQUENCE: 114

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205
```

```
Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

<210> SEQ ID NO 115
<211> LENGTH: 2207
<212> TYPE: DNA
<213> ORGANISM: Homo sapiens

<400> SEQUENCE: 115

```
ctcttgaaga gggctggtat atttgtgcct gctggaggtg gaattaacag taagaaggag     60

aaagggattg aatggactta caggaaggat ttcaagtaaa ttcagggaaa cacatttact    120

tgaatagtac aacctagagt attattttac actaagacga cacaaaagat gttaaagtta    180

tcaccaagct gccggacaga tatatattcc aacaccaagg tgcagatcag catagatctg    240

tgattcagaa atcaggattt gttttggaaa gagctcaagg gttgagaaga actcaaaagc    300

aagtgaagat tactttggga actacagttt atcagaagat caacttttgc taattcaaat    360

accaaaggcc tgattatcat aaattcatat aggaatgcat aggtcatctg atcaaataat    420

attagccgtc ttctgctaca tcaatgcagc aaaaactctt aacaactgtg gataattgga    480

aatctgagtt tcagctttct tagaaataac tactcttgac atattccaaa atatttaaaa    540

taggacagga aaatcggtga ggatgttgtg ctcagaaatg tcactgtcat gaaaaatagg    600

taaatttgtt ttttcagcta ctgggaaact gtacctccta gaaccttagg ttttttttt    660

ttttaagagg acaagaagga ctaaaaatat caacttttgc ttttggacaa aaatgcatct    720

gactgtattt ttacttaagg gtattgtggg tttcctctgg agctgctggg ttctagtggg    780

ttatgcaaaa ggaggtttgg gagacaatca tgttcactcc agttttattt atagaagact    840

acggaaccac gaaagacggg aaatacaaag ggaaattctc tctatcttgg gtttgcctca    900

cagacccaga ccattttcac ctggaaaaca agcgtcctct gcacctctct ttatgctgga    960
```

```
tctctacaat gccatgacca atgaagaaaa tcctgaagag tcggagtact cagtaagggc   1020
atccttggca gaagagacca gaggggcaag aaagggatac ccagcctctc ccaatgggta   1080
tcctcgtcgc atacagttat ctcggacgac tcctctgacc acccagagtc ctcctctagc   1140
cagcctccat gataccaact ttctgaatga tgctgacatg gtcatgagct ttgtcaactt   1200
agttgaaaga gacaaggatt tttctcacca gcgaaggcat tacaaagaat ttcgatttga   1260
tcttacccaa attcctcatg gagaggcagt gacagcagct gaattccgga tatacaagga   1320
ccggagcaac aaccgatttg aaaatgaaac aattaagatt agcatatatc aaatcatcaa   1380
ggaatacaca aatagggatg cagatctgtt cttgttagac acaagaaagg cccaagcttt   1440
agatgtgggt tggcttgtct ttgatatcac tgtgaccagc aatcattggg tgattaatcc   1500
ccagaataat ttgggcttac agctctgtgc agaaacaggg gatggacgca gtatcaacgt   1560
aaaatctgct ggtcttgtgg gaagacaggg acctcagtca aaacaaccat tcatggtggc   1620
cttcttcaag gcgagtgagg tacttcttcg atccgtgaga gcagccaaca aacgaaaaaa   1680
tcaaaaccgc aataaatcca gctctcatca ggactcctcc agaatgtcca gtgttggaga   1740
ttataacaca agtgagcaaa aacaagcctg taagaagcac gaactctatg tgagcttccg   1800
ggatctggga tggcaggact ggattatagc accagaagga tacgctgcat tttattgtga   1860
tggagaatgt tcttttccac ttaacgccca tatgaatgcc accaaccacg ctatagttca   1920
gactctggtt catctgatgt ttcctgacca cgtaccaaag ccttgttgtg ctccaaccaa   1980
attaaatgcc atctctgttc tgtactttga tgacagctcc aatgtcattt tgaaaaaata   2040
tagaaatatg gtagtacgct catgtggctg ccactaatat taaataatat tgataataac   2100
aaaaagatct gtattaaggt ttatggctgc aataaaaagc atactttcag acaaacgggg   2160
aatttcctaa aaaaaaaaaa aaaaaaaaaa aaaaaaaaaa aaaaaaa                 2207
```

<210> SEQ ID NO 116
<211> LENGTH: 454
<212> TYPE: PRT
<213> ORGANISM: Homo sapiens

<400> SEQUENCE: 116

```
Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30

His Val His Ser Ser Phe Ile Tyr Arg Arg Leu Arg Asn His Glu Arg
        35                  40                  45

Arg Glu Ile Gln Arg Glu Ile Leu Ser Ile Leu Gly Leu Pro His Arg
    50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160
```

```
Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
        355                 360                 365

Asp Trp Ile Ile Ala Pro Glu Gly Tyr Ala Ala Phe Tyr Cys Asp Gly
    370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
                405                 410                 415

Pro Cys Cys Ala Pro Thr Lys Leu Asn Ala Ile Ser Val Leu Tyr Phe
            420                 425                 430

Asp Asp Ser Ser Asn Val Ile Leu Lys Lys Tyr Arg Asn Met Val Val
        435                 440                 445

Arg Ser Cys Gly Cys His
    450
```

<210> SEQ ID NO 117
<211> LENGTH: 3105
<212> TYPE: DNA
<213> ORGANISM: Homo sapiens

<400> SEQUENCE: 117

```
caactggggg cgccccggac gaccatgaga gataaggact gagggccagg aaggggaagc     60

gagcccgccg agaggtggcg gggactgctc acgccaaggg ccacagcggc cgcgctccgg    120

cctcgctccg ccgctccacg cctcgcggga tccgcggggg cagcccggcc gggcggggat    180

gccggggctg gggcggaggg cgcagtggct gtgctggtgg tgggggctgc tgtgcagctg    240

ctgcgggccc ccgccgctgc ggccgccctt gcccgctgcc gcggccgccg ccgccggggg    300

gcagctgctg ggggacggcg ggagccccgg ccgcacggag cagccgccgc cgtcgccgca    360

gtcctcctcg ggcttcctgt accggcggct caagacgcag gagaagcggg agatgcagaa    420
```

```
ggagatcttg tcggtgctgg ggctcccgca ccggccccgg cccctgcacg gcctccaaca    480
gccgcagccc ccggcgctcc ggcagcagga ggagcagcag cagcagcagc agctgcctcg    540
cggagagccc cctcccgggc gactgaagtc cgcgcccctc ttcatgctgg atctgtacaa    600
cgccctgtcc gccgacaacg acgaggacgg ggcgtcggag gggagaggc agcagtcctg    660
gccccacgaa gcagccagct cgtcccagcg tcggcagccg cccccgggcg ccgcgcaccc    720
gctcaaccgc aagagccttc tggcccccgg atctggcagc ggcggcgcgt ccccactgac    780
cagcgcgcag gacagcgcct tcctcaacga cgcggacatg gtcatgagct ttgtgaacct    840
ggtggagtac gacaaggagt tctcccctcg tcagcgacac cacaaagagt tcaagttcaa    900
cttatcccag attcctgagg gtgaggtggt gacggctgca gaattccgca tctacaagga    960
ctgtgttatg gggagtttta aaaaccaaac ttttcttatc agcatttatc aagtcttaca   1020
ggagcatcag cacagagact ctgacctgtt tttgttggac acccgtgtag tatgggcctc   1080
agaagaaggc tggctggaat ttgacatcac ggccactagc aatctgtggg ttgtgactcc   1140
acagcataac atggggcttc agctgagcgt ggtgacaagg gatggagtcc acgtccaccc   1200
ccgagccgca ggcctggtgg gcagagacgg cccttacgac aagcagccct tcatggtggc   1260
tttcttcaaa gtgagtgagg tgcacgtgcg caccaccagg tcagcctcca gccggcgccg   1320
acaacagagt cgtaatcgct ctacccagtc ccaggacgtg gcgcgggtct ccagtgcttc   1380
agattacaac agcagtgaat tgaaaacagc ctgcaggaag catgagctgt atgtgagttt   1440
ccaagacctg ggatggcagg actggatcat tgcacccaag ggctatgctg ccaattactg   1500
tgatggagaa tgctccttcc cactcaacgc acacatgaat gcaaccaacc acgcgattgt   1560
gcagaccttg gttcacctta tgaaccccga gtatgtcccc aaaccgtgct gtgcgccaac   1620
taagctaaat gccatctcgg ttctttactt tgatgacaac tccaatgtca ttctgaaaaa   1680
atacaggaat atggttgtaa gagcttgtgg atgccactaa ctcgaaacca gatgctgggg   1740
acacacattc tgccttggat tcctagatta catctgcctt aaaaaaacac ggaagcacag   1800
ttggaggtgg gacgatgaga ctttgaaact atctcatgcc agtgccttat tacccaggaa   1860
gattttaaag gacctcatta ataatttgct cacttggtaa atgacgtgag tagttgttgg   1920
tctgtagcaa gctgagtttg gatgtctgta gcataaggtc tggtaactgc agaaacataa   1980
ccgtgaagct cttcctaccc tcctccccca aaaacccacc aaaattagtt ttagctgtag   2040
atcaagctat ttggggtgtt tgttagtaaa tagggaaaat aatctcaaag gagttaaatg   2100
tattcttggc taaaggatca gctggttcag tactgtctat caaaggtaga ttttacagag   2160
aacagaaatc ggggaagtgg ggggaacgcc tctgttcagt tcattcccag aagtccacag   2220
gacgcacagc ccaggccaca gccagggctc cacggggcgc ccttgtctca gtcattgctg   2280
ttgtatgttc gtgctggagt tttgttggtg tgaaaataca cttatttcag ccaaaacata   2340
ccatttctac acctcaatcc tccatttgct gtactctttg ctagtaccaa aagtagactg   2400
attacactga ggtgaggcta caaggggtgt gtaaccgtgt aacacgtgaa ggcaatgctc   2460
acctcttctt taccagaacg gttctttgac cagcacatta acttctggac tgccggctct   2520
agtacctttt cagtaaagtg gttctctgcc tttttactat acagcatacc acgccacagg   2580
gttagaacca acgaagaaaa taaaatgagg gtgcccagct tataagaatg gtgttagggg   2640
gatgagcatg ctgtttatga acggaaatca tgatttccct tgtagaaagt gaggctcaga   2700
ttaaatttta gaatattttc taaatgtctt tttcacaatc atgtactggg aaggcaattt   2760
```

```
catactaaac tgattaaata atacatttat aatctacaac tgtttgcact tacagctttt   2820

tttgtaaata taaactataa tttattgtct attttatatc tgttttgctg taacattgaa   2880

ggaaagacca gacttttaaa aaaaaagagt ttatttagaa agtatcatag tgtaaacaaa   2940

caaattgtac cactttgatt ttcttggaat acaagactcg tgatgcaaag ctgaagttgt   3000

gtgtacaaga ctcttgacag ttgtgcttct ctaggaggtt gggttttttt aaaaaaagaa   3060

ttatctgtga accatacgtg attaataaag atttccttta aggca                   3105


<210> SEQ ID NO 118
<211> LENGTH: 513
<212> TYPE: PRT
<213> ORGANISM: Homo sapiens

<400> SEQUENCE: 118

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
            20                  25                  30

Ala Ala Ala Ala Ala Ala Ala Gly Gly Gln Leu Leu Gly Asp Gly Gly
        35                  40                  45

Ser Pro Gly Arg Thr Glu Gln Pro Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
        275                 280                 285

Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320
```

```
Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
            340                 345                 350

Tyr Asp Lys Gln Pro Phe Met Val Ala Phe Phe Lys Val Ser Glu Val
        355                 360                 365

His Val Arg Thr Thr Arg Ser Ala Ser Ser Arg Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
        435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510

His

<210> SEQ ID NO 119
<211> LENGTH: 4049
<212> TYPE: DNA
<213> ORGANISM: Homo sapiens

<400> SEQUENCE: 119

agcgcgtacc actctggcgc tcccgaggcg gcctcttgtg cgatccaggg cgcacaaggc      60

tgggagagcg ccccggggcc cctgctatcc gcgccggagg ttggaagagg gtgggttgcc     120

gccgcccgag ggcgagagcg ccagaggagc gggaagaagg agcgctcgcc cgcccgcctg     180

cctcctcgct gcctccccgg cgttggctct ctggactcct aggcttgctg gctgctcctc     240

ccacccgcgc ccgcctcctc actcgccttt tcgttcgccg gggctgcttt ccaagccctg     300

cggtgcgccc gggcgagtgc ggggcgaggg gcccggggcc agcaccgagc agggggcggg     360

ggtccgggca gagcgcggcc ggccggggag gggccatgtc tggcgcgggc gcagcggggc     420

ccgtctgcag caagtgaccg agcggcgcgg acggccgcct gccccctctg ccacctgggg     480

cggtgcgggc ccggagcccg gagcccgggt agcgcgtaga gccggcgcga tgcacgtgcg     540

ctcactgcga gctgcggcgc cgcacagctt cgtggcgctc tgggcacccc tgttcctgct     600

gcgctccgcc ctggccgact tcagcctgga caacgaggtg cactcgagct tcatccaccg     660

gcgcctccgc agccaggagc ggcgggagat gcagcgcgag atcctctcca ttttgggctt     720

gccccaccgc ccgcgcccgc acctccaggg caagcacaac tcggcaccca tgttcatgct     780

ggacctgtac aacgccatgg cggtggagga gggcggcggg cccggcggcc agggcttctc     840

ctacccctac aaggccgtct tcagtaccca gggccccccct ctggccagcc tgcaagatag     900

ccatttcctc accgacgccg acatggtcat gagcttcgtc aacctcgtgg aacatgacaa     960
```

```
ggaattcttc cacccacgct accaccatcg agagttccgg tttgatcttt ccaagatccc   1020
agaaggggaa gctgtcacgg cagccgaatt ccggatctac aaggactaca tccgggaacg   1080
cttcgacaat gagacgttcc ggatcagcgt ttatcaggtg ctccaggagc acttgggcag   1140
ggaatcggat ctcttcctgc tcgacagccg taccctctgg gcctcggagg agggctggct   1200
ggtgtttgac atcacagcca ccagcaacca ctgggtggtc aatccgcggc acaacctggg   1260
cctgcagctc tcggtggaga cgctggatgg gcagagcatc aaccccaagt tggcgggcct   1320
gattgggcgg cacgggcccc agaacaagca gcccttcatg gtggctttct tcaaggccac   1380
ggaggtccac ttccgcagca tccggtccac ggggagcaaa cagcgcagcc agaaccgctc   1440
caagacgccc aagaaccagg aagccctgcg gatggccaac gtggcagaga acagcagcag   1500
cgaccagagg caggcctgta agaagcacga gctgtatgtc agcttccgag acctgggctg   1560
gcaggactgg atcatcgcgc ctgaaggcta cgccgcctac tactgtgagg gggagtgtgc   1620
cttccctctg aactcctaca tgaacgccac caaccacgcc atcgtgcaga cgctggtcca   1680
cttcatcaac ccggaaacgg tgcccaagcc ctgctgtgcg cccacgcagc tcaatgccat   1740
ctccgtcctc tacttcgatg acagctccaa cgtcatcctg aagaaataca gaaacatggt   1800
ggtccgggcc tgtggctgcc actagctcct ccgagaattc agaccctttg gggccaagtt   1860
tttctggatc ctccattgct cgccttggcc aggaaccagc agaccaactg ccttttgtga   1920
gaccttcccc tccctatccc caactttaaa ggtgtgagag tattaggaaa catgagcagc   1980
atatggcttt tgatcagttt ttcagtggca gcatccaatg aacaagatcc tacaagctgt   2040
gcaggcaaaa cctagcagga aaaaaaaaca acgcataaag aaaaatggcc gggccaggtc   2100
attggctggg aagtctcagc catgcacgga ctcgtttcca gaggtaatta tgagcgccta   2160
ccagccaggc cacccagccg tgggaggaag ggggcgtggc aaggggtggg cacattggtg   2220
tctgtgcgaa aggaaaattg acccggaagt tcctgtaata aatgtcacaa taaaacgaat   2280
gaatgaaaat ggttaggacg ttacagatat attttcctaa acaatttatc cccatttctc   2340
ggtttatcct gatgcgtaaa cagaagctgt gtcaagtgga gggcggggag gtccctctcc   2400
attccctaca gttttcatcc tgaggcttgc agaggcccag tgtttaccga ggtttgccca   2460
aatccaagat ctagtgggag gggaaagagc aaatgtctgc tccgaggagg gcggtgtgtt   2520
gatctttgga ggaaaaatat gttctgttgt tcagctggat ttgccgtggc agaaatgaaa   2580
ctaggtgtgt gaaatacccg cagacatttg ggattggctt ttcacctcgc cccagtggta   2640
gtaaatccat gtgaaattgc agaggggaca aggacagcaa gtaggatgga acttgcaact   2700
caaccctgtt gttaagaagc accaatgggc cgggcacagt agctcccacc tgtaatccca   2760
gcactttggg aggctgaggt gggcggatca tttgaggtca ggagttcgag accagcctgg   2820
ccaacatggt gaaaccccat ctctactaaa aatacaaaaa ttagccgggc atggtggcac   2880
gcacctgtaa tcccagctac tctggaggct gaggcaggag aattgcttga accccagagg   2940
tggaggttgc agtgagccaa gatcgtccca ctgcactcca gcttgggtga caaaacaaga   3000
ctccatctca aaagaaaaaa aaaacagcac caatgaagcc tagttctcca cgggagtggg   3060
gtgagcagga gcactgcaca tcgccccagt ggaccctctg gtctttgtct gcagtggcat   3120
tccaaggctg ggccctggca agggcacccg tggctgtctc ttcatttgca gaccctgatc   3180
agaagtctct gcaaacaaat ttgctccttg aattaagggg gagatggcat aataggaggt   3240
ctgatgggtg caggatgtgc tggacttaca ttgcaaatag aagccttgtt gagggtgaca   3300
tcctaaccaa gtgtcccgat ttggaggtgg catttctgac gtggctcttg gtgtaagcct   3360
```

```
gccttgcctt ggctggtgag tcccataaat agtatgcact cagcctccgg ccacaaacac   3420

aaggcctagg ggagggctag actgtctgca aacgttttct gcatctgtaa agaaaacaag   3480

gtgatcgaaa actgtggcca tgtggaaccc ggtcttgtgg gggactgttt ctccatcttg   3540

actcagacag ttcctggaaa caccggggct ctgtttttat tttctttgat gtttttcttc   3600

tttagtagct tgggctgcag cctccactct ctagtcactg gggaggagta tttttttgtta   3660

tgtttggttt catttgctgg cagagctggg gctttttgtg tgatccctct tggtgtgagt   3720

tttctgaccc aaccagcctc tggttagcat catttgtaca tttaaacctg taaatagttg   3780

ttacaaagca aagagattat ttatttccat ccaaagctct tttgaacacc cccccccctt   3840

taatccctcg ttcaggacga tgagcttgct ttccttcaac ctgtttgttt tcttatttaa   3900

gactatttat taatggttgg accaatgtac tcacagctgt tgcgtcgagc agtccttagt   3960

gaaaattctg tataaataga caaaatgaaa agggtttgac cttgcaataa aaggagacgt   4020

ttggttctgg caaaaaaaaa aaaaaaaaa                                     4049
```

<210> SEQ ID NO 120
<211> LENGTH: 431
<212> TYPE: PRT
<213> ORGANISM: Homo sapiens

<400> SEQUENCE: 120

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
```

```
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430


<210> SEQ ID NO 121
<211> LENGTH: 5430
<212> TYPE: DNA
<213> ORGANISM: Homo sapiens

<400> SEQUENCE: 121

aagctattga agctgacacc cacagagtta aactcagttg ctgaagccac cagctccccc      60

tcccagtcct tcttttcaga gtaggctggc agctgtccta actgcctact aaagccaaat     120

gcttgaggag agagagagag taaggagcca gccatgaatc ctttccagaa aaatgagtcc     180

aaggaaactc ttttttcacc tgtctccatt gaagaggtac cacctcgacc acctagccct     240

ccaaagaagc catctccgac aatctgtggc tccaactatc cactgagcat tgccttcatt     300

gtggtgaatg aattctgcga gcgcttttcc tattatggaa tgaaagctgt gctgatcctg     360

tatttcctgt atttcctgca ctggaatgaa gatacctcca catctatata ccatgccttc     420

agcagcctct gttattttac tcccatcctg ggagcagcca ttgctgactc gtggttggga     480

aaattcaaag tcctatcatt gatcggcctg agtctaatag ctttggggac aggaggcatc     540

aaaccctgtg tggcagcttt tggtggagac cagtttgaag aaaaacatgc agaggaacgg     600

actagatact tctcagtctt ctacctgtcc atcaatgcag ggagcttgat ttctacattt     660

atcacaccca tgctgagagg agatgtgcaa tgttttggag aagactgcta tgcattggct     720

tttggagttc caggactgct catggtaatt gcacttgttg tgtttgcaat gggaagcaaa     780

atatacaata aaccaccccc tgaaggaaac atagtggctc aagttttcaa atgtatctgg     840

tttgctattt ccaatcgttt caagaaccgt tctggagaca ttccaaagcg acagcactgg     900

ctagactggg cggctgagaa atatccaaag cagctcatta tggatgtaaa ggcactgacc     960

agggtactat tcctttatat cccattgccc atgttctggg ctcttttgga tcagcagggt    1020

tcacgatgga ctttgcaagc catcaggatg aataggaatt tggggttttt tgtgcttcag    1080
```

```
ccggaccaga tgcaggttct aaatcccctt ctggttctta tcttcatccc gttgtttgac   1140
tttgtcattt atcgtctggt ctccaagtgt ggaattaact tctcatcact taggaaaatg   1200
gctgttggta tgatcctagc atgcctggca tttgcagttg cggcagctgt agagataaaa   1260
ataaatgaaa tggccccagc ccagccaggt ccccaggagg ttttcctaca agtcttgaat   1320
ctggcagatg atgaggtgaa ggtgacagtg gtgggaaatg aaaacaattc tctgttgata   1380
gagtccatca aatcctttca gaaaacacca cactattcca aactgcacct gaaaacaaaa   1440
agccaggatt ttcacttcca cctgaaatat cacaatttgt ctctctacac tgagcattct   1500
gtgcaggaga agaactggta cagtcttgtc attcgtgaag atgggaacag tatctccagc   1560
atgatggtaa aggatacaga aagcagaaca accaatggga tgacaaccgt gaggtttgtt   1620
aacactttgc ataaagatgt caacatctcc ctgagtacag atacctctct caatgttggt   1680
gaagactatg gtgtgtctgc ttatagaact gtgcaaagag gagaataccc tgcagtgcac   1740
tgtagaacag aagataagaa cttttctctg aatttgggtc ttctagactt tggtgcagca   1800
tatctgtttg ttattactaa taacaccaat cagggtcttc aggcctggaa gattgaagac   1860
attccagcca acaaaatgtc cattgcgtgg cagctaccac aatatgccct ggttacagct   1920
ggggaggtca tgttctctgt cacaggtctt gagttttctt attctcaggc tccctctagc   1980
atgaaatctg tgctccaggc agcttggcta ttgacaattg cagttgggaa tatcatcgtg   2040
cttgttgtgg cacagttcag tggcctggta cagtgggccg aattcatttt gttttcctgc   2100
ctcctgctgg tgatctgcct gatcttctcc atcatgggct actactatgt tcctgtaaag   2160
acagaggata tgcggggtcc agcagataag cacattcctc acatccaggg gaacatgatc   2220
aaactagaga ccaagaagac aaaactctga tgactcccta gattctgtcc tgaccccaat   2280
tcctggccct gtcttgaagc atttttttc ttctactgga ttagacaaga gagatagcag   2340
catatcagag ctgatctcct ccacctttct ccaatgacag aagttccagg actggttttc   2400
cagtacatct ttaaacaagg ccccagagac tctatgtctg cccgtccatc agtgaactca   2460
ttaaaacttg tgcagtgttg ctggagctgg cctggtgtct ccaaatgacc atgaaaatac   2520
acacgtataa tggagatcat tctctgtggg tatgcaaagt tatgggaatt cctttatagg   2580
taactgccat ttaggactga tggccctaat ttttgaggtg ctgatttaga ggcaaaattg   2640
cagaataaca aagaaatggt atttcaagtt ttttttttta taagcaatgt aattatgcta   2700
ttcacagggg cctcaagaat tggtatgtat gatgtgatct ggtccagcca gggcctggct   2760
tgtcagctct ctaggtttga tatgacttta gtaaatttgt caatatagat ggtaggaagc   2820
agaatgccat tttattaaaa cacaggagaa gttatatctc tctgattatg atagtatttt   2880
atttacttat ccaaaccctc ctttctcagt atggatagat catggaaacc agattagaga   2940
tagtaagcat tagtaaacat tgttctggag aacaggaaca ggtgtaagtt gtagaaatcc   3000
tgaagagcca gtcattcttt tacagagtac attcttctta gcctctatgg cgctggtcta   3060
tgcccttcag tgaacagttg tataaacaat aattataatt tgcaaccttg tcttgtcaac   3120
cttgctgatc cagctttttc ttattattac accttgtctt gcttattgca gcaaatattc   3180
aataacaaca atgtttctat aagtccaact tcctttatta atgtttccat ttagcctcaa   3240
aaatatcaaa gtagttcctt tttgatgttg ttttcctgat ttacttttcc cataagtttt   3300
aaataccatt tctgccttga agcctagaaa ttttcttttt attcaaaaaa agttacatta   3360
atgctctagg tttgaggttc taaaatggaa atgtcaatag aggagcatgg tcctatgtga   3420
ggttcctatc aaaatttgtg ggagtaggga tggtagagca tgagggtttt gtttgtgtat   3480
```

gtgtatggtc atgaaaaaaa attgagaaac attacctcat acacaatgaa tgaatcagag 3540
gacagacacg ggaatggcac gactgtgcag tgtgttacta ggaaaaaagt tcagaatcac 3600
tgttctagag agcttcattt ccattggttt taaaacatta ttctcatgta gaacagtgtt 3660
gggtctcata ctgttaatgt taatacgtaa caatgttcat gttaacaggc acctgttaat 3720
attaacagat aatgttactg ttaacaggta agagaaattg ctctaagtgc ccaaacttta 3780
tatacttcag ttttaatgac aagcatttca gaaatataag agcggcagcc agaccaacca 3840
gtttttccag atatcttgat gtgaacctga ccctactcct ttagaagaca gcctgttcat 3900
ttttaaatag ctttaaccca aactgttcta tgaccattgt ttcaagagac attaacacag 3960
ttctgtaaat agaagtgtct atggacaaat aagtttggga aatgtggcat actgtatcct 4020
tttcttaaca tttgcatatt aaagactctg agatatcctg cagtaaagac acaagatacc 4080
ttgtttaaat taacatgtac gctgcagaac attggtttgg aaaaaactgt tgagcagttc 4140
ttccttgtaa gtgctgagct tcctctctga aacctcctac cattgttttt tttcccctgt 4200
agctaacaag aataagtata acagccggcc aggcacagtg gctcatgcct gtaatcccag 4260
cactttggga ggctgagaca ggtggatcac ctgaggtcag gagttcgaga ccagcctggc 4320
caacatggtg aaaccgtgtc tctactaaaa gtacaaaaat tagccaggtg tgatggcagg 4380
tgcctgtaat cccagctact cgggaggctg aagcagaaga attgcttgaa cccgggaggc 4440
agaggttgca atgagccgag atcacgccat cacactctag cctgggggac aagagtgaga 4500
cttcatctaa aaaaaaaaag aaaagaatat gtataccccc tttttcatgt ggcagatgtt 4560
tagctatttg ggagaacttt tcatggctct tccctaatca tcaagtattc aaggtaaaga 4620
ttctcggttc ctgtaatggt tcctcaccag gcataatttg tccttttacc atcctacttt 4680
ctgtcttctg aaaaacattc tttatctgaa atacagcaat taatattaag atatcttaat 4740
atgaagtgcc tggagtcaaa tataacattc caaagtagtc tgactggaag aactagcacc 4800
tgcctttctt caaacaatgc acttctgtta atgcagtgta aggtaacatg agttgttttt 4860
ggaaactaca tcataatgtg ggcttacatt ctagcactta tcacttaatg acagggatac 4920
atttgaggaa tgcattgtta ggcaattttg tcattatgca aacatcatag agtgtactta 4980
cacaaaccta tggtatagcc tactacacat ctaagttata tggtatagac tgtttctcca 5040
gctatatggt gtagactgtt tctcctaggc tacaaacctg cacagcatgt tactgtatta 5100
aatgctgtag gcaattgtaa cacaatggta tttttatact taaacatatc taaacataga 5160
aacggtacaa aaaactttac acattatata gatgtatcaa attattcata tgtgctctga 5220
aaatgtctat atctgttatg tatcaatttt ttaaaaagtg aatgacataa ttcatttgaa 5280
aaaatgtgga cacacaaatt ggaaaagagg tataaatgca gtattataat ctaatgggac 5340
caccatcaca tatttggtct gtcattgact gaaactgcaa tatagagttt ttcttaacat 5400
ttgcatatta aagactctga ctatatatgg 5430

<210> SEQ ID NO 122
<211> LENGTH: 698
<212> TYPE: PRT
<213> ORGANISM: Homo sapiens

<400> SEQUENCE: 122

Met Asn Pro Phe Gln Lys Asn Glu Ser Lys Glu Thr Leu Phe Ser Pro
1 5 10 15

Val Ser Ile Glu Glu Val Pro Pro Arg Pro Pro Ser Pro Pro Lys Lys

```
            20                  25                  30

Pro Ser Pro Thr Ile Cys Gly Ser Asn Tyr Pro Leu Ser Ile Ala Phe
        35                  40                  45

Ile Val Val Asn Glu Phe Cys Glu Arg Phe Ser Tyr Tyr Gly Met Lys
    50                  55                  60

Ala Val Leu Ile Leu Tyr Phe Leu Tyr Phe Leu His Trp Asn Glu Asp
65                  70                  75                  80

Thr Ser Thr Ser Ile Tyr His Ala Phe Ser Ser Leu Cys Tyr Phe Thr
                85                  90                  95

Pro Ile Leu Gly Ala Ala Ile Ala Asp Ser Trp Leu Gly Lys Phe Lys
            100                 105                 110

Val Leu Ser Leu Ile Gly Leu Ser Leu Ile Ala Leu Gly Thr Gly Gly
        115                 120                 125

Ile Lys Pro Cys Val Ala Ala Phe Gly Gly Asp Gln Phe Glu Glu Lys
    130                 135                 140

His Ala Glu Glu Arg Thr Arg Tyr Phe Ser Val Phe Tyr Leu Ser Ile
145                 150                 155                 160

Asn Ala Gly Ser Leu Ile Ser Thr Phe Ile Thr Pro Met Leu Arg Gly
                165                 170                 175

Asp Val Gln Cys Phe Gly Glu Asp Cys Tyr Ala Leu Ala Phe Gly Val
            180                 185                 190

Pro Gly Leu Leu Met Val Ile Ala Leu Val Val Phe Ala Met Gly Ser
        195                 200                 205

Lys Ile Tyr Asn Lys Pro Pro Pro Glu Gly Asn Ile Val Ala Gln Val
    210                 215                 220

Phe Lys Cys Ile Trp Phe Ala Ile Ser Asn Arg Phe Lys Asn Arg Ser
225                 230                 235                 240

Gly Asp Ile Pro Lys Arg Gln His Trp Leu Asp Trp Ala Ala Glu Lys
                245                 250                 255

Tyr Pro Lys Gln Leu Ile Met Asp Val Lys Ala Leu Thr Arg Val Leu
            260                 265                 270

Phe Leu Tyr Ile Pro Leu Pro Met Phe Trp Ala Leu Leu Asp Gln Gln
        275                 280                 285

Gly Ser Arg Trp Thr Leu Gln Ala Ile Arg Met Asn Arg Asn Leu Gly
    290                 295                 300

Phe Phe Val Leu Gln Pro Asp Gln Met Gln Val Leu Asn Pro Leu Leu
305                 310                 315                 320

Val Leu Ile Phe Ile Pro Leu Phe Asp Phe Val Ile Tyr Arg Leu Val
                325                 330                 335

Ser Lys Cys Gly Ile Asn Phe Ser Ser Leu Arg Lys Met Ala Val Gly
            340                 345                 350

Met Ile Leu Ala Cys Leu Ala Phe Ala Val Ala Ala Ala Val Glu Ile
        355                 360                 365

Lys Ile Asn Glu Met Ala Pro Ala Gln Pro Gly Pro Gln Glu Val Phe
    370                 375                 380

Leu Gln Val Leu Asn Leu Ala Asp Asp Glu Val Lys Val Thr Val Val
385                 390                 395                 400

Gly Asn Glu Asn Asn Ser Leu Leu Ile Glu Ser Ile Lys Ser Phe Gln
                405                 410                 415

Lys Thr Pro His Tyr Ser Lys Leu His Leu Lys Thr Lys Ser Gln Asp
            420                 425                 430

Phe His Phe His Leu Lys Tyr His Asn Leu Ser Leu Tyr Thr Glu His
        435                 440                 445
```

```
Ser Val Gln Glu Lys Asn Trp Tyr Ser Leu Val Ile Arg Glu Asp Gly
    450                 455                 460

Asn Ser Ile Ser Ser Met Met Val Lys Asp Thr Glu Ser Arg Thr Thr
465                 470                 475                 480

Asn Gly Met Thr Thr Val Arg Phe Val Asn Thr Leu His Lys Asp Val
                485                 490                 495

Asn Ile Ser Leu Ser Thr Asp Thr Ser Leu Asn Val Gly Glu Asp Tyr
            500                 505                 510

Gly Val Ser Ala Tyr Arg Thr Val Gln Arg Gly Glu Tyr Pro Ala Val
        515                 520                 525

His Cys Arg Thr Glu Asp Lys Asn Phe Ser Leu Asn Leu Gly Leu Leu
    530                 535                 540

Asp Phe Gly Ala Ala Tyr Leu Phe Val Ile Thr Asn Asn Thr Asn Gln
545                 550                 555                 560

Gly Leu Gln Ala Trp Lys Ile Glu Asp Ile Pro Ala Asn Lys Met Ser
                565                 570                 575

Ile Ala Trp Gln Leu Pro Gln Tyr Ala Leu Val Thr Ala Gly Glu Val
            580                 585                 590

Met Phe Ser Val Thr Gly Leu Glu Phe Ser Tyr Ser Gln Ala Pro Ser
        595                 600                 605

Ser Met Lys Ser Val Leu Gln Ala Ala Trp Leu Leu Thr Ile Ala Val
    610                 615                 620

Gly Asn Ile Ile Val Leu Val Val Ala Gln Phe Ser Gly Leu Val Gln
625                 630                 635                 640

Trp Ala Glu Phe Ile Leu Phe Ser Cys Leu Leu Leu Val Ile Cys Leu
                645                 650                 655

Ile Phe Ser Ile Met Gly Tyr Tyr Tyr Val Pro Val Lys Thr Glu Asp
            660                 665                 670

Met Arg Gly Pro Ala Asp Lys His Ile Pro His Ile Gln Gly Asn Met
        675                 680                 685

Ile Lys Leu Glu Thr Lys Lys Thr Lys Leu
    690                 695
```

<210> SEQ ID NO 123
<211> LENGTH: 1955
<212> TYPE: DNA
<213> ORGANISM: Homo sapiens

<400> SEQUENCE: 123

```
aagcacaagt ggaggacaat ccagcccggc agcgggtgag agtgggtgct ggccaggacg     60

gttccttcag agcaaacagc agggagatgc cggcccgctc cttcccagct cctccccgtg    120

cccgctaaca cagcacggcc gcctgcagtc tcctctctgg gtgattgcgc gggcctaaga    180

tgtgtcctgg ggcactgtgg gtggccctgc ccctgctgtc cctgctggct ggctccctac    240

aggggaagcc actgcagagc tggggacgag ggtctgctgg gggaaacgcc cacagcccac    300

tgggggtgcc tggaggtggg ctgcctgagc acaccttcaa cctgaagatg tttctggaga    360

acgtgaaggt ggatttcctg cgcagcctta acctgagtgg ggtcccttcg caggacaaaa    420

ccagggtgga gccgccgcag tacatgattg acctgtacaa caggtacacg tccgataagt    480

cgactacgcc agcgtccaac attgtgcgga gcttcagcat ggaagatgcc atctccataa    540

ctgccacaga ggacttcccc ttccagaagc acatcttgct cttcaacatc tccattccta    600

ggcatgagca gatcaccaga gctgagctcc gactctatgt ctcctgtcaa aatcacgtgg    660
```

```
acccctctca tgacctgaaa ggaagcgtgg tcatttatga tgttctggat ggaacagatg    720

cctgggatag tgctacagag accaagacct tcctggtgtc ccaggacatt caggatgagg    780

gctgggagac cttggaagtg tccagcgccg tgaagcgctg ggtccggtcc gactccacca    840

agagcaaaaa taagctggaa gtgactgtgg agagccacag gaagggctgc gacacgctgg    900

acatcagtgt cccccccaggt tccagaaacc tgcccttctt tgttgtcttc tccaatgacc    960

acagcagtgg gaccaaggag accaggctgg agctgaggga gatgatcagc catgaacaag   1020

agagcgtgct caagaagctg tccaaggacg gctccacaga ggcaggtgag agcagtcacg   1080

aggaggacac ggatggccac gtggctgcgg ggtcgacttt agccaggcgg aaaaggagcg   1140

ccggggctgg cagccactgt caaaagacct ccctgcgggt aaacttcgag gacatcggct   1200

gggacagctg gatcattgca cccaaggagt atgaagccta cgagtgtaag ggcggctgct   1260

tcttcccctt ggctgacgat gtgacgccga cgaaacacgc tatcgtgcag accctggtgc   1320

atctcaagtt ccccacaaag gtgggcaagg cctgctgtgt gcccaccaaa ctgagcccca   1380

tctccgtcct ctacaaggat gacatggggg tgcccaccct caagtaccat tacgagggca   1440

tgagcgtggc agagtgtggg tgcaggtagt atctgcctgc ggggctgggg aggcaggcca   1500

aaggggctcc acatgagagg tcctgcatgc ccctgggcac aacaaggact gattcaatct   1560

gcatgccagc ctggaggagg aaagggagcc tgctctccct ccccacaccc cacccaaagc   1620

atacaccgct gagctcaact gccagggaag gctaaggaaa tggggatttg agcacaacag   1680

gaaagcctgg gagggttgtt gggatgcaag gaggtgatga aaaggagaca gggggaaaaa   1740

taatccatag tcagcagaaa acaacagcag tgagccagag gagcacaggc gggcaggtca   1800

ctgcagagac tgatggaagt tagagaggtg gaggaggcca gctcgctcca aaacccttgg   1860

ggagtagagg gaaggagcag gccgcgtgtc acacccatca ttgtatgtta tttcccacaa   1920

cccagttgga ggggcatggc ttccaattta gagac                              1955

<210> SEQ ID NO 124
<211> LENGTH: 429
<212> TYPE: PRT
<213> ORGANISM: Homo sapiens

<400> SEQUENCE: 124

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
        115                 120                 125

Gln Lys His Ile Leu Leu Phe Asn Ile Ser Ile Pro Arg His Glu Gln
    130                 135                 140
```

```
Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
        195                 200                 205

Ser Ala Val Lys Arg Trp Val Arg Ser Asp Ser Thr Lys Ser Lys Asn
    210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
    290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
        355                 360                 365

Thr Pro Thr Lys His Ala Ile Val Gln Thr Leu Val His Leu Lys Phe
    370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
            420                 425
```

```
<210> SEQ ID NO 125
<211> LENGTH: 1584
<212> TYPE: DNA
<213> ORGANISM: Homo sapiens

<400> SEQUENCE: 125

ggggagagga agagtggtag ggggagggag agagagagga agagtttcca aacttgtctc     60

cagtgacagg agacatttac gttccacaag ataaaactgc cacttagagc ccagggaagc    120

taaaccttcc tggcttggcc taggagctcg agcggagtca tgggctctct ggtcctgaca    180

ctgtgcgctc ttttctgcct ggcagcttac ttggtttctg gcagccccat catgaaccta    240

gagcagtctc ctctggaaga agatatgtcc ctctttggtg atgttttctc agagcaagac    300

ggtgtcgact ttaacacact gctccagagc atgaaggatg agtttcttaa gacactaaac    360

ctctctgaca tccccacgca ggattcagcc aaggtggacc caccagagta catgttggaa    420

ctctacaaca aatttgcaac agatcggacc tccatgccct ctgccaacat cattaggagt    480

ttcaagaatg aagatctgtt ttcccagccg gtcagtttta atgggctccg aaaatacccc    540
```

```
ctcctcttca atgtgtccat tcctcaccat gaagaggtca tcatggctga acttaggcta    600

tacacactgg tgcaaaggga tcgtatgata tacgatggag tagaccggaa aattaccatt    660

tttgaagtgc tggagagcaa aggggataat gagggagaaa gaaacatgct ggtcttggtg    720

tctggggaga tatatggaac caacagtgag tgggagactt ttgatgtcac agatgccatc    780

agacgttggc aaaagtcagg ctcatccacc caccagctgg aggtccacat tgagagcaaa    840

cacgatgaag ctgaggatgc cagcagtgga cggctagaaa tagataccag tgcccagaat    900

aagcataacc ctttgctcat cgtgttttct gatgaccaaa gcagtgacaa ggagaggaag    960

gaggaactga atgaaatgat ttcccatgag caacttccag agctggacaa cttgggcctg   1020

gatagctttt ccagtggacc tggggaagag gctttgttgc agatgagatc aaacatcatc   1080

tatgactcca ctgcccgaat cagaaggaac gccaaaggaa actactgtaa gaggaccccg   1140

ctctacatcg acttcaagga gattgggtgg gactcctgga tcatcgctcc gcctggatac   1200

gaagcctatg aatgccgtgg tgtttgtaac taccccctgg cagagcatct cacacccaca   1260

aagcatgcaa ttatccaggc cttggtccac ctcaagaatt cccagaaagc ttccaaagcc   1320

tgctgtgtgc ccacaaagct agagcccatc tccatcctct atttagacaa aggcgtcgtc   1380

acctacaagt ttaaatacga aggcatggcc gtctccgaat gtggctgtag atagaagaag   1440

agtcctatgg cttatttaat aactgtaaat gtgtatattt ggtgttccta tttaatgaga   1500

ttatttaata agggtgtaca gtaatagagg cttgctgcct tcaggaaatg gacaggtcag   1560

tttgttgtag gaaatgcata tttt                                          1584
```

```
<210> SEQ ID NO 126
<211> LENGTH: 424
<212> TYPE: PRT
<213> ORGANISM: Homo sapiens

<400> SEQUENCE: 126

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
            20                  25                  30

Glu Glu Asp Met Ser Leu Phe Gly Asp Val Phe Ser Glu Gln Asp Gly
        35                  40                  45

Val Asp Phe Asn Thr Leu Leu Gln Ser Met Lys Asp Glu Phe Leu Lys
    50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
        115                 120                 125

Leu Phe Asn Val Ser Ile Pro His His Glu Glu Val Ile Met Ala Glu
    130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
```

```
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
        275                 280                 285

Ser Phe Ser Ser Gly Pro Gly Glu Glu Ala Leu Leu Gln Met Arg Ser
    290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
        355                 360                 365

His Ala Ile Ile Gln Ala Leu Val His Leu Lys Asn Ser Gln Lys Ala
    370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420
```

<210> SEQ ID NO 127
<211> LENGTH: 3936
<212> TYPE: DNA
<213> ORGANISM: Homo sapiens

<400> SEQUENCE: 127

```
agttttaatt gcttccaatg aggtcagcaa aggtatttat cgaaaagccc tgaataaaag     60

gctcacacac acacacaagc acacacgcgc tcacacacag agagaaaatc cttctgcctg    120

ttgatttatg gaaacaatta tgattctgct ggagaacttt tcagctgaga aatagtttgt    180

agctacagta gaaaggctca agttgcacca ggcagacaac agacatggaa ttcttatata    240

tccagctgtt agcaacaaaa caaaagtcaa atagcaaaca gcgtcacagc aactgaactt    300

actacgaact gtttttatga ggatttatca acagagttat ttaaggagga atcctgtgtt    360

gttatcagga actaaaagga taaggctaac aatttggaaa gagcaactac tctttcttaa    420

atcaatctac aattcacaga taggaagagg tcaatgacct aggagtaaca atcaactcaa    480

gattcatttt cattatgtta ttcatgaaca cccggagcac tacactataa tgcacaaatg    540

gatactgaca tggatcctgc caactttgct ctacagatca tgctttcaca ttatctgtct    600

agtgggtact atatctttag cttgcaatga catgactcca gagcaaatgg ctacaaatgt    660

gaactgttcc agccctgagc gacacacaag aagttatgat tacatggaag gaggggatat    720
```

```
aagagtgaga agactcttct gtcgaacaca gtggtacctg aggatcgata aaagaggcaa     780
agtaaaaggg acccaagaga tgaagaataa ttacaatatc atggaaatca ggacagtggc     840
agttggaatt gtggcaatca aaggggtgga aagtgaattc tatcttgcaa tgaacaagga     900
aggaaaactc tatgcaaaga aagaatgcaa tgaagattgt aacttcaaag aactaattct     960
ggaaaaccat tacaacacat atgcatcagc taaatggaca cacaacggag gggaaatgtt    1020
tgttgcctta aatcaaaagg ggattcctgt aagaggaaaa aaaacgaaga aagaacaaaa    1080
aacagcccac tttcttccta tggcaataac ttaattgcat atggtatata aagaaccagt    1140
tccagcaggg agatttcttt aagtggactg ttttctttct tctcaaaatt ttctttcctt    1200
ttattttta gtaatcaaga aaggctggaa aactactgaa aaactgatca agctggactt    1260
gtgcatttat gtttgtttta agacactgca ttaaagaaag atttgaaaag tatacacaaa    1320
aatcagattt agtaactaaa ggttgtaaaa aattgtaaaa ctggttgtac aatcatgatg    1380
ttagtaacag taattttttt cttaaattaa tttaccctta agagtatgtt agatttgatt    1440
atctgataat gattatttaa atattcctat ctgcttataa aatggctgct ataataataa    1500
taatacagat gttgttatat aaggtatatc agacctacag gcttctggca ggatttgtca    1560
gataatcaag ccacactaac tatggaaaat gagcagcatt ttaaatgctt tctagtgaaa    1620
aattataatc tacttaaact ctaatcagaa aaaaaattct caaaaaaact attatgaaag    1680
tcaataaaat agataattta acaaaagtac aggattagaa catgcttata cctataaata    1740
agaacaaaat ttctaatgct gctcaagtgg aaagggtatt gctaaaagga tgtttccaaa    1800
aatcttgtat ataagatagc aacagtgatt gatgataata ctgtacttca tcttacttgc    1860
cacaaaataa cattttataa atcctcaaag taaaattgag aaatctttaa gttttttca     1920
agtaacataa tctatctttg tataattcat atttgggaat atggctttta ataatgttct    1980
tcccacaaat aatcatgctt ttttcctatg gttacagcat taaactctat tttaagttgt    2040
ttttgaactt tattgttttg ttatttaagt ttatgttatt tataaaaaaa aaaccttaat    2100
aagctgtatc tgtttcatat gcttttaatt ttaaaggaat aacaaaactg tctggctcaa    2160
cggcaagttt ccctcccttt tctgactgac actaagtcta gcacacagca cttgggccag    2220
caaatcctgg aaggcagaca aaaataagag cctgaagcaa tgcttacaat agatgtctca    2280
cacagaacaa tacaaatatg taaaaaatct ttcaccacat attcttgcca attaattgga    2340
tcatataagt aaaatcatta caaatataag tatttacagg attttaaagt tagaatatat    2400
ttgaatgcat gggtagaaaa tatcatattt taaaactatg tatatttaaa tttagtaatt    2460
ttctaatctc tagaaatctc tgctgttcaa aaggtggcag cactgaaagt tgttttcctg    2520
ttagatggca agagcacaat gcccaaaata gaagatgcag ttaagaataa ggggccctga    2580
atgtcatgaa ggcttgaggt cagcctacag ataacaggat tattacaagg atgaatttcc    2640
acttcaaaag tctttcattg gcagatcttg gtagcacttt atatgttcac caatgggagg    2700
tcaatattta tctaatttaa aaggtatgct aaccactgtg gttttaattt caaaatattt    2760
gtcattcaag tccctttaca taaatagtat ttggtaatac atttatagat gagagttata    2820
tgaaaaggct aggtcaacaa aaacaataga ttcatttaat tttcctgtgg ttgacctata    2880
cgaccaggat gtagaaaact agaaagaact gcccttcctc agatatactc ttgggagaga    2940
gcatgaatgg tattctgaac tatcacctga ttcaaggact ttgctagcta ggttttgagg    3000
tcaggcttca gtaactgtag tcttgtgagc atattgaggg cagaggagga cttagttttt    3060
catatgtgtt tccttagtgc ctagcagact atctgttcat aatcagtttt cagtgtgaat    3120
```

```
tcactgaatg tttatagaca aaagaaaata cacactaaaa ctaatcttca ttttaaaagg   3180
gtaaaacatg actatacaga aatttaaata gaaatagtgt atatacatat aaaatacaag   3240
ctatgttagg accaaatgct ctttgtctat ggagttatac ttccatcaaa ttacatagca   3300
atgctgaatt aggcaaaacc aacatttagt ggtaaatcca ttcctggtag tataagtcac   3360
ctaaaaaaga cttctagaaa tatgtacttt aattatttgt ttttctccta tttttaaatt   3420
tattatgcaa attttagaaa ataaaatttg ctctagttac acacctttag aattctagaa   3480
tattaaaact gtaaggggcc tccatccctc ttactcattt gtagtctagg aaattgagat   3540
tttgatacac ctaaggtcac gcagctgggt agatatacag ctgtcacaag agtctagatc   3600
agttagcaca tgctttctac tcttcgatta ttagtattat tagctaatgg tctttggcat   3660
gtttttgttt tttatttctg ttgagatata gcctttacat ttgtacacaa atgtgactat   3720
gtcttggcaa tgcacttcat acacaatgac taatctatac tgtgatgatt tgactcaaaa   3780
ggagaaaaga aattatgtag ttttcaattc tgattcctat tcaccttttg tttatgaatg   3840
gaaagctttg tgcaaaatat acatataagc agagtaagcc ttttaaaaat gttctttgaa   3900
agataaaatt aaatacatga gtttctaaca attaga                             3936
```

<210> SEQ ID NO 128
<211> LENGTH: 194
<212> TYPE: PRT
<213> ORGANISM: Homo sapiens

<400> SEQUENCE: 128

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr
```

<210> SEQ ID NO 129
<211> LENGTH: 627
<212> TYPE: DNA

<213> ORGANISM: Homo sapiens

<400> SEQUENCE: 129

```
atgtggaaat ggatactgac acattgtgcc tcagcctttc cccacctgcc cggctgctgc     60
tgctgctgct ttttgttgct gttcttggtg tcttccgtcc ctgtcacctg ccaagccctt    120
ggtcaggaca tggtgtcacc agaggccacc aactcttctt cctcctcctt ctcctctcct    180
tccagcgcgg gaaggcatgt gcggagctac aatcaccttc aaggagatgt ccgctggaga    240
aagctattct ctttcaccaa gtactttctc aagattgaga agaacgggaa ggtcagcggg    300
accaagaagg agaactgccc gtacagcatc ctggagataa catcagtaga aatcggagtt    360
gttgccgtca aagccattaa cagcaactat tacttagcca tgaacaagaa ggggaaactc    420
tatggctcaa aagaatttaa caatgactgt aagctgaagg agaggataga ggaaaatgga    480
tacaatacct atgcatcatt taactggcag cataatggga ggcaaatgta tgtggcattg    540
aatggaaaag gagctccaag gagaggacag aaaacacgaa ggaaaaacac ctctgctcac    600
tttcttccaa tggtggtaca ctcatag                                        627
```

<210> SEQ ID NO 130
<211> LENGTH: 208
<212> TYPE: PRT
<213> ORGANISM: Homo sapiens

<400> SEQUENCE: 130

```
Met Trp Lys Trp Ile Leu Thr His Cys Ala Ser Ala Phe Pro His Leu
1               5                   10                  15

Pro Gly Cys Cys Cys Cys Cys Phe Leu Leu Leu Phe Leu Val Ser Ser
            20                  25                  30

Val Pro Val Thr Cys Gln Ala Leu Gly Gln Asp Met Val Ser Pro Glu
        35                  40                  45

Ala Thr Asn Ser Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205
```

<210> SEQ ID NO 131
<211> LENGTH: 2157
<212> TYPE: DNA
<213> ORGANISM: Homo sapiens

<400> SEQUENCE: 131

```
gctcccagcc aagaacctcg gggccgctgc gcggtgggga ggagttcccc gaaacccggc     60
cgctaagcga ggcctcctcc tcccgcagat ccgaacggcc tgggcggggt caccccggct    120
gggacaagaa gccgccgcct gcctgcccgg gcccggggag ggggctgggg ctggggccgg    180
aggcggggtg tgagtgggtg tgtgcggggg gcggaggctt gatgcaatcc cgataagaaa    240
tgctcgggtg tcttgggcac ctacccgtgg ggcccgtaag gcgctactat ataaggctgc    300
cggcccggag ccgccgcgcc gtcagagcag gagcgctgcg tccaggatct agggccacga    360
ccatcccaac ccggcactca cagccccgca gcgcatcccg gtcgccgccc agcctcccgc    420
acccccatcg ccggagctgc gccgagagcc ccagggaggt gccatgcgga gcgggtgtgt    480
ggtggtccac gtatggatcc tggccggcct ctggctggcc gtggccgggc gcccccctcgc    540
cttctcggac gcggggcccc acgtgcacta cggctggggc gaccccatcc gcctgcggca    600
cctgtacacc tccggccccc acgggctctc cagctgcttc ctgcgcatcc gtgccgacgg    660
cgtcgtggac tgcgcgcggg gccagagcgc gcacagtttg ctggagatca aggcagtcgc    720
tctgcggacc gtggccatca agggcgtgca cagcgtgcgg tacctctgca tgggcgccga    780
cggcaagatg caggggctgc ttcagtactc ggaggaagac tgtgctttcg aggaggagat    840
ccgcccagat ggctacaatg tgtaccgatc cgagaagcac cgcctcccgg tctccctgag    900
cagtgccaaa cagcggcagc tgtacaagaa cagaggcttt cttccactct ctcatttcct    960
gcccatgctg cccatggtcc cagaggagcc tgaggacctc aggggccact tggaatctga   1020
catgttctct tcgcccctgg agaccgacag catggaccca tttgggcttg tcaccggact   1080
ggaggccgtg aggagtccca gctttgagaa gtaactgaga ccatgcccgg gcctcttcac   1140
tgctgccagg ggctgtggta cctgcagcgt gggggacgtg cttctacaag aacagtcctg   1200
agtccacgtt ctgtttagct ttaggaagaa acatctagaa gttgtacata ttcagagttt   1260
tccattggca gtgccagttt ctagccaata gacttgtctg atcataacat tgtaagcctg   1320
tagcttgccc agctgctgcc tgggccccca ttctgctccc tcgaggttgc tggacaagct   1380
gctgcactgt ctcagttctg cttgaatacc tccatcgatg gggaactcac ttcctttgga   1440
aaaattctta tgtcaagctg aaattctcta attttttctc atcacttccc caggagcagc   1500
cagaagacag gcagtagttt taatttcagg aacaggtgat ccactctgta aaacagcagg   1560
taaatttcac tcaaccccat gtgggaattg atctatatct ctacttccag ggaccatttg   1620
cccttcccaa atccctccag gccagaactg actggagcag gcatggccca ccaggcttca   1680
ggagtagggg aagcctggag ccccactcca gccctgggac aacttgagaa ttcccccctga   1740
ggccagttct gtcatggatg ctgtcctgag aataacttgc tgtcccggtg tcacctgctt   1800
ccatctccca gcccaccagc cctctgccca cctcacatgc ctccccatgg attggggcct   1860
cccaggcccc ccaccttatg tcaacctgca cttcttgttc aaaaatcagg aaaagaaaag   1920
atttgaagac cccaagtctt gtcaataact tgctgtgtgg aagcagcggg ggaagaccta   1980
gaaccctttc cccagcactt ggttttccaa catgatattt atgagtaatt tattttgata   2040
tgtacatctc ttattttctt acattattta tgcccccaaa ttatatttat gtatgtaagt   2100
gaggtttgtt ttgtatatta aaatggagtt tgtttgtaaa aaaaaaaaaa aaaaaaa      2157
```

<210> SEQ ID NO 132
<211> LENGTH: 216
<212> TYPE: PRT
<213> ORGANISM: Homo sapiens

<400> SEQUENCE: 132

```
Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 133
<211> LENGTH: 1220
<212> TYPE: DNA
<213> ORGANISM: Homo sapiens

<400> SEQUENCE: 133

```
gggagcgggc gagtaggagg gggcgccggg ctatatatat agcggctcgg cctcgggcgg      60

gcctggcgct cagggaggcg cgcactgctc ctcagagtcc cagctccagc cgcgcgcttt     120

ccgcccggct cgccgctcca tgcagccggg gtagagcccg gcgcccgggg gccccgtcgc     180

ttgcctcccg cacctcctcg gttgcgcact cctgcccgag gtcggccgtg cgctcccgcg     240

ggacgccaca ggcgcagctc tgccccccag cttcccgggc gcactgaccg cctgaccgac     300

gcacggccct cgggccggga tgtcggggcc cgggacggcc gcggtagcgc tgctcccggc     360

ggtcctgctg gccttgctgg cgccctgggc gggccgaggg ggcgccgccg cacccactgc     420

acccaacggc acgctggagg ccgagctgga gcgccgctgg gagagcctgg tggcgctctc     480

gttggcgcgc ctgccggtgg cagcgcagcc caaggaggcg gccgtccaga gcggcgccgg     540

cgactacctg ctgggcatca agcggctgcg gcggctctac tgcaacgtgg gcatcggctt     600

ccacctccag gcgctccccg acggccgcat cggcggcgcg cacgcggaca cccgcgacag     660

cctgctggag ctctcgcccg tggagcgggg cgtggtgagc atcttcggcg tggccagccg     720

gttcttcgtg gccatgagca gcaagggcaa gctctatggc tcgcccttct tcaccgatga     780
```

```
gtgcacgttc aaggagattc tccttcccaa caactacaac gcctacgagt cctacaagta    840

ccccggcatg ttcatcgccc tgagcaagaa tgggaagacc aagaagggga accgagtgtc    900

gcccaccatg aaggtcaccc acttcctccc caggctgtga ccctccagag gacccttgcc    960

tcagcctcgg gaagcccctg ggagggcagt gccgagggtc accttggtgc actttcttcg   1020

gatgaagagt ttaatgcaag agtaggtgta agatatttaa attaattatt taaatgtgta   1080

tatattgcca ccaaattatt tatagttctg cgggtgtgtt ttttaatttt ctggggggaa   1140

aaaaagacaa aacaaaaaac caactctgac ttttctggtg caacagtgga gaatcttacc   1200

attggatttc tttaacttgt                                               1220
```

```
<210> SEQ ID NO 134
<211> LENGTH: 206
<212> TYPE: PRT
<213> ORGANISM: Homo sapiens

<400> SEQUENCE: 134

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205
```

```
<210> SEQ ID NO 135
<211> LENGTH: 1548
<212> TYPE: DNA
<213> ORGANISM: Homo sapiens

<400> SEQUENCE: 135

gacctttcag agccaggagg gctttcgggg gcgtggggcg cgctgcggag cggagccgcg     60

gctcgacggc ggtgcgctgg cggcgagtgt atgcagacgg cgcccggccc gaacccccgag    120

ccccgcgggg ctccccaccc gccggcctcc cgcccctccc gcgcctccgc ctggggacca    180

cgtcggcctt ttgttggcga accgtccttt ctttcagcgc tttgcgcagc aacggaaatt    240
```

```
tcattgctcc tgggtggaaa ttaaagggac tcgcgttccc tctctccctc tccctctccc    300

actctccctc tctttctctc tctcgcccac ccttccccct tcttccccca cctttcccgc    360

gaagccggag tcagcatctc caggcgcggg atcccgctcc gagcacctcg cagctgtccg    420

gctgccgccc cttccatggg cgccgcgctc gcctgcagcc gccgccgccg cggggcgggc    480

gcgatgccac gatgggccta atctggctgc tactgctcag cctgctggag cccggctggc    540

ccgcagcggg ccctggggcg cggttgcggc gcgatgcggg cggccgtggc ggcgtctacg    600

agcaccttgg cggggcgccc cggcgccgca agctctactg cgccacgaag taccacctcc    660

agctgcaccc gagcggccgc gtcaacggca gcctggagaa cagcgcctac agtattttgg    720

agataacggc agtggaggtg ggcattgtgg ccatcagggg tctcttctcc gggcggtacc    780

tggccatgaa caagagggga cgactctatg cttcggagca ctacagcgcc gagtgcgagt    840

ttgtggagcg gatccacgag ctgggctata atacgtatgc ctcccggctg taccggacgg    900

tgtctagtac gcctggggcc cgccggcagc ccagcgccga gagactgtgg tacgtgtctg    960

tgaacggcaa gggccggccc cgcaggggct tcaagacccg ccgcacacag aagtcctccc   1020

tgttcctgcc ccgcgtgctg gaccacaggg accacgagat ggtgcggcag ctacagagtg   1080

ggctgcccag accccctggt aagggggtcc agccccgacg gcggcggcag aagcagagcc   1140

cggataacct ggagccctct cacgttcagg cttcgagact gggctcccag ctggaggcca   1200

gtgcgcacta gctgggcctg gtggccaccg ccagagctcc tggcgacatc ttggcgtggc   1260

agcctcttga ctctgactct cctccttgag cccttgcccc tgcgtcccgc gtctgggttc   1320

tcagctattt ccagagccag ctcaaatcag ggtccagtgg gaactgaaga gggcccaagt   1380

cggagctcgg agggggctgc ctgcaatgca gggcatttgt gggtctgtgt ggcaggaagc   1440

cggcagggaa gggcctgagt gccagccctg gcagactgag gagcctccca ggagcagcgg   1500

ggcagtgtgg ggctttgtgt catcacaaca ttaaagtatt ttattcta                1548


<210> SEQ ID NO 136
<211> LENGTH: 239
<212> TYPE: PRT
<213> ORGANISM: Homo sapiens

<400> SEQUENCE: 136

Met Gly Leu Ile Trp Leu Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
            20                  25                  30

Gly Gly Val Tyr Glu His Leu Gly Gly Ala Pro Arg Arg Arg Lys Leu
        35                  40                  45

Tyr Cys Ala Thr Lys Tyr His Leu Gln Leu His Pro Ser Gly Arg Val
    50                  55                  60

Asn Gly Ser Leu Glu Asn Ser Ala Tyr Ser Ile Leu Glu Ile Thr Ala
65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
            100                 105                 110

Ala Glu Cys Glu Phe Val Glu Arg Ile His Glu Leu Gly Tyr Asn Thr
        115                 120                 125

Tyr Ala Ser Arg Leu Tyr Arg Thr Val Ser Ser Thr Pro Gly Ala Arg
    130                 135                 140
```

```
Arg Gln Pro Ser Ala Glu Arg Leu Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Asp His Arg Asp His Glu Met Val Arg
            180                 185                 190

Gln Leu Gln Ser Gly Leu Pro Arg Pro Pro Gly Lys Gly Val Gln Pro
        195                 200                 205

Arg Arg Arg Arg Gln Lys Gln Ser Pro Asp Asn Leu Glu Pro Ser His
    210                 215                 220

Val Gln Ala Ser Arg Leu Gly Ser Gln Leu Glu Ala Ser Ala His
225                 230                 235


<210> SEQ ID NO 137
<211> LENGTH: 5408
<212> TYPE: DNA
<213> ORGANISM: Homo sapiens

<400> SEQUENCE: 137

gtgccagcgc ccatgcaaat ctgctgtgca tccagagagc aaagtgggat gatctgtcac     60

tacacctgca gcaccacgct cggaggacag ctcctgcctg cagcttccag acccaggaag    120

cctgaggga aggaaggaag tacgggcgaa atcatcagat tggcttccca gatttgggaa    180

tctgaagcgg gcccacatct tccggccaac ttccattgaa cttcccagca ctcgaaaggg    240

accgaaatgg agagcaaaga accccagctc aaagggattg tgacaaggtt attcagccag    300

cagggatact tcctgcagat gcacccagat ggtaccattg atgggaccaa ggacgaaaac    360

agcgactaca ctctcttcaa tctaattccc gtgggcctgc gtgtagtggc catccaagga    420

gtgaaggcta gcctctatgt ggccatgaat ggtgaaggct atctctacag ttcagatgtt    480

ttcactccag aatgcaaatt caaggaatct gtgtttgaaa actactatgt gatctattct    540

tccacactgt accgccagca agaatcaggc cgagcttggt ttctgggact caataaagaa    600

ggtcaaatta tgaaggggaa cagagtgaag aaaaccaagc cctcatcaca ttttgtaccg    660

aaacctattg aagtgtgtat gtacagagaa ccatcgctac atgaaattgg agaaaaacaa    720

gggcgttcaa ggaaaagttc tggaacacca accatgaatg gaggcaaagt tgtgaatcaa    780

gattcaacat agctgagaac tctccccttc ttccctctct catcccttcc ccttcccttc    840

cttcccattt acccatttcc ttccagtaaa tccacccaag gagaggaaaa taaaatgaca    900

acgcaagacc tagtggctaa gattctgcac tcaaaatctt cctttgtgta ggacaagaaa    960

attgaaccaa agcttgcttg ttgcaatgtg gtagaaaatt cacgtgcaca aagattagca   1020

cacttaaaag caaaggaaaa aataaatcag aactccataa atattaaatt aaactgtatt   1080

gttattagta gaaggctaat tgtaatgaag acattaataa agatgaaata aacttattac   1140

tttaaaggaa aggatttgga gaattgaact cacaaactga tgttatatac tcaatagctt   1200

aaactcatga taatgctgcg atgtgtggtt ttgcttgatt ttgtatttta tttgggcatc   1260

tggaattgac acaccattac attctgtttg caggattttt tttgtaacca tgaaattgaa   1320

catttccaaa ttataaacta tgttaatacc tataaaatat atagccagga accatttatc   1380

atcaagaaaa gtgtaagaaa ttatttttga gatgtaattt aagattgttt tatgtaaaag   1440

gaaaatcttg tatggcatcg aatagcctta atgagtttaa ttctttcaca aaaatgattt   1500

caaattatcc tagagtataa catttttatc aaagatatta tttccggagt tcttctttct   1560

ttcttttttt ttttttttta gtaatttagc aaaaacatta ctgttctaat gctgaagtga   1620
```

```
cttttgccag tgccatgtcc aggtggtgag gtataagtta cttgctctta gcatttggtc   1680
tgattttttt gctttgtgga cacctttgag agtatccaca aagcaatgtc tcaggtgtgg   1740
acacctgaga gcatgtttta gaaagctttg taccctgtct tgtggcagga aagaaagaac   1800
aggggtttta cataaggaaa taagtcctag gaaattagtc aacgcaaatt gcatttgcgt   1860
ttgtacctta ccacagtctt atattgtttt ttaaactctg ccatgaaatt tggagacatg   1920
actgtgaaat tcctaactta ctatcttaca aagccagtag ctaatttgtt gctctatgta   1980
tgatcctgtt acaagtccag tttgcaattc atttgtttcc tagaacacag aagggtacca   2040
gtaatacact aaattttcaa ggtgtgtaga gaaataatat ggaattagca gctatgactc   2100
caacagacag gattgtgtga gcagctgaaa ggagcaaaaa agaactcagt gtaagagaag   2160
gcacatacat agttaagaat actaaagtat ttttaaaaat caaggaagaa ataaatgtta   2220
cacaatttgc attggaataa atagatctat ttagtcctac aaatcaggag tggtgtagag   2280
acatccaaat ttaaagaaaa aaaaacacaa aacagaatgt taaaaaatgt atgcagattt   2340
atggatatta tcaatgagaa gacatagcat gtaacttctc ctatatctct actgtccagc   2400
atgtattgtt ccaaatatga ctccctaaaa tatatacact ttgcagaagc tctaggccct   2460
cacctcaaac cttgccattg gttgccgtat ttcaaggtca atatagtttc cctcacttta   2520
cacaatcatt attcttcaat agtggaccat atccttcacc aggtatccta tttctgttat   2580
ctagaggtta gcagaaaatg aaatgaagga atttccctaa gcagttggga agaacaaatt   2640
gtatgcatgt aggcaaagat tttgaagata catttgcaag agatatttgt ttaaccaaaa   2700
tatttggaaa gtaacaaata aagacattta aattttctaa aaatggactt gctcttctag   2760
gaaaagaata cccctggggc aaaaatataa ctctagctgt atttcttctt gtcactcttg   2820
attcaacttg attataaata cacctgtcac taccagaacc aaaaaaaaaa agaaaaaaat   2880
cccaagcaca aagcttattt tatttgaaaa aaataaaaaa gaaacttcaa cactatggga   2940
cactggctct tttagcatga aatgacttga gcttttgtag tgatgataca catacacact   3000
catcagtaaa acgatggttt cataaataac acaattgatg caaatcataa aaatcaatta   3060
caattatgat ttcatgacaa aatatattta attaagtttg ttatgaaaaa aatagagata   3120
tgaatcacta acaaaattcc tccattttca gtggctattc atcatttatc atctagactc   3180
acatttgtct ccttcctgat agcagttaag aaaaaattct aaccacacaa tttgtatatt   3240
gtttttctcc gtattatgtt aagcaaatgt tcactgcagt aaaatgtttt ggaaattagc   3300
tttgtcttat ttccagttta gttcagagaa ttaattggaa acctgatttc ttttacacat   3360
aaacctgaca aaaaatgtag cttagagcaa agggtgaatg tttgcttaac tcctgcttac   3420
ttctcaagta catgaaaact ttaatagaat atgccagtat tcactgagtt tttaaaaata   3480
ttaccatgtg taaacatata atatccaact tcatccaaaa atatggttga gtttaagtac   3540
tttgtttttc aggcttattt caagtataat aattctttga ttttcattgt tctgatttct   3600
gggtcttcaa ttcattcgtc acttttcctt tttaagtaaa ataagctttt tttttttttt   3660
tttttttttt ttggagttgc attgggattt ttcccaggaa aaaatatggc ttttagtaat   3720
gctttgcaat tggctacgca gatataaatt aagatatgtt tattctgagt tcttattgga   3780
ataagtttca aaatcaacga gcttaagaat gaaaacaaaa cttttgagag tctcacaaaa   3840
tagctttctg gtcaatacac cttacttgat ttttaagctc gcagaataaa gtatagaaac   3900
aaatggagct gaagttccat ttgctaattc agagactttt gtgcttccgc aaattggagg   3960
```

```
gcagcaagcc atcctattct catagtaatc gttttggctt tgaaatttac atacaattta    4020

atagcacatt tttagccatt atggattggc gcaataaaga gatatcaatg taatgcaatg    4080

tgatgcttta tgggcctcat tctaattcag aaagcttgtt taaaagaact aagactcttc    4140

tgtttaataa aatagcaaca atctaatatc tagattggta gtcctgcggt gccactagtg    4200

ggagatgaga gtattaagac aagagtaagg acaaggaaag acttaaaggt tgcatattga    4260

aaagtttgga attcctaatt tgggagcact gatttcttgg tgaagaagta agtatgacta    4320

cgttgccagt aatttttttaa aaacatagac ccagaaatag caaatcgatt tcaccctcat    4380

accttagtct acaaggcctt gctcttgaga aggttttcca tgatattgct taatttcatc    4440

tgcacaagat gagacacaaa cataaaaatt ccctgctcat tttaatacca taaaaggctg    4500

aggttatttc tctgtcataa aattgtaaat agcatttttt aagtcaaaat tacatttaaa    4560

acagtggatt gttctacaaa tatatatgtg tatatataca tatgcttctg aaataaggat    4620

atattatatg agtttttatt tgatttgtgg tctttagtca taggtaatca aaaataaaga    4680

gatttgaatg caaaacttta tacattaatg tacatttcta atgatggtac aaattgccac    4740

tttataataa aaaagaaaca ggtgggaata ataatcaaag cacgtgttcc ttcagtactt    4800

tggtgatttt taatccccct tgtgatgcac aggaaattat tttttagtta caaaaagtta    4860

tcttagaaat ctatacttcc caatacagat ttcatgttaa gtcatatcaa attgagaatt    4920

tgtggtgaaa gaataggaaa aggatgctag atgctgatct ttctttttca ggattttttcc    4980

tggagcccaa gttaaaaatt caatacttaa atctaagtta agtgaaaatt aataatgttc    5040

agaatgatgt attgagcttt agtaacagac ggaagcaaaa aaaaataaga atatttaaca    5100

ttatgataat agccttaaaa taatgtaata aaaattgcat cattaaatgt tctattagtt    5160

ggaaagaatg agctgatgtt tctttgtctt tgctccaagt acaatttaaa gacagtgaca    5220

ttcattttac ttaaaattgt tcaaaaagtc caaaacatac tcccatggct agaattggta    5280

ttagctccaa tacaaggtta aatgttacaa tcttaagaaa ttattgacac tgaaatgttt    5340

agtaaacatg ttgtatgaga aactaaacaa attaatgttt cattttttcca ttaaagcaca    5400

gattattc                                                              5408
```

```
<210> SEQ ID NO 138
<211> LENGTH: 181
<212> TYPE: PRT
<213> ORGANISM: Homo sapiens

<400> SEQUENCE: 138

Met Glu Ser Lys Glu Pro Gln Leu Lys Gly Ile Val Thr Arg Leu Phe
1               5                   10                  15

Ser Gln Gln Gly Tyr Phe Leu Gln Met His Pro Asp Gly Thr Ile Asp
            20                  25                  30

Gly Thr Lys Asp Glu Asn Ser Asp Tyr Thr Leu Phe Asn Leu Ile Pro
        35                  40                  45

Val Gly Leu Arg Val Val Ala Ile Gln Gly Val Lys Ala Ser Leu Tyr
    50                  55                  60

Val Ala Met Asn Gly Glu Gly Tyr Leu Tyr Ser Ser Asp Val Phe Thr
65                  70                  75                  80

Pro Glu Cys Lys Phe Lys Glu Ser Val Phe Glu Asn Tyr Tyr Val Ile
                85                  90                  95

Tyr Ser Ser Thr Leu Tyr Arg Gln Gln Glu Ser Gly Arg Ala Trp Phe
            100                 105                 110
```

```
Leu Gly Leu Asn Lys Glu Gly Gln Ile Met Lys Gly Asn Arg Val Lys
        115                 120                 125

Lys Thr Lys Pro Ser Ser His Phe Val Pro Lys Pro Ile Glu Val Cys
    130                 135                 140

Met Tyr Arg Glu Pro Ser Leu His Glu Ile Gly Glu Lys Gln Gly Arg
145                 150                 155                 160

Ser Arg Lys Ser Ser Gly Thr Pro Thr Met Asn Gly Gly Lys Val Val
                165                 170                 175

Asn Gln Asp Ser Thr
            180


<210> SEQ ID NO 139
<211> LENGTH: 1354
<212> TYPE: DNA
<213> ORGANISM: Homo sapiens

<400> SEQUENCE: 139

cccctcctcc tccctctttt ctctcctcct cctcccettt ctctcctcct cgcccccctg      60

aaaacctgtg gctcggagag accttggctt ctctgggact ctacccctgg ggacttccca     120

catctgctcc tgagcttggg ggcagggggg caaccgcctg aggaacctct ccagcgatgg     180

gagccgcccg cctgctgccc aacctcactc tgtgcttaca gctgctgatt ctctgctgtc     240

aaactcagta cgtgagggac cagggcgcca tgaccgacca gctgagcagg cggcagatcc     300

gcgagtacca actctacagc aggaccagtg gcaagcacgt gcaggtcacc gggcgtcgca     360

tctccgccac cgccgaggac ggcaacaagt ttgccaagct catagtggag acggacacgt     420

ttggcagccg ggttcgcatc aaaggggctg agagtgagaa gtacatctgt atgaacaaga     480

ggggcaagct catcgggaag cccagcggga agagcaaaga ctgcgtgttc acggagatcg     540

tgctggagaa caactatacg gccttccaga acgcccggca cgagggctgg ttcatggcct     600

tcacgcggca ggggcggccc cgccaggctt cccgcagccg ccagaaccag cgcgaggccc     660

acttcatcaa gcgcctctac caaggccagc tgcccttccc caaccacgcc gagaagcaga     720

agcagttcga gtttgtgggc tccgccccca cccgccggac caagcgcaca cggcggcccc     780

agcccctcac gtagtctggg aggcaggggg cagcagcccc tgggccgcct ccccacccct     840

ttcccttctt aatccaagga ctgggctggg gtggcgggag gggagccaga tccccgaggg     900

aggaccctga gggccgcgaa gcatccgagc ccccagctgg gaaggggcag gccggtgccc     960

caggggcggc tggcacagtg ccccttcccc ggacgggtgg caggccctgg agaggaactg    1020

agtgtcaccc tgatctcagg ccaccagcct ctgccggcct cccagccggg ctcctgaagc    1080

ccgctgaaag gtcagcgact gaaggccttg cagacaaccg tctggaggtg gctgtcctca    1140

aaatctgctt ctcggatctc cctcagtctg cccccagccc ccaaactcct cctggctaga    1200

ctgtaggaag ggacttttgt ttgtttgttt gtttcaggaa aaaagaaagg gagagagagg    1260

aaaatagagg gttgtccact cctcacattc cacgacccag gcctgcaccc cacccccaac    1320

tcccagcccc ggaataaaac cattttcctg caaa                                1354


<210> SEQ ID NO 140
<211> LENGTH: 205
<212> TYPE: PRT
<213> ORGANISM: Homo sapiens

<400> SEQUENCE: 140

Met Gly Ala Ala Arg Leu Leu Pro Asn Leu Thr Leu Cys Leu Gln Leu
1               5                   10                  15
```

```
Leu Ile Leu Cys Cys Gln Thr Gln Tyr Val Arg Asp Gln Gly Ala Met
            20                  25                  30

Thr Asp Gln Leu Ser Arg Arg Gln Ile Arg Glu Tyr Gln Leu Tyr Ser
        35                  40                  45

Arg Thr Ser Gly Lys His Val Gln Val Thr Gly Arg Arg Ile Ser Ala
    50                  55                  60

Thr Ala Glu Asp Gly Asn Lys Phe Ala Lys Leu Ile Val Glu Thr Asp
65                  70                  75                  80

Thr Phe Gly Ser Arg Val Arg Ile Lys Gly Ala Glu Ser Glu Lys Tyr
                85                  90                  95

Ile Cys Met Asn Lys Arg Gly Lys Leu Ile Gly Lys Pro Ser Gly Lys
            100                 105                 110

Ser Lys Asp Cys Val Phe Thr Glu Ile Val Leu Glu Asn Asn Tyr Thr
        115                 120                 125

Ala Phe Gln Asn Ala Arg His Glu Gly Trp Phe Met Ala Phe Thr Arg
    130                 135                 140

Gln Gly Arg Pro Arg Gln Ala Ser Arg Ser Arg Gln Asn Gln Arg Glu
145                 150                 155                 160

Ala His Phe Ile Lys Arg Leu Tyr Gln Gly Gln Leu Pro Phe Pro Asn
                165                 170                 175

His Ala Glu Lys Gln Lys Gln Phe Glu Phe Val Gly Ser Ala Pro Thr
            180                 185                 190

Arg Arg Thr Lys Arg Thr Arg Arg Pro Gln Pro Leu Thr
        195                 200                 205
```

<210> SEQ ID NO 141
<211> LENGTH: 744
<212> TYPE: DNA
<213> ORGANISM: Homo sapiens

<400> SEQUENCE: 141

```
tttagggcca ttaattctga ccacgtgcct gagaggcaag gtggatggcc ctgggacaga     60

aactgttcat cactatgtcc cggggagcag gacgtctgca gggcacgctg tgggctctcg    120

tcttcctagg catcctagtg ggcatggtgg tgccctcgcc tgcaggcacc cgtgccaaca    180

acacgctgct ggactcgagg ggctggggca ccctgctgtc caggtctcgc gcggggctag    240

ctggagagat tgccggggtg aactgggaaa gtggctattt ggtggggatc aagcggcagc    300

ggaggctcta ctgcaacgtg ggcatcggct ttcacctcca ggtgctcccc gacggccgga    360

tcagcgggac ccacgaggag aacccctaca gcctgctgga aatttccact gtggagcgag    420

gcgtggtgag tctctttgga gtgagaagtg ccctcttcgt tgccatgaac agtaaaggaa    480

gattgtacgc aacgcccagc ttccaagaag aatgcaagtt cagagaaacc ctcctgccca    540

acaattacaa tgcctacgag tcagacttgt accaagggac ctacattgcc ctgagcaaat    600

acggacgggt aaagcggggc agcaaggtgt ccccgatcat gactgtcact catttccttc    660

ccaggatcta aggacccaca aaagaaggct tacagattta aagcatcatc tgttcgattg    720

aaattttgca ccagcgaaga attc                                           744
```

<210> SEQ ID NO 142
<211> LENGTH: 208
<212> TYPE: PRT
<213> ORGANISM: Homo sapiens

<400> SEQUENCE: 142

```
Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
            20                  25                  30

Gly Met Val Val Pro Ser Pro Ala Gly Thr Arg Ala Asn Asn Thr Leu
        35                  40                  45

Leu Asp Ser Arg Gly Trp Gly Thr Leu Leu Ser Arg Ser Arg Ala Gly
    50                  55                  60

Leu Ala Gly Glu Ile Ala Gly Val Asn Trp Glu Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
        115                 120                 125

Ser Leu Phe Gly Val Arg Ser Ala Leu Phe Val Ala Met Asn Ser Lys
    130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205
```

<210> SEQ ID NO 143
<211> LENGTH: 751
<212> TYPE: DNA
<213> ORGANISM: Homo sapiens

<400> SEQUENCE: 143

```
gcccgggagc gacgagcgcg cagcgaaccg ggtgccgggt catgcgccgc cgcctgtggc     60

tgggcctggc ctggctgctg ctggcgcggg cgccggacgc cgcgggaacc ccgagcgcgt    120

cgcggggacc gcgcagctac ccgcacctgg agggcgacgt gcgctggcgg cgcctcttct    180

cctccactca cttcttcctg cgcgtggatc ccggcggccg cgtgcagggc acccgctggc    240

gccacggcca ggacagcatc ctggagatcc gctctgtaca cgtgggcgtc gtggtcatca    300

aagcagtgtc ctcaggcttc tacgtggcca tgaaccgccg gggccgcctc tacgggtcgg    360

ttccgggagc gcatcgaaga gaacggccac aacacctacg cctcacagcg ctggcgccgc    420

cgcggccagc ccatgttcct ggcgctggac aggagggggg ggccccggcc aggcggccgg    480

acgcggcggt accacctgtc cgcccacttc ctgcccgtcc tggtctcctg aggccctgag    540

aggccggcgg ctccccaagg tgcctgggct ggtggcgagg ggcccggcca cgcttgttct    600

tccccctgcg ggctctgtaa gcgctgagtg cccaccgtgt gcgggcgctg tggacacagc    660

ccaggagccc tccagggggg tcccagcctg agggggtggt ggccaccaag caggttcaat    720

cctgagttgg ggacctcgag gacccaacag g                                   751
```

<210> SEQ ID NO 144
<211> LENGTH: 165
<212> TYPE: PRT
<213> ORGANISM: Homo sapiens

<400> SEQUENCE: 144

```
Met Arg Arg Arg Leu Trp Leu Gly Leu Ala Trp Leu Leu Leu Ala Arg
1               5                   10                  15

Ala Pro Asp Ala Ala Gly Thr Pro Ser Ala Ser Arg Gly Pro Arg Ser
            20                  25                  30

Tyr Pro His Leu Glu Gly Asp Val Arg Trp Arg Arg Leu Phe Ser Ser
        35                  40                  45

Thr His Phe Phe Leu Arg Val Asp Pro Gly Gly Arg Val Gln Gly Thr
    50                  55                  60

Arg Trp Arg His Gly Gln Asp Ser Ile Leu Glu Ile Arg Ser Val His
65                  70                  75                  80

Val Gly Val Val Val Ile Lys Ala Val Ser Ser Gly Phe Tyr Val Ala
                85                  90                  95

Met Asn Arg Arg Gly Arg Leu Tyr Gly Ser Val Pro Gly Ala His Arg
            100                 105                 110

Arg Glu Arg Pro Gln His Leu Arg Leu Thr Ala Leu Ala Pro Pro Arg
        115                 120                 125

Pro Ala His Val Pro Gly Ala Gly Gln Glu Gly Gly Ala Pro Ala Arg
    130                 135                 140

Arg Pro Asp Ala Ala Val Pro Pro Val Arg Pro Leu Pro Ala Arg Pro
145                 150                 155                 160

Gly Leu Leu Arg Pro
                165
```

<210> SEQ ID NO 145
<211> LENGTH: 2414
<212> TYPE: DNA
<213> ORGANISM: Homo sapiens

<400> SEQUENCE: 145

```
ctctgagtag gaccgggccc ccacgtgact cagcctgcct ctccatctcc tcagctccca      60

ccccccatat ccttgatgaa tgtctctctc tccagagcct cagctcaaag gcatcgtcac     120

caaactgttc tgccgccagg gtttctacct ccaggcgaat cccgacggaa gcatccaggg     180

caccccagag gataccagct ccttcaccca cttcaacctg atccctgtgg gcctccgtgt     240

ggtcaccatc cagagcgcca agctgggtca ctacatggcc atgaatgctg agggactgct     300

ctacagttcg ccgcatttca cagctgagtg tcgctttaag gagtgtgtct ttgagaatta     360

ctacgtcctg tacgcctctg ctctctaccg ccagcgtcgt tctggccggg cctggtacct     420

cggcctggac aaggagggcc aggtcatgaa gggaaaccga gttaagaaga ccaaggcagc     480

tgcccacttt ctgcccaagc tcctggaggt ggccatgtac caggagcctt ctctccacag     540

tgtccccgag gcctcccctt ccagtccccc tgccccctga aatgtagtcc ctggactgga     600

ggttccctgc actcccagtg agccagccac caccacaacc tgtctcccag tcctgctctc     660

acccctgctg ccacacacat gccctgagca gccaggtccc actaggtgct ctaccctgag     720

ggagcctagg ggctgactgt gacttccgag gctgctgaga cccttagatc tttgggccta     780

ggagggagtc agagaggggg atgtctgaag atggtcctgg ctgatcactt ctttctttcc     840

acactcacac aaccccatgc cttttcctga gatggcgctg ggagttccca catggacagc     900

cagggcataa acacttccca ccccggctca gccagttcct ggagtcctgt gccccttttc     960

attgccactg agccatttct agattcactg gagctcagga ttcatgtgtc cttctttccc    1020

tactctacct tctaccttgg tctggacaca ttctggaaca ctggacaccc tcgccagggc    1080
```

```
cacttctgca ctagggctct gtgctggaac ccaggcatgc tgccagcctt ttctctggat   1140

ctgtcaggcc tctgtcattg actcagatgg accccctggtt tccaagtaga aagaggctag   1200

atttgggcct tgtctagctg ttggctttgg cctgaaccgg aaccagtctc agatgaccac   1260

gggtttaacc ttcttatccc agagacaccc aattctagag ctttatggag ccgtacttcc   1320

ccctgaatcc tagctctagg acatagatca tgactctcag cccttttacc caggatggag   1380

ctggggcctg tatagccata ttattgttct aagtaagttc tagccccacc ctcccgcctt   1440

cttgagtgat acctattacg gatgagttct ggaaaagacc cagctatgat tcataaaaac   1500

acttctggat gaatcaagaa ccatttcttg tttttcctag ataattctct aaaaatatga   1560

ttcttccata tagaatgcta agcttatttt tacatgcagt ttctagctcc ttcaacccag   1620

ctgaggtcgt gccagggaga cagagtctgg agaagggcag aggaattttg gaaggatccc   1680

tggctcatag tagggaagct gggatggggg aggggtcaaa attatggcat gactgaacct   1740

gcatctgtgt tgggtggaca tgaatactta gctacctcag caggaattcc ttccaggtcc   1800

cctttaaagc tgaggtcctt agagtaatat gtccttaata aaaaggacaa atggatacag   1860

ccttgaccct cccagtgagg agaccccaat tcagcaataa gtctcaccct tctcccctac   1920

aggtcaggcc aagaagggtg aaggcctctt gcactccaga cctcatacgc cccaacagct   1980

tctaattgga tagaacttgc tttaccttac agctcacaac ctcagctggg ttttaggtac   2040

ccaaaaaggg cctgtctaga tttttcaga aaaacgtgga gtgctagggg cagcctggaa   2100

aagatgggga acctgctagt gaactaggag ggagacttcc atagcctcag acttggatag   2160

ggtaggctga gggggcccta agggagggac taaggctcca aggcaggtca cttttcctta   2220

ggctgttcta cttctggctt gttgcaagag gagtagatgc cccctcaccc acacaaaccc   2280

cactcagtct ccacccaact cctggcactg ctcccagggg atcgggtctc cactccagct   2340

ttctcaatta aagacgattt atacaaaaaa aaaaaaaaaa aaaaaaaaaa aaaaaaaaaa   2400

aaaaaaaaaa aaaa                                                      2414
```

<210> SEQ ID NO 146
<211> LENGTH: 166
<212> TYPE: PRT
<213> ORGANISM: Homo sapiens

<400> SEQUENCE: 146

```
Met Ser Leu Ser Pro Glu Pro Gln Leu Lys Gly Ile Val Thr Lys Leu
1               5                   10                  15

Phe Cys Arg Gln Gly Phe Tyr Leu Gln Ala Asn Pro Asp Gly Ser Ile
            20                  25                  30

Gln Gly Thr Pro Glu Asp Thr Ser Ser Phe Thr His Phe Asn Leu Ile
        35                  40                  45

Pro Val Gly Leu Arg Val Val Thr Ile Gln Ser Ala Lys Leu Gly His
    50                  55                  60

Tyr Met Ala Met Asn Ala Glu Gly Leu Leu Tyr Ser Ser Pro His Phe
65                  70                  75                  80

Thr Ala Glu Cys Arg Phe Lys Glu Cys Val Phe Glu Asn Tyr Tyr Val
                85                  90                  95

Leu Tyr Ala Ser Ala Leu Tyr Arg Gln Arg Arg Ser Gly Arg Ala Trp
            100                 105                 110

Tyr Leu Gly Leu Asp Lys Glu Gly Gln Val Met Lys Gly Asn Arg Val
        115                 120                 125

Lys Lys Thr Lys Ala Ala Ala His Phe Leu Pro Lys Leu Leu Glu Val
```

```
    130                 135                 140

Ala Met Tyr Gln Glu Pro Ser Leu His Ser Val Pro Glu Ala Ser Pro
145                 150                 155                 160

Ser Ser Pro Pro Ala Pro
                165


<210> SEQ ID NO 147
<211> LENGTH: 6774
<212> TYPE: DNA
<213> ORGANISM: Homo sapiens

<400> SEQUENCE: 147

cggccccaga aaacccgagc gagtaggggg cggcgcgcag gagggaggag aactgggggc      60

gcgggaggct ggtgggtgtg gggggtggag atgtagaaga tgtgacgccg cggcccggcg     120

ggtgccagat tagcggacgc ggtgcccgcg gttgcaacgg gatcccgggc gctgcagctt     180

gggaggcggc tctccccagg cggcgtccgc ggagacaccc atccgtgaac cccaggtccc     240

gggccgccgg ctcgccgcgc accaggggcc ggcggacaga agagcggccg agcggctcga     300

ggctggggga ccgcgggcgc ggccgcgcgc tgccgggcgg gaggctgggg ggccggggcc     360

ggggccgtgc cccggagcgg gtcggaggcc ggggccgggg ccgggggacg gcggctcccc     420

gcgcggctcc agcggctcgg ggatcccggc cgggccccgc agggaccatg gcagccggga     480

gcatcaccac gctgcccgcc ttgcccgagg atggcggcag cggcgccttc ccgcccggcc     540

acttcaagga ccccaagcgg ctgtactgca aaaacggggg cttcttcctg cgcatccacc     600

ccgacggccg agttgacggg gtccgggaga agagcgaccc tcacatcaag ctacaacttc     660

aagcagaaga gagaggagtt gtgtctatca aaggagtgtg tgctaaccgt tacctggcta     720

tgaaggaaga tggaagatta ctggcttcta aatgtgttac ggatgagtgt ttcttttttg     780

aacgattgga atctaataac tacaatactt accggtcaag gaaatacacc agttggtatg     840

tggcactgaa acgaactggg cagtataaac ttggatccaa aacaggacct gggcagaaag     900

ctatactttt tcttccaatg tctgctaaga gctgatttta atggccacat ctaatctcat     960

ttcacatgaa agaagaagta tattttagaa atttgttaat gagagtaaaa gaaaataaat    1020

gtgtatagct cagtttggat aattggtcaa acaatttttt atccagtagt aaaatatgta    1080

accattgtcc cagtaaagaa aaataacaaa agttgtaaaa tgtatattct cccttttata    1140

ttgcatctgc tgttacccag tgaagcttac ctagagcaat gatctttttc acgcatttgc    1200

tttattcgaa aagaggcttt taaaatgtgc atgtttagaa acaaaatttc ttcatggaaa    1260

tcatatacat tagaaaatca cagtcagatg tttaatcaat ccaaaatgtc cactatttct    1320

tatgtcattc gttagtctac atgtttctaa acatataaat gtgaatttaa tcaattcctt    1380

tcatagtttt ataattctct ggcagttcct tatgatagag tttataaaac agtcctgtgt    1440

aaactgctgg aagttcttcc acagtcaggt caattttgtc aaacccttct ctgtacccat    1500

acagcagcag cctagcaact ctgctggtga tgggagttgt attttcagtc ttcgccaggt    1560

cattgagatc catccactca catcttaagc attcttcctg gcaaaaattt atggtgaatg    1620

aatatggctt taggcggcag atgatataca tatctgactt cccaaaagct ccaggatttg    1680

tgtgctgttg ccgaatactc aggacggacc tgaattctga ttttatacca gtctcttcaa    1740

aaacttctcg aaccgctgtg tctcctacgt aaaaaaagag atgtacaaat caataataat    1800

tacactttta gaaactgtat catcaaagat tttcagttaa agtagcatta tgtaaaggct    1860

caaaacatta ccctaacaaa gtaaagtttt caatacaaat tctttgcctt gtggatatca    1920
```

```
agaaatccca aaatattttc ttaccactgt aaattcaaga agcttttgaa atgctgaata   1980
tttctttggc tgctacttgg aggcttatct acctgtacat ttttggggtc agctcttttt   2040
aacttcttgc tgctcttttt cccaaaaggt aaaaatatag attgaaaagt taaaacattt   2100
tgcatggctg cagttccttt gtttcttgag ataagattcc aaagaactta gattcatttc   2160
ttcaacaccg aaatgctgga ggtgtttgat cagttttcaa gaaacttgga atataaataa   2220
ttttataatt caacaaaggt tttcacattt tataaggttg atttttcaat taaatgcaaa   2280
tttgtgtggc aggattttta ttgccattaa catattttttg tggctgcttt ttctacacat   2340
ccagatggtc cctctaactg ggctttctct aattttgtga tgttctgtca ttgtctccca   2400
aagtatttag gagaagccct ttaaaaagct gccttcctct accactttgc tggaaagctt   2460
cacaattgtc acagacaaag atttttgttc caatactcgt tttgcctcta tttttcttgt   2520
ttgtcaaata gtaaatgata tttgcccttg cagtaattct actggtgaaa aacatgcaaa   2580
gaagaggaag tcacagaaac atgtctcaat tcccatgtgc tgtgactgta gactgtctta   2640
ccatagactg tcttacccat cccctggata tgctcttgtt ttttccctct aatagctatg   2700
gaaagatgca tagaaagagt ataatgtttt aaaacataag gcattcgtct gccatttttc   2760
aattacatgc tgacttccct tacaattgag atttgcccat aggttaaaca tggttagaaa   2820
caactgaaag cataaaagaa aaatctaggc cgggtgcagt ggctcatgcc tatattccct   2880
gcactttggg aggccaaagc aggaggatcg cttgagccca ggagttcaag accaacctgg   2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa   3060
ggttgcagtg agccataatc gtgccactgc agtccagcct aggcaacaga gtgagacttt   3120
gtctcaaaaa aagagaaatt ttccttaata agaaaagtaa tttttactct gatgtgcaat   3180
acatttgtta ttaaatttat tatttaagat ggtagcacta gtcttaaatt gtataaaata   3240
tcccctaaca tgtttaaatg tccattttta ttcattatgc tttgaaaaat aattatgggg   3300
aaatacatgt ttgttattaa atttattatt aaagatagta gcactagtct taaatttgat   3360
ataacatctc ctaacttgtt taaatgtcca tttttattct ttatgtttga aaataaatta   3420
tggggatcct atttagctct tagtaccact aatcaaaagt tcggcatgta gctcatgatc   3480
tatgctgttt ctatgtcgtg gaagcaccgg atgggggtag tgagcaaatc tgccctgctc   3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggattt caagatgaat   3720
tgaaattttt aatcaagata gtgtgcttta ttctgttgta ttttttatta ttttaatata   3780
ctgtaagcca aactgaaata acatttgctg ttttataggt ttgaagaaca taggaaaaac   3840
taagaggttt tgtttttatt tttgctgatg aagagatatg tttaaatatg ttgtattgtt   3900
ttgtttagtt acaggacaat aatgaaatgg agtttatatt tgttatttct attttgttat   3960
atttaataat agaattagat tgaaataaaa tataatggga aataatctgc agaatgtggg   4020
ttttcctggt gtttccctct gactctagtg cactgatgat ctctgataag gctcagctgc   4080
tttatagttc tctggctaat gcagcagata ctcttcctgc cagtggtaat acgatttttt   4140
aagaaggcag tttgtcaatt ttaatcttgt ggataccttt atactcttag ggtattattt   4200
tatacaaaag ccttgaggat tgcattctat tttctatatg accctcttga tatttaaaaa   4260
```

```
acactatgga taacaattct tcatttacct agtattatga aagaatgaag gagttcaaac   4320
aaatgtgttt cccagttaac tagggtttac tgtttgagcc aatataaatg tttaactgtt   4380
tgtgatggca gtattcctaa agtacattgc atgttttcct aaatacagag tttaaataat   4440
ttcagtaatt cttagatgat tcagcttcat cattaagaat atcttttgtt ttatgttgag   4500
ttagaaatgc cttcatatag acatagtctt tcagacctct actgtcagtt ttcatttcta   4560
gctgctttca gggttttatg aattttcagg caaagcttta atttatacta agcttaggaa   4620
gtatggctaa tgccaacggc agtttttttc ttcttaattc cacatgactg aggcatatat   4680
gatctctggg taggtgagtt gttgtgacaa ccacaagcac tttttttttt tttaaagaaa   4740
aaaaggtagt gaatttttaa tcatctggac tttaagaagg attctggagt atacttaggc   4800
ctgaaattat atatatttgg cttggaaatg tgtttttctt caattacatc tacaagtaag   4860
tacagctgaa attcagagga cccataagag ttcacatgaa aaaaatcaat ttatttgaaa   4920
aggcaagatg caggagagag gaagccttgc aaacctgcag actgcttttt gcccaatata   4980
gattgggtaa ggctgcaaaa cataagctta attagctcac atgctctgct ctcacgtggc   5040
accagtggat agtgtgagag aattaggctg tagaacaaat ggccttctct ttcagcattc   5100
acaccactac aaaatcatct tttatatcaa cagaagaata agcataaact aagcaaaagg   5160
tcaataagta cctgaaacca agattggcta gagatatatc ttaatgcaat ccattttctg   5220
atggattgtt acgagttggc tatataatgt atgtatggta ttttgatttg tgtaaaagtt   5280
ttaaaaatca agctttaagt acatggacat ttttaaataa aatatttaaa gacaatttag   5340
aaaattgcct taatatcatt gttggctaaa tagaataggg gacatgcata ttaaggaaaa   5400
ggtcatggag aaataatatt ggtatcaaac aaatacattg atttgtcatg atacacattg   5460
aatttgatcc aatagtttaa ggaataggta ggaaaatttg gtttctattt ttcgatttcc   5520
tgtaaatcag tgacataaat aattcttagc ttattttata tttccttgtc ttaaatactg   5580
agctcagtaa gttgtgttag gggattattt ctcagttgag actttcttat atgacatttt   5640
actatgtttt gacttcctga ctattaaaaa taaatagtag atacaatttt cataaagtga   5700
agaattatat aatcactgct ttataactga ctttattata tttatttcaa agttcattta   5760
aaggctacta ttcatcctct gtgatggaat ggtcaggaat ttgttttctc atagtttaat   5820
tccaacaaca atattagtcg tatccaaaat aacctttaat gctaaacttt actgatgtat   5880
atccaaagct tctcattttc agacagatta atccagaagc agtcataaac agaagaatag   5940
gtggtatgtt cctaatgata ttatttctac taatggaata aactgtaata ttagaaatta   6000
tgctgctaat tatatcagct ctgaggtaat ttctgaaatg ttcagactca gtcggaacaa   6060
attggaaaat ttaaattttt attcttagct ataaagcaag aaagtaaaca cattaatttc   6120
ctcaacattt ttaagccaat taaaaatata aaagatacac accaatatct tcttcaggct   6180
ctgacaggcc tcctggaaac ttccacatat ttttcaactg cagtataaag tcagaaaata   6240
aagttaacat aactttcact aacacacaca tatgtagatt tcacaaaatc cacctataat   6300
tggtcaaagt ggttgagaat atattttta gtaattgcat gcaaaatttt tctagcttcc   6360
atcctttctc cctcgtttct tcttttttg ggggagctgg taactgatga aatcttttcc   6420
caccttttct cttcaggaaa tataagtggt tttgtttggt taacgtgata cattctgtat   6480
gaatgaaaca ttggagggaa acatctactg aatttctgta atttaaaata ttttgctgct   6540
agttaactat gaacagatag aagaatctta cagatgctgc tataaataag tagaaaatat   6600
aaatttcatc actaaaatat gctattttaa aatctatttc ctatattgta tttctaatca   6660
```

```
gatgtattac tcttattatt tctattgtat gtgttaatga ttttatgtaa aaatgtaatt   6720

gcttttcatg agtagtatga ataaaattga ttagtttgtg ttttcttgtc tccc         6774


<210> SEQ ID NO 148
<211> LENGTH: 288
<212> TYPE: PRT
<213> ORGANISM: Homo sapiens

<400> SEQUENCE: 148

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285


<210> SEQ ID NO 149
<211> LENGTH: 3018
<212> TYPE: DNA
<213> ORGANISM: Homo sapiens

<400> SEQUENCE: 149

cggcaaaaag gagggaatcc agtctaggat cctcacacca gctacttgca agggagaagg     60

aaaaggccag taaggcctgg gccaggagag tcccgacagg agtgtcaggt ttcaatctca    120
```

-continued

```
gcaccagcca ctcagagcag ggcacgatgt tgggggcccg cctcaggctc tgggtctgtg    180
ccttgtgcag cgtctgcagc atgagcgtcc tcagagccta tcccaatgcc tccccactgc    240
tcggctccag ctggggtggc ctgatccacc tgtacacagc cacagccagg aacagctacc    300
acctgcagat ccacaagaat ggccatgtgg atggcgcacc ccatcagacc atctacagtg    360
ccctgatgat cagatcagag gatgctggct ttgtggtgat tacaggtgtg atgagcagaa    420
gatacctctg catggatttc agaggcaaca tttttggatc acactatttc gacccggaga    480
actgcaggtt ccaacaccag acgctggaaa acgggtacga cgtctaccac tctcctcagt    540
atcacttcct ggtcagtctg ggccgggcga agagagcctt cctgccaggc atgaacccac    600
ccccgtactc ccagttcctg tcccggagga acgagatccc cctaattcac ttcaacaccc    660
ccataccacg gcggcacacc cggagcgccg aggacgactc ggagcgggac cccctgaacg    720
tgctgaagcc ccgggcccgg atgaccccgg ccccggcctc ctgttcacag gagctcccga    780
gcgccgagga caacagcccg atggccagtg acccattagg ggtggtcagg ggcggtcgag    840
tgaacacgca cgctggggga acgggcccgg aaggctgccg ccccttcgcc aagttcatct    900
agggtcgctg gaagggcacc ctctttaacc catccctcag caaacgcagc tcttcccaag    960
gaccaggtcc cttgacgttc cgaggatggg aaaggtgaca ggggcatgta tggaatttgc   1020
tgcttctctg gggtcccttc cacaggaggt cctgtgagaa ccaacctttg aggcccaagt   1080
catggggttt caccgccttc ctcactccat atagaacacc tttcccaata ggaaacccca   1140
acaggtaaac tagaaatttc cccttcatga aggtagagag aaggggtctc tcccaacata   1200
tttctcttcc ttgtgcctct cctctttatc acttttaagc ataaaaaaaa aaaaaaaaaa   1260
aaaaaaaaaa aaaagcagtg ggttcctgag ctcaagactt tgaaggtgta gggaagagga   1320
aatcggagat cccagaagct tctccactgc cctatgcatt tatgttagat gccccgatcc   1380
cactggcatt tgagtgtgca aaccttgaca ttaacagctg aatggggcaa gttgatgaaa   1440
acactacttt caagccttcg ttcttccttg agcatctctg gggaagagct gtcaaaagac   1500
tggtggtagg ctggtgaaaa cttgacagct agacttgatg cttgctgaaa tgaggcagga   1560
atcataatag aaaactcagc ctccctacag ggtgagcacc ttctgtctcg ctgtctccct   1620
ctgtgcagcc acagccagag ggcccagaat ggccccactc tgttcccaag cagttcatga   1680
tacagcctca ccttttggcc ccatctctgg tttttgaaaa tttggtctaa ggaataaata   1740
gcttttacac tggctcacga aaatctgccc tgctagaatt tgcttttcaa aatggaaata   1800
aattccaact ctcctaagag gcatttaatt aaggctctac ttccaggttg agtaggaatc   1860
cattctgaac aaactacaaa aatgtgactg ggaagggggc tttgagagac tgggactgct   1920
ctgggttagg ttttctgtgg actgaaaaat cgtgtccttt tctctaaatg aagtggcatc   1980
aaggactcag gggaaagaa atcaggggac atgttataga agttatgaaa agacaaccac    2040
atggtcaggc tcttgtctgt ggtctctagg gctctgcagc agcagtggct cttcgattag   2100
ttaaaactct cctaggctga cacatctggg tctcaatccc cttggaaatt cttggtgcat   2160
taaatgaagc cttaccccat tactgcggtt cttcctgtaa gggggctcca ttttcctccc   2220
tctctttaaa tgaccaccta aaggacagta tattaacaag caaagtcgat tcaacaacag   2280
cttcttccca gtcacttttt tttttctcac tgccatcaca tactaacctt atactttgat   2340
ctattctttt tggttatgag agaaatgttg ggcaactgtt tttacctgat ggttttaagc   2400
tgaacttgaa ggactggttc ctattctgaa acagtaaaac tatgtataat agtatatagc   2460
catgcatggc aaatatttta atatttctgt tttcatttcc tgttggaaat attatcctgc   2520
```

```
ataatagcta ttggaggctc ctcagtgaaa gatcccaaaa ggattttggt ggaaaactag   2580

ttgtaatctc acaaactcaa cactaccatc aggggttttc tttatggcaa agccaaaata   2640

gctcctacaa tttcttatat ccctcgtcat gtggcagtat ttatttattt atttggaagt   2700

ttgcctatcc ttctatattt atagatattt ataaaaatgt aaccccttt tcctttcttc   2760

tgtttaaaat aaaaataaaa tttatctcag cttctgttag cttatcctct ttgtagtact   2820

acttaaaagc atgtcggaat ataagaataa aaaggattat gggaggggaa cattagggaa   2880

atccagagaa ggcaaaattg aaaaaaagat tttagaattt taaaattttc aaagatttct   2940

tccattcata aggagactca atgattttaa ttgatctaga cagaattatt taagttttat   3000

caatattgga tttctggt                                                   3018
```

<210> SEQ ID NO 150
<211> LENGTH: 251
<212> TYPE: PRT
<213> ORGANISM: Homo sapiens

<400> SEQUENCE: 150

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 151
<211> LENGTH: 4162
<212> TYPE: DNA

<213> ORGANISM: Homo sapiens

<400> SEQUENCE: 151

```
agaagtccat tcggctcaca catttgcccc aagacaaacc acgttaaaat aacacccagg     60
gtagctgctg ccaccgtctt ctgtctctac ctccctcctg gctggccaat ggctctgtgt    120
tcctgggcct gctgctggct gtccagagta ggggttgctt agagctgtgt gcatccctgc    180
gggtggtgtg ggagtgggcg gttgtctaaa ggcaggtccc ctctactgat aaacaaggac    240
cggagataga cctagaggct gacattcttg gctcccccag cctacacccc ccccacctcg    300
atttcccaca gagccctagg gacgggtagc cagctctgtg gcatggtatc tggaggcagg    360
ccagcaacct gatgtgcatg ccacggcccg tccctctccc cactcagagc tgcagtagcc    420
tggaggttca gagagccggg ctactctgag aagaagacac caagtggatt ctgcttcccc    480
tgggacagca ctgagcgagt gtggagagag gtacagccct cggcctacaa gctctttagt    540
cttgaaagcg ccacaagcag cagctgctga gccatggctg aaggggaaat caccaccttc    600
acagccctga ccgagaagtt taatctgcct ccagggaatt acaagaagcc caaactcctc    660
tactgtagca acgggggcca cttcctgagg atccttccgg atggcacagt ggatgggaca    720
agggacagga gcgaccagca cattcagctg cagctcagtg cggaaagcgt gggggaggtg    780
tatataaaga gtaccgagac tggccagtac ttggccatgg acaccgacgg gcttttatac    840
ggctcacaga caccaaatga ggaatgtttg ttcctggaaa ggctggagga gaaccattac    900
aacacctata tatccaagaa gcatgcagag aagaattggt ttgttggcct caagaagaat    960
gggagctgca aacgcggtcc tcggactcac tatggccaga aagcaatctt gtttctcccc   1020
ctgccagtct cttctgatta aagagatctg ttctgggtgt tgaccactcc agagaagttt   1080
cgaggggtcc tcacctggtt gacccaaaaa tgttcccttg accattggct gcgctaaccc   1140
ccagcccaca gagcctgaat ttgtaagcaa cttgcttcta aatgcccagt tcacttcttt   1200
gcagagcctt ttacccctgc acagtttaga acagagggac caaattgctt ctaggagtca   1260
actggctggc cagtctgggt ctgggtttgg atctccaatt gcctcttgca ggctgagtcc   1320
ctccatgcaa aagtggggct aaatgaagtg tgttaagggg tcggctaagt gggacattag   1380
taactgcaca ctatttccct ctactgagta aaccctatct gtgattcccc caaacatctg   1440
gcatggctcc cttttgtcct tcctgtgccc tgcaaatatt agcaaagaag cttcatgcca   1500
ggttaggaag gcagcattcc atgaccagaa acagggacaa agaaatcccc ccttcagaac   1560
agaggcattt aaaatggaaa agagagattg gattttggtg ggtaacttag aaggatggca   1620
tctccatgta gaataaatga agaaagggag gcccagccgc aggaaggcag aataaatcct   1680
tgggagtcat taccacgcct tgaccttccc aaggttactc agcagcagag agccctgggt   1740
gacttcaggt ggagagcact agaagtggtt tcctgataac aagcaaggat atcagagctg   1800
ggaaattcat gtggatctgg ggactgagtg tgggagtgca gagaaagaaa gggaaactgg   1860
ctgaggggat accataaaaa gaggatgatt tcagaaggag aaggaaaaag aaagtaatgc   1920
cacacattgt gcttggcccc tggtaagcag aggctttggg gtcctagccc agtgcttctc   1980
caacactgaa gtgcttgcag atcatctggg gacctggttt gaatggagat tctgattcag   2040
tgggttgggg gcagagtttc tgcagttcca tcaggtcccc cccaggtgca ggtgctgaca   2100
atactgctgc cttacccgcc atacattaag gagcagggtc ctggtcctaa agagttattc   2160
aaatgaaggt ggttcgacgc cccgaacctc acctgacctc aactaaccct taaaaatgca   2220
cacctcatga gtctacctga gcattcaggc agcactgaca atagttatgc ctgtactaag   2280
```

```
gagcatgatt ttaagaggct ttggcccaat gcctataaaa tgcccatttc gaagatatac   2340

aaaaacatac ttcaaaaatg ttaaaccctt accaacagct tttcccagga gaccatttgt   2400

attaccatta cttgtataaa tacacttcct gcttaaactt gacccaggtg gctagcaaat   2460

tagaaacacc attcatctct aacatatgat actgatgcca tgtaaaggcc tttaataagt   2520

cattgaaatt tactgtgaga ctgtatgttt taattgcatt taaaaatata tagcttgaaa   2580

gcagttaaac tgattagtat tcaggcactg agaatgatag taataggata caatgtataa   2640

gctactcact tatctgatac ttatttacct ataaaatgag atttttgttt tccactgtgc   2700

tattacaaat tttcttttga aagtaggaac tcttaagcaa tggtaattgt gaataaaaat   2760

tgatgagagt gttagctcct gtttcatatg aaattgaagt aattgttaac taaaaacaat   2820

tccttagtaa ctgaactgtc atatttagaa tggaaggaaa atgacagttt gtgaaagttc   2880

aaagcaatag tgcaattgaa gaattgacct aagtaagctg acattatggt taataatagt   2940

attttagatt tgtgcagcaa aataatttca taactttttt gtttttgtta cttggataag   3000

atcaatctgt tttattttag taaatctttg caggcaagtt agagaaaatg cagtgtggct   3060

taacgtctct ttagtatgaa gatttggcca gaaaaagata cccagagagg aaatctaaga   3120

taattataat ggtccatact ttttattgta tgaatcaaac tcaagcataa cattggccaa   3180

ggaaaattaa ataccattgc taacttgtga aatggaagtc tgtgatttcg gagatgcaaa   3240

gcattgtagt aaaaacacca atgtgacctc gaccatctca gcccagatat cattcatata   3300

tctgttcaat gactattaag gtgcctactg tgtgctaggc actgtactgg atactgggga   3360

ccttgtctgt ctggtttgct gctgtatctt ctcccagggc attatattta tgatgaaaga   3420

tgctgtggat tcaattcttt cagtcaagaa taaacacaga ctttgtaggt tcctgctgaa   3480

taaagcaaat cccagaaacc cagattttgg aagaatcagc aaccccagca taaaataaac   3540

ccctatcaaa atgtcagagg acatggcaag gtaaacttag cattttcaac tttagaaccg   3600

ggtcagcttc agggggactg ctttcaaatc agccaaagag cctgtcagat cttcttagaa   3660

ggaagaggtt ggtagttccc tgctctgttt tgaacatgct ctagtttatt aacctgggga   3720

cattcccatt gctgtcttaa gtaagtctca tagccagctc ctgtcacgtg actctcatat   3780

ggattcattt tcgggccagc tctgaacaaa gcatcatgaa catatgtgct tttggtcgtt   3840

tgcaatgtga tggtggtgga ggtaggtatt ggtttccttg gaaggcatga taagaaagat   3900

tcacaatggc caacagtgtg tatgaacaaa aaactgattg gagcatcagc tagtactgaa   3960

ggtccttgct ttgtgtcaga ggcaaaggaa cccaaggcgc caagtcctca gccttgagtg   4020

tactgctgac aactaaactc acaggctgca aagcagacct ctgatgaaga tgcctgttat   4080

ttcacatcac tgtctttttg tgtatcatag tctgcacctt acaaatatta ataaatgttc   4140

caataatagg tgaaaaaaaa aa                                              4162
```

```
<210> SEQ ID NO 152
<211> LENGTH: 155
<212> TYPE: PRT
<213> ORGANISM: Homo sapiens

<400> SEQUENCE: 152

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30
```

```
Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 153
<211> LENGTH: 940
<212> TYPE: DNA
<213> ORGANISM: Homo sapiens

<400> SEQUENCE: 153

ctgtcagctg aggatccagc cgaaagagga gccaggcact caggccacct gagtctactc     60

acctggacaa ctggaatctg gcaccaattc taaaccactc agcttctccg agctcacacc    120

ccggagatca cctgaggacc cgagccattg atggactcgg acgagaccgg gttcgagcac    180

tcaggactgt gggtttctgt gctggctggt cttctgctgg gagcctgcca ggcacacccc    240

atccctgact ccagtcctct cctgcaattc gggggccaag tccggcagcg gtacctctac    300

acagatgatg cccagcagac agaagcccac ctggagatca gggaggatgg gacggtgggg    360

ggcgctgctg accagagccc cgaaagtctc ctgcagctga aagccttgaa gccgggagtt    420

attcaaatct tgggagtcaa gacatccagg ttcctgtgcc agcggccaga tggggccctg    480

tatggatcgc tccactttga ccctgaggcc tgcagcttcc gggagctgct tcttgaggac    540

ggatacaatg tttaccagtc cgaagcccac ggcctcccgc tgcacctgcc agggaacaag    600

tccccacacc gggaccctgc accccgagga ccagctcgct tcctgccact accaggcctg    660

ccccccgcac tcccggagcc acccggaatc ctggcccccc agccccccga tgtgggctcc    720

tcggaccctc tgagcatggt gggaccttcc cagggccgaa gccccagcta cgcttcctga    780

agccagaggc tgtttactat gacatctcct ctttatttat taggttattt atcttattta    840

ttttttttatt tttcttactt gagataataa agagttccag aggagaaaaa aaaaaaaaaa    900

aaaaaaaaaa aaaaaaaaaa aaaaaaaaaa aaaaaaaaaa                          940


<210> SEQ ID NO 154
<211> LENGTH: 209
<212> TYPE: PRT
<213> ORGANISM: Homo sapiens

<400> SEQUENCE: 154

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
```

```
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser


<210> SEQ ID NO 155
<211> LENGTH: 856
<212> TYPE: DNA
<213> ORGANISM: Homo sapiens

<400> SEQUENCE: 155

accttgcgtc cgcagtaccg acccgcacgc tcttcagcgc atccctagtg aaggaggttc     60

tcccccagcc cgtggctgtt gcacttgctg gtcctctgcc tccaagccca gcatgtgagg    120

gagcagagcc tggtgacgga tcagctcagc cgccgcctca tccggaccta ccaactctac    180

agccgcacca gcgggaagca cgtgcaggtc ctggccaaca agcgcatcaa cgccatggca    240

gaggacggcg accccttcgc aaagctcatc gtggagacgg acacctttgg aagcagagtt    300

cgagtccgag gagccgagac gggcctctac atctgcatga acaagaaggg gaagctgatc    360

gccaagagca acggcaaagg caaggactgc gtcttcacgg agattgtgct ggagaacaac    420

tacacagcgc tgcagaatgc caagtacgag ggctggtaca tggccttcac ccgcaagggc    480

cggccccgca agggctccaa gacgcggcag caccagcgtg aggtccactt catgaagcgg    540

ctgccccggg gccaccacac caccgagcag agcctgcgct tcgagttcct caactacccg    600

cccttcacgc gcagcctgcg cggcagccag aggacttggg cccccgagcc ccgataggtg    660

ctgcctggcc ctccccacaa tgccagaccg cagagaggct catcctgtag ggcacccaaa    720

actcaagcaa gatgagctgt gcgctgctct gcaggctggg gaggtgctgg gggagccctg    780

ggttccggtt gttgatattg tttgctgttg ggtttttgct gttttttttt tttttttttt    840

ttttaaaaca aaagag                                                    856


<210> SEQ ID NO 156
<211> LENGTH: 140
<212> TYPE: PRT
<213> ORGANISM: Homo sapiens

<400> SEQUENCE: 156
```

```
Met Ala Glu Asp Gly Asp Pro Phe Ala Lys Leu Ile Val Glu Thr Asp
1               5                   10                  15

Thr Phe Gly Ser Arg Val Arg Val Arg Gly Ala Glu Thr Gly Leu Tyr
            20                  25                  30

Ile Cys Met Asn Lys Lys Gly Lys Leu Ile Ala Lys Ser Asn Gly Lys
        35                  40                  45

Gly Lys Asp Cys Val Phe Thr Glu Ile Val Leu Glu Asn Asn Tyr Thr
    50                  55                  60

Ala Leu Gln Asn Ala Lys Tyr Glu Gly Trp Tyr Met Ala Phe Thr Arg
65                  70                  75                  80

Lys Gly Arg Pro Arg Lys Gly Ser Lys Thr Arg Gln His Gln Arg Glu
                85                  90                  95

Val His Phe Met Lys Arg Leu Pro Arg Gly His His Thr Thr Glu Gln
            100                 105                 110

Ser Leu Arg Phe Glu Phe Leu Asn Tyr Pro Pro Phe Thr Arg Ser Leu
        115                 120                 125

Arg Gly Ser Gln Arg Thr Trp Ala Pro Glu Pro Arg
    130                 135                 140
```

<210> SEQ ID NO 157
<211> LENGTH: 4545
<212> TYPE: DNA
<213> ORGANISM: Homo sapiens

<400> SEQUENCE: 157

```
actctgcgcg ccggcggggg ctgcgcagga ggagcgctcc gcccggctac aacgctccgc      60

gagccggcgc ggcaacacct gttcgcggca gcctgggcgg cacgcgagct cccggacgcg     120

gctctcctcg ctcgccgctc gccacccgtt ctaagccaat ggacatctgc cgagcctctg     180

gagaatcctg gatactagct ttggacgcct aaagtttctt cttcttttg ttttattatt      240

attatcattt tttggagggg ggaccgggag gggagatttg tcgccgccac caacgtgaga     300

ttttttttc cccttgaagg attcatgctg atgtctgcag agtcggttag agagtaaaaa      360

cagcgcatgc cttcctggag tcaggatccg taaattctga cgtagcccgt gcatcttaaa     420

aatccctata ataacgccta ggcatttaag ttgctatggt cattctgatc tcaaaccaaa     480

tggagaaact acggattttt tttccttatt acggtcggat gggatgaaga ccttcctgcc     540

tgctaagagc tggggatcta tctatagaga tacatagata tgtttatcaa tatgtcagtg     600

tgtgagtata aagtggtggt ttcttagact atcagtggtt tgaccttgaa cctgtgccag     660

tgaaacagca gattactttt atttatgcat ttaatggatt gaagaaaaga accttttttt     720

tctctctctc tctgcaactg cagtaaggga ggggagttgg atatacctcg cctaatatct     780

cctgggttga caccatcatt attgtttatt cttgtgctcc aaaagccgag tcctctgatg     840

gctcccttag gtgaagttgg gaactatttc ggtgtgcagg atgcggtacc gtttgggaat     900

gtgcccgtgt tgccggtgga cagcccggtt ttgttaagtg accacctggg tcagtccgaa     960

gcaggggggc tccccagggg acccgcagtc acggacttgg atcatttaaa ggggattctc    1020

aggcggaggc agctatactg caggactgga tttcacttag aaatcttccc caatggtact    1080

atccagggaa ccaggaaaga ccacagccga tttggcattc tggaatttat cagtatagca    1140

gtgggcctgg tcagcattcg aggcgtggac agtggactct acctcgggat gaatgagaag    1200

ggggagctgt atggatcaga aaaactaacc caagagtgtg tattcagaga acagttcgaa    1260

gaaaactggt ataatacgta ctcatcaaac ctatataagc acgtggacac tggaaggcga    1320
```

```
tactatgttg cattaaataa agatgggacc ccgagagaag ggactaggac taaacggcac   1380
cagaaattca cacatttttt acctagacca gtggaccccg acaaagtacc tgaactgtat   1440
aaggatattc taagccaaag ttgacaaaga cagtttcttc acttgagccc ttaaaaaagt   1500
aaccactata aaggtttcac gcggtgggtt cttattgatt cgctgtgtca tcacatcagc   1560
tccactgttg ccaaactttg tcgcatgcat aatgtatgat ggaggcttgg atgggaatat   1620
gctgattttg ttctgcactt aaaggcttct cctcctggag ggctgcctag ggccacttgc   1680
ttgatttatc atgagagaag aggagagaga gagagactga gcgctaggag tgtgtgtatg   1740
tgtgtgtgtg tgtgtgtgtg tgtgtgtgta tgtgtgtagc gggagatgtg ggcggagcga   1800
gagcaaaagg actgcggcct gatgcatgct ggaaaaagac acgcttttca tttctgatca   1860
gttgtacttc atcctatatc agcacagctg ccatacttcg acttatcagg attctggctg   1920
gtggcctgcg cgagggtgca gtcttactta aaagactttc agttaattct cactggtatc   1980
atcgcagtga acttaaagca aagacctctt agtaaaaaat aaaaaaaaat aaaaaataaa   2040
aataaaaaaa gttaaattta tttatagaaa ttccaaaggc aacattttat ttattttata   2100
tatttattta ttatatagag tttattttta atgaaacatg tacaggccag ataggcattt   2160
tggaagcttt aggctctgta agcattaaat ggcaaagtcc gctatgaacc tgtggtaaat   2220
tcatgcaagt agatataatg gtgcatggat ataagaaatt ctaatgaccc taatgtacta   2280
aaggcgacaa tctcttttgt gcccatatta ttgtaaactt atgcacatcg ctcatgacac   2340
tgagtattca ctcttcagac tgcttgtttc atagcttatc ccagaggatt aaagataaac   2400
tgggtctcaa actttgattc tgtgtctgca atatttcctc tctcataagt gactccacta   2460
ttgtaacttc atggttggaa aatatgaggg ttgatatatg tcttacttgt ttaaatctgt   2520
cgcagaatat accaaagcta aataataact atgctttcat tttagccgat ctccagaatg   2580
acagtattaa catcaaacat tgtattgatt tagaattctc aaaaaaggaa aaaaaagtac   2640
atagcacaga ctattttttt taaagacgta agaatcagat taacaggatc atacttgtaa   2700
actttttttg gttcacttgg ctatcaaata tgaaattata gaagtatcat aggggtcatt   2760
gtaacatctt ttagagaaaa tggctatcag tgtgaactgt cataattacg tggtaatagc   2820
acccttagta aaacttgcaa aatgaaacta ataaatcgtt atcaataatg acaatgaggg   2880
ggaaagtatt atacttgttg actgtgtttt gtttttttaaa atggtctcca caagcgctca   2940
atttttttag aggggatatt actatataga atatctttta caaggctttt ataacatttt   3000
atgctgaaaa gcataagaat acgtatttct ttagtagcaa taattttgga acttgccctt   3060
gggcaagcga gactatttct tactatatac taaggagaaa agagccaaat tcttaaagca   3120
atatttaaga aaaaaggaat ttataacaaa ttctcatcta catatgacac tttctagcca   3180
gttgtgttga gaagtgcaaa gtgacggttt aaacatgtgt tgggatttat tgaactaatt   3240
ttaaaattta ctattcaaac tttattttgc tctgatgcac attctctatg aaaaataaaa   3300
gtgtgtcact ggtgagtgac agctgttatg agctagaagc gcatgactta ttgtgacgat   3360
gtcttgcctt tctgtggtcc aagttggagt acatggcaat gccctcctgc tgatgtgcat   3420
taaggaaaat ctaagtctaa tatttggaat taagatatat tttaggggga ggggacagaa   3480
gcaatgtaaa atagttgatt tatgataaag ctcagaatgt cctcttcatt tattttcttg   3540
ttttattttc ctttctaaac agaaactgca tttaattcca aaaagtagta ttcttattta   3600
ttatttaacc ctttgctgct gctaaaatgt gcacatattc aggctttagt ttttccaaaa   3660
```

```
ggcatttttt ttttggctga aaaatattaa acatttgacc acagggaaga atcaagtttc   3720

taggatgtca taggtatact atgtagcact gaaaaaattg attttaggtg acagccaaaa   3780

gtagtcttaa agtagcatga gaccttagat aatcgaccta aaagaaagaa aattgtgaaa   3840

aagacaaaaa tcttcatgca ttcctataaa acgctacttt aaggtctact tttggagtta   3900

attttgtttg gtactttttt ttttttaag acgagcaaat tgttatatgc ttttggcaat   3960

tgatacaata aactgtaatg gtctgtaaat aaataaatat tgactcatgc gatttatgta   4020

aatagtggaa ctgggagagt ggatggctca gggtttcggt gtgggcattg tctcttgggc   4080

agtagagtga gtcatcccca gctcatgggt ttgcatccag ttcttgtctt aagagaccca   4140

aagcccagtg aatggcagcc ctgagccact gtggaatggg ggttctggtt tcacaaacag   4200

atgcttagat agccaaacca ctgtcttgtt ggtgccaaca cttgcactgt ggtcaaagac   4260

ttaccgagca tgggctgaac aaccttccca tctgtcatgt gaatgtcccc aagcagtggt   4320

gaaggacatg ctaggtcagt gttggggaac ctgccctgcc aggtcctgtt ttgtagataa   4380

acaaatggct gccttctggt gtttttattc tatttcatct cattaacact acaaccttgt   4440

gttatttact tgataatctg taattgtatg taaatacata caggattatg taatttgtgt   4500

aaatacataa ttacagagtt ttgaaaactg aaaaaaaaaa aaaaa                   4545
```

```
<210> SEQ ID NO 158
<211> LENGTH: 208
<212> TYPE: PRT
<213> ORGANISM: Homo sapiens

<400> SEQUENCE: 158

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

<210> SEQ ID NO 159
```

<211> LENGTH: 5118
<212> TYPE: DNA
<213> ORGANISM: Homo sapiens

<400> SEQUENCE: 159

```
ctcagtaggg ccagatcgct cttccagcgc gggttggtcc accaggcaga gccccagcca     60
gggcctgtca ggtacccagg gagaccggaa atgtagccag gagacagcag cgctcacagt    120
cacctggttt cagtgtcagc ctggttgctc ctagatgttc ctaacttgct ccatctcaga    180
ccaaagactc cacgggccat tgggctcctt cttacacagg ctccagagga gcgtggacac    240
caccggcggt ctgaagattt ggcagccagc agtctccaga ggggggtcgg aggcgcgcaa    300
gtgggtgttt tggaaatatt tgctgtgtct caggggattg taggaatacg aggagttttc    360
agcaacaaat ttttagcgat gtcaaaaaaa ggaaaactcc atgcaagtgc caagttcaca    420
gatgactgca agttcaggga gcgttttcaa gaaaatagct ataataccta tgcctcagca    480
atacatagaa ctgaaaaaac agggcgggag tggtatgtgg ccctgaataa aagaggaaaa    540
gccaaacgag ggtgcagccc ccgggttaaa ccccagcata tctctaccca ttttctgcca    600
agattcaagc agtcggagca gccagaactt tctttcacgg ttactgttcc tgaaaagaaa    660
aagccaccta gccctatcaa gccaaagatt cccctttctg cacctcggaa aaataccaac    720
tcagtgaaat acagactcaa gtttcgcttt ggataatatt cctcttggcc ttgtgagaaa    780
ccattctttc ccctcaggag tttctatagg tgtcttcaga gttctgaaga aaaattactg    840
gacacagctt cagctatact tacactgtat tgaagtcacg tcatttgttt caatgtgact    900
gaaacaaaat gtttttttgat aggaaggaaa ctggaattct ttgtactaat acagggagca    960
cactccttca gttcagcaag acataaagcc ttttgcttta tgcttgaggg atatttagaa   1020
ctttgtattt tcggaaagtt aaataacagg gactacgtat ttttctgact tttacagatt   1080
aacctgaaag aacatacatg atacattttt atttttggtt tccaaagaat attttgatgc   1140
agataaaata ttttgttaac ttttgttttt ttttgtttgt tttcttaaaa gtacctctgc   1200
attgagcata ttttcttact tttattattt taattaatat gacataagca atcattttat   1260
gctgtttatg aattataaat gtgtttatag ctcatttgta atatggaaat cttttacatt   1320
tttcctattc actgcacttt tttattgttt ttatttctag ccatacctca gataatatgt   1380
ttagttttac attttaaaat gtttaaattc tctttcacag caccaaaggc tcagcttgga   1440
tttgtgtgta tgtgtatgtc aattcatgac attatgtgga atcctaaacc tttggtggct   1500
gggatatgat gggttagaag caaggagaaa atataaggac tttttgatgg aattaaatgt   1560
gggaggtaag gaaaaggatt tagaggtaaa agtacactaa gtttgcaaca tttattgaga   1620
tctaagtctg tcttgccttc atttctcttt ttatctcccc cttgccctca ttcttgaaca   1680
gctggaggaa tacattttat tctgtccatg aagcatacac tatgaaattc aagtgcttaa   1740
aaatacttct atgactctct gctatcccac tgtatagatc cacagggagc aaacacttag   1800
aaatgataga gaactgaagg agatcaatgg tttaacagtt atccatgcca agtcccattg   1860
tcagaaatat tcttattact cagtcaaaca ctctttgagc ttcccttcct aaaggtaacc   1920
aatccagtga atagatgtgc ccttttataa ggaaacttct gatgtttatt aaaaaaactg   1980
gccttttgat agaggtaact taatttggga atttgttgtg ttgaaatggc atttaatttc   2040
aacctaaata ctgactgctg gacataaatc acagaaaatt taacttaaga aaatttacaa   2100
aatttattct caggtaatca ttttaataaa gttctgcaaa atacacgttt atcttacatt   2160
cagaaatgtg gcaaaaaagg catagctaaa ggctaaacat atggctttag tagtaacaaa   2220
```

```
agggttcata gaaacttcat ggtttgcatt taaacatgtt taaagtgtac ttataaacta   2280
tttttttctt aaagcaaact atgatttatt ttggtgcaca aatacaaagt ggaaacttac   2340
caaaattgaa ctagctacca tataagcaga ttgctttaat ttgatgggaa aatagtacac   2400
acatatatat aacaaataat atattaaaaa acccatccat caactaaaac attatatgta   2460
tacatcagta tagtgtttta ttataaagcc aattatctga ttaagcattc tttccactga   2520
atgcataatg tttaaatagc ataaaatgaa atgctacaaa aattgaacta atttatactt   2580
taaagtattt ctgggttaaa tgaaacaatg aaatttttta gtatgttcaa ctctcatcca   2640
aatggcatat gaccctgttt acacagccta aagctaaaaa tattactcta gtttattcta   2700
atctattgtt aagtattgtg cactgtatac caagttctta gggcacatga aaaattttag   2760
ctgccaaaca ggaactagta aacatatgtt cctaataagt gaagggaaag ataataatga   2820
tggtcaacaa taagccacgt caatgcataa gttgtatagg ctaaatgttg cttgtaggct   2880
acattaaact caaatgtaat agtttatctt atactcctgg tttgatttga ttagcatatt   2940
aacgtgaaag taggatagct actaaatata tattatgcaa gtcaggaatc attaatttca   3000
aaatttaaag ccatgctaaa attaaaaaga aaatattaaa ttacacaatt acacttgtct   3060
ttactggcca tacaaaatga tttttttttt tttttgaga cagagtcttg ctctgtcacc   3120
aggctggagt gcagtggcat gatctcggct cactgcaacc tccaactccc tggtttaagg   3180
gattctcctg cctcagcctc ccaagtagct gggattacag actcatgcca ccacgccagc   3240
taatttttgt atttttagta gagacggggt ttcaccatgt tggtcaggat ggtctcaatc   3300
ctggcctctt gatagtcctg acctcatgat ctgcccacct cggcctcccc aaagtgctgg   3360
gattacaggt acaatgatgt ataattaatg cttagtgaag cataaagtta cctacatcaa   3420
ttaattaaat gaacttatgt acagaaaaca tgtataaata taagtctata ctaatgctta   3480
caactttcta agagggttct tgcttatgta gctttttatt attttaagta actagaacca   3540
ccaaatatca aataaaatta tttggttatg gttatgttca tctaaacaca acaataactt   3600
ttatattaat atttaggagt ctattttgtc tataggtgac aaacatctcc agactaacat   3660
gtcagtttta tcaattatat tatgtttaat tatttaagat ttctttatgt ggaacatcta   3720
tagagataaa tagaaatttt caataagatg tagtaacact gtgatttatc tttcaagagt   3780
ctctcttcac ttccttctaa agagactaat ttgagagtac aggtgcatat taattttctt   3840
ggttctttca gctgaattat attggtccag aagttcaaaa tcatgtgaca ataataaggg   3900
atactgacag aagttatttc caagtttgtg tatatattat aaaaattaca tatataaaac   3960
taaggctttt atttctgtta tttttaagct tttatttctt gtagctaaaa ataaaacatc   4020
ataaatctgg taggtaaatt tcttattaaa tcaatcttga aatagaaaat gtaataactt   4080
tcttaccatt aacatttttt acccttccat agaagggagg gaataaatca tgacttatcc   4140
cattttcaat aacaaaacga aactatggca ctaaccaaaa acttgcattc tggcataatt   4200
tttacagttg cagagaattg tttctgggct cattaaaaaa agtagtattg cagacattgc   4260
tgcaatggga agcagacaat aacttcttaa aggaattcta cacctccttt aagatttact   4320
taattgctac atctaaattc tgataattta aaatccattt taggtgataa aatttttttaa  4380
aagttttgaa ggaaacctct ggataaatgg acaaggccta atttttttttt gtagtcaatc  4440
caactgtact ggccaatttt tgaaataaga ttatatgatt aggtattagc agagacaaag   4500
agttacctcc tccatcttac tctgccctat ttgaaagtct caggggagaa aagggaacaa   4560
```

```
gatgctgatc caacctgagt ggagtcaggt gaggcatctt tacatctaag aatttttttt   4620

taaattttat tattattata cttcaagttc tagggtacat gtccacaatg cacatgtctg   4680

tcacacatgc acacatgtgc catgctggtg tgctgcaccc accaacctgt catccagcat   4740

taggtatatc tcctaatgct atccctcccc tctccaccca ccccacagca ggccccggta   4800

tgtgatgttc cccttcgtgt gtccatgtgt tcttattgtt caattcccac ctatgagtga   4860

gaatatgtgg tgtttggttt ttggtccttg caatagtttg ctgagaatga tggtttccag   4920

cttcatccat gtccctacaa agaacatgaa ctcatcattt tttatggctg catagtattc   4980

catggtgtat atgtgccaca ttttcttaat ccagtctatc attgttggac atttgggttg   5040

gttccaagtc tttgctattg tgaatagtgc tgcaataaac atatgtgtgc atgtgtcttt   5100

aaaaaaaaaa aaaaaaaa                                                  5118
```

<210> SEQ ID NO 160
<211> LENGTH: 125
<212> TYPE: PRT
<213> ORGANISM: Homo sapiens

<400> SEQUENCE: 160

```
Met Ser Lys Lys Gly Lys Leu His Ala Ser Ala Lys Phe Thr Asp Asp
1               5                   10                  15

Cys Lys Phe Arg Glu Arg Phe Gln Glu Asn Ser Tyr Asn Thr Tyr Ala
            20                  25                  30

Ser Ala Ile His Arg Thr Glu Lys Thr Gly Arg Glu Trp Tyr Val Ala
        35                  40                  45

Leu Asn Lys Arg Gly Lys Ala Lys Arg Gly Cys Ser Pro Arg Val Lys
    50                  55                  60

Pro Gln His Ile Ser Thr His Phe Leu Pro Arg Phe Lys Gln Ser Glu
65                  70                  75                  80

Gln Pro Glu Leu Ser Phe Thr Val Thr Val Pro Glu Lys Lys Lys Pro
                85                  90                  95

Pro Ser Pro Ile Lys Pro Lys Ile Pro Leu Ser Ala Pro Arg Lys Asn
            100                 105                 110

Thr Asn Ser Val Lys Tyr Arg Leu Lys Phe Arg Phe Gly
        115                 120                 125
```

<210> SEQ ID NO 161
<211> LENGTH: 2172
<212> TYPE: DNA
<213> ORGANISM: Homo sapiens

<400> SEQUENCE: 161

```
gtggctctct aggaccggag agttctttgg aaggagagcg cgagcgaggg agcgggcgag     60

ctccgagggg gtgtgggtgt agggagagag agaaagagag caggcagcgg cggcggcggc    120

agcggtgggg aaaagcggat tccgccccga accacaccga ggggagctcg tggtcgagac    180

ttgccgccct aagcactctc ccaagtccga cccgctcggc gaggacttcc gtcttctgag    240

cgaaccttgt caagcaagct gggatctatg agtggaaagg tgaccaagcc caaagaggag    300

aaagatgctt ctaaggagcc tcagcttaag ggtatagtta ccaagctata cagccgacaa    360

ggctaccact tgcagctgca ggcggatgga accattgatg gcaccaaaga tgaggacagc    420

acttacactc tgtttaacct catccctgtg ggtctgcgag tggtggctat ccaaggagtt    480

caaaccaagc tgtacttggc aatgaacagt gagggatact tgtacacctc ggaacttttc    540

acacctgagt gcaaattcaa agaatcagtg tttgaaaatt attatgtgac atattcatca    600
```

```
atgatatacc gtcagcagca gtcaggccga gggtggtatc tgggtctgaa caaagaagga    660

gagatcatga aaggcaacca tgtgaagaag aacaagcctg cagctcattt tctgcctaaa    720

ccactgaaag tggccatgta caaggagcca tcactgcacg atctcacgga gttctcccga    780

tctggaagcg ggaccccaac caagagcaga agtgtctctg gcgtgctgaa cggaggcaaa    840

tccatgagcc acaatgaatc aacgtagcca gtgagggcaa aagaagggct ctgtaacaga    900

accttacctc caggtgctgt tgaattcttc tagcagtcct tcacccaaaa gttcaaattt    960

gtcagtgaca tttaccaaac aaacaggcag agttcactat tctatctgcc attagacctt   1020

cttatcatcc atactaaagc ccattattt agattgagct tgtgcataag aatgccaagc    1080

atttagtga actaaatctg agagaaggac tgccaaattt tctcatgatc tcacctatac    1140

tttggggatg ataatccaaa agtatttcac agcactaatg ctgatcaaaa tttgctctcc   1200

caccaagaaa atgtaaaaga ccacaattgt tcttcaaaaa caaacaaaac aaaacaaaac   1260

aaaattaact gcttaaatgt tttgtcgggg caaacaaaat tatgtgaatt gtgttgtttt   1320

cttggcttga tgttttctat ctacgcttga ttcacatgta ctcttttctt tggcatagtg   1380

caactttatg atttctgaaa ttcaatggtt ctattgactt tttgcgtcac ttaatccaaa   1440

tcaaccaaat tcagggttga atctgaattg gcttctcagg ctcaaggtaa cagtgttctt   1500

gtggtttgac caattgtttt tctttctttt tttttttttt tagatttgtg gtattctggt   1560

caagttattg tgctgtactt tgtgcgtaga aattgagttg tattgtcaac cccagtcagt   1620

aaagagaact tcaaaaaatt atcctcaagt gtagatttct cttaattcca tttgtgtatc   1680

atgttaaact attgttgtgg cttcttgtgt aaagacagga actgtggaac tgtgatgttg   1740

tcttttgtgt tgttaaaata agaaatgtct tatctgtata tgtatgagtc ttcctgtcat   1800

tgtatttggc acatgaatat tgtgtacaag gaattgttaa gactggtttt ccctcaacaa   1860

catatattat acttgctact ggaaaagtgt ttaagactta gctaggtttc catttagatc   1920

ttcatatctg ttgcatggaa gaaagttggg ttcttggcat agagttgcat gatatgtaag   1980

attttgtgca ttcataattg ttaaaaatct gtgttccaaa agtggacata gcatgtacag   2040

gcagttttct gtcctgtgca caaaaagttt aaaaaagttg tttaatattt gttgttgtat   2100

acccaaatac gcaccgaata aactctttat attcattcaa agaaaaaaaa aaaaaaaaaa   2160

aaaaaaaaaa aa                                                       2172
```

<210> SEQ ID NO 162
<211> LENGTH: 199
<212> TYPE: PRT
<213> ORGANISM: Homo sapiens

<400> SEQUENCE: 162

```
Met Ser Gly Lys Val Thr Lys Pro Lys Glu Glu Lys Asp Ala Ser Lys
1               5                   10                  15

Glu Pro Gln Leu Lys Gly Ile Val Thr Lys Leu Tyr Ser Arg Gln Gly
            20                  25                  30

Tyr His Leu Gln Leu Gln Ala Asp Gly Thr Ile Asp Gly Thr Lys Asp
        35                  40                  45

Glu Asp Ser Thr Tyr Thr Leu Phe Asn Leu Ile Pro Val Gly Leu Arg
    50                  55                  60

Val Val Ala Ile Gln Gly Val Gln Thr Lys Leu Tyr Leu Ala Met Asn
65                  70                  75                  80

Ser Glu Gly Tyr Leu Tyr Thr Ser Glu Leu Phe Thr Pro Glu Cys Lys
```

```
                85                  90                  95

Phe Lys Glu Ser Val Phe Glu Asn Tyr Tyr Val Thr Tyr Ser Ser Met
            100                 105                 110

Ile Tyr Arg Gln Gln Gln Ser Gly Arg Gly Trp Tyr Leu Gly Leu Asn
        115                 120                 125

Lys Glu Gly Glu Ile Met Lys Gly Asn His Val Lys Lys Asn Lys Pro
    130                 135                 140

Ala Ala His Phe Leu Pro Lys Pro Leu Lys Val Ala Met Tyr Lys Glu
145                 150                 155                 160

Pro Ser Leu His Asp Leu Thr Glu Phe Ser Arg Ser Gly Ser Gly Thr
                165                 170                 175

Pro Thr Lys Ser Arg Ser Val Ser Gly Val Leu Asn Gly Gly Lys Ser
            180                 185                 190

Met Ser His Asn Glu Ser Thr
        195


<210> SEQ ID NO 163
<211> LENGTH: 1999
<212> TYPE: DNA
<213> ORGANISM: Homo sapiens

<400> SEQUENCE: 163

cacggccgga gagacgcgga ggaggagaca tgagccggcg ggcgcccaga cggagcggcc     60

gtgacgcttt cgcgctgcag ccgcgcgccc cgaccccgga gcgctgaccc ctggccccac    120

gcagctccgc gcccgggccg gagagcgcaa ctcggcttcc agacccgccg cgcatgctgt    180

ccccggactg agccgggcag ccagcctccc acggacgccc ggacggccgg ccggccagca    240

gtgagcgagc ttccccgcac cggccaggcg cctcctgcac agcggctgcc gccccgcagc    300

ccctgcgcca gcccggaggg cgcagcgctc gggaggagcc gcgcggggcg ctgatgccgc    360

agggcgcgcc gcggagcgcc ccggagcagc agagtctgca gcagcagcag ccggcgagga    420

gggagcagca gcagcggcgg cggcggcggc ggcggcggcg gaggcgcccg gtcccggccg    480

cgcggagcgg acatgtgcag gctgggctag gagccgccgc ctccctcccg cccagcgatg    540

tattcagcgc cctccgcctg cacttgcctg tgtttacact tcctgctgct gtgcttccag    600

gtacaggtgc tggttgccga ggagaacgtg gacttccgca tccacgtgga gaaccagacg    660

cgggctcggg acgatgtgag ccgtaagcag ctgcggctgt accagctcta cagccggacc    720

agtgggaaac acatccaggt cctgggccgc aggatcagtg cccgcggcga ggatggggac    780

aagtatgccc agctcctagt ggagacagac accttcggta gtcaagtccg gatcaagggc    840

aaggagacgg aattctacct gtgcatgaac cgcaaaggca agctcgtggg gaagcccgat    900

ggcaccagca aggagtgtgt gttcatcgag aaggttctgg agaacaacta cacggccctg    960

atgtcggcta agtactccgg ctggtacgtg ggcttcacca agaaggggcg gccgcggaag   1020

ggccccaaga cccgggagaa ccagcaggac gtgcatttca tgaagcgcta ccccaagggg   1080

cagccggagc ttcagaagcc cttcaagtac acgacggtga ccaagaggtc ccgtcggatc   1140

cggcccacac accctgccta ggccaccccg ccgcggcccc tcaggtcgcc ctggccacac   1200

tcacactccc agaaaactgc atcagaggaa tatttttaca tgaaaaataa ggaagaagct   1260

ctatttttgt acattgtgtt taaaagaaga caaaaactga accaaaactc ttgggggggag   1320

gggtgataag gattttattg ttgacttgaa acccccgatg acaaaagact cacgcaaagg   1380

gactgtagtc aacccacagg tgcttgtctc tctctaggaa cagacaactc taaactcgtc   1440
```

```
cccagaggag gacttgaatg aggaaaccaa cactttgaga aaccaaagtc ctttttccca   1500

aaggttctga aaggaaaaaa aaaaaaaaca aaaaaaaaga aaaacaaaga gaaagtagta   1560

ctccgcccac caacaaactc cccctaactt tcccaatcct ctgttcctgc cccaaactcc   1620

aacaaaaatc gctctctggt ttgcagtcat ttatttattg tccgctgcaa gctgccccga   1680

gacaccgcgc agggaaggcg tgcccctggg aattctccgc gcctcgacct cccgacgaca   1740

gacgcctcgt ccaatcatgg tgaccctgcc ttgctcgcag ttctggagga tgctgctatc   1800

gaccttccgt gactcacgtg acctagtaca ccaatgataa gggaatattt taaaaccagc   1860

tatattatat atattatata tatataagct atttatttca cctctctgta tattgcagtt   1920

tcatgaacca agtattactg cctcaacaat taaaaacaac agacaaatta tttaaaaaac   1980

caaaaaaaaa aaaaaaaaa                                                1999
```

<210> SEQ ID NO 164
<211> LENGTH: 207
<212> TYPE: PRT
<213> ORGANISM: Homo sapiens

<400> SEQUENCE: 164

```
Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205
```

<210> SEQ ID NO 165
<211> LENGTH: 1016
<212> TYPE: DNA
<213> ORGANISM: Homo sapiens

<400> SEQUENCE: 165

```
agcgacctca gaggagtaac cgggccttaa ctttttgcgc tcgttttgct ataatttttc     60

tctatccacc tccatcccac ccccacaaca ctctttactg ggggggtctt ttgtgttccg    120
```

```
gatctccccc tccatggctc ccttagccga agtcgggggc tttctgggcg gcctggaggg    180
cttgggccag caggtgggtt cgcatttcct gttgcctcct gccggggagc ggccgccgct    240
gctgggcgag cgcaggagcg cggcggagcg gagcgcgcgc ggcgggccgg gggctgcgca    300
gctggcgcac ctgcacggca tcctgcgccg ccggcagctc tattgccgca ccggcttcca    360
cctgcagatc ctgcccgacg gcagcgtgca gggcacccgg caggaccaca gcctcttcgg    420
tatcttggaa ttcatcagtg tggcagtggg actggtcagt attagaggtg tggacagtgg    480
tctctatctt ggaatgaatg acaaaggaga actctatgga tcagagaaac ttacttccga    540
atgcatcttt agggagcagt ttgaagagaa ctggtataac acctattcat ctaacatata    600
taaacatgga gacactggcc gcaggtattt tgtggcactt aacaaagacg gaactccaag    660
agatggcgcc aggtccaaga ggcatcagaa atttacacat ttcttaccta gaccagtgga    720
tccagaaaga gttccagaat tgtacaagga cctactgatg tacacttgaa gtgcgatagt    780
gacattatgg aagagtcaaa ccacaaccat tctttcttgt catagttccc atcataaaat    840
aatgacccaa ggagacgttc aaaatattaa agtctatttt ctactgagag actggatttg    900
gaaagaatat tgagaaaaaa aaccaaaaaa aattttgact agaaatagat catgatcact    960
ctttatatgt ggattaagtt cccttagata cattggatta gtccttacca gtagac       1016
```

<210> SEQ ID NO 166
<211> LENGTH: 211
<212> TYPE: PRT
<213> ORGANISM: Homo sapiens

<400> SEQUENCE: 166

```
Met Ala Pro Leu Ala Glu Val Gly Gly Phe Leu Gly Gly Leu Glu Gly
1               5                   10                  15

Leu Gly Gln Gln Val Gly Ser His Phe Leu Leu Pro Pro Ala Gly Glu
            20                  25                  30

Arg Pro Pro Leu Leu Gly Glu Arg Arg Ser Ala Ala Glu Arg Ser Ala
        35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210
```

<210> SEQ ID NO 167
<211> LENGTH: 2720
<212> TYPE: DNA
<213> ORGANISM: Homo sapiens

<400> SEQUENCE: 167

```
atggccgcgg ccatcgctag cggcttgatc cgccagaagc ggcaggcgcg ggagcagcac      60
tgggaccggc cgtctgccag caggaggcgg agcagcccca gcaagaaccg cgggctctgc     120
aacggcaacc tggtggatat cttctccaaa gtgcgcatct tcggcctcaa gaagcgcagg     180
ttgcggcgcc aagatcccca gctcaagggt atagtgacca ggttatattg caggcaaggc     240
tactacttgc aaatgcaccc cgatggagct ctcgatggaa ccaaggatga cagcactaat     300
tctacactct tcaacctcat accagtggga ctacgtgttg ttgccatcca gggagtgaaa     360
acagggttgt atatagccat gaatggagaa ggttacctct acccatcaga actttttacc     420
cctgaatgca agtttaaaga atctgttttt gaaaattatt atgtaatcta ctcatccatg     480
ttgtacagac aacaggaatc tggtagagcc tggtttttgg gattaaataa ggaagggcaa     540
gctatgaaag ggaacagagt aaagaaaacc aaaccagcag ctcattttct acccaagcca     600
ttggaagttg ccatgtaccg agaaccatct ttgcatgatg ttggggaaac ggtcccgaag     660
cctggggtga cgccaagtaa aagcacaagt gcgtctgcaa taatgaatgg aggcaaacca     720
gtcaacaaga gtaagacaac atagccagat cctcacaggt gttgtgactt attcgtcctg     780
agcacagttg agtgatttat cctcaccaga cattcctgct ccgtggctga agagcagcag     840
gaagtaagct aatgcttatt ctttgctgtc tccgaacttc tctgttgcaa gtggataaat     900
ctcaacctgt tgcacccccc acaacaagaa gacacctgga taaccagcta aactcagacc     960
atggaatgcc ctaccagata tggaatgcct ttttaatatc ttttctgtga ctgtgacact    1020
tcatgtgaat gacatacttc acaagtacac tcgatacctt gcctgctgac agctacccat    1080
aatccttttt gagtcctgtt tcagcgaaat ctatgtgttt aagttcaatt ttgtagcaca    1140
caaataatat tgagtaattt ctagttagac gctgtaaacc tgtgctatta cggatttctc    1200
ttcttcccat ttttacaggg ctgctcgctc cactgtctgt gaccttttgc agggattttg    1260
ttcctctaaa tcttaaatgt tgcagttggc ttaggtcgga gagcaatcag ggaatcagga    1320
agccttctaa acctattatt acaaattgca tctataaaga aagattaaga aagattgttg    1380
tctctggctc acactatcga ttaaacacac atatacgctc tgtccagtag cagatactgt    1440
gctcccaagg tcggcattgc ctgggtggga aatggctcaa acacaatcca gggaagctct    1500
ctatgatatg tgtttgacat ccccctctag tttctttgtg tgtgtgtgtt ttatacatat    1560
cacaagctta ctggtaatgg taacatttgc cttgcccagc gagcaagacc cactggtttt    1620
tgagaaagtg ggtccaaaga tttctgtagg ccttgtaggc ctgattaagg ttcatttttc    1680
atctattaat tctcattatt tggaaaaaaa aaaaaaggaa aatcagtaat tataacctac    1740
aagaattgcg ctacctaaat ccatttcaga tatactccgt cctgttttta atgaaccaaa    1800
cttaacgcca tccccgtttc tggctgcgtt cccctcatac tcagcagagc atgggcaaga    1860
cggctgttgt gttctttcct gcagcagcaa tgcaaacgtt agttataaat taattagact    1920
ttaatatttt tggtgtttaa tgacaagttt ttaaactgga catattagga aaaatatttt    1980
ttttagctca gcatgctgag tccggtactg tgtatttcac cagtacatgc ctctagctca    2040
gcatctgggg ctcatgttgc ccagtggctg ggttagaggt gccttgccat gatctcagaa    2100
```

```
tacagtctgt tgaattatcc tagatgaaaa taaaggcaaa ccaacacatt catccatgag   2160

gattttggtc cattccattt attttctttt attttgcatt cttaatttcc tttttagttt   2220

aacactgttt gtttgagctt agggaagaca actaccaaga aaggccagga acagttgact   2280

acacaatgaa gattccatgc aaaatgttca atattggatc taaaggggtt caaaatgttt   2340

catactaaac tgtttgggaa tttatttgtt aactctgtgt acacctaata aaattcaatg   2400

ttttcttctc agaagagttc attgagacca aactgaacct catttattga aaattatatg   2460

tgggatcaat gtactggcct cttgttattc tttctatgtg ggaggatgac ccagtcatca   2520

ttttccccat ctgcactgta tttattggga aattattttg tcactgcttt cataaatctt   2580

cttcatgaca gcccttgccc agcattaaaa aattctggcc tgcttagctg attaaaggtt   2640

tagtagaaat ttaactgttt gtttatgctt atttcatttt catattggat tctacttgaa   2700

taaataaaaa gttagcagaa                                                2720


<210> SEQ ID NO 168
<211> LENGTH: 247
<212> TYPE: PRT
<213> ORGANISM: Homo sapiens

<400> SEQUENCE: 168

Met Ala Ala Ala Ile Ala Ser Gly Leu Ile Arg Gln Lys Arg Gln Ala
1               5                   10                  15

Arg Glu Gln His Trp Asp Arg Pro Ser Ala Ser Arg Arg Arg Ser Ser
            20                  25                  30

Pro Ser Lys Asn Arg Gly Leu Cys Asn Gly Asn Leu Val Asp Ile Phe
        35                  40                  45

Ser Lys Val Arg Ile Phe Gly Leu Lys Lys Arg Arg Leu Arg Arg Gln
    50                  55                  60

Asp Pro Gln Leu Lys Gly Ile Val Thr Arg Leu Tyr Cys Arg Gln Gly
65                  70                  75                  80

Tyr Tyr Leu Gln Met His Pro Asp Gly Ala Leu Asp Gly Thr Lys Asp
                85                  90                  95

Asp Ser Thr Asn Ser Thr Leu Phe Asn Leu Ile Pro Val Gly Leu Arg
            100                 105                 110

Val Val Ala Ile Gln Gly Val Lys Thr Gly Leu Tyr Ile Ala Met Asn
        115                 120                 125

Gly Glu Gly Tyr Leu Tyr Pro Ser Glu Leu Phe Thr Pro Glu Cys Lys
    130                 135                 140

Phe Lys Glu Ser Val Phe Glu Asn Tyr Tyr Val Ile Tyr Ser Ser Met
145                 150                 155                 160

Leu Tyr Arg Gln Gln Glu Ser Gly Arg Ala Trp Phe Leu Gly Leu Asn
                165                 170                 175

Lys Glu Gly Gln Ala Met Lys Gly Asn Arg Val Lys Lys Thr Lys Pro
            180                 185                 190

Ala Ala His Phe Leu Pro Lys Pro Leu Glu Val Ala Met Tyr Arg Glu
        195                 200                 205

Pro Ser Leu His Asp Val Gly Glu Thr Val Pro Lys Pro Gly Val Thr
    210                 215                 220

Pro Ser Lys Ser Thr Ser Ala Ser Ala Ile Met Asn Gly Gly Lys Pro
225                 230                 235                 240

Val Asn Lys Ser Lys Thr Thr
                245
```

```
<210> SEQ ID NO 169
<211> LENGTH: 2175
<212> TYPE: DNA
<213> ORGANISM: Homo sapiens

<400> SEQUENCE: 169

agtacagtat aaaacttcac agtgccaata ccatgaagag gagctcagac agctcttacc      60

acatgataca agagccggct ggtggaagag tggggaccag aaagagaatt tgctgaagag     120

gagaaggaaa aaaaaaacac caaaaaaaaa aataaaaaaa tccacacaca caaaaaaacc     180

tgcgcgtgag gggggaggaa aagcagggcc ttttaaaaag gcaatcacaa caacttttgc     240

tgccaggatg cccttgcttt ggctgagagg atttctgttg gcaagttgct ggattatagt     300

gaggagttcc cccaccccag gatccgaggg gcacagcgcg gcccccgact gtccgtcctg     360

tgcgctggcc gccctcccaa aggatgtacc caactctcag ccagagatgg tggaggccgt     420

caagaagcac attttaaaca tgctgcactt gaagaagaga cccgatgtca cccagccggt     480

acccaaggcg gcgcttctga acgcgatcag aaagcttcat gtgggcaaag tcggggagaa     540

cgggtatgtg gagatagagg atgacattgg aaggagggca gaaatgaatg aacttatgga     600

gcagacctcg gagatcatca cgtttgccga gtcaggaaca gccaggaaga cgctgcactt     660

cgagatttcc aaggaaggca gtgacctgtc agtggtggag cgtgcagaag tctggctctt     720

cctaaaagtc cccaaggcca acaggaccag gaccaaagtc accatccgcc tcttccagca     780

gcagaagcac ccgcagggca gcttggacac aggggaagag gccgaggaag tgggcttaaa     840

gggggagagg agtgaactgt tgctctctga aaaagtagta gacgctcgga agagcacctg     900

gcatgtcttc cctgtctcca gcagcatcca gcggttgctg gaccagggca agagctccct     960

ggacgttcgg attgcctgtg agcagtgcca ggagagtggc gccagcttgg ttctcctggg    1020

caagaagaag aagaaagaag aggaggggga agggaaaaag aagggcggag gtgaaggtgg    1080

ggcaggagca gatgaggaaa aggagcagtc gcacagacct ttcctcatgc tgcaggcccg    1140

gcagtctgaa gaccaccctc atcgccggcg tcggcggggc ttggagtgtg atggcaaggt    1200

caacatctgc tgtaagaaac agttctttgt cagtttcaag gacatcggct ggaatgactg    1260

gatcattgct ccctctggct atcatgccaa ctactgcgag ggtgagtgcc cgagccatat    1320

agcaggcacg tccgggtcct cactgtcctt ccactcaaca gtcatcaacc actaccgcat    1380

gcggggccat agcccctttg ccaacctcaa atcgtgctgt gtgcccacca agctgagacc    1440

catgtccatg ttgtactatg atgatggtca aaacatcatc aaaaaggaca ttcagaacat    1500

gatcgtggag gagtgtgggt gctcatagag ttgcccagcc caggggggaaa gggagcaaga    1560

gttgtccaga gaagacagtg gcaaaatgaa gaaattttta aggtttctga gttaaccaga    1620

aaaatagaaa ttaaaaacaa aacaaaaaaa aaaacaaaaa aaaacaaaag taaattaaaa    1680

acaaaacctg atgaaacaga tgaaggaaga tgtggaaaaa atccttagcc agggctcaga    1740

gatgaagcag tgaaagagac aggaattggg agggaaaggg agaatggtgt accctttatt    1800

tcttctgaaa tcacactgat gacatcagtt gtttaaacgg ggtattgtcc tttcccccct    1860

tgaggttccc ttgtgagcct tgaatcaacc aatctagtct gcagtagtgt ggactagaac    1920

aacccaaata gcatctagaa agccatgagt ttgaaagggc ccatcacagg cactttccta    1980

cccaattacc caggtcataa ggtatgtctg tgtgacactt atctctgtgt atatcagcat    2040

acacacacac acacacacac acacacacac acacaggcat ttccacacat tacatatata    2100

cacatactgg taaaagaaca atcgtgtgca ggtggtcaca cttccttttt ctgtaccact    2160
```

```
tttgcaacaa aacaa                                                        2175


<210> SEQ ID NO 170
<211> LENGTH: 426
<212> TYPE: PRT
<213> ORGANISM: Homo sapiens

<400> SEQUENCE: 170

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365
```

```
His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425


<210> SEQ ID NO 171
<211> LENGTH: 2583
<212> TYPE: DNA
<213> ORGANISM: Homo sapiens

<400> SEQUENCE: 171

agccggtccc cgccgccgcc gcccttcgcg ccctgggcca tctccctccc acctccctcc      60

gcggagcagc cagacagcga gggccccggc cgggggcagg ggggacgccc cgtccggggc     120

acccccccgg ctctgagccg cccgcggggc cggcctcggc ccggagcgga ggaaggagtc     180

gccgaggagc agcctgaggc cccagagtct gagacgagcc gccgccgccc ccgccactgc     240

ggggaggagg gggaggagga gcgggaggag ggacgagctg gtcgggagaa gaggaaaaaa     300

acttttgaga cttttccgtt gccgctggga gccggaggcg cggggacctc ttggcgcgac     360

gctgccccgc gaggaggcag gacttgggga ccccagaccg cctccctttg ccgccgggga     420

cgcttgctcc ctccctgccc cctacacggc gtccctcagg cgcccccatt ccggaccagc     480

cctcgggagt cgccgacccg gcctcccgca aagacttttc cccagacctc gggcgcaccc     540

cctgcacgcc gccttcatcc ccggcctgtc tcctgagccc ccgcgcatcc tagacccttt     600

ctcctccagg agacggatct ctctccgacc tgccacagat cccctattca agaccaccca     660

ccttctggta ccagatcgcg cccatctagg ttatttccgt gggatactga gacacccccg     720

gtccaagcct cccctccacc actgcgccct tctccctgag gacctcagct ttccctcgag     780

gccctcctac cttttgccgg gagaccccca gcccctgcag ggcggggcc tccccaccac     840

accagccctg ttcgcgctct cggcagtgcc ggggggcgcc gcctccccca tgccgccctc     900

cgggctgcgg ctgctgccgc tgctgctacc gctgctgtgg ctactggtgc tgacgcctgg     960

ccggccggcc gcgggactat ccacctgcaa gactatcgac atggagctgg tgaagcggaa    1020

gcgcatcgag gccatccgcg gccagatcct gtccaagctg cggctcgcca gcccccgag    1080

ccagggggag gtgccgcccg gcccgctgcc cgaggccgtg ctcgccctgt acaacagcac    1140

ccgcgaccgg gtggccgggg agagtgcaga accggagccc gagcctgagg ccgactacta    1200

cgccaaggag gtcacccgcg tgctaatggt ggaaacccac aacgaaatct atgacaagtt    1260

caagcagagt acacacagca tatatatgtt cttcaacaca tcagagctcc gagaagcggt    1320

acctgaaccc gtgttgctct cccgggcaga gctgcgtctg ctgaggctca agttaaaagt    1380

ggagcagcac gtggagctgt accagaaata cagcaacaat tcctggcgat acctcagcaa    1440

ccggctgctg gcacccagcg actcgccaga gtggttatct tttgatgtca ccggagttgt    1500

gcggcagtgg ttgagccgtg gaggggaaat tgagggcttt cgccttagcg cccactgctc    1560

ctgtgacagc agggataaca cactgcaagt ggacatcaac gggttcacta ccggccgccg    1620

aggtgacctg gccaccattc atggcatgaa ccggcctttc ctgcttctca tggccacccc    1680

gctggagagg gcccagcatc tgcaaagctc ccggcaccgc cgagccctgg acaccaacta    1740

ttgcttcagc tccacggaga agaactgctg cgtgcggcag ctgtacattg acttccgcaa    1800
```

```
ggacctcggc tggaagtgga tccacgagcc caagggctac catgccaact tctgcctcgg   1860

gccctgcccc tacatttgga gcctggacac gcagtacagc aaggtcctgg ccctgtacaa   1920

ccagcataac ccgggcgcct cggcggcgcc gtgctgcgtg ccgcaggcgc tggagccgct   1980

gcccatcgtg tactacgtgg gccgcaagcc caaggtggag cagctgtcca acatgatcgt   2040

gcgctcctgc aagtgcagct gaggtcccgc cccgccccgc cccgccccgg caggcccggc   2100

cccaccccgc cccgcccccg ctgccttgcc catgggggct gtatttaagg acacccgtgc   2160

cccaagccca cctggggccc cattaaagat ggagagagga ctgcggatct ctgtgtcatt   2220

gggcgcctgc ctggggtctc catccctgac gttcccccac tcccactccc tctctctccc   2280

tctctgcctc ctcctgcctg tctgcactat tcctttgccc ggcatcaagg cacaggggac   2340

cagtggggaa cactactgta gttagatcta tttattgagc accttgggca ctgttgaagt   2400

gccttacatt aatgaactca ttcagtcacc atagcaacac tctgagatgc agggactctg   2460

ataacaccca ttttaaaggt gaggaaacaa gcccagagag gttaagggag gagttcctgc   2520

ccaccaggaa cctgctttag tgggggatag tgaagaagac aataaaagat agtagttcag   2580

gcc                                                                 2583
```

<210> SEQ ID NO 172
<211> LENGTH: 390
<212> TYPE: PRT
<213> ORGANISM: Homo sapiens

<400> SEQUENCE: 172

```
Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220
```

```
Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390
```

<210> SEQ ID NO 173
<211> LENGTH: 5966
<212> TYPE: DNA
<213> ORGANISM: Homo sapiens

<400> SEQUENCE: 173

```
gtgatgttat ctgctggcag cagaaggttc gctccgagcg gagctccaga agctcctgac      60

aagagaaaga cagattgaga tagagataga aagagaaaga gagaaagaga cagcagagcg     120

agagcgcaag tgaaagaggc aggggagggg gatggagaat attagcctga cggtctaggg     180

agtcatccag gaacaaactg aggggctgcc cggctgcaga caggaggaga cagagaggat     240

ctattttagg gtggcaagtg cctacctacc ctaagcgagc aattccacgt tggggagaag     300

ccagcagagg ttgggaaagg gtgggagtcc aagggagccc ctgcgcaacc ccctcaggaa     360

taaaactccc cagccagggt gtcgcaaggg ctgccgttgt gatccgcagg gggtgaacgc     420

aaccgcgacg gctgatcgtc tgtggctggg ttggcgtttg gagcaagaga aggaggagca     480

ggagaaggag ggagctggag gctggaagcg tttgcaagcg gcggcggcag caacgtggag     540

taaccaagcg ggtcagcgcg cgcccgccag ggtgtaggcc acggagcgca gctcccagag     600

caggatccgc gccgcctcag cagcctctgc ggcccctgcg gcacccgacc gagtaccgag     660

cgccctgcga agcgcaccct cctccccgcg gtgcgctggg ctcgccccca gcgcgcgcac     720

acgcacacac acacacacac acacacacgc acgcacacac gtgtgcgctt ctctgctccg     780

gagctgctgc tgctcctgct ctcagcgccg cagtggaagg caggaccgaa ccgctccttc     840

tttaaatata taaatttcag cccaggtcag cctcggcggc ccccctcacc gcgctcccgg     900

cgcccctccc gtcagttcgc cagctgccag ccccgggacc ttttcatctc ttcccttttg     960

gccggaggag ccgagttcag atccgccact ccgcacccga gactgacaca ctgaactcca    1020

cttcctcctc ttaaatttat ttctacttaa tagccactcg tctctttttt tccccatctc    1080

attgctccaa gaattttttt cttcttactc gccaaagtca gggttccctc tgcccgtccc    1140
```

```
gtattaatat ttccactttt ggaactactg gccttttctt tttaaaggaa ttcaagcagg   1200
atacgttttt ctgttgggca ttgactagat tgtttgcaaa agtttcgcat caaaaacaac   1260
aacaacaaaa aaccaaacaa ctctccttga tctatacttt gagaattgtt gatttctttt   1320
ttttattctg acttttaaaa acaacttttt tttccacttt tttaaaaaat gcactactgt   1380
gtgctgagcg cttttctgat cctgcatctg gtcacggtcg cgctcagcct gtctacctgc   1440
agcacactcg atatggacca gttcatgcgc aagaggatcg aggcgatccg cgggcagatc   1500
ctgagcaagc tgaagctcac cagtccccca gaagactatc ctgagcccga ggaagtcccc   1560
ccggaggtga tttccatcta caacagcacc agggacttgc tccaggagaa ggcgagccgg   1620
agggcggccg cctgcgagcg cgagaggagc gacgaagagt actacgccaa ggaggtttac   1680
aaaatagaca tgccgccctt cttcccctcc gaaactgtct gcccagttgt tacaacaccc   1740
tctggctcag tgggcagctt gtgctccaga cagtcccagg tgctctgtgg gtaccttgat   1800
gccatcccgc ccactttcta cagaccctac ttcagaattg ttcgatttga cgtctcagca   1860
atggagaaga atgcttccaa tttggtgaaa gcagagttca gagtctttcg tttgcagaac   1920
ccaaaagcca gagtgcctga acaacggatt gagctatatc agattctcaa gtccaaagat   1980
ttaacatctc caacccagcg ctacatcgac agcaaagttg tgaaaacaag agcagaaggc   2040
gaatggctct ccttcgatgt aactgatgct gttcatgaat ggcttcacca taaagacagg   2100
aacctgggat ttaaaataag cttacactgt ccctgctgca cttttgtacc atctaataat   2160
tacatcatcc caaataaaag tgaagaacta gaagcaagat ttgcaggtat tgatggcacc   2220
tccacatata ccagtggtga tcagaaaact ataaagtcca ctaggaaaaa aaacagtggg   2280
aagaccccac atctcctgct aatgttattg ccctcctaca gacttgagtc acaacagacc   2340
aaccggcgga agaagcgtgc tttggatgcg gcctattgct ttagaaatgt gcaggataat   2400
tgctgcctac gtccacttta cattgatttc aagagggatc tagggtggaa atggatacac   2460
gaacccaaag ggtacaatgc caacttctgt gctggagcat gcccgtattt atggagttca   2520
gacactcagc acagcagggt cctgagctta tataatacca taaatccaga agcatctgct   2580
tctccttgct gcgtgtccca agatttagaa cctctaacca ttctctacta cattggcaaa   2640
acacccaaga ttgaacagct ttctaatatg attgtaaagt cttgcaaatg cagctaaaat   2700
tcttggaaaa gtggcaagac caaaatgaca atgatgatga taatgatgat gacgacgaca   2760
acgatgatgc ttgtaacaag aaaacataag agagccttgg ttcatcagtg ttaaaaaatt   2820
tttgaaaagg cggtactagt tcagacactt tggaagtttg tgttctgttt gttaaaactg   2880
gcatctgaca caaaaaaagt tgaaggcctt attctacatt tcacctactt tgtaagtgag   2940
agagacaaga agcaaatttt ttttaaagaa aaaaataaac actggaagaa tttattagtg   3000
ttaattatgt gaacaacgac aacaacaaca acaacaacaa acaggaaaat cccattaagt   3060
ggagttgctg tacgtaccgt tcctatcccg cgcctcactt gatttttctg tattgctatg   3120
caataggcac ccttcccatt cttactctta gagttaacag tgagttattt attgtgtgtt   3180
actatataat gaacgtttca ttgcccttgg aaaataaaac aggtgtataa agtggagacc   3240
aaatactttg ccagaaactc atggatggct taaggaactt gaactcaaac gagccagaaa   3300
aaaagaggtc atattaatgg gatgaaaacc caagtgagtt attatatgac cgagaaagtc   3360
tgcattaaga taaagaccct gaaaacacat gttatgtatc agctgcctaa ggaagcttct   3420
tgtaaggtcc aaaaactaaa aagactgtta ataaaagaaa ctttcagtca gaataagtct   3480
gtaagttttt ttttttcttt ttaattgtaa atggttcttt gtcagtttag taaaccagtg   3540
```

```
aaatgttgaa atgttttgac atgtactggt caaacttcag accttaaaat attgctgtat   3600
agctatgcta taggtttttt cctttgtttt ggtatatgta accataccta tattattaaa   3660
atagatggat atagaagcca gcataattga aaacacatct gcagatctct tttgcaaact   3720
attaaatcaa aacattaact actttatgtg taatgtgtaa atttttacca tatttttat    3780
attctgtaat aatgtcaact atgatttaga ttgacttaaa tttgggctct ttttaatgat   3840
cactcacaaa tgtatgtttc ttttagctgg ccagtacttt tgagtaaagc ccctatagtt   3900
tgacttgcac tacaaatgca tttttttttt aataacattt gccctacttg tgctttgtgt   3960
ttctttcatt attatgacat aagctacctg ggtccacttg tcttttcttt tttttgtttc   4020
acagaaaaga tgggttcgag ttcagtggtc ttcatcttcc aagcatcatt actaaccaag   4080
tcagacgtta acaaattttt atgttaggaa aaggaggaat gttatagata catagaaaat   4140
tgaagtaaaa tgttttcatt ttagcaagga tttagggttc taactaaaac tcagaatctt   4200
tattgagtta agaaaagttt ctctaccttg gtttaatcaa tatttttgta aaatcctatt   4260
gttattacaa agaggacact tcataggaaa catctttttc tttagtcagg tttttaatat   4320
tcagggggaa attgaaagat atatatttta gtcgattttt caaaagggga aaaaagtcca   4380
ggtcagcata agtcattttg tgtatttcac tgaagttata aggtttttat aaatgttctt   4440
tgaaggggaa aaggcacaag ccaatttttc ctatgatcaa aaaattcttt ctttcctctg   4500
agtgagagtt atctatatct gaggctaaag tttaccttgc tttaataaat aatttgccac   4560
atcattgcag aagaggtatc ctcatgctgg ggttaataga atatgtcagt ttatcacttg   4620
tcgcttattt agctttaaaa taaaaattaa taggcaaagc aatggaatat ttgcagtttc   4680
acctaaagag cagcataagg aggcgggaat ccaaagtgaa gttgtttgat atggtctact   4740
tctttttggg aatttcctga ccattaatta aagaattgga tttgcaagtt tgaaaactgg   4800
aaaagcaaga gatgggatgc cataatagta aacagccctt gtgttggatg taacccaatc   4860
ccagatttga gtgtgtgttg attatttttt tgtcttccac ttttctatta tgtgtaaatc   4920
acttttattt ctgcagacat tttcctctca gataggatga cattttgttt tgtattattt   4980
tgtctttcct catgaatgca ctgataatat tttaaatgct ctattttaag atctcttgaa   5040
tctgtttttt tttttttaa tttgggggtt ctgtaaggtc tttatttccc ataagtaaat    5100
attgccatgg gaggggggtg gaggtggcaa ggaaggggtg aagtgctagt atgcaagtgg   5160
gcagcaatta tttttgtgtt aatcagcagt acaatttgat cgttggcatg gttaaaaaat   5220
ggaatataag attagctgtt ttgtattttg atgaccaatt acgctgtatt ttaacacgat   5280
gtatgtctgt ttttgtggtg ctctagtggt aaataaatta tttcgatgat atgtggatgt   5340
ctttttccta tcagtaccat catcgagtct agaaaacacc tgtgatgcaa taagactatc   5400
tcaagctgga aaagtcatac cacctttccg attgccctct gtgctttctc ccttaaggac   5460
agtcacttca gaagtcatgc tttaaagcac aagagtcagg ccatatccat caaggataga   5520
agaaatccct gtgccgtctt tttattccct tatttattgc tatttggtaa ttgtttgaga   5580
tttagtttcc atccagcttg actgccgacc agaaaaaatg cagagagatg tttgcaccat   5640
gctttggctt tctggttcta tgttctgcca acgccagggc caaaagaact ggtctagaca   5700
gtatcccctg tagccccata acttggatag ttgctgagcc agccagatat aacaagagcc   5760
acgtgctttc tggggttggt tgtttgggat cagctacttg cctgtcagtt tcactggtac   5820
cactgcacca caaacaaaaa aacccaccct atttcctcca attttttgg ctgctaccta    5880
```

```
caagaccaga ctcctcaaac gagttgccaa tctcttaata aataggatta ataaaaaaag   5940

taattgtgac tcaaaaaaaa aaaaaa                                         5966


<210> SEQ ID NO 174
<211> LENGTH: 442
<212> TYPE: PRT
<213> ORGANISM: Homo sapiens

<400> SEQUENCE: 174

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Thr Val Cys Pro Val Val Thr Thr Pro Ser Gly Ser Val
        115                 120                 125

Gly Ser Leu Cys Ser Arg Gln Ser Gln Val Leu Cys Gly Tyr Leu Asp
    130                 135                 140

Ala Ile Pro Pro Thr Phe Tyr Arg Pro Tyr Phe Arg Ile Val Arg Phe
145                 150                 155                 160

Asp Val Ser Ala Met Glu Lys Asn Ala Ser Asn Leu Val Lys Ala Glu
                165                 170                 175

Phe Arg Val Phe Arg Leu Gln Asn Pro Lys Ala Arg Val Pro Glu Gln
            180                 185                 190

Arg Ile Glu Leu Tyr Gln Ile Leu Lys Ser Lys Asp Leu Thr Ser Pro
        195                 200                 205

Thr Gln Arg Tyr Ile Asp Ser Lys Val Val Lys Thr Arg Ala Glu Gly
    210                 215                 220

Glu Trp Leu Ser Phe Asp Val Thr Asp Ala Val His Glu Trp Leu His
225                 230                 235                 240

His Lys Asp Arg Asn Leu Gly Phe Lys Ile Ser Leu His Cys Pro Cys
                245                 250                 255

Cys Thr Phe Val Pro Ser Asn Asn Tyr Ile Ile Pro Asn Lys Ser Glu
            260                 265                 270

Glu Leu Glu Ala Arg Phe Ala Gly Ile Asp Gly Thr Ser Thr Tyr Thr
        275                 280                 285

Ser Gly Asp Gln Lys Thr Ile Lys Ser Thr Arg Lys Lys Asn Ser Gly
    290                 295                 300

Lys Thr Pro His Leu Leu Leu Met Leu Leu Pro Ser Tyr Arg Leu Glu
305                 310                 315                 320

Ser Gln Gln Thr Asn Arg Arg Lys Lys Arg Ala Leu Asp Ala Ala Tyr
                325                 330                 335

Cys Phe Arg Asn Val Gln Asp Asn Cys Cys Leu Arg Pro Leu Tyr Ile
            340                 345                 350

Asp Phe Lys Arg Asp Leu Gly Trp Lys Trp Ile His Glu Pro Lys Gly
```

```
        355                 360                 365

Tyr Asn Ala Asn Phe Cys Ala Gly Ala Cys Pro Tyr Leu Trp Ser Ser
    370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
                405                 410                 415

Thr Ile Leu Tyr Tyr Ile Gly Lys Thr Pro Lys Ile Glu Gln Leu Ser
            420                 425                 430

Asn Met Ile Val Lys Ser Cys Lys Cys Ser
        435                 440


<210> SEQ ID NO 175
<211> LENGTH: 3183
<212> TYPE: DNA
<213> ORGANISM: Homo sapiens

<400> SEQUENCE: 175

gacagaagca atggccgagg cagaagacaa gccgaggtgc tggtgaccct gggcgtctga     60

gtggatgatt ggggctgctg cgctcagagg cctgcctccc tgccttccaa tgcatataac    120

cccacacccc agccaatgaa gacgagaggc agcgtgaaca aagtcattta gaaagccccc    180

gaggaagtgt aaacaaaaga gaaagcatga atggagtgcc tgagagacaa gtgtgtcctg    240

tactgccccc acctttagct gggccagcaa ctgcccggcc ctgcttctcc ccacctactc    300

actggtgatc ttttttttt tacttttttt tccctttct tttccattct cttttcttat    360

tttctttcaa ggcaaggcaa ggattttgat tttgggaccc agccatggtc cttctgcttc    420

ttctttaaaa tacccacttt ctccccatcg ccaagcggcg tttggcaata tcagatatcc    480

actctattta tttttaccta aggaaaaact ccagctccct tcccactccc agctgccttg    540

ccacccctcc cagccctctg cttgccctcc acctggcctg ctgggagtca gagcccagca    600

aaacctgttt agacacatgg acaagaatcc cagcgctaca aggcacacag tccgcttctt    660

cgtcctcagg gttgccagcg cttcctggaa gtcctgaagc tctcgcagtg cagtgagttc    720

atgcaccttc ttgccaagcc tcagtctttg ggatctgggg aggccgcctg gttttcctcc    780

ctccttctgc acgtctgctg ggtctcttc ctctccaggc cttgccgtcc ccctggcctc    840

tcttcccagc tcacacatga agatgcactt gcaaagggct ctggtggtcc tggccctgct    900

gaactttgcc acggtcagcc tctctctgtc cacttgcacc accttggact tcggccacat    960

caagaagaag agggtggaag ccattagggg acagatcttg agcaagctca ggctcaccag   1020

ccccccctgag ccaacggtga tgacccacgt cccctatcag gtcctggccc tttacaacag   1080

cacccgggag ctgctggagg agatgcatgg ggagagggag gaaggctgca cccaggaaaa   1140

caccgagtcg gaatactatg ccaaagaaat ccataaattc gacatgatcc aggggctggc   1200

ggagcacaac gaactggctg tctgccctaa aggaattacc tccaaggttt tccgcttcaa   1260

tgtgtcctca gtggagaaaa atagaaccaa cctattccga gcagaattcc gggtcttgcg   1320

ggtgcccaac cccagctcta agcggaatga gcagaggatc gagctcttcc agatccttcg   1380

gccagatgag cacattgcca aacagcgcta tatcggtggc aagaatctgc ccacacgggg   1440

cactgccgag tggctgtcct ttgatgtcac tgacactgtg cgtgagtggc tgttgagaag   1500

agagtccaac ttaggtctag aaatcagcat tcactgtcca tgtcacacct ttcagcccaa   1560

tggagatatc ctggaaaaca ttcacgaggt gatggaaatc aaattcaaag gcgtggacaa   1620
```

```
tgaggatgac catggccgtg gagatctggg gcgcctcaag aagcagaagg atcaccacaa   1680
ccctcatcta atcctcatga tgattccccc acaccggctc gacaacccgg gccagggggg   1740
tcagaggaag aagcgggctt tggacaccaa ttactgcttc cgcaacttgg aggagaactg   1800
ctgtgtgcgc cccctctaca ttgacttccg acaggatctg ggctggaagt gggtccatga   1860
acctaagggc tactatgcca acttctgctc aggcccttgc ccatacctcc gcagtgcaga   1920
cacaacccac agcacggtgc tgggactgta caacactctg aaccctgaag catctgcctc   1980
gccttgctgc gtgccccagg acctggagcc cctgaccatc ctgtactatg ttgggaggac   2040
ccccaaagtg gagcagctct ccaacatggt ggtgaagtct tgtaaatgta gctgagaccc   2100
cacgtgcgac agagagaggg gagagagaac caccactgcc tgactgcccg ctcctcggga   2160
aacacacaag caacaaacct cactgagagg cctggagccc acaaccttcg gctccgggca   2220
aatggctgag atggaggttt ccttttggaa catttctttc ttgctggctc tgagaatcac   2280
ggtggtaaag aaagtgtggg tttggttaga ggaaggctga actcttcaga acacacagac   2340
tttctgtgac gcagacagag gggatgggga tagaggaaag ggatggtaag ttgagatgtt   2400
gtgtggcaat gggatttggg ctaccctaaa gggagaagga agggcagaga atggctgggt   2460
cagggccaga ctggaagaca cttcagatct gaggttggat ttgctcattg ctgtaccaca   2520
tctgctctag ggaatctgga ttatgttata caaggcaagc attttttttt tttttttaaa   2580
gacaggttac gaagacaaag tcccagaatt gtatctcata ctgtctggga ttaagggcaa   2640
atctattact tttgcaaact gtcctctaca tcaattaaca tcgtgggtca ctacagggag   2700
aaaatccagg tcatgcagtt cctggcccat caactgtatt gggccttttg gatatgctga   2760
acgcagaaga aagggtggaa atcaaccctc tcctgtctgc cctctgggtc cctcctctca   2820
cctctccctc gatcatattt ccccttggac acttggttag acgccttcca ggtcaggatg   2880
cacatttctg gattgtggtt ccatgcagcc ttggggcatt atgggttctt cccccacttc   2940
ccctccaaga ccctgtgttc atttggtgtt cctggaagca ggtgctacaa catgtgaggc   3000
attcggggaa gctgcacatg tgccacacag tgacttggcc ccagacgcat agactgaggt   3060
ataaagacaa gtatgaatat tactctcaaa atctttgtat aaataaatat ttttggggca   3120
tcctggatga tttcatcttc tggaatattg tttctagaac agtaaaagcc ttattctaag   3180
gtg                                                                 3183
```

```
<210> SEQ ID NO 176
<211> LENGTH: 412
<212> TYPE: PRT
<213> ORGANISM: Homo sapiens

<400> SEQUENCE: 176

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Glu Gly Cys Thr Gln Glu Asn Thr
                85                  90                  95
```

```
Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410
```

```
<210> SEQ ID NO 177
<211> LENGTH: 2085
<212> TYPE: DNA
<213> ORGANISM: Homo sapiens

<400> SEQUENCE: 177

gtcctttcta gacagccccc tcctccaggc tcagggacct gtctggctgt gagctcccag      60

gaggtcccag gggtgtgacc tccctccctc cctccctccc tcttcccttc accccaggcc     120

agcccagggc cagctataaa gctggcccag cctggctctc agcacaccca gctgcctgag     180

accctccttc aacctcccta gaggacagcc ccactctgcc tcctgctccc ccagggcagc     240

accatgtggc cctgtggct ctgctgggca ctctgggtgc tgcccctggc tggccccggg     300
```

```
gcggccctga ccgaggagca gctcctgggc agcctgctgc ggcagctgca gctcagcgag    360

gtgcccgtac tggacagggc cgacatggag aagctggtca tccccgccca cgtgagggcc    420

cagtatgtag tcctgctgcg gcgcagccac ggggaccgct cccgcggaaa gaggttcagc    480

cagagcttcc gagaggtggc cggcaggttc ctggcgtcgg aggccgcgct gcacaggcac    540

gggcggctgt ccccgcgcag cgcccaggcc cgggtgaccg tcgagtggct gcgcgtccgc    600

gacgacggct ccaaccgcac ctccctcatc gactccaggc tggtgtccgt ccacgagagc    660

ggctggaagg ccttcgacgt gaccgaggcc gtgaacttct ggcagcagct gagccggccc    720

cggcagccgc tgctgctaca ggtgtcggtg cagagggagc atctgggccc gctggcgtcc    780

ggcgcccaca agctggtccg ctttgcctcg caggggggcgc cagccgggct tggggagccc    840

cagctggagc tgcacaccct ggacctcagg gactatggag ctcagggcga ctgtgaccct    900

gaagcaccaa tgaccgaggg cacccgctgc tgccgccagg agatgtacat tgacctgcag    960

gggatgaagt gggccaagaa ctgggtgctg gagcccccgg gcttcctggc ttacgagtgt   1020

gtgggcacct gccagcagcc cccggaggcc ctggccttca attggccatt tctggggccg   1080

cgacagtgta tcgcctcgga gactgcctcg ctgcccatga tcgtcagcat caaggaggga   1140

ggcaggacca ggccccaggt ggtcagcctg cccaacatga gggtgcagaa gtgcagctgt   1200

gcctcggatg ggcgctcgt gccaaggagg ctccagccat aggcgcctgg tgtatccatt    1260

gagccctcta actgaacgtg tgcatagagg tggtcttaat gtaggtctta actttatact   1320

tagcaagtta ctccatccca atttagtgct cctgtgtgac cttcgccctg tgtccttcca   1380

tttcctgtct ttcccgtcca tcacccatcc taagcactta cgtgagtaaa taatgcagct   1440

cagatgctga gctctagtag gaaatgctgg catgctgatt acaagataca gctgagcaat   1500

gcacacattt tcagctggga gtttctgttc tctggcaaat tcttcactga gtctggaaca   1560

ataataccct atgattagaa ctggggaaac agaactgaat tgctgtgtta tatgaggaat   1620

taaaaccttc aaatctctat ttcccccaaa tactgaccca ttctggactt ttgtaaacat   1680

acctaggccc ctgttcccct gagagggtgc taagaggaag gatgaagggc ttcaggctgg   1740

gggcagtgga cagggaattg ggatacctgg attctggttc tgacagggcc acaagctagg   1800

atctctaaca aacgcagaag gctttggctc gtcatttcct cttaaaaagg aggagctggg   1860

cttcagctct aagaacttca ttgccctggg gatcagacag cccctaccta cccctgccca   1920

ctcctctgga gactgagcct tgcccgtgca tatttaggtc atttcccaca ctgtcttaga   1980

gaacttgtca ccagaaacca catgtatttg catgtttttt gttaatttag ctaaagcaat   2040

tgaatgtaga tactcagaag aaataaaaaa tgatgtttca ctctg                   2085
```

<210> SEQ ID NO 178
<211> LENGTH: 332
<212> TYPE: PRT
<213> ORGANISM: Homo sapiens

<400> SEQUENCE: 178

```
Met Trp Pro Leu Trp Leu Cys Trp Ala Leu Trp Val Leu Pro Leu Ala
1               5                   10                  15

Gly Pro Gly Ala Ala Leu Thr Glu Glu Gln Leu Leu Gly Ser Leu Leu
            20                  25                  30

Arg Gln Leu Gln Leu Ser Glu Val Pro Val Leu Asp Arg Ala Asp Met
        35                  40                  45
```

-continued

```
Glu Lys Leu Val Ile Pro Ala His Val Arg Ala Gln Tyr Val Val Leu
    50                  55                  60

Leu Arg Arg Ser His Gly Asp Arg Ser Arg Gly Lys Arg Phe Ser Gln
65                  70                  75                  80

Ser Phe Arg Glu Val Ala Gly Arg Phe Leu Ala Ser Glu Ala Ala Leu
                85                  90                  95

His Arg His Gly Arg Leu Ser Pro Arg Ser Ala Gln Ala Arg Val Thr
            100                 105                 110

Val Glu Trp Leu Arg Val Arg Asp Asp Gly Ser Asn Arg Thr Ser Leu
        115                 120                 125

Ile Asp Ser Arg Leu Val Ser Val His Glu Ser Gly Trp Lys Ala Phe
    130                 135                 140

Asp Val Thr Glu Ala Val Asn Phe Trp Gln Gln Leu Ser Arg Pro Arg
145                 150                 155                 160

Gln Pro Leu Leu Leu Gln Val Ser Val Gln Arg Glu His Leu Gly Pro
                165                 170                 175

Leu Ala Ser Gly Ala His Lys Leu Val Arg Phe Ala Ser Gln Gly Ala
            180                 185                 190

Pro Ala Gly Leu Gly Glu Pro Gln Leu Glu Leu His Thr Leu Asp Leu
        195                 200                 205

Arg Asp Tyr Gly Ala Gln Gly Asp Cys Asp Pro Glu Ala Pro Met Thr
    210                 215                 220

Glu Gly Thr Arg Cys Cys Arg Gln Glu Met Tyr Ile Asp Leu Gln Gly
225                 230                 235                 240

Met Lys Trp Ala Lys Asn Trp Val Leu Glu Pro Pro Gly Phe Leu Ala
                245                 250                 255

Tyr Glu Cys Val Gly Thr Cys Gln Gln Pro Pro Glu Ala Leu Ala Phe
            260                 265                 270

Asn Trp Pro Phe Leu Gly Pro Arg Gln Cys Ile Ala Ser Glu Thr Ala
        275                 280                 285

Ser Leu Pro Met Ile Val Ser Ile Lys Glu Gly Gly Arg Thr Arg Pro
    290                 295                 300

Gln Val Val Ser Leu Pro Asn Met Arg Val Gln Lys Cys Ser Cys Ala
305                 310                 315                 320

Ser Asp Gly Ala Leu Val Pro Arg Arg Leu Gln Pro
                325                 330
```

METHODS FOR DIFFERENTIATION

CROSS-REFERENCE TO RELATED APPLICATIONS

This application is a continuation under 35 U.S.C. § 120 of co-pending U.S. application Ser. No. 15/317,205 filed Dec. 8, 2016, which is a 35 U.S.C. § 371 National Phase Entry Application of International Application No. PCT/US2015/034849 filed Jun. 9, 2015, which designates the U.S. and claims benefit under 35 U.S.C. § 119(e) of U.S. Provisional Application No. 62/010,244 filed Jun. 10, 2014, the contents of which are incorporated herein by reference in their entireties.

GOVERNMENT SUPPORT

This invention was made with federal funding under Grant No. GM26875 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on May 28, 2015, is named 002806-081571-PCT_SL.txt and is 314,859 bytes in size.

TECHNICAL FIELD

The technology described herein relates to methods of differentiation, e.g. differentiating stem cells.

BACKGROUND

As cells differentiate during embryonic development, they progress through a sequence of events, starting with stem cells, to intermediate cell types, and finally, to terminally differentiated cell types. This differentiation process can be induced in vitro. However, in vitro differentiation can be a time-consuming process with a significant lag time before differentiated cells are obtained.

SUMMARY

Described herein are methods relating to the inventors' discovery that early and simultaneous inhibition of the cell cycle as well as the introduction of differentiation factors can significantly reduce the time required for cells to differentiate in vitro.

In one aspect, described herein is a method of differentiating a stem cell, the method comprising: i) contacting the stem cell with one or more ectopic differentiation factors; and ii) inhibiting the cell cycle of the stem cell; wherein steps i) and ii) occur within 15 days of each other.

In some embodiments, steps i) and ii) occur within 14 days of each other. In some embodiments, steps i) and ii) occur within 13 days of each other. In some embodiments, steps i) and ii) occur within 12 days of each other. In some embodiments, steps i) and ii) occur within 11 days of each other. In some embodiments, steps i) and ii) occur within 10 days of each other. In some embodiments, steps i) and ii) occur within 9 days of each other. In some embodiments, steps i) and ii) occur within 8 days of each other. In some embodiments, steps i) and ii) occur within 7 days of each other. In some embodiments, steps i) and ii) occur within 6 days of each other. In some embodiments, steps i) and ii) occur within 5 days of each other. In some embodiments, steps i) and ii) occur within 4 days of each other. In some embodiments, steps i) and ii) occur within 3 days of each other. In some embodiments, steps i) and ii) occur within 2 days of each other. In some embodiments, steps i) and ii) occur within 24 hours of each other. In some embodiments, steps i) and ii) occur simultaneously.

In some embodiments, the differentiation factor is a terminal transcription factor. In some embodiments, the terminal transcription factor is selected from Table 1.

In some embodiments, the cell cycle is inhibited by one or more of the following: reducing or removing growth factors; reducing serum levels; reducing serum levels below 5%; contacting the cell with a PI3K inhibitor; contacting the cell with an E2F family transcription factor inhibitor; contacting the cell with a Myc inhibitor; contacting the cell with a MAPK inhibitor; contacting the cell with a MEK1/2 inhibitor; contacting the cell with a CDK inhibitor; contacting the cell with an Id inhibitor; contacting the cell with a Rb agonist; contacting the cell with a Ink family agonist; contacting the cell with a Cip/Kip family agonist; and culturing the cell in a media lacking a factor selected from the group consisting of: LIF; Bmp; Fgf; Activin; or TGFβ. In some embodiments, the PI3K inhibitor is LY294002. In some embodiments, the E2F transcription factor inhibitor is HLM006474. In some embodiments, the Myc inhibitor is JQ1 or 10058-F4. In some embodiments, the MAPK inhibitor is PD98059. In some embodiments, the CDK inhibitor is a CDK4 or CDK2 inhibitor. In some embodiments, the CDK inhibitor is p16, p15, p18, or p19. In some embodiments, the CDK inhibitor is p21, p27, or p57.

In some embodiments, the stem cell is an embryonic stem cell. In some embodiments, steps i) and ii) result in a population of cells comprising one or more terminally-differentiated cell types. In some embodiments, steps i) and ii) result in a population of cells comprising no more than 2 terminally-differentiated cell types. In some embodiments, steps i) and ii) result in a population of cells of which at least 50% are terminally-differentiated cells. In some embodiments, steps i) and ii) result in a population of cells of which at least 60% are terminally-differentiated cells. In some embodiments, steps i) and ii) result in a population of cells of which at least 70% are terminally-differentiated cells. In some embodiments, steps i) and ii) result in a population of cells of which at least 80% are terminally-differentiated cells.

BRIEF DESCRIPTION OF THE DRAWINGS

FIG. 1A depicts a schematic reconstructed summary of main network components and interactions in normal somatic cycling cells. Extracellular growth factors (GFs) either purified or in serum activate downstream signaling pathways (PI3K, MAPK), which then trigger a transcriptional activation (Myc, E2F) that drives the core cell cycle machinery (Cyclins and Cyclin-dependent kinases). For a full explanation and justification of the summary see FIGS. 7A-7C. The cellular behavior associated with this model is normal oscillatory cycling. FIG. 1B depicts a schematic of changes to the network that occur during terminal division arrest and differentiation. Cells switch to insulin signaling for survival and growth, and shut down cycling activity. Terminal transcription factors become fully active, leading to complete differentiation. FIG. 1C depicts a schematic composite adaptation of network for ES cells. ES cells are normally maintained by LIF and high serum or LIF and Bmp4. This hyper-activates PI3K, Myc, E2F, CDK2, and Id family activities. Meanwhile, MAPK, CDK4, p16 family, p21 family, and Rb family activities are highly suppressed. This leads to an ultra-rapid proliferation and short G1 phase.

FIG. 2A depicts a differentiation time course of ES cells to skeletal muscle when exposed to low serum vs high serum conditions. MyoD overexpression was initially induced with tamoxifen starting at Day −1 for 24 hours under ES conditions. LIF was removed at Day 0. Low serum was then initiated at different starting times beginning with Day 0. Cells were then fixed and immunostained for myosin heavy chain (MHC) expression. Differentiating cells in high serum were continuously split to prevent overgrowth. FIG. 2B depicts a comparison of differentiation efficiency generated by two types of defined media (N2B27) and 20% KOSR, low serum media (2% horse serum+insulin), and high serum media (15% FBS). Cells were removed from standard ES media (LIF and serum) and incubated in the specified media starting from Day 0 to Day 4. Continuation of LIF (1000 U/ml) or addition of Bmp4 (10 ng/ml) results in a strong block to muscle differentiation.

FIG. 8 depicts microscopy images demonstrating the morphology of differentiated muscle myotubes stained for myosin heavy chain and sarcomeric a-actinin.

FIG. 11A demonstrates rapid neuron formation from iNIL ES cells Beta-3 tubulin (terminal neuron marker) mRNA expression after 4 days in media of different growth factor content. FIG. 11B depicts a time course of gene expression for neuronal lineage factors and motor neuron terminal differentiation markers in growth factor-free (N2B27) media.

FIG. 12A demonstrates rapid kinetics of cardiomyocyte formation from GATA5-overexpressing ES cells. Cardiac troponin (terminal cardiomyocyte marker) mRNA expression after 4 days in media of different growth factor content. FIG. 12B depicts a time course of gene expression for cardiac lineage factors and cardiomyocyte terminal differentiation markers in growth factor-free (N2B27) media.

FIG. 13A demonstrates hepatoblast formation from Hnf4α-overexpressing ES cells. Alpha-fetoprotein mRNA expression after 4 days in media of different growth factor content. FIG. 13B depicts a time course of gene expression for hepatic lineage factors and hepatocyte markers in growth factor-free (N2B27) media.

DETAILED DESCRIPTION

Figure 1A:
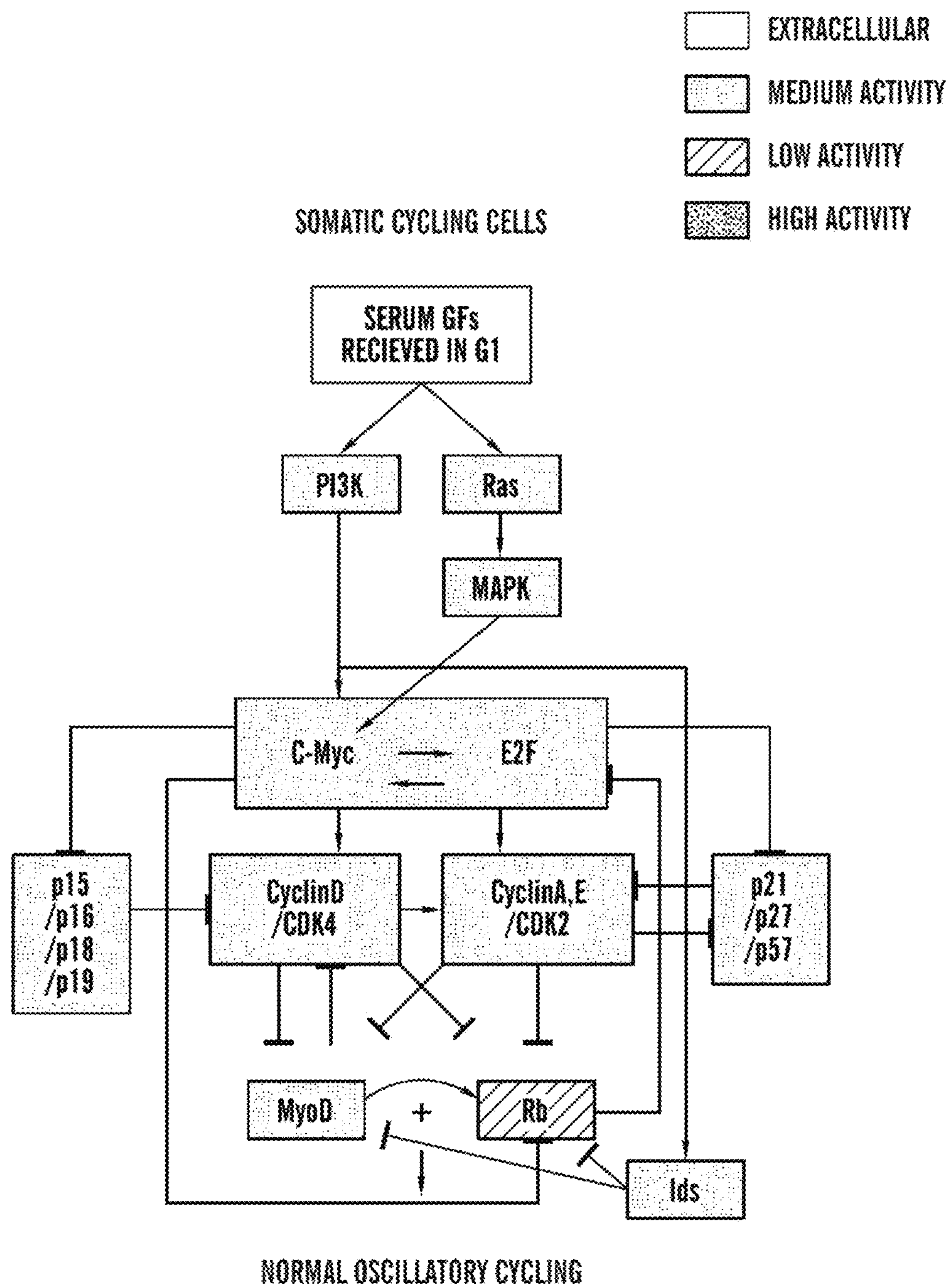
FIGS. 1A-1C depict an illustrative summary of the proliferation/differentiation network adapted for ES cells.

As described herein, the inventors's have found that inhibiting the cell cycle and introducing differentiation factors, when both steps are performed early in the differentiation process, significantly increases the rate of differentiation (e.g. the differentiation of stem cells to terminally differentiated cells). In one aspect, described herein is a method of differentiating a stem cell, the method comprising (i) contacting the stem cell with one or more ectopic differentiation factors and (ii) inhibiting the cell cycle of the stem cell. In some embodiments, the stem cell can be an embryonic stem cell. In some embodiments, the stem cell can be an adult stem cell. In some embodiments, the stem cell can be an induced pluripotent stem cell.

Accordingly, in some embodiments, step (i) (i.e., contacting the stem cell with one or more ectopic differentiation factors) and step (ii) (i.e., inhibiting the cell cycle of the stem cell) are performed within about 15 days or less of each other, e.g. within about 14 days or less of each other, within about 13 days or less of each other, within about 12 days or less of each other, within about 11 days or less of each other, within about 10 days or less of each other, within about 9 days or less of each other, within about 8 days or less of each other, within about 7 days or less of each other, within about 6 days or less of each other, within about 5 days or less of each other, within about 4 days or less of each other, within about 3 days or less of each other, within about 2 days or less of each other, or within about 1 day or less of each other. In some embodiments, steps (i) and (ii) can be performed about simultaneously.

In some embodiments, step (i) (i.e., contacting the stem cell with one or more ectopic differentiation factors) and step (ii) (i.e., inhibiting the cell cycle of the stem cell) are performed within 15 days of each other, e.g. within 14 days of each other, within 13 days of each other, within 12 days of each other, within 11 days of each other, within 10 days of each other, within 9 days of each other, within 8 days of each other, within 7 days of each other, within 6 days of each other, within 5 days of each other, within 4 days of each other, within 3 days of each other, within 2 days of each other, or within 1 day (e.g. within 24 hours) of each other. In some embodiments, steps (i) and (ii) can be performed simultaneously.

In some embodiments, steps (i) and (ii) can both be performed before the stem cell differentiates to an intermediate and/or terminally differentiated cell, e.g. while the stem cell still evidences a stem cell phenotype. In some embodiments, a stem cell can be an undifferentiated cell exhibiting both pluripotency (or totipotent) and capable of self-renewal. In some embodiments, a stem cell can be a cell expressing stem cell markers. Stem cell markers are known in the art and can include, by way of non-limiting example, Nanog, SSEA-1, TDGF-1, Sox2, Oct4, (for further detail see, e.g., Pazhianisamy MATER METHODS 2013 3:200 and Zhao et al. Molecules 2013 17:6196-6236; each of which is incorporated by reference herein in its entirety). Kits for determining if a cell expresses stem cell markers are commercially available, e.g. Cat No. ab109884 from AbCam, Cambridge, Mass.

As used herein, "ectopic differentiation factor" refers to an ectopic agent that increases and/or promotes the process of differentiation. Ectopic differentiation factors are known in the art and can include, e.g. nucleic acids encoding polypeptides, polypeptides, small molecules, growth factors, cytokines, and the like. The identity of the ectopic differentiation factor will vary according to the type of differentiated cell that is desired. Appropriate ectopic differentiation factors that permit the differentiation of specific differentiated cell types are known in the art, see, e.g. Examples of various differentiation agents are disclosed in U.S. patent application Ser. No. 2003/0022367, or Gimble et al., 1995; Lennon et al., 1995; Majumdar et al., 1998; Caplan and Goldberg, 1999; Ohgushi and Caplan, 1999; Pittenger et al., 1999; Caplan and Bruder, 2001; Fukuda, 2001; Worster et al., 2001; Zuk et al., 2001; Rosenbauer and Tenen Nature Reviews Immunology 2007 7:105-117; Hughes et al. Periodontology 2006 41:48-72; Loregger et al. Placenta 2003

A:S104-110; Florini et al. Ann Rev of Physiology 1991 53:201-216; Yamamizu et al. Stem Cell Reports 2013 1:545-559; James. Scientifica 2013 684736; and Mummery et al. Circulation Research 2012 111:344-358; each of which is incorporated by reference herein in its entirety.

In some embodiments, the ectopic differentiation factor can be a terminal transcription factor. As used herein, the term "terminal transcription factor" refers to a transcription factor that promotes the differentiation of a stem cell and/or intermediate or partially differentiated cell into a terminally differentiated cell. A cell that is contacted with a terminal transcription factor can be contacted with either an ectopic nucleic acid encoding a terminal transcription factor and/or an ectopic terminal transcription factor polypeptide.

Terminal transcription factors, and the differentiated phenotypes they promote are known in the art. Non-limiting examples of terminal transcription factors can include MyoD; MyoG, Myf5, Mrf4, Ngn family (e.g. Ngn1-3), NeuroD family (e.g. NeuroD1-3), Ascl family (e.g. Ascl1-2), Hb9, Zic1, Brn2, Myt11, Nurr1, Lmx1a, Gata family (e.g. Gatal, 2, 4, 5, 6), Tbx5, Mef2 family (e.g. Mef2a,b,c), Mesp1, Hnf/FoxA family (e.g. Hnf4α, FoxA2), Pdx1, MafA, Runx family (e.g. Runx2, Runx1t1), Mitf, Spi1, Nkx family (e.g. Nkx2.1, 2.2), C/EBP family (e.g. C/EBPα, β), Prdm family (e.g. Prdm1, 16), PPARγ, Sc1, Lmo2, Ldb1, E2A, Ebf, Sox9, Hlf, Prdm5, Pbx1, Zfp37, Isl1, Lhx3, Phox2a, Fezf2, Olig family (e.g. 1 and 2), Elf5, Irf2, Elf1, Tgif1, Ets1, Sox family (e.g. Sox4, 6, 9, 17), Bach2, Cdx2, Smyd1, Pax family (e.g. Pax3, 6, 7), Klf family (e.g. Klf4), basic helix-loop-helix factors. A non-limiting list of exemplary terminal transcription factors is provided in Table 1.

TABLE 1

Exemplary Terminal Transcription Factors

| Exemplary Associated Differentiated Cell Type | Terminal Transcription Factor | NCBI Gene ID for Human Gene |
|---|---|---|
| Myoblast | MyoD | 4654 |
| | MyoG | 4656 |
| | Myf5 | 4617 |
| | Mrf4 | 4618 |
| | Gata4 | 2626 |
| | Tbx5 | 6910 |
| | Mef2a | 4205 |
| | Mef2b | 100271849 |
| | Mef2c | 4208 |
| | Mesp1 | 55897 |
| | Pax7 | 5081 |
| | Smyd1 | 150572 |
| Neuron | Ngn1 | 4762 |
| | Ngn2 | 63973 |
| | Ngn3 | 50674 |
| | NeuroD1 | 4760 |
| | NeuroD2 | 4761 |
| | NeuroD3 | 4762 |
| | Ascl1 | 429 |
| | Ascl2 | 430 |
| | Zic1 | 7545 |
| | Brn2 | 5454 |
| | Nurr1 | 4929 |
| | Mytl1 | 23040 |
| | Lmx1a | 4009 |
| | Hlf | 3131 |
| | Zfp37 | 7539 |
| | Phox2a | 401 |
| | Fezf2 | 55079 |
| Motor neurons/Pancreatic cells | Hb9 | 3110 |
| | Isl1 | 3670 |
| Erythroid | Gata1 | 2623 |
| | Ldb1 | 8861 |
| Haemotopoietic and Endocrine lineages | Gata2 | 2624 |

TABLE 1-continued

Exemplary Terminal Transcription Factors

| Exemplary Associated Differentiated Cell Type | Terminal Transcription Factor | NCBI Gene ID for Human Gene |
|---|---|---|
| Myocardial and endodermal lineages | Gata5 | 140628 |
| Endodermal and Mesodermal lineages | Gata6 | 2627 |
| Hepatocyte (also liver, kidney, & intestinal cells) | Hnf4α | 3172 |
| Hepatocytes | FoxA2 | 3170 |
| Pancreatic | Pdx1 | 3651 |
| | MafA | 389692 |
| Osteoblast | Runx2 | 860 |
| | Prdm5 | 11107 |
| | Pbx1 | 5087 |
| Melanocytes | Mitf | 4286 |
| Myeloid, B lymphoid | Spi1 | 6688 |
| Thyroid | Nkx2.1 | 7080 |
| Central Nervous System | Nkx2.2 | 4821 |
| Adipocytes | C/EBPα | 1050 |
| | Prdm16 | 63976 |
| | C/EBPβ | 1051 |
| | PPARγ | 5468 |
| Trophoblasts, plasma cells | Prdm1 | 639 |
| Osteoblast, neurons, haemotopoietic lineages | Scl | 6886 |
| Haemotopoietic | Lmo2 | 4005 |
| | Runx1t1 | 862 |
| | Bach2 | 60468 |
| | Irf2 | 3660 |
| | Sox4 | 6659 |
| Lymphocytes | E2A | 6929 |
| | Elf1 | 1997 |
| B cells | Ebf | 1879 |
| Chondrocytes | Sox9 | 6662 |
| Motor Neurons | Lhx3 | 8022 |
| Oligodendrocytes | Olig1 | 116448 |
| | Olig2 | 10215 |
| Epithelial lineage | Elf5 | 2001 |
| | Klf4 | 9314 |
| Myeloid | Tgif1 | 7050 |
| Haemotopoietic and Epithelial lineages | Ets1 | 2113 |
| Neurons and chondrocytes | Sox6 | 55553 |
| Endoderm and Haemotopoietic lineages | Sox17 | 64321 |
| Intestinal | Cdx2 | 1045 |
| Muscle cells | Pax3 | 5077 |
| Nervous system and eye cells | Pax6 | 5080 |
| Skeletal muscle cells | MyoD | 4654 |
| Spinal motor neurons | Ngn2 | 63973 |
| | Isl1 | 3670 |
| | Lhx3 | 8022 |
| Cardiomyocytes | Gata5 | 140628 |
| Hepatocytes/Hepatoblasts | Hnf4α | 3172 |

In some embodiments, the stem cell is to be differentiated to a skeletal muscle phenotype and is contacted with the terminal transcription factor MyoD. In some embodiments, the stem cell is to be differentiated to a skeletal muscle phenotype and is contacted with the terminal transcription factor MyoD and the cell cycle is inhibited by reducing or removing growth factors. In some embodiments, the stem cell is to be differentiated to a skeletal muscle phenotype and is contacted with the terminal transcription factor MyoD and the cell cycle is inhibited by culturing the cell in a media lacking a factor selected from the group consisting of: LIF; Bmp; Fgf; Activin; or TGFβ. In some embodiments, the stem cell is to be differentiated to a skeletal muscle phenotype and is contacted with the terminal transcription factor MyoD and the cell cycle is inhibited by culturing the cell in a media lacking LIF.

In some embodiments, the stem cell is to be differentiated to a spinal motor neuron phenotype and is contacted with a terminal transcription factor selected from the group consisting of: Ngn2; Isl1; and Lhx3. In some embodiments, the stem cell is to be differentiated to a spinal motor neuron phenotype and is contacted with a terminal transcription factor selected from the group consisting of: Ngn2; Isl1; and Lhx3 and the cell cycle is inhibited by reducing or removing growth factors. In some embodiments, the stem cell is to be differentiated to a spinal motor neuron phenotype and is contacted with a terminal transcription factor selected from the group consisting of: Ngn2; Isl1; and Lhx3 and the cell cycle is inhibited by culturing the cell in a media lacking a factor selected from the group consisting of: LIF; Bmp; Fgf; Activin; or TGFβ. In some embodiments, the stem cell is to be differentiated to a spinal motor neuron phenotype and is contacted with a terminal transcription factor selected from the group consisting of: Ngn2; Isl1; and Lhx3 and the cell cycle is inhibited by culturing the cell in a media lacking LIF. In some embodiments, the stem cell is to be differentiated to a spinal motor neuron phenotype and is contacted with the terminal transcription factors Ngn2; Isl1; and Lhx3. In some embodiments, the stem cell is to be differentiated to a spinal motor neuron phenotype and is contacted with the terminal transcription factors Ngn2; Isl1; and Lhx3 and the cell cycle is inhibited by reducing or removing growth factors. In some embodiments, the stem cell is to be differentiated to a spinal motor neuron phenotype and is contacted with the terminal transcription factors Ngn2; Isl1; and Lhx3 and the cell cycle is inhibited by culturing the cell in a media lacking a factor selected from the group consisting of: LIF; Bmp; Fgf; Activin; or TGFβ. In some embodiments, the stem cell is to be differentiated to a spinal motor neuron phenotype and is contacted with the terminal transcription factors Ngn2; Isl1; and Lhx3 and the cell cycle is inhibited by culturing the cell in a media lacking LIF.

In some embodiments, the stem cell is to be differentiated to a cardiomyocyte phenotype and is contacted with the terminal transcription factor Gata5. In some embodiments, the stem cell is to be differentiated to a cardiomyocyte phenotype and is contacted with the terminal transcription factor Gata5 and the cell cycle is inhibited by reducing or removing growth factors. In some embodiments, the stem cell is to be differentiated to a cardiomyocyte phenotype and is contacted with the terminal transcription factor Gata5 and the cell cycle is inhibited by culturing the cell in a media lacking a factor selected from the group consisting of: LIF; Bmp; Fgf; Activin; or TGFβ. In some embodiments, the stem cell is to be differentiated to a cardiomyocyte phenotype and is contacted with the terminal transcription factor Gata5 and the cell cycle is inhibited by culturing the cell in a media lacking LIF.

In some embodiments, the stem cell is to be differentiated to a hepatocyte or hepatoblast phenotype and is contacted with the terminal transcription factor Hnf4α. In some embodiments, the stem cell is to be differentiated to a hepatocyte or hepatoblast phenotype and is contacted with the terminal transcription factor Hnf4α and the cell cycle is inhibited by reducing or removing growth factors. In some embodiments, the stem cell is to be differentiated to a hepatocyte or hepatoblast phenotype and is contacted with the terminal transcription factor Hnf4α and the cell cycle is inhibited by culturing the cell in a media lacking a factor selected from the group consisting of: LIF; Bmp; Fgf; Activin; or TGFβ. In some embodiments, the stem cell is to be differentiated to a hepatocyte or hepatoblast phenotype and is contacted with the terminal transcription factor Hnf4α and the cell cycle is inhibited by culturing the cell in a media lacking LIF.

In some embodiments, the ectopic differentiation factor can be a polypeptide. In some embodiments, the ectopic differentiation factor can be a terminal transcription factor polypeptide. In some embodiments, the ectopic differentiation factor can be a variant of a terminal transcription factor polypeptide. In some embodiments, the ectopic differentiation factor can be a functional fragment of a terminal transcription factor polypeptide.

As used herein, a given "polypeptide" can include the human polypeptide, as well as homologs from other species, including but not limited to bovine, dog, cat chicken, murine, rat, porcine, ovine, turkey, horse, fish, baboon and other primates. The terms also refer to fragments or variants of a polypeptide that maintain at least 50% of the activity or effect, e.g. transcriptional activation and/or suppression of a full-length polypeptide. Conservative substitution variants that maintain the activity of wildtype polypeptides will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by transcriptional activity assays and/or differentiation assays.

In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of an activity of the wildtype polypeptide. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of the wildtype polypeptide, e.g. 110%, 125%, 150%, 175%, 200%, 500%, 1000% or more.

One method of identifying amino acid residues which can be substituted is to align, for example, a human polypeptide with a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, a polypeptide, can comprise one or more amino acid substitutions or modifications. In some embodiments, the substitutions and/or modifications can prevent or reduce proteolytic degradation and/or prolong half-life of the polypeptide. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide as described herein can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide, as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

In some embodiments, the polypeptide can be a functional fragment of one of the amino acid sequences described herein. As used herein, a "functional fragment" is a fragment or segment of a polypeptide which retains the activity, e.g. the transcriptional activity, of the wildtype polypeptide. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

In some embodiments, a cell can be contacted with multiple ectopic differentiation factors, e.g. two or more terminal transcription factors, or a terminal transcription factor and cytokine.

As used herein "cell cycle" refers to the series of events involving the growth, replication, and division of a eukaryotic cell. A "phase of a cell cycle" or "cell cycle phase" refers to a distinct phase or period of the cell cycle, such as the mitosis phase (M phase), the first gap phase (G1 phase), the DNA synthesis phase (S phase), and the second gap phase (G2 phase). A "complete cell cycle" refers to entire single cell cycle including a G1 phase, S phase, G2 phase, and an M phase. Analysis of a complete cell cycle does not require beginning at a particular phase within the cell cycle. For example, a "complete cellcycle phase" may begin with an S phase and end at completion of G1 phase, or likewise, a "complete cell cycle phase" may begin with an M phase and end with completion of G2 phase. Inhibition of the cell cycle can comprise slowing the progression of a cell through the cycle, slowing the progression of a cell through a particular stage of the cell cycle, and/or arresting the cell at a particular point in the cell cycle. Slowing the progression of the cell constitutes a decrease in the rate at which the cell progresses through the cell cycle.

Methods of inhibiting the cell cycle can comprise contacting the cell with an agent that inhibits the cell cycle and/or removing an agent that promotes progression through the cell cycle. Agents for promoting or inhibiting cell cycle progression are known in the art. By way of non-limiting example, the cell cycle can be inhibited by: reducing or removing growth factors; reducing serum levels; reducing serum levels below about 5%; reducing serum levels below 5%; contacting the cell with a PI3K inhibitor; contacting the cell with an E2F family transcription factor inhibitor; contacting the cell with a Myc inhibitor; contacting the cell with a MAPK inhibitor; contacting the cell with a MEK1/2 inhibitor; contacting the cell with a CDK inhibitor; contacting the cell with an Id inhibitor; contacting the cell with a Rb agonist; contacting the cell with a Ink family agonist; contacting the cell with a Cip/Kip family agonist; culturing the cell in a media lacking a factor selected from the group consisting of: LIF; Bmp; Fgf; Activin; or TGFβ.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor, e.g. its ability to decrease the level and/or activity of the target, can be determined, e.g. by measuring the level of an expression product of and/or the activity of the target. Methods for measuring the level of a given mRNA and/or polypeptide are known to one of skill in the art, e.g. RTPCR can be used to determine the level of RNA and Western blotting with an antibody can be used to determine the level of a polypeptide. The activity of a target can be determined using methods known in the art and described herein, e.g. transcriptional activity assays. In some embodiments, the inhibitor can be an inhibitory nucleic acid; an aptamer; an antibody reagent; an antibody; or a small molecule.

As used herein, the term "agonist" refers to any agent that increases the level and/or activity of the target, e.g., of Rb, Ink family polypeptides, and/or Cip/Kip family polypeptides. As used herein, the term "agonist" refers to an agent which increases the expression and/or activity of the target by at least 10% or more, e.g. by 10% or more, 50% or more, 100% or more, 200% or more, 500% or more, or 1000% or more.

Phosphoinositide 3-kinases are a family of related enzymes that are capable of phosphorylating the 3 position hydroxyl group of the inositol ring of phosphatidylinositol. They are also known as phosphatidylinositol-3-kinases. PI3Ks interact with the IRS (Insulin receptor substrate) in order to regulate glucose uptake through a series of phosphorylation events. The phosphoinositol-3-kinase family is composed of Class I, II and Class III, with Class I the only ones able to convert PI(4,5)P2 to PI(3,4,5)P3 on the inner leaflet of the plasma membrane. As used herein, a "PI3K inhibitor" refers to an agent that inhibits the activity of PI3K, as measured by the level of phosphorylation of the 3 position hydroxyl group of the inositol ring of phosphatidylinositol, or as measured by the activity and/or phosphorylation (where increased phosphorylation indicates PI3K activity) of molecules downstream of PI3K. Examples of such downstream molecules are known in the art and can include, but are not limited to AKT, SGK, mTOR, GSK3β, PSD-95, S6, and 4EBP1. Methods of measuring the activity of PI3K, directly or indirectly are well known in the art, and include, by way of non-limiting example determining the level of phosphorylation of a molecule downstream of PI3K using phospho-isoform specific antibodies, which are commercially available (e.g. anti-phospho-AKT antibody, Cat No. ab66138 Abcam, Cambridge, Mass.). Non-limiting examples of PI3K inhibitors can include LY294002; BGT226; BEZ235; PI103, PI828. wortmannin, demethoxyviridin, IC486068, IC87114, GDC-0941, perifosine, CAL101, PX-866, IPI-145, BAY 80-6946, P6503, TGR1202, SF1126, INK1117, BKM120, IL147, XL765, Palomid 529, GSK1059615, ZSTK474, PWT33597, TG100-115, CAL263, GNE-447, CUDC-907, and AEZS-136.

An inhibitor of E2F family transcription factors can be an agent that inhibits the activity of a E2F transcription factor, as measured by the level of transcription of E2F targets (e.g. CCNA1, MYB, EB1, BRCA1, and TP53). Assays for E2F activity are known in the art and are commercially available (e.g. Cat. No. CCS-003L, Qiagen Valencia, Calif.). Non-limiting examples of E2F family transcription factors can include HLM006474.

An inhibitor of Myc can be an agent that inhibits the activity and/or level of Myc. Myc is a transcription factor that participates in cell proliferation and DNA replication. The sequence of Myc is known in a number of species, e.g. human Myc (NCBI Gene ID: 4609) mRNA (NCBI Ref Seq: NM_002467 (SEQ ID NO: 85)) and polypeptide (NP_002458 (SEQ ID NO: 86)) sequences. Myc activity can be measured, e.g. by the level of transcription of genes activated (e.g. CDK or MNT) or suppressed (e.g. Miz1) by Myc. Assays for Myc activity are known in the art and are commercially available (e.g. Cat. No. CCS-012L; Qiagen Valencia, Calif.). Non-limiting examples of Myc inhibitors can include JQ1; 10058-F4; and CAS 403811-55-21.

An inhibitor of MAPK can be an agent that inhibits the activity of a mitogen-activated protein kinase (MAPK), as measured by the level of phosphorylation of MAPK targets (e.g. ELK1 is a substrate of ERK1 and MK2 and MK3 are targets of p38 kinases). Assays for MAPK activity are known in the art and are commercially available (e.g. Cat. No. CS0250 from Sigma-Aldrich, St. Louis, Mo.). Non-limiting examples of MAPK inhibitors can include PD98059; SB203580; SB202190; and SP600125.

An inhibitor of CDK can be an agent that inhibits the activity of a cyclin-dependent kinase (CDK), as measured by the level of phosphorylation of CDK targets (e.g. CDK2 targets Rb, p53 and E2F are substrates of CDK2 and RB1 and MEP50 are substrates of CDK4). Assays for CDK activity are known in the art and are commercially available (e.g. Cat. No. PV3343 Invitrogen, Carlsbad, Calif.). In some embodiments, an inhibitor of CDK can inhibit CDK4 and/or CDK2. In some embodiments, an inhibitor of CDK can specifically inhibit CDK4 and/or CDK2. Non-limiting examples of CDK inhibitors can include p16; p15; p18; p19; p21; p27; p57; p1446A-05; PD-0332991; flavopiridol; aloisine A; AT7519; BS-181; butyrolactone I; purvalanol A; pruvalanol B; roscovitine; and WHI-P 180.

An inhibitor of Id can be an agent that inhibits the level and/or activity of inhibitor of DNA binding 1 (Id). Id forms heterodimers with helix-loop-helix transcription factors and inhibits their activyt. The sequence of Id is known in a number of species, e.g. human Id (NCBI Gene ID: 3397) mRNA (NCBI Ref Seq: NM_002165 (SEQ ID NO: 87)) and polypeptide (NP_002156 (SEQ ID NO: 88)) sequences. Id activity can be measured, e.g. by measuring the inhibition of DNA binding and/or transcriptional activation of helix-loop-helix transcription factors that can bind with Id. Non-limiting examples of Id inhibitors can include caveolin-1.

An agonist of Rb can be an agent that increases the level and/or activity of retinoblastoma 1 (Rb). Rb binds to and inhibits E2F transcription factors, thereby preventing progress through the cell cycle. The sequence of Rb is known in a number of species, e.g. human Rb (NCBI Gene ID: 5925) mRNA (NCBI Ref Seq: NM_000321 (SEQ ID NO: 89)) and polypeptide (NP_000312 (SEQ ID NO: 90)) sequences. Rb activity can be measured, e.g., by measuring binding to E2F transcription factors and/or transcription of E2F factors. Non-limiting examples of agonists of Rb can include Rb polypeptides or agonist fragments thereof and nucleic acids encoding a Rb polypeptide.

An agonist of Ink family proteins can be an agent that increase the level and/or activity of Ink family proteins (e.g. INK4 family, INK4A (NCBI Gene ID: 1029 (SEQ ID NOS 91-92)), INK4B (NCBI Gene ID: 1030 (SEQ ID NOS 93-94)), INK4C (NCBI Gene ID: 1031 (SEQ ID NOS 95-96)), and INK4D (NCBI Gene ID: 1032 (SEQ ID NOS 97-98))). INK family proteins bind and inhibit CDK4 and CDK6. Ink protein activity can be measured by measuring, e.g. the activity of CDK4 and/or CDK6 as described elsewhere herein and/or binding to CDK4 and/or CDK6. Non-limiting examples of agonists of Ink family polypeptides can include Ink family polypeptides or agonist fragments thereof and nucleic acids encoding an Ink family polypeptide.

An agonist of Cip/Kip family proteins can be an agent that increase the level and/or activity of Cip/Kip family proteins (e.g. Cip/Kip family, KIP1 (NCBI Gene ID: 1027 (SEQ ID NOS 99-100)), KIP2 (NCBI Gene ID: 1028 (SEQ ID NOS 101-102)), and CIP1 (NCBI Gene ID: 1026 (SEQ ID NOS 103-104))). Cip/Kip family proteins bind and inhibit CDK2. Cip/Kip protein activity can be measured by measuring, e.g. the activity of CDK2 as described elsewhere herein. Non-limiting examples of agonists of Cip/Kip family polypeptides can include Cip/Kip family polypeptides or agonist fragments thereof and nucleic acids encoding an Cip/Kip family polypeptide.

In some embodiments, inhibition of the cell cycle can be accomplished by removing and/or reducing the level of growth and/or signaling factors, e.g. by culturing the cell in media lacking or having reduced levels of one or more growth and/or signaling factors that promote the cell cycle. Non-limiting examples of such growth and/or signaling factors can include LIF (e.g., NCBI Gene ID: 3976 (SEQ ID NOS 105-106)), Bmp (e.g. NCBI Gene ID: 649 (SEQ ID NOS 107-108), 650 (SEQ ID NOS 109-110), 651 (SEQ ID NOS 111-112), 652 (SEQ ID NOS 113-114), 653 (SEQ ID NOS 115-116), 654 (SEQ ID NOS 117-118), 655 (SEQ ID NOS 119-120), 6565 (SEQ ID NOS 121-122), 51423 (SEQ ID NOS 123-124), and 27302 (SEQ ID NOS 125-126)), Fgf (e.g. one or more of NCBI Gene IDs: 2252 (SEQ ID NOS 127-128), 2255 (SEQ ID NOS 129-130), 9965 (SEQ ID NOS 131-132), 2249 (SEQ ID NOS 133-134), 2248 (SEQ ID NOS 135-136), 2257 (SEQ ID NOS 137-138), 8822 (SEQ ID NOS 139-140), 2251 (SEQ ID NOS 141-142), 27006 (SEQ ID NOS 143-144), 2256 (SEQ ID NOS 145-146), 2247 (SEQ ID NOS 147-148), 8074 (SEQ ID NOS 149-150), 2246 (SEQ ID NOS 151-152), 26291 (SEQ ID NOS 153-154), 2253 (SEQ ID NOS 155-156), 2254 (SEQ ID NOS 157-158), 2250 (SEQ ID NOS 159-160), 2258 (SEQ ID NOS 161-162), 8817 (SEQ ID NOS 163-164), 26281 (SEQ ID NOS 165-166), and 2259 (SEQ ID NOS 167-168)) Avtivin (e.g., NBCI Gene ID: 3624 (SEQ ID NOS 169-170)), and TGFβ (e.g. one or more of NCBI Gene IDs: 7040 (SEQ ID NOS 171-172), 7042 (SEQ ID NOS 173-174), 7043 (SEQ ID NOS 175-176), and 7044 (SEQ ID NOS 177-178)). In some embodiments, inhibiting the cell cycle can comprise culturing the cell in a media lacking one or more factors selected from the group consisting of: LIF; Bmp; Fgf; Activin; or TGFβ, e.g. lacking 1 of the factors, 2 of the factors, 3 of the factors, 4 of the factors, 5 of the factors, or more of the factors.

In some embodiments, contacting a cell with an agent can comprise contacting the cell with one dose of the agent. In some embodiments, contacting a cell with an agent can comprise contacting the cell with repeated doses of the agent. In some embodiments, contacting a cell with an agent can comprise maintaining a given concentration of the agent in the cell's environment, e.g. in the culture media. In some embodiments, contacting a cell with an agent can comprise maintaining at least a given minimum concentration of the agent in the cell's environment, e.g. in the culture media.

In some embodiments, the methods described herein can result in a population of cells comprising one or more terminally-differentiated cell types, e.g. 1 terminally-differentiated cell type, 2 terminally-differentiated cell types, 3 terminally-differentiated cell types, 4 terminally-differentiated cell types, 5 terminally-differentiated cell types, or more terminally-differentiated cell types. When discussing a population of cells that results from the methods described herein, the resulting population can be the population of cells existing at about 1 day to about 30 days after both steps (i) and (ii) have been performed.

In some embodiments, the methods described herein can result in a population of cells comprising no more than 2 terminally-differentiated cell types, e.g. 1 terminally-differentiated cell type or 2 terminally-differentiated cell types.

In some embodiments, the methods described herein can result in a population of cells of which at least about 50% of the cells are terminally-differentiated cell, e.g. about 50% or more of the cells are terminally-differentiated cells, about 60% or more of the cells are terminally-differentiated cells, about 70% or more of the cells are terminally-differentiated cells, about 80% or more of the cells are terminally-differentiated cells, about 90% or more of the cells are terminally-differentiated cells, about 95% or more of the cells are terminally-differentiated cells, or about 98% or more of the cells are terminally-differentiated cells. In some embodiments, the methods described herein can result in a population of cells of which at least 50% of the cells are terminally-differentiated cell, e.g. 50% or more of the cells are terminally-differentiated cells, 60% or more of the cells are terminally-differentiated cells, 70% or more of the cells are terminally-differentiated cells, 80% or more of the cells are terminally-differentiated cells, 90% or more of the cells are terminally-differentiated cells, 95% or more of the cells are terminally-differentiated cells, or 98% or more of the cells are terminally-differentiated cells.

Differentiated cells obtained in accordance with the methods described herein can be used, e.g. for cell therapy, autologous cell therapy, transplantation, wound healing or repair, in vitro studies of cell function, cell growth, cell differentiation, and/or screens for modulators of cell function and behavior (e.g. therapeutics, drug candidates, inhibitors or agonists of growth, function, and differentiation).

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon—carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, "ectopic" refers to a substance that is found in an unusual location and/or amount. An ectopic substance can be one that is normally found in a given cell, but at a much lower amount and/or at a different time.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The polypeptides of the present invention can be synthesized by using well known methods including recombinant methods and chemical synthesis. Recombinant methods of producing a polypeptide through the introduction of a vector including nucleic acid encoding the polypeptide into a suitable host cell are well known in the art, e.g., as described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

In some embodiments, the technology described herein relates to a nucleic acid encoding a polypeptide as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules include DNA, including genomic DNA or cDNA. Other suitable nucleic acid molecules include RNA, including mRNA. The nucleic acid molecule can be naturally occurring, as in genomic DNA, or it may be synthetic, i.e., prepared based upon human action, or may be a combination of the two. The nucleic acid molecule can also have certain modification(s) such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are linked between the 2'-oxygen and the 4'-carbon atoms with a methylene unit as described in U.S. Pat. No. 6,268,490, wherein both patent and patent application are incorporated herein by reference in their entirety.

In some embodiments, a nucleic acid encoding a polypeptide as described herein is comprised by a vector. In some of the aspects described herein, a nucleic acid sequence encoding a polypeptide as described herein is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

The term "progenitor cell" is used herein to refers to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only.

The term "embryonic stem cell" is used to refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. As indicated above, stem cells have been found resident in virtually every tissue. Accordingly, the technology described herein appreciates that stem cell populations can be isolated from virtually any animal tissue. As used herein, the term "adult cell" refers to a cell found throughout the body after embryonic development.

As used herein, the terms "iPS cell" and "induced pluripotent stem cell" are used interchangeably and refers to a pluripotent cell artificially derived (e.g., induced by complete or partial reversal) from a differentiated somatic cell (i.e. from a non-pluripotent cell). A pluripotent cell can differentiate to cells of all three developmental germ layers.

The term "derived from" used in the context of a cell derived from another cell means that a cell has stemmed from (e.g. changed from or was produced by) a cell which is a different cell type. In some instances, for example, a cell derived from an iPS cell refers to a cell which has differentiated from an iPS cell. Alternatively, a cell can be converted from one cell type to a different cell type by a process referred to as transdifferention or direct reprogramming. Alternatively, in the terms of iPS cells, a cell (e.g. an iPS cell) can be derived from a differentiated cell by a process referred to in the art as dedifferentiation or reprogramming.

The term "pluripotent" as used herein refers to a cell that can give rise to any type of cell in the body except germ line cells. The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages. Pluripotency is also evidenced by the expression of embryonic stem (ES) cell markers, although the preferred test for pluripotency is the demonstration of the capacity to differentiate into cells of all three germ layers, as detected using, for example, a nude mouse teratoma formation assay. iPS cells are pluripotent cells. Pluripotent cells undergo further differentiation into multipotent cells that are committed to give rise to cells that have a particular function. For example, multipotent cardiovascular stem cells give rise to the cells of the heart, including cardiomyocytes, as well as other cells involved in the vasculature of the heart.

The term "phenotype" refers to one or a number of total biological characteristics that define the cell or organism under a particular set of environmental conditions and factors, regardless of the actual genotype.

The term "lineages" as used herein refers to a term to describe cells with a common ancestry, for example cells that are derived from the same cardiovascular stem cell or other stem cell, or cells with a common developmental fate. By way of an example only, when referring to a cell that is of endoderm origin or is "endodermal linage," this means the cell was derived from an endodermal cell and can differentiate along the endodermal lineage restricted pathways, such as one or more developmental lineage pathways which give rise to definitive endoderm cells, which in turn can differentiate into liver cells, thymus, pancreas, lung and intestine.

In the context of cell ontogeny, the term "differentiated", or "differentiating" is a relative term. A "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an atrial precursor), and then to an end-stage differentiated cell, such as atrial cardiomyocytes or smooth muscle cells, which play a characteristic role in a certain tissue type, and may or may not retain the capacity to proliferate further. The term "differentiated cell" refers to any primary cell that is not, in its native form, pluripotent as that term is defined herein. The term a "differentiated cell" also encompasses cells that are partially differentiated, such as multipotent cells, or cells that are stable non-pluripotent partially reprogrammed cells. In some embodiments, a differentiated cell is a cell that is a stable intermediate cell, such as a non-pluripotent partially reprogrammed cell. It should be noted that placing many primary cells in culture can lead to some loss of fully differentiated characteristics. However, simply culturing such primary cells, e.g., after removal or isolateion from a tissue or organism does not render these cells non-differentated cells (e.g. undifferentiated cells) or pluripotent cells. The transition of a differentiated cell (including stable non-pluripotent partially reprogrammed cell intermediates) to pluripotency requires a reprogramming stimulus beyond the stimuli that lead to partial loss of differentiated character in culture.

The term "differentiation" as referred to herein refers to the process whereby a cell moves further down the developmental pathway and begins expressing markers and phenotypic characteristics known to be associated with a cell that are more specialized and closer to becoming terminally differentiated cells. The pathway along which cells progress from a less committed cell to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a more specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, in the context of this specification, the terms "differentiation" or "differentiated" refer to cells that are more specialized in their fate or function than at one time in their development. For example in the context of this application, a differentiated cell includes a cardiomyocyte which has differentiated from cardiovascular progenitor cell, where such cardiovascular progenitor cell can in some instances be derived from the differentiation of an ES cell, or alternatively from the differentiation of an induced pluripotent stem (iPS) cell, or in some embodiments from a human ES cell line. A cell that is "differentiated" relative to a progenitor cell has one or more phenotypic differences relative to that progenitor cell and characteristic of a more mature or specialized cell type. Phenotypic differences include, but are not limited to morphologic differences and differences in gene expression and biological activity, including not only the presence or absence of an expressed marker, but also differences in the amount of a marker and differences in the co-expression patterns of a set of markers.

The term "contacting" or "contact" as used herein in connection with contacting a cell with an agent as described herein, includes subjecting the cell to a culture medium which comprises that agent.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of differentiating a stem cell, the method comprising:
   i) contacting the stem cell with one or more ectopic differentiation factors; and
   ii) inhibiting the cell cycle of the stem cell;
   wherein steps i) and ii) occur within 15 days of each other.
2. The method of paragraph 1, wherein steps i) and ii) occur within 14 days of each other.
3. The method of paragraph 1, wherein steps i) and ii) occur within 13 days of each other.
4. The method of paragraph 1, wherein steps i) and ii) occur within 12 days of each other.
5. The method of paragraph 1, wherein steps i) and ii) occur within 11 days of each other.
6. The method of paragraph 1, wherein steps i) and ii) occur within 10 days of each other.
7. The method of paragraph 1, wherein steps i) and ii) occur within 9 days of each other.
8. The method of paragraph 1, wherein steps i) and ii) occur within 8 days of each other.
9. The method of paragraph 1, wherein steps i) and ii) occur within 7 days of each other.
10. The method of paragraph 1, wherein steps i) and ii) occur within 6 days of each other.
11. The method of paragraph 1, wherein steps i) and ii) occur within 5 days of each other.
12. The method of paragraph 1, wherein steps i) and ii) occur within 4 days of each other.

13. The method of paragraph 1, wherein steps i) and ii) occur within 3 days of each other.
14. The method of paragraph 1, wherein steps i) and ii) occur within 2 days of each other.
15. The method of paragraph 1, wherein steps i) and ii) occur within 24 hours of each other.
16. The method of paragraph 1, wherein steps i) and ii) occur simultaneously.
17. The method of any of paragraphs 1-16, wherein the differentiation factor is a terminal transcription factor.
18. The method of paragraph 17, wherein the terminal transcription factor is selected from Table 1.
19. The method of any of paragraphs 17-18, wherein the stem cell is to be differentiated to a skeletal muscle phenotype and is contacted with the terminal transcription factor MyoD.
20. The method of any of paragraphs 17-18, wherein the stem cell is to be differentiated to a spinal motor neuron phenotype and is contacted with a terminal transcription factor selected from the group consisting of: Ngn2; Isl1; and Lhx3.
21. The method of any of paragraphs 17-18, wherein the stem cell is to be differentiated to a spinal motor neuron phenotype and is contacted with the terminal transcription factors Ngn2; Isl1; and Lhx3.
22. The method of any of paragraphs 17-18, wherein the stem cell is to be differentiated to a cardiomyocyte phenotype and is contacted with the terminal transcription factor Gata5.
23. The method of any of paragraphs 17-18, wherein the stem cell is to be differentiated to a hepatocyte or hepatoblast phenotype and is contacted with the terminal transcription factor Hnf4α.
24. The method of any of paragraphs 1-23, wherein the cell cycle is inhibited by one or more of the following: reducing or removing growth factors; reducing serum levels; reducing serum levels below 5%; contacting the cell with a PI3K inhibitor; contacting the cell with an E2F family transcription factor inhibitor; contacting the cell with a Myc inhibitor;
contacting the cell with a MAPK inhibitor; contacting the cell with a MEK1/2 inhibitor; contacting the cell with a CDK inhibitor; contacting the cell with an Id inhibitor; contacting the cell with a Rb agonist; contacting the cell with a Ink family agonist; contacting the cell with a Cip/Kip family agonist; and culturing the cell in a media lacking a factor selected from the group consisting of:
LIF; Bmp; Fgf; Activin; or TGFβ.
25. The method of paragraph 24, wherein the cell cycle is inhibited by reducing or removing growth factors.
26. The method of paragraph 24, wherein the cell cycle is inhibited by culturing the cell in a media lacking a factor selected from the group consisting of:
LIF; Bmp; Fgf; Activin; or TGFβ.
27. The method of paragraph 26, wherein the cell cycle is inhibited by culturing the cell in a media lacking LIF.
28. The method of paragraph 24, wherein the PI3K inhibitor is LY294002.
29. The method of paragraph 24, wherein the E2F transcription factor inhibitor is HLM006474.
30. The method of paragraph 24, wherein the Myc inhibitor is JQ1 or 10058-F4.
31. The method of paragraph 24, wherein the MAPK inhibitor is PD98059.
32. The method of paragraph 24, wherein the CDK inhibitor is a CDK4 or CDK2 inhibitor.
33. The method of paragraph 24, wherein the CDK inhibitor is p16, p15, p18, or p19.
34. The method of paragraph 24, wherein the CDK inhibitor is p21, p27, or p57.
35. The method of any of paragraphs 1-34, wherein the stem cell is an embryonic stem cell.
36. The method of any of paragraphs 1-35, wherein steps i) and ii) result in a population of cells comprising one or more terminally-differentiated cell types.
37. The method of any of paragraphs 1-35, wherein steps i) and ii) result in a population of cells comprising no more than 2 terminally-differentiated cell types.
38. The method of any of paragraphs 1-35, wherein steps i) and ii) result in a population of cells of which at least 50% are terminally-differentiated cells.
39. The method of any of paragraphs 1-35, wherein steps i) and ii) result in a population of cells of which at least 60% are terminally-differentiated cells.
40. The method of any of paragraphs 1-35, wherein steps i) and ii) result in a population of cells of which at least 70% are terminally-differentiated cells.
41. The method of any of paragraphs 1-35, wherein steps i) and ii) result in a population of cells of which at least 80% are terminally-differentiated cells.

EXAMPLES

Example 1: Molecular Ties Between the Cell Cycle and Differentiation in Embryonic Stem Cells Attainment of the differentiated state during the final stages of somatic cell differentiation is closely tied to cell cycle progression. Much less is known about the role of the cell cycle at very early stages of embryonic development. It is demonstrated herein that molecular pathways involving the cell cycle can be engineered to strongly affect embryonic stem cell differentiation at early stages in vitro. Strategies based on perturbing these pathways can shorten the rate and simplify the lineage path of ES differentiation. These results make it likely that pathways involving cell proliferation intersect at various points with pathways that regulate cell lineages in embryos and demonstrate that this knowledge can be used profitably to guide the path and effectiveness of cell differentiation of pluripotent cells.

As cells differentiate during embryonic development, they progress through a stereotypical sequence of events, starting from highly potent embryonic precursors to germ layer intermediates, then to lineage-restricted progenitors, and finally, to terminally differentiated cell types. Any of these stages may consist of further states of differentiation and may be difficult to recognize. Most of our knowledge about the differentiation process comes from studies in the latter stages of differentiation (i.e. terminal model systems), where cells are one step away from their final fate and are usually restricted to differentiate to one type of cell. Less is known about what happens during early embryonic stages, where the differentiation process is just beginning and many alternative pathways of differentiation may still be available.

In terminal somatic cell culture models, inhibition of the cell cycle is almost always a requisite for differentiation. Forced inhibition of the cell cycle very often induces terminal differentiation and vice versa (1-3). The molecular pathways that couple the cell cycle to differentiation involve molecules of the G1/S transition including growth factors, downstream signaling pathways, Myc, the Rb/E2F pathway, and the CDK inhibitors (e.g. p21). The role of G1 length on embryonic stem cell self-renewal was investigated and it was found that in contrast to the terminal stages it did not accelerate the loss of pluripotency or facilitate differentiation (4). Described herein is the state of the cell cycle molecular network in the ES cell system and how the cell cycle may be re-coupled to differentiation to re-direct lineage pathways, e.g., for practical benefit.

Results

Figure 7A:
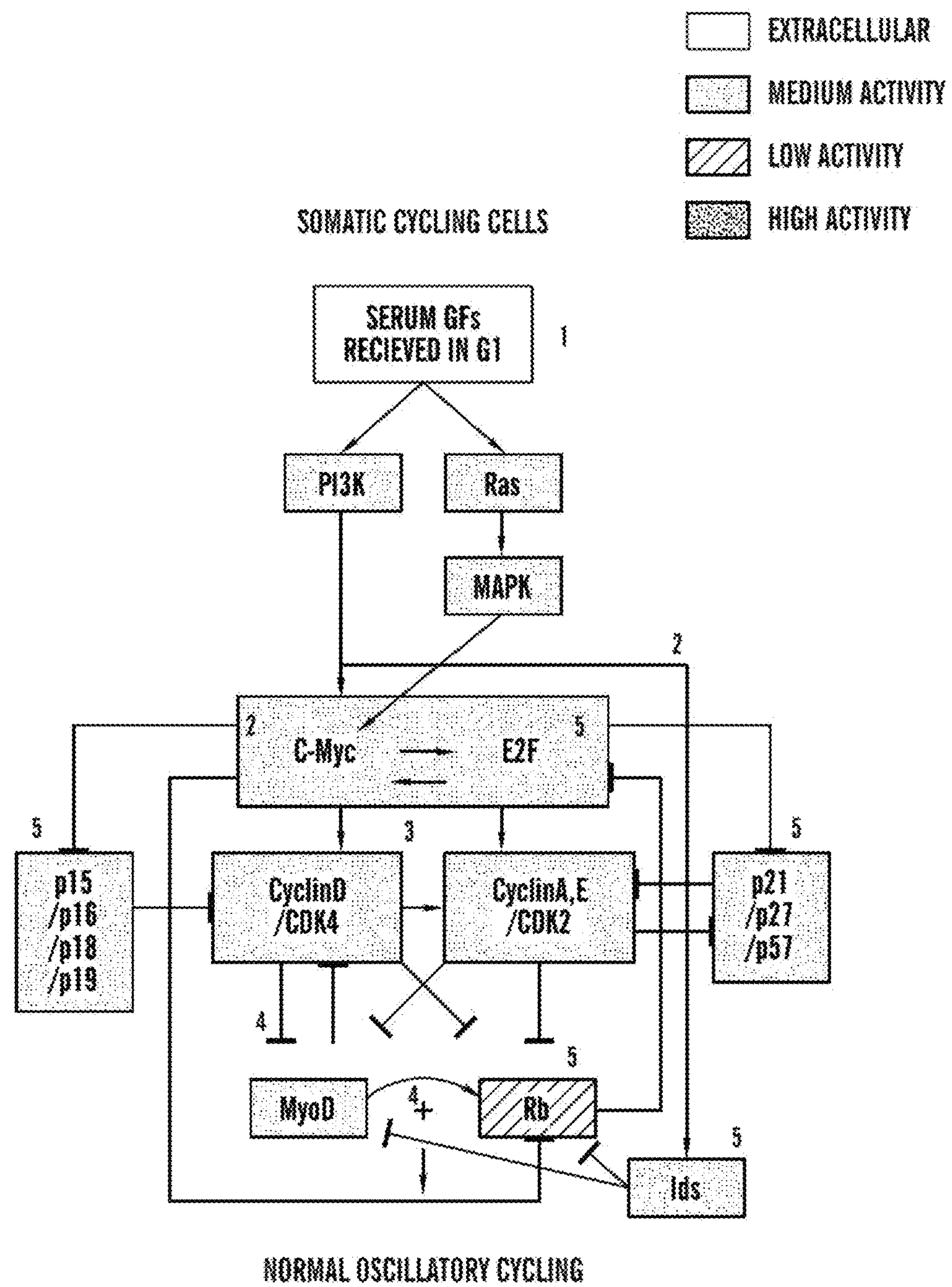
FIGS. 7A-7C depict schematics of cell cycle control. Schematics are adapted from Morgan, D. O. The cell cycle: principles of control. Sinauer associates, Sunderland, 2007 p. 207-210; which is incorporated by reference herein in its entirety. 1. Growth factors (GFs)/mitogens are received in G1 before the restriction point 2. The immediate-early response genes are initiated in response to mitogens. Myc then induces Cyclin D transcription and E2F activity. Entry into S-phase by Myc requires E2F activity. Myc also can induce Inhibitor of differentiation (Id) family proteins. 3. E2F activity reciprocally promotes Myc activity. Box represents that Myc and E2F share a transcriptional function to activate pro-proliferative genes. 4. MyoD interacts with G1/S transition components in several ways. MyoD directly interacts with Cyclin D/Cdk4, suppressing its activity. MyoD is also phosphorylated by CDKs leading to its ubiquitination and destruction. Rb interacts with MyoD as a co-factor on DNA. Finally, MyoD transcriptionally increases the expression of Rb RNA. 5. Grouped together are family members of the Ink4 CDK inhibitors, Cip/Kip CDK inhibitors, Rb pocket proteins (Rb1, p107, p130), Inhibitor of DNA binding (Id) proteins, and E2F transcription factors. It is recognized that individual family members have unique features, however this complexity is not represented in this model. 6. In mES cells, LIF drives Myc activity through Jak/Stat signaling. LIF also increases PI3K activity. 7. Bmp signaling leads to upregulation of Inhibitor of differentiation (Id) proteins, which are predicted to inhibit Rb and MyoD 8. c-Myc has been observed to bind Rb in vitro, but not in vivo. On the other hand, p107 does interact with Myc in vivo. In mES cells, Myc is expressed at high levels and may be inhibiting Rb family members. 9. In certain cases, Myc or E2F overexpression leads to a reduction in Cyclin D1 levels. It is contemplated that the extra activation of these factors in mES cells decreases Cyclin D1 levels. 10. c-Myc has been suspected to independently suppress myod outside of cell transformation.
Figure 7B:
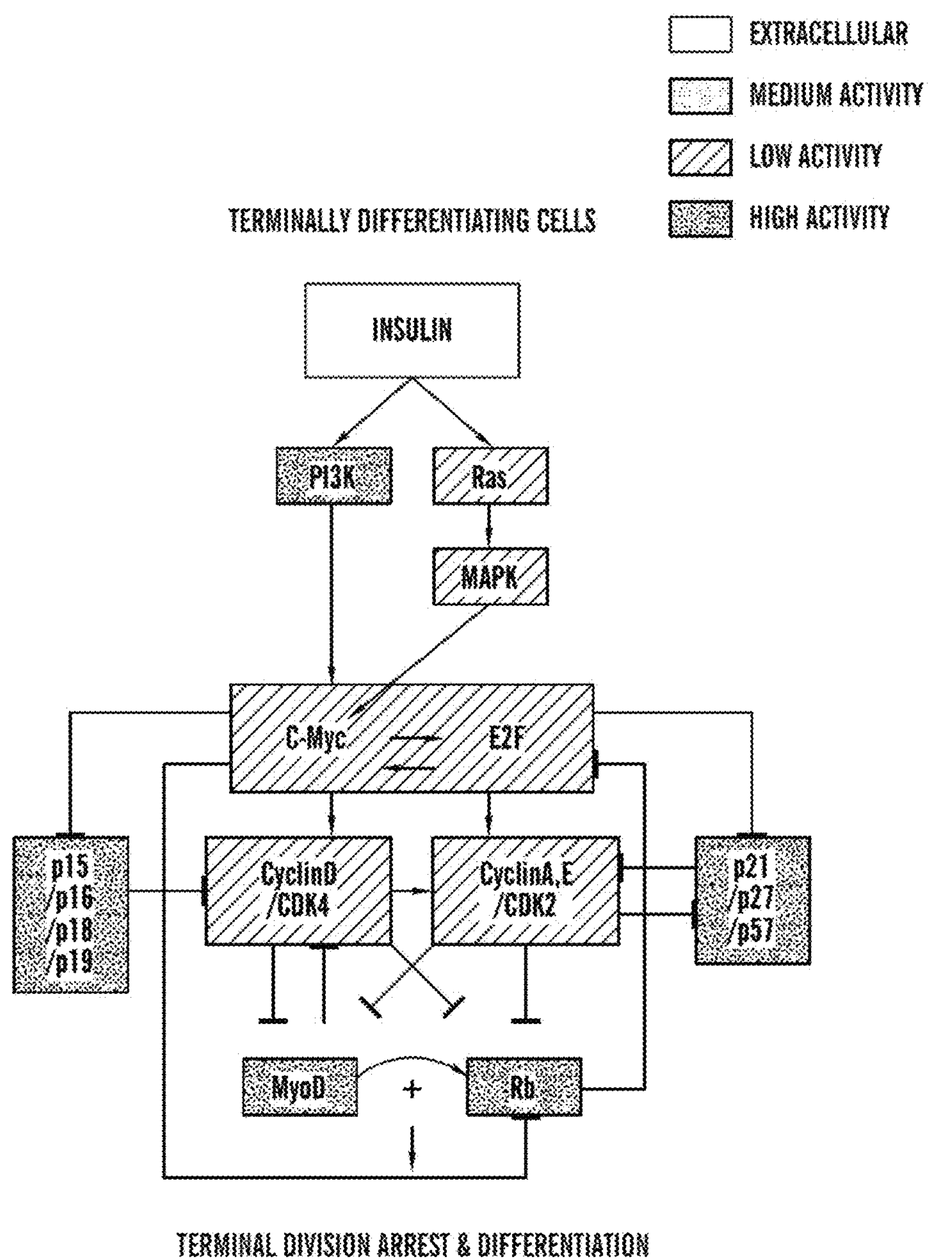
Figure 7C:
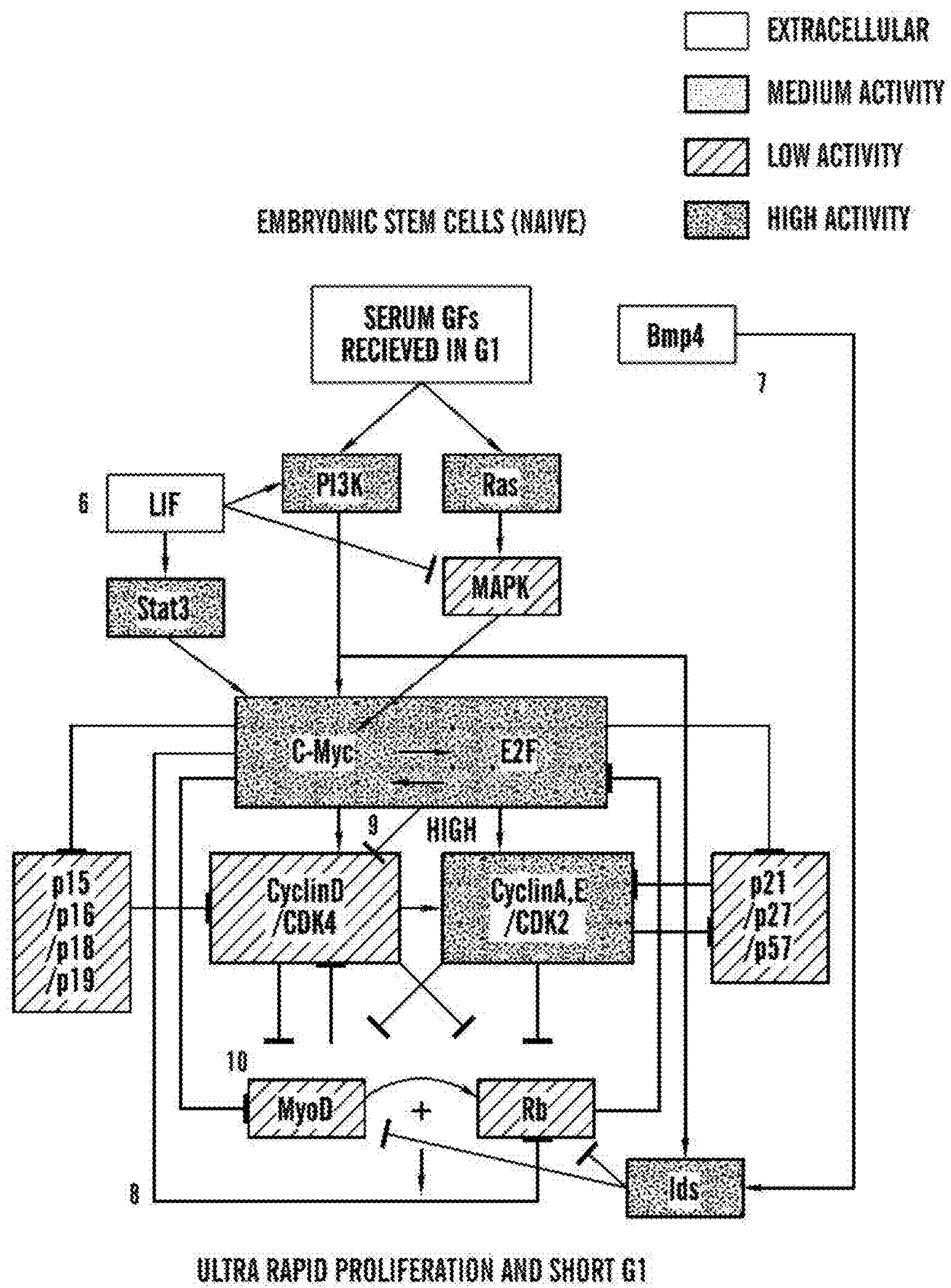
Figure 8A:
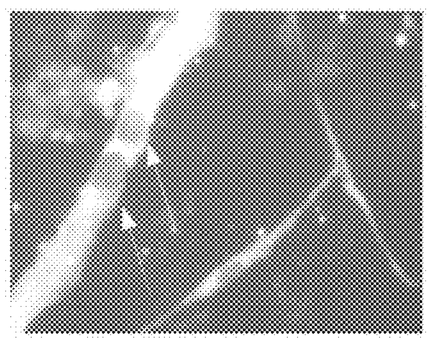
FIG. 8A depicts myosin heavy chain staining is in white coloring in the cytoplasm. Myotubes exhibit an elongated, multinucleated morphology. Arrows point to nuclei in a binucleate myotube. This particular image was taken on day 8 of the low serum time course started on day 0.
Figure 8B:
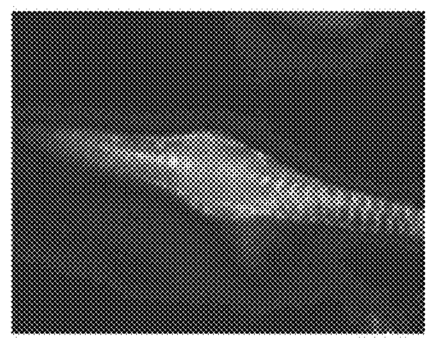
FIGS. 8B-8D depict sarcomeric a-actinin staining of myofibrillar striations in differentiated myotubes. These particular images were taken on day 13.
Figure 8C:
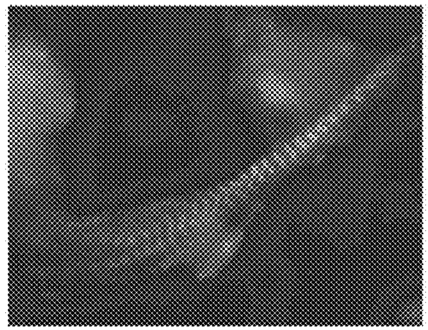
Figure 8D:
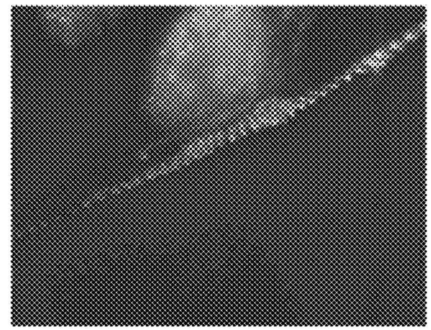

In terminally differentiated cells the cell cycle and differentiation are linked together through a molecular network rooted in the G1/S transition. A wiring diagram summarizing such a network is shown in FIG. 1A, with explanations and justifications provided in FIGS. 7A-7C, which was constructed from known or postulated relationships in normal somatic cycling cells, and interactions between the cell cycle machinery and terminal transcription factors, such as MyoD.

Figure 1B:
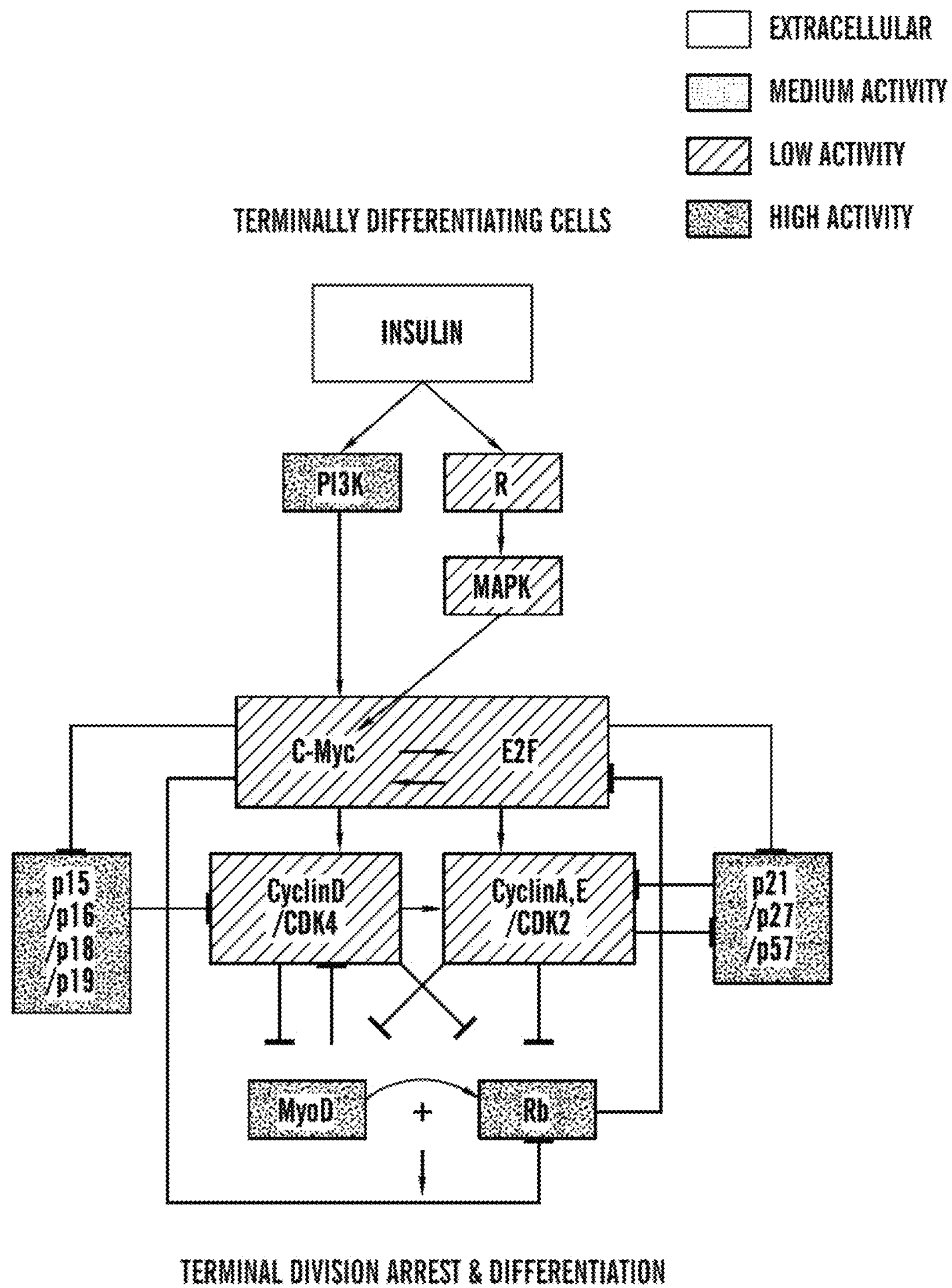
Figure 1C:
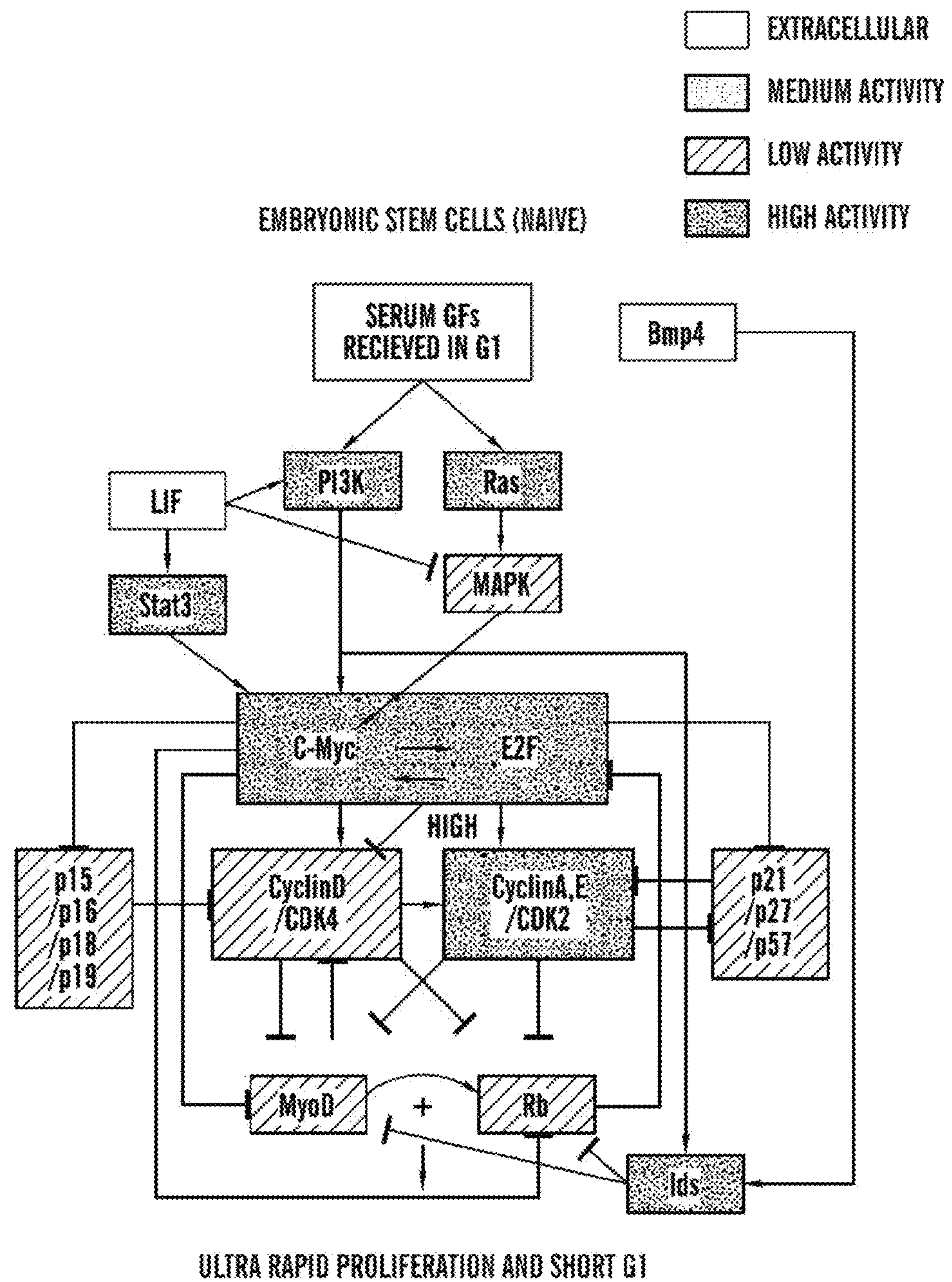

During the process of differentiation, the network changes. For cultured cells at the terminal stage of differentiation, this involves an exit from the cell cycle, activation of terminal transcription factors, and a shift towards insulin signaling away from other growth factors for survival and growth. These changes to the network are shown in FIG. 1B. At the other end of the differentiation process are embryonic stem cells, which have a number of unique features. They can be maintained in an undifferentiated state with the combination of Leukemia Inhibitory Factor (LIF) and high amounts of serum, or LIF and Bmp4, as shown in FIG. 1C. The actual differentiation process from ES cells to terminally differentiated cells spans at least three states in a defined order (ES to somatic cycling cells to terminal differentiation), but may pass through other intermediate stages of differentiation, expressing genes and behavior different from terminal cells and pluripotent stem cells; little is known concerning the cell cycle and their state of differentiation in these largely uncharacterized cell cycle states (FIG. 1D).

Guided Differentiation and Cell Cycle Manipulation of ES Cells.

Figure 2A:
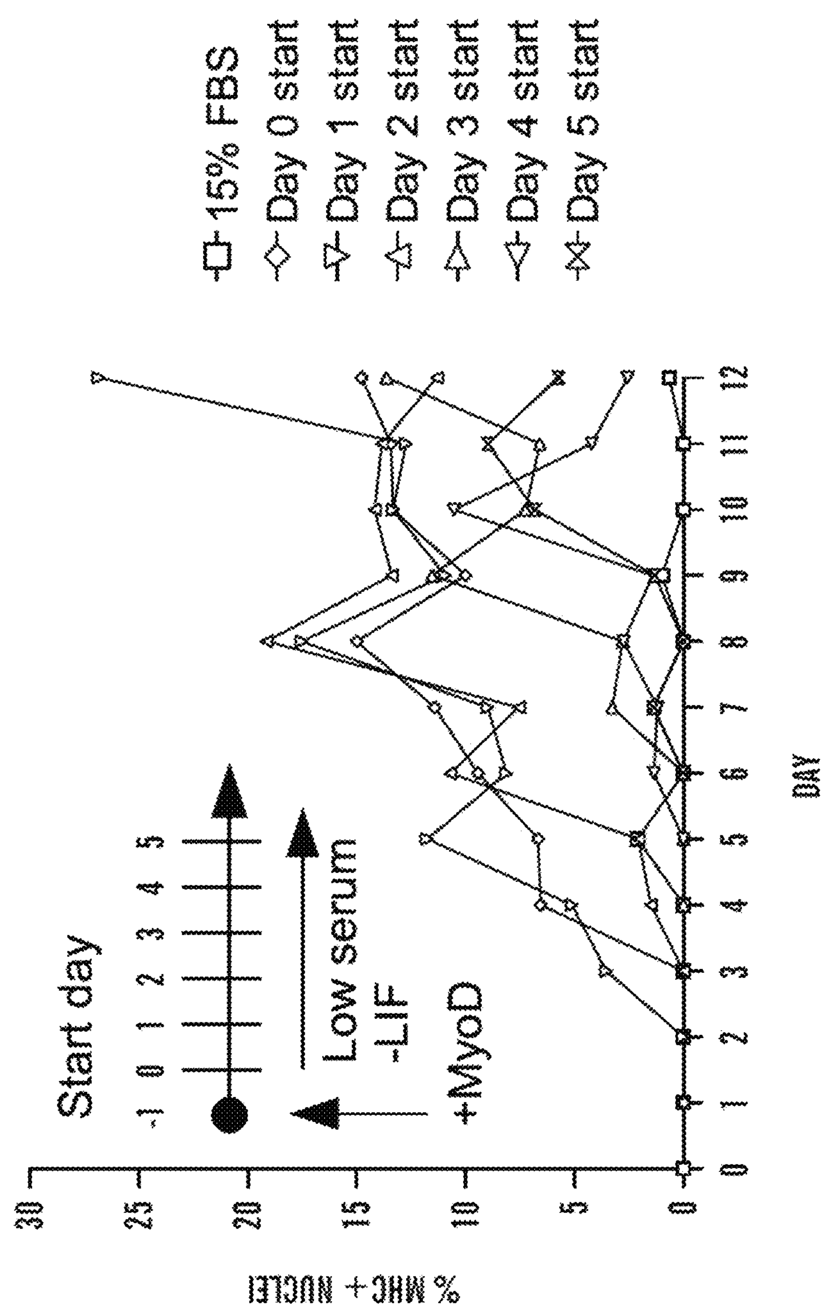
FIGS. 2A-2B demonstrate that gfactor/serum reduction drives a direct terminal skeletal muscle differentiation program.

To probe the effect of the cell cycle on differentiation an ES cell line was used that constitutively over-expressed the transcription factor MyoD driven off an EF1alpha promoter (5) activated by tamoxifen-induced Cre recombination. The use of this cell line facilitated the analysis by channeling differentiation away from a diverse collection of phenotypes into a more uniform population of cells expressing muscle genes, such as myosin heavy chain (MHC). The first cell cycle manipulation was growth factor or serum withdrawal. Using the cell line that continuously expressed MyoD, LIF was removed at what is referred to herein as zero time to initiate differentiation and serum was reduced at various times thereafter from the standard 15% serum to 2% with additional insulin (10 μg/ml). As shown in FIG. 2A, in the continuous presence of 15% serum, MHC is completely suppressed, despite constitutive MyoD overexpression. When serum is reduced one day after MyoD induction, MHC begins to accumulate four days later. By day 12, 20-30 percent of cells express MHC and show characteristic morphology of mature skeletal muscle fibers including elongation, increase in volume, and significant multi-nucleation (FIG. 8). If serum removal is delayed relative to LIF removal, the cells still begin to express MHC with a 2 to 4 day delay after serum reduction. Thus serum reduction strongly potentiates terminal muscle differentiation in a very short time under the conditions studied.

Figure 2B:
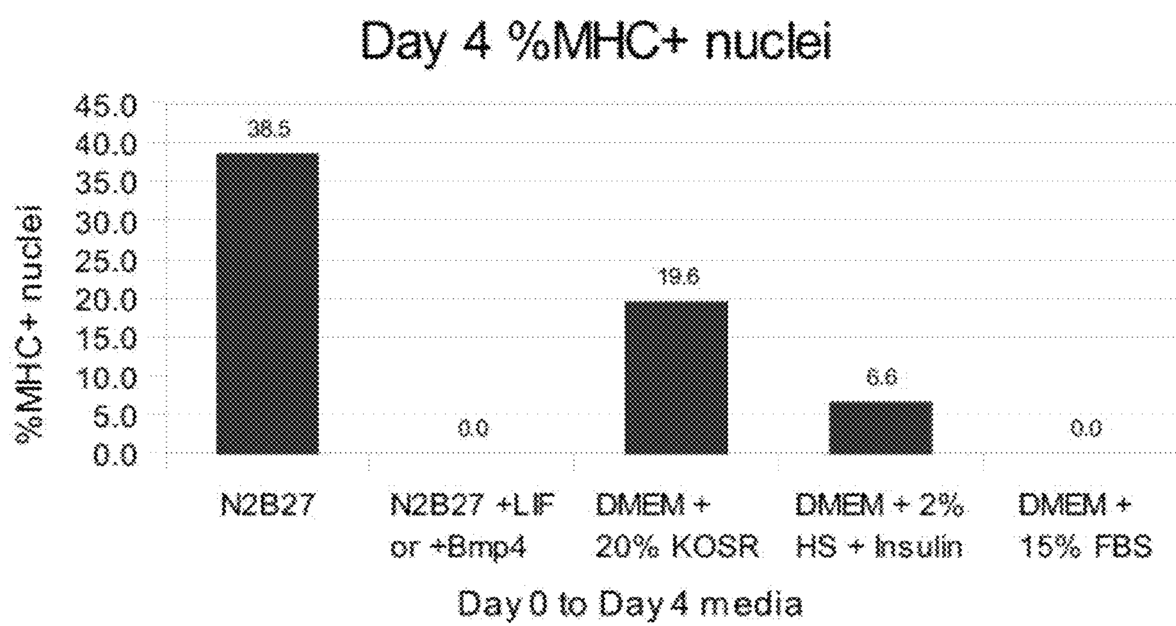
Figure 3:
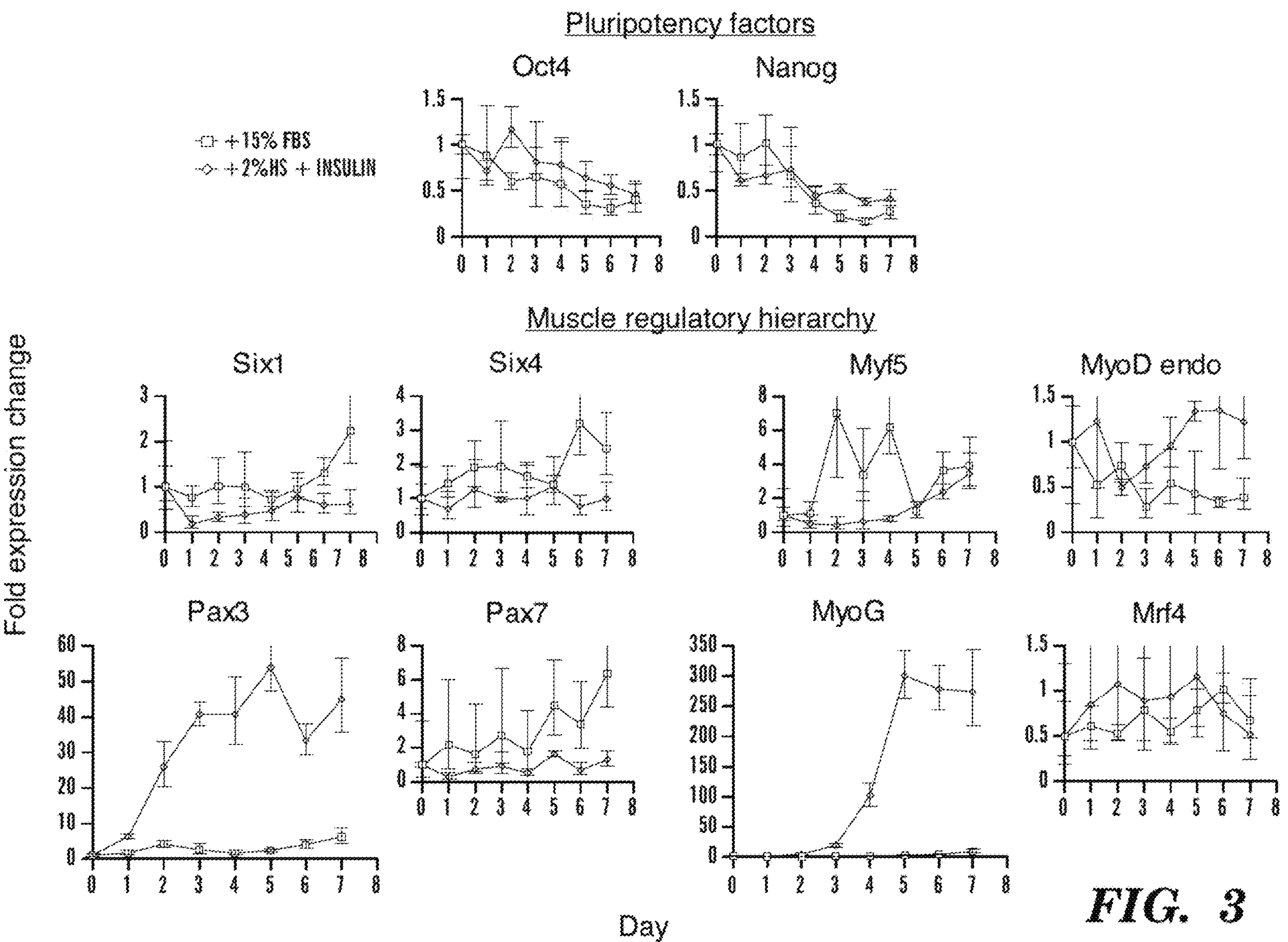
FIG. 3 demonstrates that growth factor/serum withdrawal drives a condensed gene expression program of early Pax3 expression and subsequent MyoG expression, but does not affect kinetics of Oct4 or Nanog loss. Gene expression time courses of differentiation over 7 days. In this experiment, low serum was initiated at Day 0, one day after induction of MyoD expression in ES media, and maintained over the course of differentiation. The rate of decline of Oct4 and Nanog mRNA levels are not strongly affected by cell cycle inhibition. In the muscle regulatory hierarchy, only Pax3 and MyoG are strongly upregulated. Upregulation of additional terminal markers of skeletal muscle terminal differentiation can be found in FIG. 9. Ct values were normalized to glyceraldehyde 3-phosphate dehydrogenase (GADPH). Error values reflect S.E.M. (n=3).

From the cell cycle summary in FIG. 1A, MyoD activation and hence muscle differentiation from ES cells should be blocked by either the action of LIF, which activates Myc, or Bmp4, which promotes Id protein family expression. However any implication of growth factor effects through the manipulation of serum can be fraught with the inconsistencies and complexities of serum. To avoid these problems more defined conditions were examined with two types of basal insulin-containing media, N2B27 and DMEM plus 20% Knock-out Serum Replacement (KOSR), neither of which contains growth factors. Use of both media in ES cells led to activation of MyoD and terminal myogenesis similar to the 2% low serum media, with some improvement (FIG. 2B; assessed on Day 4). The N2B27 media produced approximately 38.5% MHC+ nuclei while 20% KOSR produced approximately 19.6%. As expected when LIF or Bmp4 was added back to N2B27 differentiation was blocked (0%; FIG. 2B). These results confirm the expectation that the reduction of LIF and BMP in the setting of no other growth factors, produces highly effective conditions for ES differentiation.

The lineage from ES cells to terminal differentiation first involves the loss of pluripotency factors, followed by passage through intermediate cell types, identifiable by expression of specific transcription factors. It was found that the decline in Oct4 and Nanog mRNA levels induced by LIF removal was completely unaffected by serum reduction. This is similar to results showing that extension of G1 had no effect on Nanog levels (4).

Figure 9:
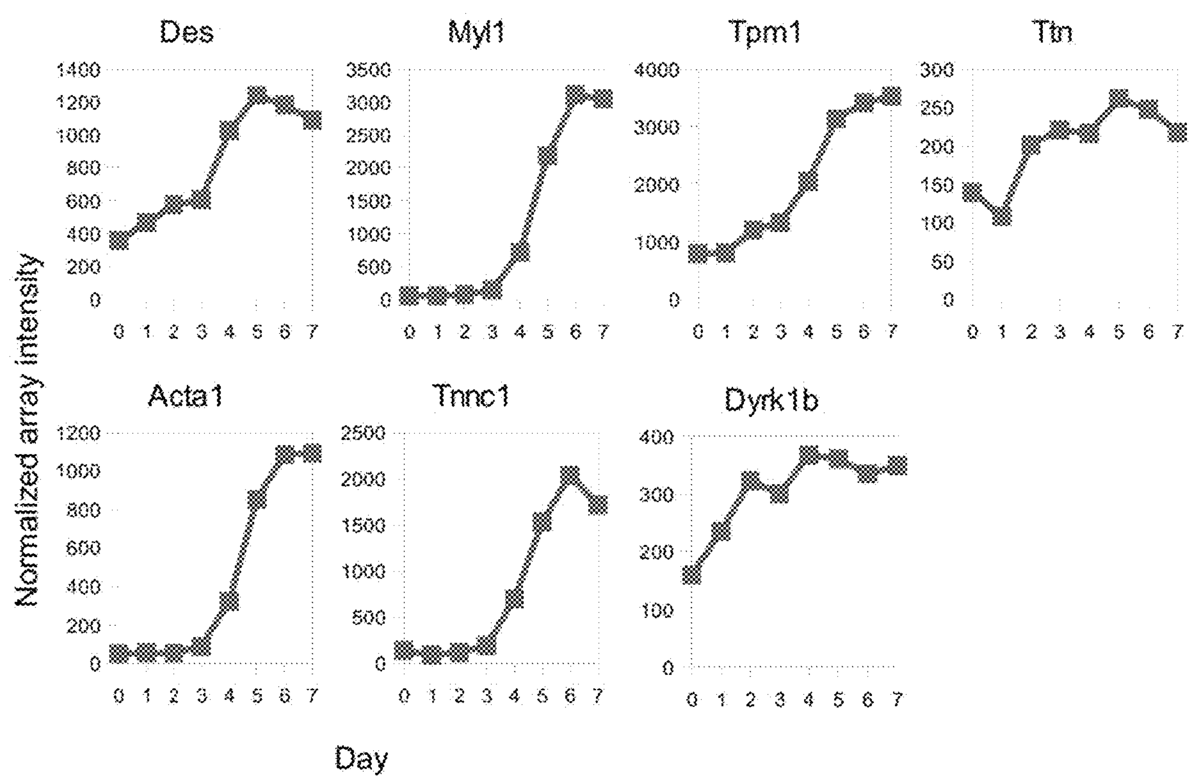
FIG. 9 demonstrates additional muscle genes upregulated by growth factor/serum removal. Microarray data confirm expression of skeletal muscle genes during MyoD differentiation by low serum Desmin (Des), Myosin light chain (My11), skeletal muscle actin (Acta1), troponin (Tnnc1), tropomyosin (Tpm1), Mirk/Dyrk1b, and titin (Ttn) get upregulated during the differentiation time course. In this experiment, MyoD overexpression is activated at Day −1 in ES media. LIF is then removed at Day 0 and the media is switched to low serum.

By contrast, beyond the loss of pluripotency factors there is a dramatic effect of serum removal on the differentiation cascade toward muscle. From studies in embryos, there is a prescribed sequence of steps in setting up the myogenic lineage involving the specification of the mesoderm, the sub-specification of the myotome, and the steps leading to overt cell differentiation (6-7). When the mRNA levels of genes within this hierarchy were examined using the above protocol of serum reduction, it was found that Pax3, which is expressed in the dermomyotome, rose dramatically (to a peak of ~50 fold) and very prematurely within 2 days of serum reduction. The pre-myogenic homeodomain factors Six1 (8) and Six4 (9), which are normally upstream of Pax3, are not affected or modestly suppressed, as was the case for the paired-box domain protein Pax7, which is expressed in the dermomyotome and somites during embryogenesis (10). There are small effects of serum reduction on the myogenic regulatory factor (MRF) genes, like Myf5, MRF4 and endogenous MyoD, but there is a massive (300 fold) upregulation of myogenin (MyoG), which plays a key role in very late-stage skeletal myogenesis during the period of days 3 to 7 (11). Other muscle lineage markers also respond rapidly to serum withdrawal in the presence of MyoD, indicating that the entire suite of terminal muscle lineage is induced very prematurely. Seven of these—desmin, skeletal muscle actin, troponin, myosin light chain, tropomyosin, the myoblast fusion regulator Dyrk1b (12), and titin—are shown in FIG. 9. The dramatic overexpression of Pax3 and MyoG depend on the over-expressed exogenous MyoD, as without the induction of MyoD, their expression is lower. These results document the extraordinarily rapid production of some downstream muscle differentiation factors and definitive muscle proteins in the setting of growth factor or serum withdrawal.

Promoting Differentiation by Perturbing Intracellular Pathways.

Figure 4:
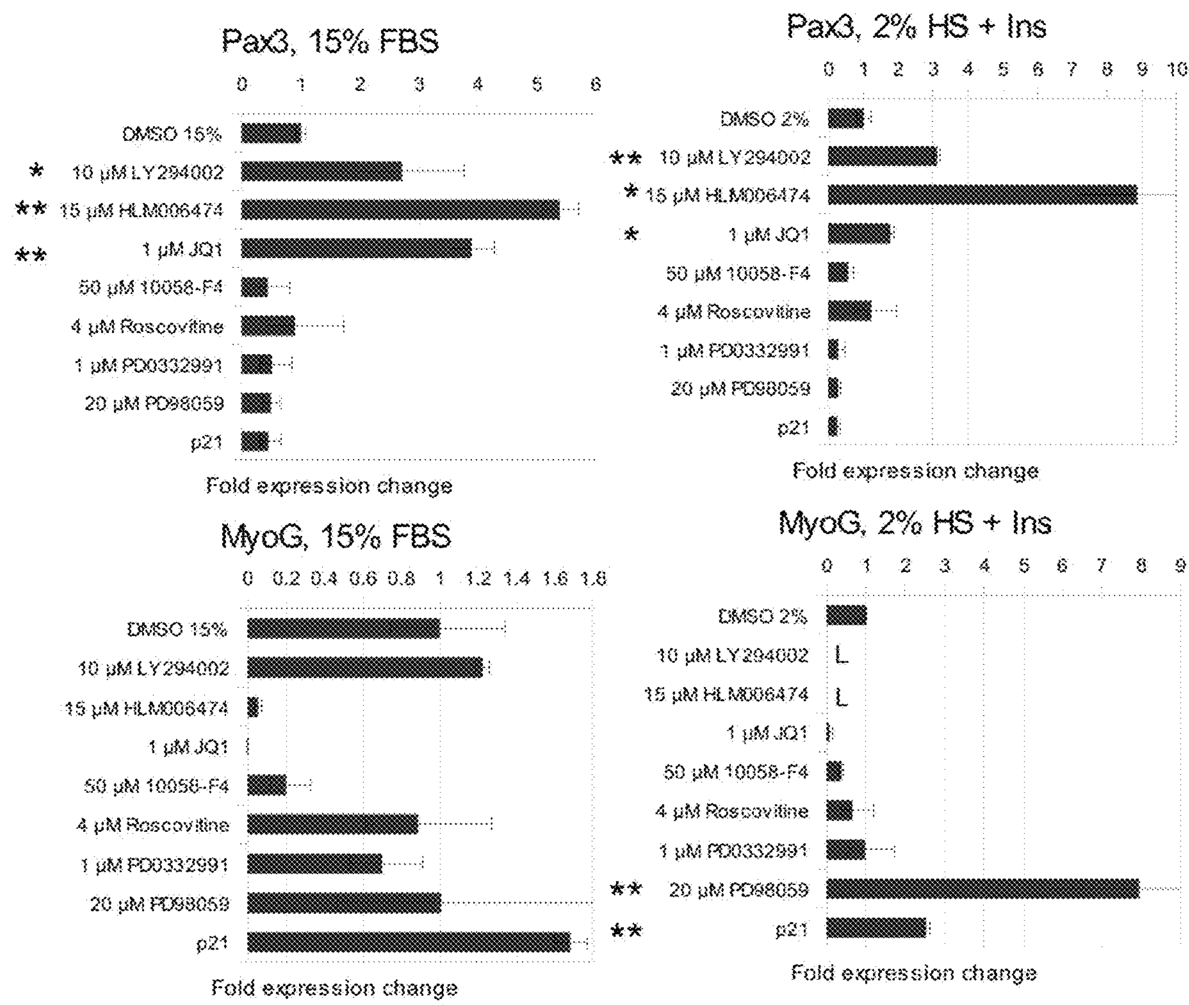
FIG. 4 demonstrates that specific cell cycle inhibitors have stage and condition-specific effects on Pax3 and MyoG expression. Time courses of differentiation were run for 7 days similarly to the previous growth factor withdrawal experiments. MyoD was induced at Day −1, and LIF was removed at Day 0. Cells were kept in either high serum (15% FBS) or low serum (2% HS+Insulin) media throughout the time course. Drug treatments were applied continuously at the designated concentrations for the entire duration of the time course, with daily media change. mRNA expression levels were measured by qRT-PCR. Pax3 was measured on Day 3 (since it is upregulated early) and MyoG was measured on Day 7 (since it is upregulated late). All measurements are relative to a DMSO control for the specific condition (i.e. low serum values are still higher than in high serum). L=lethal; drug had strong anti-survival effects so no data was collected. Error bars indicate S.E.M. (n=2).

Based on suggestions from the pathway diagrams in FIGS. 1A-1D, a few critical components of cell cycle control were focused on and their effects on the two markers strongly perturbed by serum withdrawal, Pax3 and MyoG, were measured. Perturbations were made both under high and low serum conditions and were extended throughout the time course of differentiation. LY294002 is a potent broad inhibitor of phosphoinositide-3-kinases (PI3Ks), and when applied continuously to ES cells over 7 days induced a significant 2.7 fold increase in Pax3 mRNA expression (FIG. 4). This increase was observed both in high serum and low serum media. However, continuing treatment with LY294002 led to cell death and no expression of myogenin was observed (FIG. 4, bottom panels). A similar situation was observed with HLM006474, which broadly inhibits E2F family transcription factors in their interaction with DP proteins. Myc drives cell cycle progression and growth. Its activity can be inhibited by two compounds: JQ1, a newly-identified compound that specifically inhibits bromodomains but subsequently results in Myc downregulation, and 10058-F4, an inhibitor that blocks the dimerization of Myc-Max complexes. Both are indirect inhibitors of Myc activity; as yet there are no direct pharmacologic inhibitors of the Myc protein. The effects of JQ1 were similar to LY294002 and HLM00647: an increase in Pax3 early expression, but later suppression of MyoG expression. Out of all drugs the Myc-bromodomain inhibitor JQ1 had the largest effect in inducing Pax3, whereas the Myc-Max dimerization inhibitor 10058-F4 had suppressive effects on both Pax3 and MyoG.

The effects of inhibiting cyclin-dependent kinases (kinases that are more centrally involved in cell cycle control) and MAP kinase, which very often is involved in cell cycle regulation, were also examined. Roscovitine is a broad CDK inhibitor that blocks a number of family members, including CDK1, CDK2, and CDK5. After continuous treatment throughout the 7 days of differentiation in the time course, roscovitine had no effect on Pax3 expression (FIG. 4). It also had little effect on the later expression of MyoG, either under high or low serum conditions. This lack of effect on Pax3 and MyoG was also observed for the more specific CDK4 inhibitor PD0332991. However, the MAPK inhibitor PD98059, which blocks MEK1/2, had no effect on Pax3 and induced MyoG only under low serum conditions (FIG. 4 bottom). The protein CDK inhibitor p21, which is much more specific than roscovitine, blocks CDK2 and prevents entry into S-phase. In ES cells p21 is expressed at low levels, but gradually increases during the course of ES cell differentiation (13). An mES cell line that constitutively overexpresses the p21 protein bicistronically with a mCherry tag (fused to the C-terminus with a 2A peptide) was developed. This line exhibits an elongated G1 and can be propagated in standard LIF+serum media. When induced to differentiate by the removal of LIF, this line upregulated MyoG under low serum media, but had no effect on Pax3, a behavior similar to the MAPK inhibitor. Thus, within the set of cell cycle inhibitors examined, stage-specific and condition-specific effects on gene expression were observed.

Induction of Unguided Differentiation.

Figure 5:
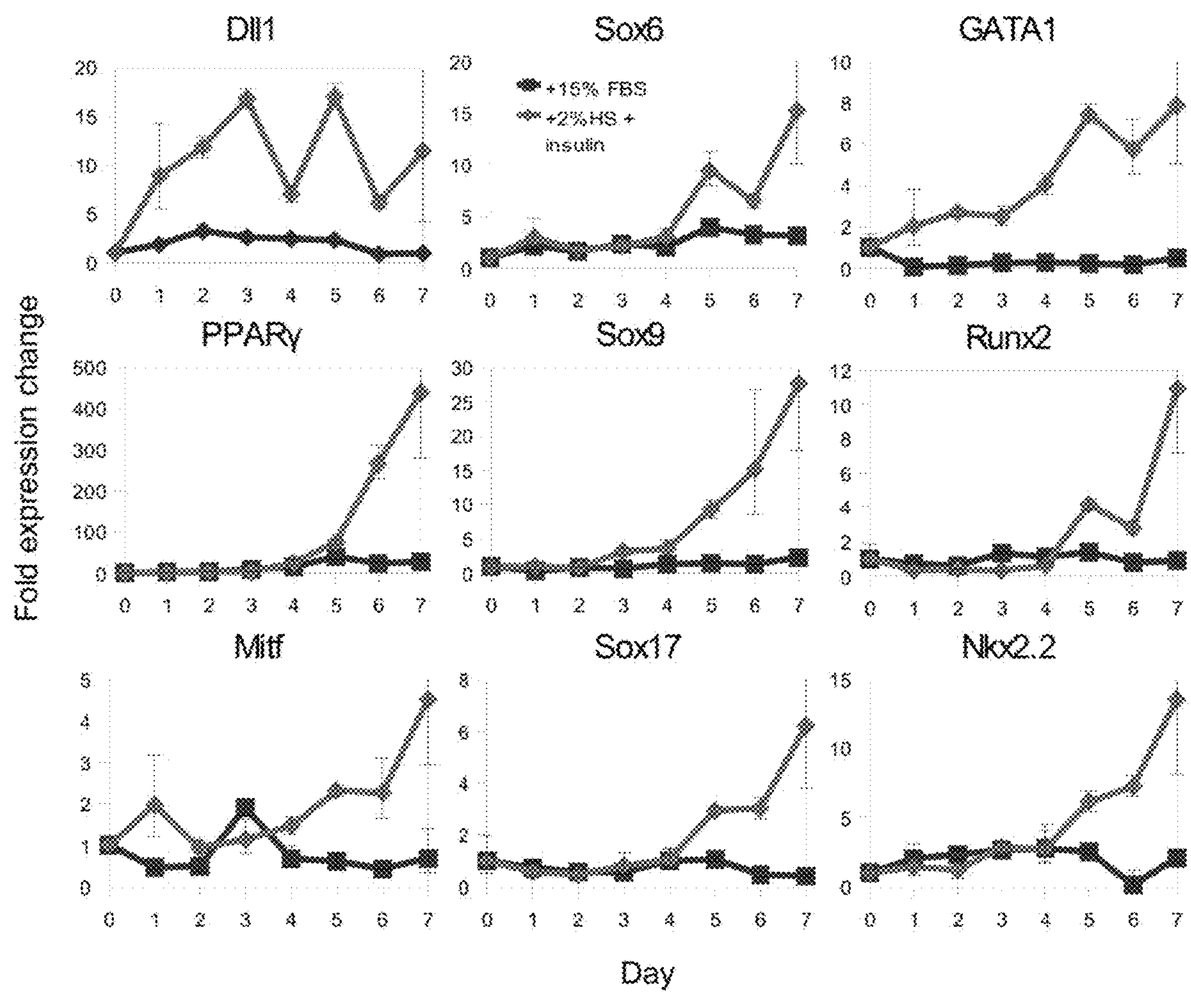
FIG. 5 demonstrates that in an unguided or heterogeneous differentiation setting, growth factor/serum withdrawal upregulates the expression of numerous genes associated with differentiated cell types. Gene expression time courses of unguided (without MyoD) differentiation after release from ES cell media at Day 0. Low or high serum was applied at Day 0 for the full time course. Upregulated factors include D111, Sox6, GATA1, PPARγ, Sox9, Runx2, Mitf, Sox17, and Nkx2.2 (continued in FIG. 10). These genes are involved in the differentiation of multiple cell types, including neurons, chondrocytes, erythrocytes, adipocytes, cardiomyocytes, osteoblasts, melanocytes, and beta-cells. Error values indicate S.E.M. (n=2).

Although forced expression of MyoD nicely served to focus differentiation into the skeletal muscle cell lineage, it was also desired to examine what happens in ES cells that are not guided in their differentiation path by MyoD. When LIF is removed in ES cells without MyoD, there is differentiation into a heterogeneous mixture of cell types. Under standard culture conditions of 15% serum, which promotes expansion, ES cells deprived of LIF normally differentiate first into general mesodermal, endodermal, and ectodermal tissues, and then later into a heterogeneous mixture of terminal cell types (7, 14). The effects of serum withdrawal on this system were examined. When high and low serum time courses in ES cells differentiating without exogenous MyoD were compared over a period of 7 days there was premature expression of genes that are normally associated with multiple cell lineages (FIG. 5). Low serum induced the expression of many lineage-specific factors. For example, an increase in the neural marker Delta (D111) was observed. The cardiac muscle factors Sox6, Smyd1, GATA4, GATA6 all increased, as well as the neural/muscle transcription factor Mef2c. For adipose genes, a very large increase in PPARγ expression (>400 fold) was detected. The early endoderm genes Sox17 and Nkx2.2 also were elevated in low serum compared to high serum. Similarly, increases in Runx2 (osteoblast differentiation), Mitf (melanocyte), and Sox9 (chondrocyte differentiation) were also observed. For hematopoietic factors, increases in the erythrocyte factor GATA1 (FIG. 5) and the progenitor factor GATA2 (FIG. 10) were observed. A full list of factors that were profiled and their time course data is available in FIG. 10.

Figure 10:
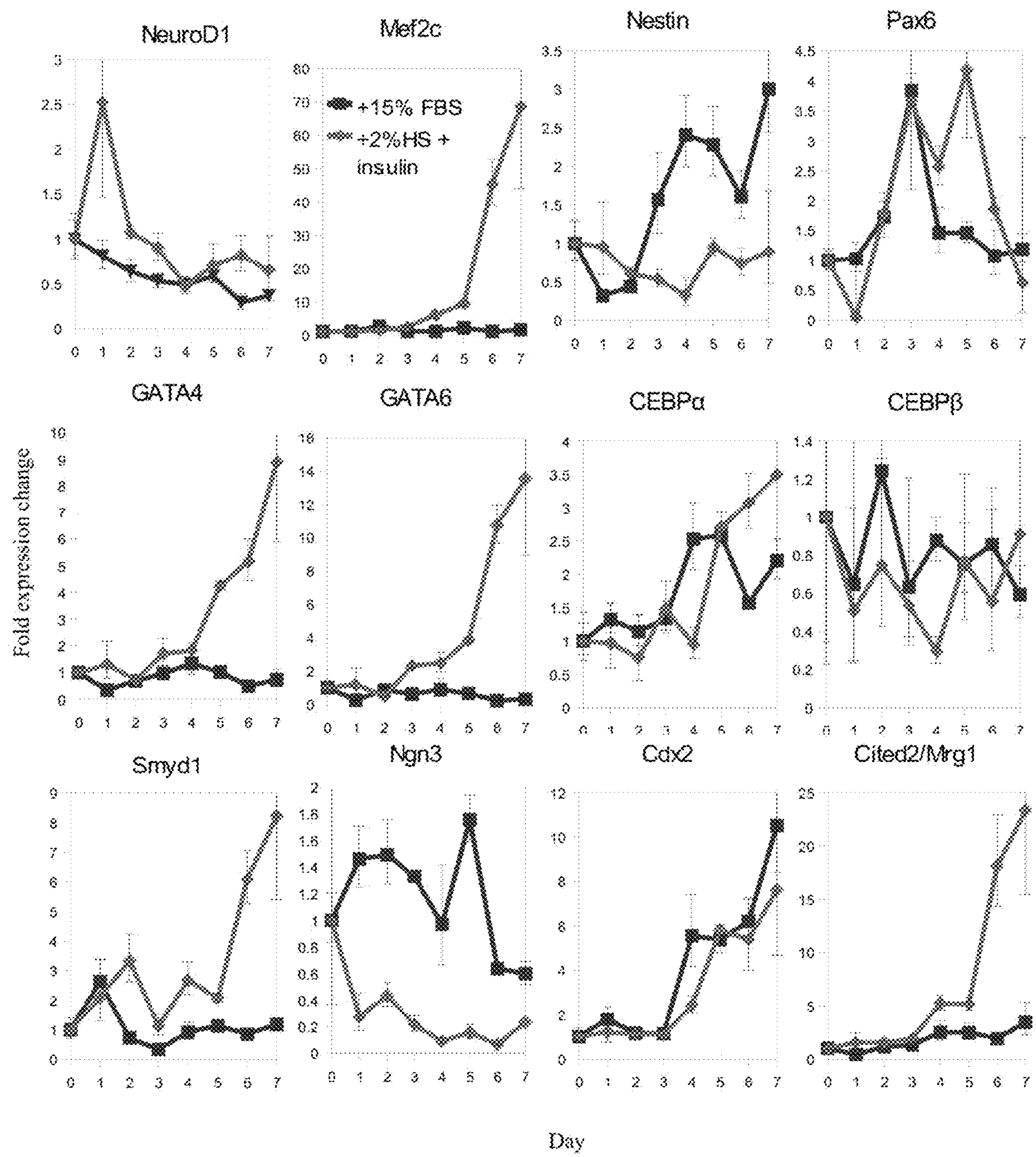
FIG. 10 demonstrates additional time courses of lineage-specific factors differentiated by low serum and LIF removal (no MyoD).
Figure 10:
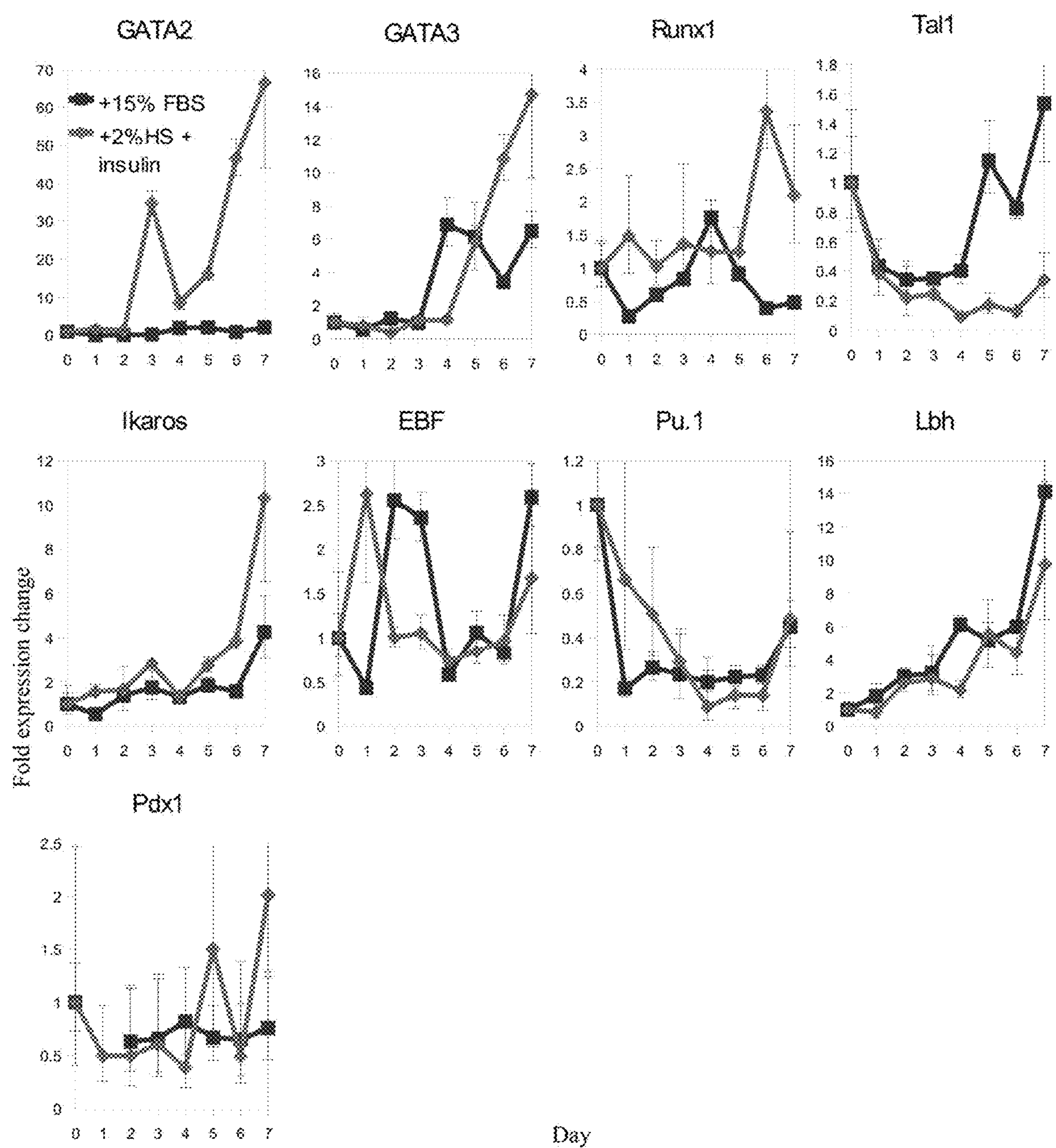

The early upregulation of such a large number of somatic lineage factors indicates that growth factor/serum reduction is permissive for a wide variety of differentiated gene expression. Many of the upregulated factors have been reported to function in terminal differentiation. Perhaps most interesting is the failure to express many of the markers of the early lineages. As seen in the MyoD-guided system, only Pax3 and MyoG were significantly activated, but not other factors in the muscle lineage hierarchy. In the unguided system, in addition to the terminal factors that were upregulated, there were numerous intermediate lineage factors that were not (e.g. Pax6, C/EBPα, C/EBPβ, Pdx1, Cdx2, etc.) (FIG. 10 and Table 3).

Discussion

Our understanding of cell differentiation comes mainly from two different sources: studies of cell culture systems and studies of embryonic systems. Although the embryo remains the gold standard for the functional process of embryogenesis, there is today a strong incentive to understand alternative in vitro pathways that can be exploited for therapeutic purposes. Furthermore there is no reason why we should consider embryonic lineages as mechanistically the most informative. Embryos have to accomplish feats other than differentiation, such as morphogenesis and cell proliferation, and many intermediate behaviors of cells may reflect those roles.

Much ingenuity and decades of effort has resulted in the discovery of ways to manipulate cells isolated and cultured from various tissues so that they can differentiate into one or a very few cell types. It is now recognized that these processes take cells from an already determined state and drive them to a state of clear expression of specific markers, rather than starting from a very early precursor state. Such manipulations can drive presumptive myoblasts to muscle, neuroblasts to neurons, fibroblasts to adipocytes, etc. A very different source of cells are pluripotent ES cells of the mouse and now of human. These cells start at an earlier state and can be driven to differentiate either by re-creating some early embryonic state through embryoid bodies or by going through a series of steps in culture, thought to parallel the various intermediate states of differentiation found in the embryo itself. As work in stem cells and ES cells in particular exploded in the last few years there has been a serious effort to identify and recreate in culture the series of signals that drive the pluripotent state to the differentiated state. In the embryo, these include the addition and removal of factors like Wnts, Nodals, BMPs, EGFs, etc. There is both a practical side to this endeavor: to either generate differentiated cells that can generate replacement tissues and organs or to find ways to stimulate the body's regenerative potential to repair worn or diseased cells.

There has also been a long standing interest in understanding how the cell cycle could further the process of differentiation. Inhibition of cell proliferation in G1 is almost always accompanied by cell differentiation. The work described herein was designed to determine whether this effect of cell cycle inhibition can be observed early in the differentiation process and whether the paths taken are the same as seen in the absence of cell cycle inhibition.

Described herein are cell cycle perturbations, starting with a reduction or removal of growth factors/serum, change the timing and the course of differentiation to muscle in a model that involves the continuous expression of MyoD. Notably none of the perturbations had an effect on exit from the ES cell state as reflected in the loss of Oct4 and Nanog. Surprisingly, this progression to the differentiated state seemed not to seem to follow the normal sequence of gene expressions seen in ES cells in culture or by embryonic lineages in the embryo. More than one path to differentiation was found, as described herien.

Described herein are heuristic descriptions of somatic cycling cells, terminally differentiating cells, and embryonic stem cells (FIGS. 1A-1D). Terminally differentiated cells typically maintain their size or grow slowly, stimulated commonly by the insulin pathway. In this cell cycle state the drivers of the cell cycle are inhibited and the expression of cell cycle inhibitors are stimulated, leading to the expression of terminally differentiated genes like MyoD, neurogenin, etc. The proliferative state that preceded terminal differentiation is reduced in the expression of CDK inhibitors and particularly in the activity of Rb. In this case MyoD activity is also reduced. Lastly, the pluripotent embryonic state has new extracellular players: LIF, serum growth factors, and BMP4. In this state, there is more complete suppression of Rb and MyoD through the activation of proliferative signals in the cell cycle and the downstream suppression of anti-proliferative factors such as CDK inhibitors.

Figure 6:
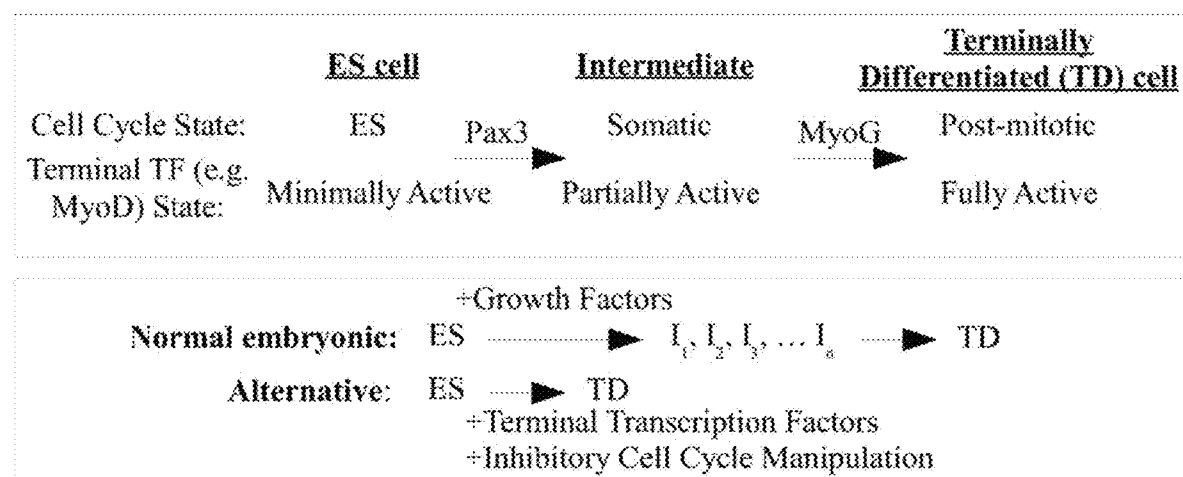
FIG. 6 demonstrates that use of network-based cell cycle manipulation may provide an alternative strategy to generating terminal cell types that is more efficient than recapitulating embryogenesis. (Top Box) Analytical scheme of how cell cycle states drive activation of a terminal transcription factor. Without wishing to be bound by theory, it is contemplated that in the MyoD overexpression system, transitions from the 3 states of ES to somatic cycling to a terminally differentiated state influence the subsequent activation of MyoD and hence the progression of differentiation. The first transition is correlated with Pax3 activation and the second transition is correlated with MyoG activation. Accelerating the cell cycle transitions accelerates the differentiation process. (Lower Box) Current strategies of differentiating ES cells into cells involves growth-factor based recapitulation of embryogenesis. The alternative strategy described herein (and shown in the case of skeletal muscle), is to artificially induce differentiation by accelerating cell cycle inhibition combined with addition of a terminal transcription factor. Since ES cells are susceptible to cell cycle-related pathways, this permits a faster, more efficient differentiation.

The results described herein indicate that in the MyoD-guided system there are minimally 3 states and two transitions (FIG. 6, top box). The first stable state is pluripotency. When the cell cycle is suppressed there is a rapid transition to an intermediate somatic state, which correlates with an upregulation in Pax3. Manipulations that promote this transition also promote Pax3 upregulation. For example, this transition could be facilitated by growth factor/serum withdrawal, LY294002 (PI3K inhibition), HLM006474 (E2F inhibition), and JQ1 (Bromodomain/Myc inhibition). Subsequently there is a second transition to the terminally differentiating state, which correlates with upregulation of MyoG. Manipulations that promote this transition also promote MyoG. MyoG could be facilitated by PD98059 (MEK1/2 inhibitor), and p21 (CDK inhibitor) when combined with low serum, but not with roscovitine (broad CDK family inhibitor) or PD0332991 (CDK4 inhibitor).

Though this scheme is likely to be a simplification for any lineage and may differ in different lineages, it nevertheless helped to make sense of a number of observations. The removal of extracellular factors in the form of LIF and Bmp4, and the replacement of serum with insulin leads to activation of MyoD and full induction of terminal myogenesis. When applied early, this leads to a very direct form of ES-to-terminal differentiation, and Pax3 and MyoG upregulation is observed. PI3K inhibition is predicted to activate MyoD by removing the stimulus to Myc, but is also expected to be inhibitory on the last steps of terminal differentiation as it becomes necessary for metabolic cell growth of the final differentiated cell. Accordingly, LY294002 upregulated Pax3 but promoted poor survival, which could have suppressed MyoG expression. This suggests that the step of MyoG upregulation corresponds to what happens in the terminal phase in this model, which is consistent with what is known about myogenin's role from terminal models. From the heuristic description, it is also expected that Myc or E2F suppression would help activate MyoD. JQ1 and HLM006474 both induced Pax3, which is consistent with this prediction. However, it was also noticed that they suppressed MyoG expression.

The cell cycle schemes also correctly predict that some CDK inhibitors and the MAPK inhibitor would have little effect on Pax3 expression by themselves, but would facilitate MyoG expression. This is due to the fact that in ES cells Myc and Id proteins are highly expressed and can independently repress the expression of endogenous MyoD and other myogenic regulatory factors outside of CDK activity (FIG. 1C). As ES cells differentiate, they transition to the somatic cell cycling state and then to the terminally differentiated model (FIG. 1D). Throughout this transition Myc and Id activity decline until CDK activity is the predominant factor blocking differentiation. Hence at the early stage of Pax3 activation CDK inhibition is not expected to have a significant effect, whereas at the late stage of MyoG activation the expectation is that it will. Moreover, CDK4 activity is suppressed in ES cells, so additional inhibition of their activity by PD0332991 should reveal no effect on Pax3. MAPK (MEK1/2) activity is also suppressed in ES cells, but is upregulated during differentiation. Thus its inhibition should stimulate MyoG induction, but not Pax3 induction.

It is described herein that the CDK inhibitors and the MAPK inhibitor promote differentiation only under low serum conditions, as high levels of growth factor/serum conditions are expected to induce higher levels of Myc and Id expression. It is further described herein that different CDK inhibitors can have different effects. The p21 protein is highly effective at promoting MyoG expression, but not roscovitine or PD0332991. Without wishing to be bound by theory, this may have to do with the differing specificities of the kinase inhibitors used.

It is specifically contemplated herein that the methods described herein can permit the differentiation of other cell types, e.g., with other terminal factors in place of MyoD. Indeed, many terminal cell systems couple cell cycle inhibition with differentiation (1), and many potent transcription factors interact with cell cycle components in ways similar to MyoD, including Ngn2, Pdx1, Smad3, Mitf, Runx2, PU.1, Hnf4α, and C/EBPβ (17-24). Expression of several genes associated with diverse differentiated cell types could be stimulated by cell cycle inhibition in a heterogeneous differentiation system where MyoD was not expressed (FIG. 5).

The forced silencing of proliferative pathways and the resulting rapid differentiation in vitro described herein is a useful strategy to generate terminal cell types as compared to trying to recapitulate embryonic differentiation pathways, which often takes weeks (FIG. 6, bottom box)(26-31).

Materials and Methods

ES culture and differentiation. The ES cells contain MyoD (and associated puromycin resistance marker) expressed from a EF1alpha promoter (5). MyoD could be expressed once a loxP segment inserted between the promoter and transgene was excised by a cre recombinase fused to the estrogen receptor. ES cells were cultured in LIF and standard conditions containing 15% FBS, non-essential amino acids, L-glutamine, penicillin/streptomycin, and beta-mercaptoethanol. To induce MyoD, cells were treated for 24 hrs with 1 μM 4OHT (Sigma) in ES media. Reduced serum media consisted of DMEM and 2% horse serum (Invitrogen) plus 10 μg/ml insulin (to maintain cell survival)(Sigma) with sodium pyruvate and penicillin/streptomycin. During differentiation, cells were treated with 1 μg/ml puromycin continuously to select for cells which maintained MyoD expression. N2B27 components/supplements and Knock-out serum replacement were purchased from Invitrogen. LIF was used at a 1000 U/ml and Bmp4 at 10 ng/ml.

Drugs. The PI3K inhibitor LY294002, Roscovitine, the MEK1/2 inhibitor PD98059, and 10058-F4 were purchased from Sigma. The E2F inhibitor HLM006474 was purchased from Millipore. PD0332991 was purchased from Selleck-Chem. JQ1 was purchased from ApexBio.

Immunostaining Myosin heavy chain expression was detected with use of the MF20 antibody (R&D systems). Cells were fixed in 4% PFA, permeabilized in 0.1% Triton-X, and co-stained with antibody and DAPI (Sigma).

RNA isolation and RT-PCR. RNA was isolated using RNAeasy plus kit (Qiagen). Reverse transcription was performed using iScript™ cDNA synthesis (Bio-rad). Real-time quantitative PCR was done on a CFX96™ PCR machine using SYBR green supermix (Bio-rad). A complete list of primers used is provided in the Supplementary Methods.

Microarray analysis. RNA time-course samples were hybridized to Illumina Ref8 BeadChip™ arrays. Data analysis was performed with GenomeStudio™ software and the help of the BCH IDDRC Molecular Genetics Core.

Cloning. The mouse p21 open reading frame was cloned into the pmCherry-N1™ plasmid (Clontech) with a self-cleaving P2A peptide and mCherry fused to its C-terminus. The plasmid was transfected into the MyoD-inducible ES cell line and selected by G418. The final line was derived from the picking of a single cell clone colony.

REFERENCES

1. Muñoz-Alonso M, and León J (2003) G1 phase control and cell differentiation. In G1 Phase Progression, ed Boonstra J (Landes Bioscience, Georgetown, Tex.), pp. 236-264.
2. Budirahardja Y, and Gönczy P (2009) Coupling the cell cycle to development. Development 136:2861-2872.
3. Hindley C, and Philpott A (2012) Co-ordination of cell cycle and differentiation in the developing nervous system. *J. Biochem.* 444:375-82.
4. Li V C, Ballabeni A, and Kirschner M W (2012) Gap 1 phase length and mouse embryonic stem cell self-renewal. *P.N.A.S.* 109:12550-12555.
5. Thoma E C, Maurus K, Wagner T U, and Schartl M (2012) Parallel differentiation of embryonic stem cells into different cell types by a single gene-based differentiation system. *Cellular Reprogramming* 14:106-111.
6. Bentzinger C F, Wang Y X, and Rudnicki M A (2012) Building muscle: molecular regulation of myogenesis. *Cold Spring Harb Perspect Biol.* 4:pii:a008342.
7. Keller G (2005) Embryonic stem cell differentiation: emergence of a new era in biology and medicine. *Genes Dev.* 19:1129-55.
8. Gianakopoulos P J, et al. (2011) MyoD directly up-regulates premyogenic mesoderm factors during induction of skeletal myogenesis in stem cells. *J. Biol. Chem.* 286:2517-25.
9. Niro C, et al. (2010) Six1 and Six4 gene expression is necessary to activate the fast-type muscle gene program in the mouse primary myotome. *Dev. Biol.* 338:168-82.
10. Galli L M, et al. (2008) Identification and characterization of subpopulations of Pax3 and Pax7 expressing cells in developing chick somites and limb buds. *Dev. Dyn.* 237:182-74.
11. Venuti J M, et al. (1995) Myogenin is required for late but not early aspects of myogenesis during mouse development. *J. Cell Biol.* 128:563-76.
12. Deng X, et al. (2003) Mirk/dyrk1B is a Rho-induced kinase active in skeletal muscle differentiation. *J. Biol. Chem.* 278:41347-54.
13. White J, et al. (2005) Developmental Activation of the Rb-E2F Pahtway and Establishment of Cell Cycle-regulated Cyclin-dependent kinase Activity during Embryonic Stem Cell Differentiation. *Mol. Biol. Cell.* 16:2018-27.
14. Odorico J S, Kaufman D S, and Thomson J A (2001) Multilineage differentiation from human embryonic stem cell lines. *Stem cells* 19:193-204.
15. Hall B K (1981) The induction of neural crest-derived cartilage and bone by embryonic epithelia: an analysis of the mode of action of an epithelial-mesenchymal interaction. *J. Embryol. Exp. Morphol.* 64:305-20.
16. Ordahl C P, and Le Douarin N M (1992) Two myogenic lineages within the developing somite. *Development* 114: 339-53.
17. Ali F, et al. (2011) Cell cycle-regulated multi-site phosphorylation of Neurogenin 2 coordinates cell cycling with differentiation during neurogenesis. *Development* 138: 4267-77.
18. Kim Y C, et al. (2011) RB regulates pancreas development by stabilizing Pdx1. *EMBO J.* 30:1563-76.
19. Matsuura I, et al. (2004) Cyclin-depedent kinases regulate the antiproliferative function of Smads. *Nature* 430: 226-31.
20. Carreira S, et al. (2005) Mitf cooperates with Rb1 and activates p21Cip1 expression to regulate cell cycle progression. *Nature* 433:764-9.
21. Thomas D M, et al. (2001) The retinoblastoma protein acts as a transcriptional coactivator required for osteogenic differentiation. *Mol. Cell* 8, 303-316
22. Rekhtman N, et al. (2003) Pu.1 and pRB interact and cooperate to repress GATA-1 and block erythroid differentiation. *Mol. Cell Biol.* 23:7460-74,
23. Hanse E A, et al. (2012) Cyclin D1 inhibits hepatic lipogenesis via repression of carbohydrate response element binding protein and hepatocyte nuclear factor 4α. *Cell Cycle* 11:2681-90.
24. Chen P L, Riley D J, Chen Y, and Lee W H (1996) Retinoblastoma protein positively regulates terminal adipocyte differentiation through direct interaction with C/EBPs. *Genes Dev.* 10:2794-804.
25. Singh A M, and Dalton S (2009) The cell cycle and Myc intersect with mechanisms that regulate pluripotency and reprogramming. *Cell Stem Cell* 5:141-9.
26. Mallanna S K and Duncan S A (2013) Differentiation of Hepatocytes from Pluripotent Stem Cells. *Current Protocols in Stem Cell Biology.* 26:1G.4.1-1G.4.13.
27. Lian X, et al. (2013) Directed cardiomyocyte differentiation from human pluripotent stem cells by modulating Wnt/β-catenin signaling under fully defined conditions. *Nat. Protoc.* 8:162-75.

28. Oldershaw R A, et al. (2010) Directed differentiation of human embryonic stem cells toward chondrocytes. *Nat. Biotechnol.* 28:1187-94.

29. Lu S J, Feng Q, Park J S, Lanza R (2010) Direction differentiation of red blood cells from human embryonic stem cells. *Methods Mol. Biol.* 636:105-21.

30. Hosoya M, Kunisada Y, Kurisaki A, Asashima M (2012) Induction of differentiation of undifferentiated cells into pancreatic beta cells in vertebrates. *Int. J. Dev. Biol.* 56:313-23.

31. Albini S, et al. (2013) Epigenetic reprogramming of human embryonic stem cells into skeletal muscle cells and generation of contractile myospheres. *Cell Rep.* 3:661-670.

References Relevant to Schematics Presented in FIGS. 1A-1C And 7A-7C

Leone G, et al. (2001) Myc requires distinct E2F activities to induce S phase and apoptosis. Mol. Cell. 8:105-113).

Lasorella, A., Noseda, M., Beyna, M., Yokota, Y. & Iavarone, A. Id2 is a retinoblastoma protein target and mediates signalling by Myc oncoproteins. Nature 407, 592-598 (2000)

La Rocca S A, Crouch D H, Gillespie D (1994) c-Myc inhibits myogenic differentiation and myoD expression by a mechanism which can be dissociated from cell transformation. Oncogene 9:3499-508.

Philipp A, et al. (1994) Repression of cyclin D1: a novel function of Myc? Mol. Cell Biol. 14:4032-4043.

Watanabe G, et al. (1998) Inhibition of cyclin D1 kinase activity is associated with E2F-mediated inhibition of cyclin D1 promoter activity through E2F and Sp1. Mol. Cell Biol. 18:3212-3222

Jirmanova L, et al. (2002) Differential contributions of ERK and PI3-kinase to the regulation of cyclin D1 expression and to the control of the G1/S transition in mouse embryonic stem cells. Oncogene 21:5515-5528.

Oswald F, et al. (1994) E2F-dependent regulation of human Myc: transactivation by Cyclin D1 and Cyclin A overrides tumour suppressor protein functions. Oncogene 9:2029-2036.

Tintignac L A et al. (2000) Cyclin E-cdk2 phosphorylation promotes late G1-phase degradation of MyoD in muscle cells. Experimental Cell Research 259:300-307

Lassar A B, Skapek S X, and Novitch B (1994) Regulatory mechanisms that coordinate skeletal muscle differentiation and cell cycle withdrawal. Curr. Opin. Cell Biol. 6:788-794.

Kitzmann M, and Fernandez A (2001) Crosstalk between cell cycle regulators and the myogenic factor MyoD in skeletal myoblasts. Cell. Mol. Life Sci. 58:571-579.

Cartwright P, et al. (2005) LIF/STAT3 controls ES-cell self-renewal and pluripotency by a Myc-dependent mechanism. Development 132:885-96.

Paling N R D, Wheadon H, Bone H K and Welham M J. (2005) Regulation of embryonic stem cell self-renewal by phosphoinositide 3-kinase dependent signalling. J. Biol. Chem. 279:48063-48070.

Ying Q L, Nichols J, Chambers I, Smith A (2003) BMP induction of Id proteins suppresses differentiation and sustains embryonic stem cell self-renewal in collaboration with STAT3. Cell 115:281-292.

Sakamuro D and Prendergast G C (1999) New Myc-interacting proteins: a second Myc network emerges. Oncogene 18:2942-2954.

TABLE 2 qRT-PCR Primer list. Primers are labelled (Gene name_)(F or R) depending on forward or reverse

| Primer | Primer Sequence | SEQ ID NO |
|---|---|---|
| GAPDH_F | GTGTTCCTACCCCCAATGTGT | 01 |
| GAPDH_R | GTTGAAGTCGCAGGAGACAAC | 02 |
| NeuroD1_F | ACAGACGCTCTGCAAAGGTTT | 03 |
| NeuroD1_R | GGACTGGTAGGAGTAGGGATG | 04 |
| Pax6_F | TACCAGTGTCTACCAGCCAAT | 05 |
| Pax6_R | TGCACGAGTATGAGGAGGTCT | 06 |
| Dll1_F | GCAGGACCTTCTTTCGCGTAT | 07 |
| Dll1_R | AAGGGGAATCGGATGGGGTT | 08 |
| Pparg_F | TTTTCCGAAGAACCATCCGATT | 09 |
| Pparg_R | ATGGCATTGTGAGACATCCCC | 010 |
| Nkx2.2_F | AAGCATTTCAAAACCGACGGA | 011 |
| Nkx2.2_R | CCTCAAATCCACAGATGACCAGA | 012 |
| Ngn3_F | CCAAGAGCGAGTTGGCACT | 013 |
| Ngn3_R | CGGGCCATAGAAGCTGTGG | 014 |
| CEBPa_F | GATAAGAACAGCAACGAGTACCG | 015 |
| CEBPa_R | GTCACTGGTCAACTCCAACACC | 016 |
| CEBPb_F | CATCGACTTCAGCCCCTACC | 017 |
| CEBPb_R | GGCTCACGTAACCGTAGTCG | 018 |
| MeF2c_F | TCTCCGCGTTCTTATCCCAC | 019 |
| MeF2c_R | AGGAGTTGCTACGGAAACCAC | 020 |
| Pdx1_F | CCCCAGTTTACAAGCTCGCT | 021 |
| Pdx1_R | CTCGGTTCCATTCGGGAAAGG | 022 |
| Nestin_F | CCCTGAAGTCGAGGAGCTG | 023 |
| Nestin_R | CTGCTGCACCTCTAAGCGA | 024 |
| Sox6_F | TCAACCTGCCAAACAAAAGC | 025 |
| Sox6_R | GCTGGATCTGTTCTCGCATC | 026 |
| Smyd1_F | TCCGAGGGTTTGTATCACGAG | 027 |
| Smyd1_R | CCTCCTGGCATAATGTGAGGC | 028 |
| Runx2_F | CCAAGGAACAAACCGTCAAA | 029 |
| Runx2_R | AAGCGGGTCTGCAGAGTGTA | 030 |
| EBF_F | AGATTCCAGGTCGTGGTGTCTA | 031 |
| EBF_R | ACAGGGAGTAGCATGTTCCAGA | 032 |
| Tal1_F | GGTCCTCACACCAAAGTAGTGC | 033 |
| Tal1_R | CGGAGGATCTCATTCTTGCTTA | 034 |
| Gata4_F | ATAATCTCCTTCACCCCAGCTC | 035 |
| Gata4_R | GGGCAGGGCTTCTATGTCTAGT | 036 |
| Mrg1_F | ATTTGTTGGCTGCATGATCTTT | 037 |

TABLE 2-continued qRT-PCR Primer list. Primers are labelled (Gene name_)(F or R) depending on forward or reverse

| Primer | Primer Sequence | SEQ ID NO |
|---|---|---|
| Mrg1_R | CGGTATGACTTTTCCTGATCCA | 038 |
| Mitf_F | AGGCAGAAAAAGGACAATCACA | 039 |
| Mitf_R | CTTCCGGATGTAGTCCACAGAG | 040 |
| Gata2_F | AAGCGAAAACCAAACTGCATAA | 041 |
| Gata2_R | CCAAGAACCACTCAAAGGACTG | 042 |
| Gata3_F | TCCCATTTGTGAATAAGCCATT | 043 |
| Gata3_R | TCCTTCATGCCTTTCTTACAGC | 044 |
| Runx1_F | CTCCCAATAGCCCTTCTCACTT | 045 |
| Runx1_R | AGCAAGAGAATGGCTGACTCAC | 046 |
| PU1_F | ACAGATGCACGTCCTCGATACT | 047 |
| PU1_R | CTTCTCCATCAGACACCTCCAG | 048 |
| Sox9_F | TCTCCCCCTTTTCTTTGTTGTT | 049 |
| Sox9_R | ACGCACACATCCACATACAGTC | 050 |
| Lbh_F | CTTGCTTCCACTCTGCTCTGTT | 051 |
| Lbh_R | ACGGCAAGACCAAGACAGATAA | 052 |
| Gata1_F | CAGAATAGCCTTGACCTTGTGG | 053 |
| Gata1_R | AGGAAAATGTCAGGCATAGCAA | 054 |
| Ikaros_F | GTTTGTTGCCCAGTAAGACGAG | 055 |
| Ikaros_R | GCTTTGGCTTCCAAGAAGTTTT | 056 |
| Gata6_F | CCAAATCATGTGCTTCTTGTGA | 057 |
| Gata6_R | TATTCTTGTTGAGACCCCAGGA | 058 |
| Oct4_F | ATGGCATACTGTGGACCTC | 059 |
| Oct4_R | AGCAGCTTGGCAAACTGTTC | 060 |
| Nanog_F | CAGCAGATGCAAGAACTCTCC | 061 |
| Nanog_R | GGATACTCCACTGGTGCTGAG | 062 |
| Brachyury_F | CTCTAATGTCCTCCCTTGTTGCC | 063 |
| Brachyury_R | TGCAGATTGTCTTTGGCTACTT | 064 |
| Sox17_F | ACAACGCAGAGCTAAGCAAGAT | 065 |
| Sox17_R | GTACTTGTAGTTGGGGTGGTCCT | 066 |
| Cdx2_F | AAAAGACAAATACCGGGTGGTG | 067 |
| Cdx2_R | TGATTTTCCTCTCCTTGGCTCT | 068 |
| Pax3_F | CATCCGACCTGGTGCCATC | 069 |
| Pax3_R | ATTTCCCAGCTAAACATGCCC | 070 |
| Pax7_F | TGGGGTCTTCATCAACGGTC | 071 |
| Pax7_R | ATCGGCACAGAATCTTGGAGA | 072 |
| Myf5_F | CACCACCAACCCTAACCAGAG | 073 |
| Myf5_R | AGGCTGTAATAGTTCTCCACCTG | 074 |
| MyoG_F | GCAGGCTCAAGAAAGTGAATGA | 075 |
| MyoG_R | TAGGCGCTCAATGTACTGGAT | 076 |
| MRF4_F | AGAGGGCTCTCCTTTGTATCC | 077 |
| MRF4_R | CTGCTTTCCGACGATCTGTGG | 078 |
| MyoD1endo_F | CTGCAGCAGCAGAGGGCGCACCA | 079 |
| MyoD1endo_R | GAAGAACGGCTTCGAAAGGACAGTTGG | 080 |
| Six1_F | GAAAGGGAGAACACCGAAAACA | 081 |
| Six1_R | GTGGCCCATATTGCTCTGGA | 082 |
| Six4_F | ACCCCAGTACCGAGGATGAAT | 083 |
| Six4_R | AACTCCAGACGAGCTTAGTGA | 084 |

Table 3: List of factors affected by cell cycle inhibition during unguided differentiation and the cell type lineages in which they play a role. Lineages refer to differentiation systems in which the factors have been reported to be involved. The effect of low serum compared to high serum is listed as increased, decreased, or same/similar. Over the seven day time course, when the effect of low serum occurs is referred to as the stage. If the effect occurs within Days 1-3, the stage is referred to as early, or else mid (Days 3-4), or late (Days 5-7).

| Gene | Lineage | Increase or Decrease | Stage |
|---|---|---|---|
| NeuroD1 | Neural | Increase | Early |
| Dll1 | Neural | Increase | Mid |
| Pax6 | Neural | Increase | Mid |
| Nestin | Neural | Decrease | Mid/Late |
| Sox6 | Cardiac | Increase | Late |
| Smyd1 | Cardiac | Increase | Late |
| Mef2c | Cardiac | Increase | Late |
| Gata4 | Cardiac | Increase | Mid/Late |
| Gata6 | Cardiac | Increase | Mid/Late |
| C/EBPβ | Adipocyte | Same | N/A |
| PPARγ | Adipocyte | Increase | Late |
| CEBPα | Adipocyte | Increase | Late |
| Sox17 | Pancreatic | Increase | Late |
| Nkx2.2 | Pancreatic | Increase | Late |
| Pdx1 | Pancreatic | Same | N/A |
| Ngn3 | Pancreatic | Decrease | Mid/Late |
| Runx2 | Osteoblast | Increase | Late |

-continued

| Gene | Lineage | Increase or Decrease | Stage |
|---|---|---|---|
| Cdx2 | Placental | Same | N/A |
| Cited2 | Multiple | Increase | Late |
| Mitf | Melanocyte | Increase | Late |
| Sox9 | Chondrocyte | Increase | Mid/Late |
| Lbh | Chondrocyte | Same | N/A |
| Runx1 | Blood | Increase | Late |
| Pu1 | Blood | Decrease | Early |
| Gata2 | Blood | Increase | Mid/Late |
| Gata3 | Blood | Increase | Late |
| Tal1 | Blood | Decrease | Late |
| EBF | Blood | Altered | N/A |
| Gata1 | Blood | Increase | Early to late |
| Ikaros | Blood | Similar | N/A |

Example 2: The Generality of Direct Embryonic Stem Cell Programming

Described above herein is a principle for the direct programming of cell fates. Further described herein is a demonstration that this programming principle can be extended from skeletal muscle to spinal motor neurons, cardiomyocytes, and hepatoblast-like cells. The broad applicability of this principle to these cell types indicates a common differentiation structure is shared across multiple lineages, and indicates that cell cycle-associated processes serve a fundamental role in regulating the rate and path of embryonic differentiation.

The induction of cell fates during embryogenesis is orchestrated through the action of developmental signals, such as growth factors (1). Proper exposure to these signals leads to the normal patterning and growth of the embryo. It is described herein that the major point of this signaling, with respect to differentiation, is to align two properties within the cell: 1. its transcriptional state, which determines the lineage and cell type to be specified, and 2. its appropriate "cell cycle" state, which determines the rate of differentiation (2). Given the alignment of these two properties, it can be possible to induce cells to turn into any fate, even through transformations that do not occur naturally. This decomposition of the normal differentiation process helps us understand the critical elements required for cell fate changes and the roles they play, which cannot be understood by only studying normal embryonic differentiation. Moreover, it could improve our ability to alter cell fates for regenerative medicine Described herein are methods relating to the combination of the appropriate transcriptional state with the appropriate "cell cycle" state to determine a specific cell fate. Neither of these two components is sufficient alone. However, when combined together, these two conditions lead to a rapid and direct conversion. This was first demonstrated in experiments where mouse embryonic stem (ES) cells are rapidly and effectively converted into skeletal muscle. Normally, a standard strategy of differentiating ES cells into skeletal muscle would require sequential treatment of growth factors to recapitulate intermediate embryonic progenitor stages, such as mesoderm (3). This need to reconstitute a series of intermediate stages can be avoided by engineering the ES cell to overexpress MyoD (the transcriptional component, which by itself does not trigger muscle differentiation) and simultaneously using methods of inhibiting the cell cycle (such as growth factor withdrawal)(2). Out of the usual myogenic regulatory hierarchy, which includes Six1, Six4, Pax3, Pax7, MyoG, Myf5, and Mrf4, only Pax3 and MyoG appear to be significantly upregulated in addition to the exogenous MyoD.

Setting the transcriptional state can be achieved by overexpressing an appropriate transcription factor. Setting the "cell cycle" state can be achieved by manipulating cell cycle pathways. The pathways that normally connect extracellular growth factors to the intracellular G1/S machinery and their nuclear effectors (e.g. Myc, Rb) are highly involved (summarized in network models in ref. 2). Withdrawing growth factors delivers a strong inhibitory signal, whereas inhibiting downstream pathways has effects that are differentiation stage-specific. The skeletal muscle system has been a model for cell differentiation, and initial studies were performed on this system.

Described herein is the demonstration that other lineages share a similar capacity to be directly programmed. MyoD was replaced with transcription factors for three additional cell types. The results indicate a much greater generality of the process of direct programming.

Results

Spinal Motor Neurons

To generate spinal motor neurons, a mouse ES cell line that overexpressed a combination of three transcription factor lineage specifiers (Ngn2, Isl1, Lhx3) was used. This combination was previously shown to specify spinal motor neuron identity (4). These iNIL cells, as they are also called, upon doxycycline stimulation express the three transcription factors from a single open reading frame coupled by 2A peptides. Growth factor withdrawal was used as the method of cell cycle manipulation in the experiments described in this Example.

Figures 11A, 11B:
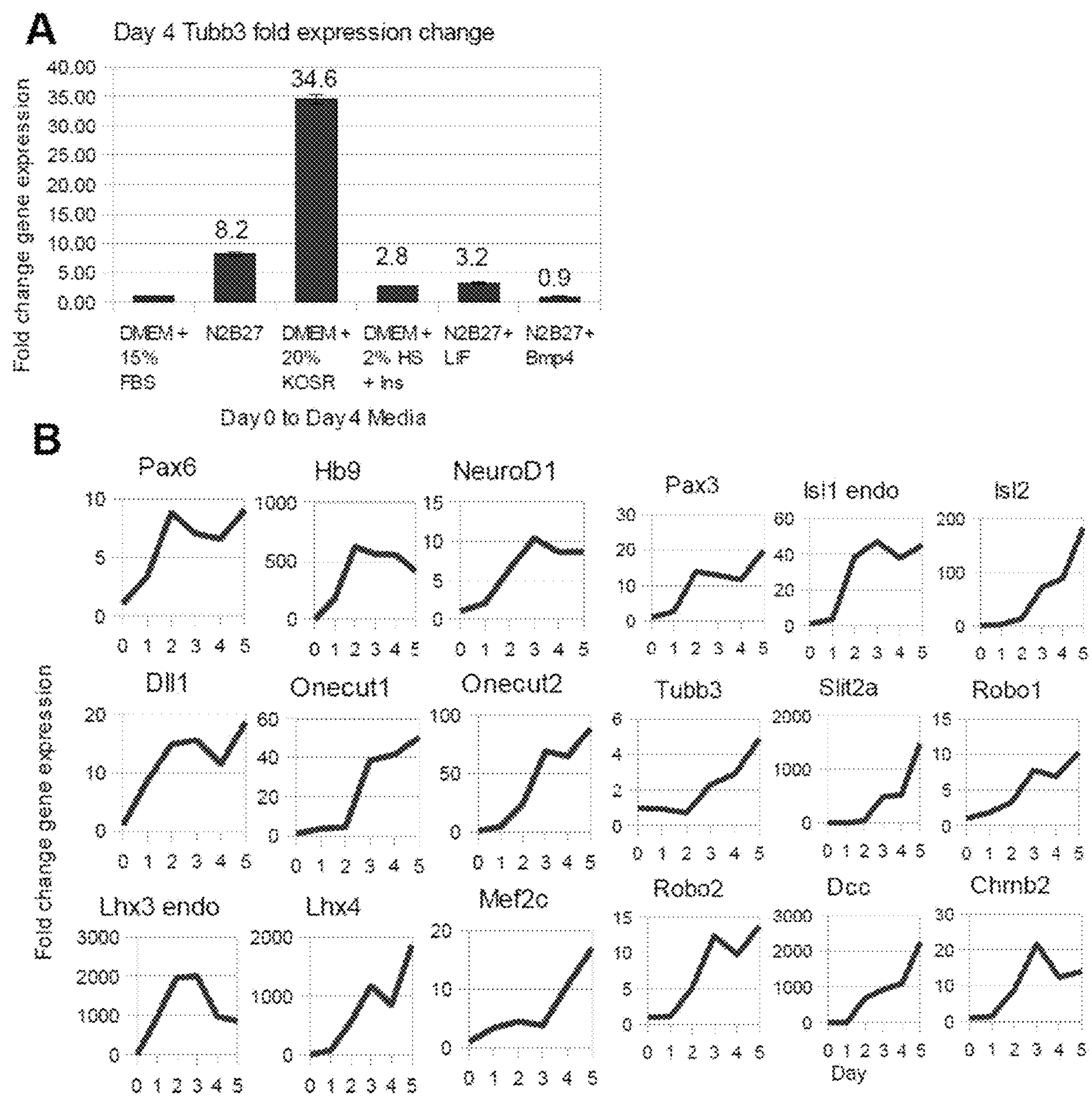
FIGS. 11A-11B depict spinal motor neurons.
Figure 14:
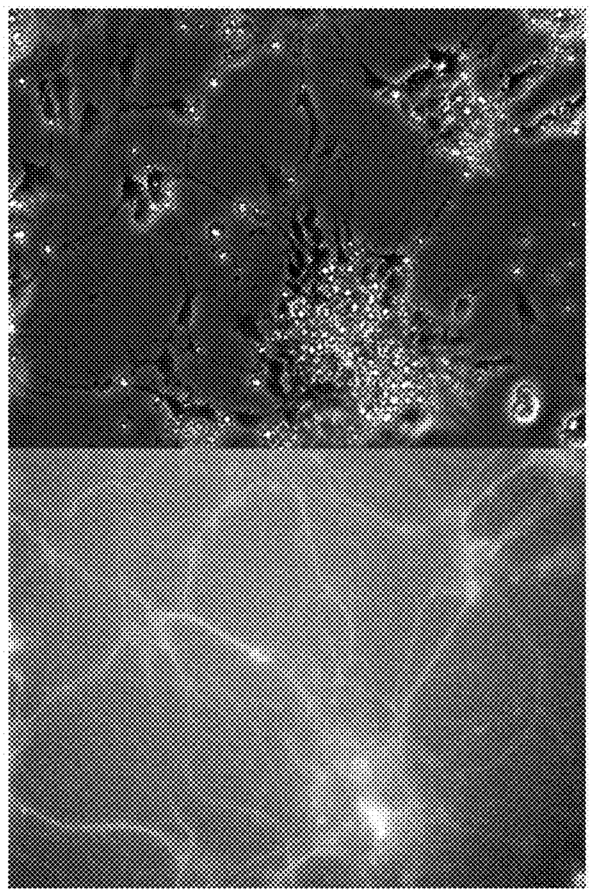
FIG. 14 depicts pictures of spinal motor neurons. Top: Phase contrast image of Day 5 neurons differentiated in growth factor-free N2B27 media. Bottom: Same neurons immunostained with antibody against neuronal beta3-tubulin (Tubb3).

As expected from the results on skeletal muscle myotubes, neurons rapidly formed from ES cells upon switching to different types of growth factor-free media. Four days after removing LIF and adding doxycycline (Day 0), ES cells that had been differentiated in growth factor-free (N2B27 or 20% Knockout Serum Replacement/KOSR) or growth factor-reduced media (2% horse serum/HS with insulin) expressed much higher levels of the terminal neuron differentiation marker beta-3 tubulin (Tubb3) than in high growth factor media (15% FBS), and displayed morphological characteristics of neurons, which was not seen in high serum (FIG. 11A and FIG. 14). Tubb3 expression was confirmed by immunostaining. When either of the ES cell growth factors LIF or Bmp4 were added back into growth factor-free media, there was a strong block on neuronal differentiation.

To see which genes are induced during this rapid differentiation process, the mRNA expression of neural lineage genes was profiled across the time course of differentiation (first 5 days). As before, LIF was removed, the media changed to N2B27, and doxycycline added at Day 0. Many neural genes were upregulated in the growth factor-free N2B27 media (FIG. 11B). These include Pax6, which had a sustained activation that increased during the five days of differentiation. Hb9 and NeuroD1 were also activated, as were endogenous Lhx3 and Lhx4. Other genes that were similarly activated include D111, Onecut1, Onecut2, Mef2c, and Pax3. Some of these genes were upregulated even at day one. In contrast, most of the activation of terminal genes occurred slightly later, around day 2-3. These include Tubb3, neuronal guidance molecule Slit2a, axon guidance receptors Robo1 and Robo2, receptor Dcc, and cholinergic receptor Chrnb2. Similar increases were not observed under the high serum condition.

Cardiomyocytes

Figures 12A, 12B:
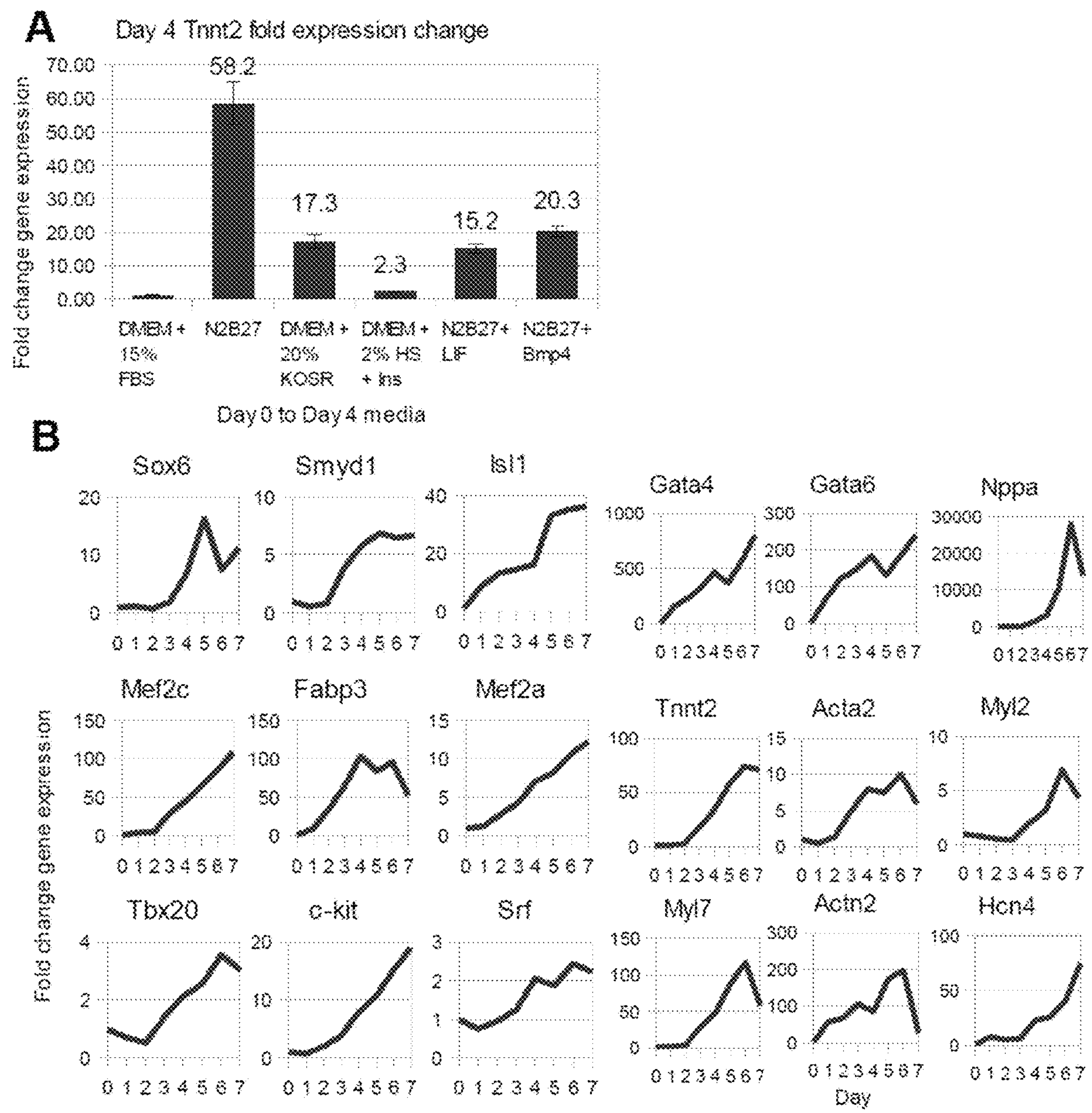
FIGS. 12A-12B depict cardiomyocytes.
Figure 15:
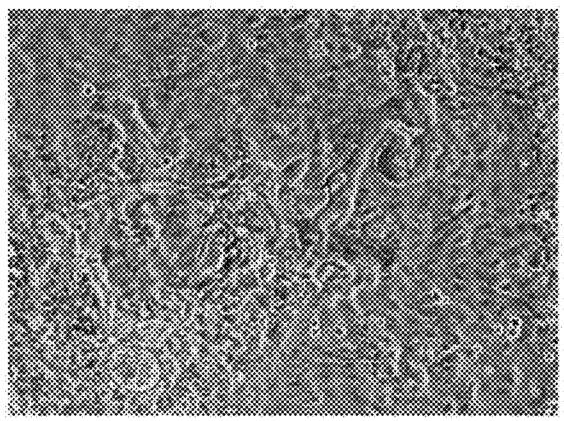
FIG. 15 depicts an image of a cluster of cardiomyocytes differentiated after 9 days beating in the dish.

Similar experiments were performed on an ES cell line that overexpressed the transcription factor Gata5. The Gata4/5/6 family of transcription factors have been shown to specify cardiomyocytes previously (5). The earliest terminal marker expression for cardiomyocytes in growth factor media could be detected by day 3 after LIF removal and dox addition. Similar to neurons, ES cells differentiated in growth factor-free or growth factor-reduced media displayed higher levels of genes involved with cardiomyocyte terminal differentiation, such as cardiac troponin (Tnnt2) by day 4, compared with high serum (FIG. 12A). The earliest spontaneously beating cardiomyocyte clusters could be observed at day 5, although this is a rare event. More commonly, beating clusters could be observed starting at day 8-9 (FIG. 15). This may reflect a requirement for aggregation.

Several cardiac lineage genes in N2B27 media were upregulated (FIG. 12B). These include the lineage specifiers Sox6, Smyd1, Isl1, and Mef2c, as well as Fabp3, Mef2a, Tbx20, c-kit, Srf, and the Gata5 related family members 4 and 6. Terminal differentiation genes were also upregulated with rapid kinetics, including natriuretic peptide A, cardiac troponin, smooth muscle actin (Acta2), Myosin light chains 2 and 7 (Myl2/7), alpha-actinin (Actn2), and the potassium channel Hcn4, all rose within 3-5 days.

Hepatoblast-Like Cells

Figures 13A, 13B:
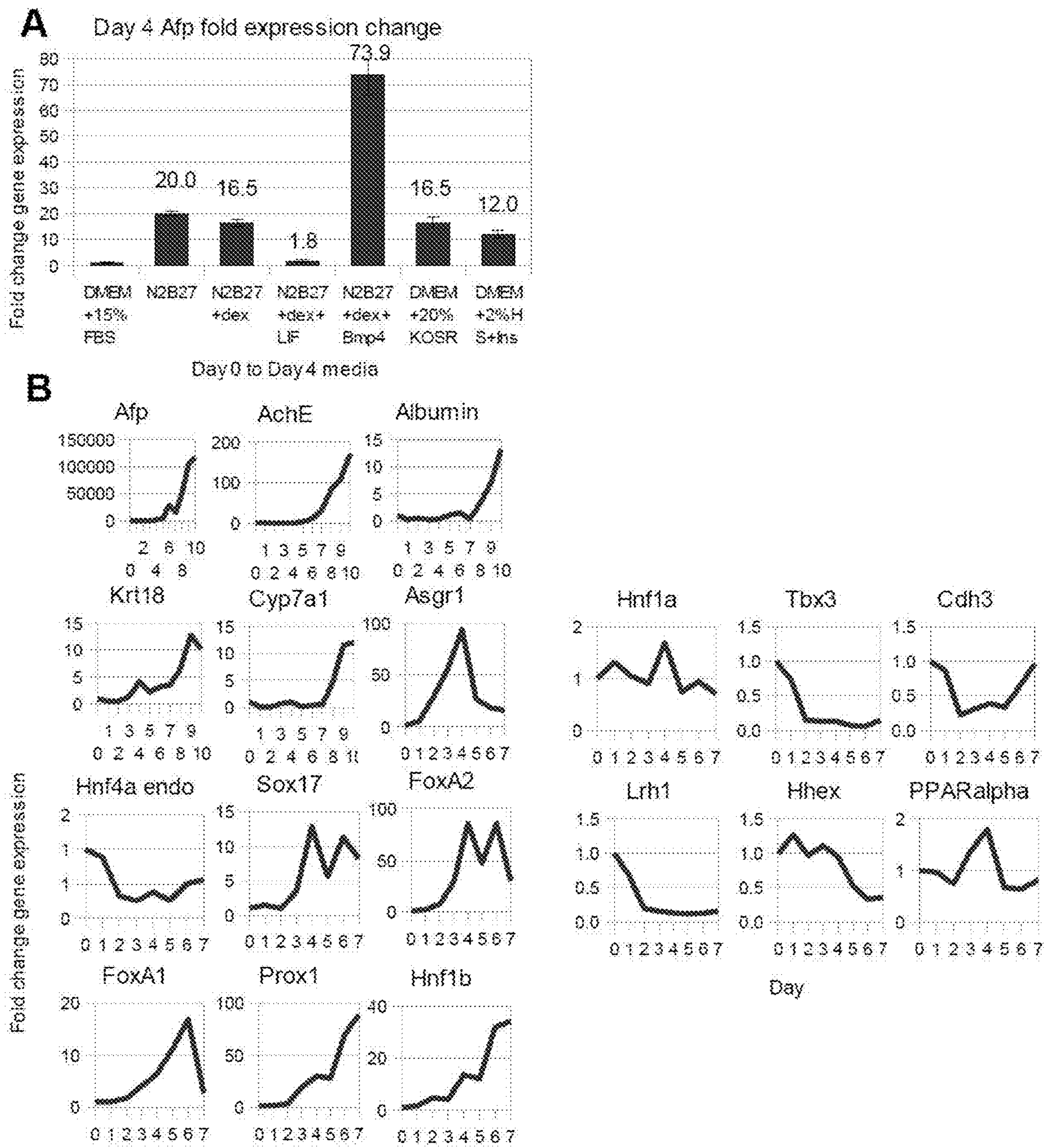
FIGS. 13A-13B depict hepatoblast-like cells.
Figure 16:
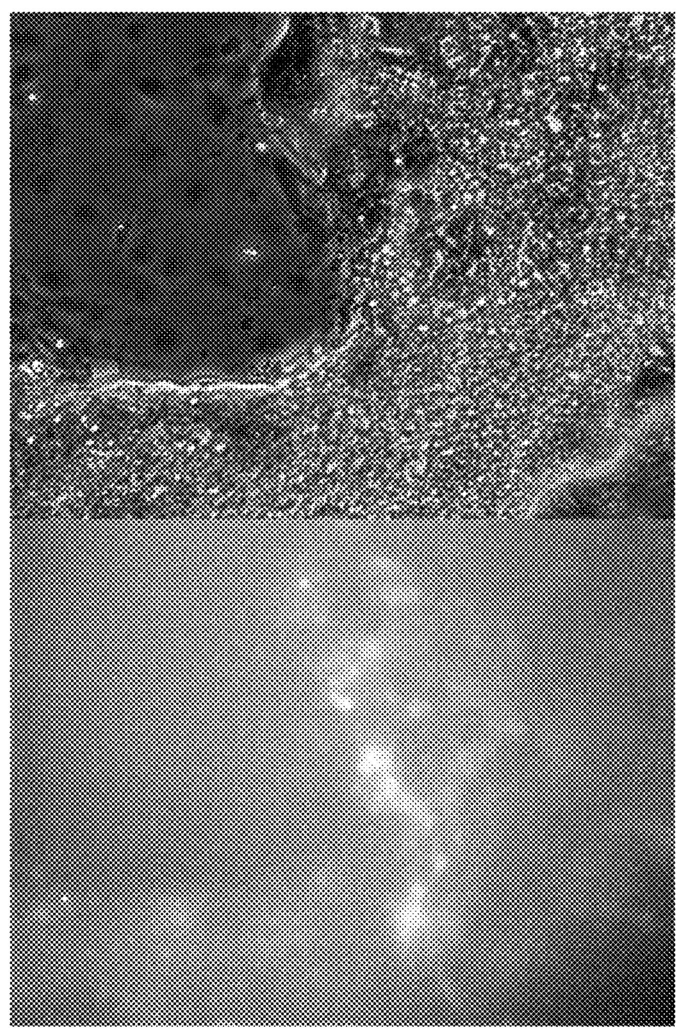
FIG. 16 depicts pictures of hepatoblast-like cells. Top: Phase contrast image of Day 5 hepatoblast-like cells differentiated in growth factor-free N2B27 media. Image is crowded due to the continued proliferation of these cells in growth factor-free media. Bottom: Same hepatoblast-like cells immunostained with antibody against alpha fetoprotein (AFP

One essential lineage specifying factor for hepatocytes is hepatic nuclear factor 4α (Hnf4α)(6). Switching of Hnf4α-overexpressing ES cells to growth factor-free or growth factor-reduced media led to the activation of a subset of hepatic genes. At day 0, LIF and doxycycline were removed and the media was either switched or kept to 15% FBS. By day 4, there were high levels of alphafetoprotein (AFP) that could be detected in the cells differentiated in the growth factor-free or growth factor-reduced media and less than 10% the level of AFP in cells in 15% FBS (FIG. 13A and FIG. 16). AFP expression could be confirmed by immunostaining. While this activation by growth factor withdrawal was similar to the pattern seen in previous cell types, there was an additional interesting point of variation compared to other lineages examined so far. The re-addition of Bmp4 did not reduce the amount of AFP expression, although the re-addition of LIF did, as usually observed. Hnf4α-overexpressing cells continued to divide for several days even after incubation in growth factor-free N2B27 media. The AFP expression and continuous division indicate that the cells have characteristics of hepatoblasts, rather than hepatocytes. Dexamethasone (a corticosteroid) often helps maintain hepatocyte survival in culture. However, it did not have any additional effect on AFP expression. Many hepatic genes upregulated, including acetylcholinesterase (AchE), endogenous Hnf4α (from days 5-7), Foxa2 (from days 2-5), Foxa1, Asgr1, and Prox1 (FIG. 13B). Albumin production was also detected, as was Sox17, Pparα, Cdh3, Tbx3, Krt18, Hhex, Lrh1, C/EBPα, Hnf1a, and Hnf1b.

Discussion

The results presented herein from from skeletal muscle, spinal motor neurons, cardiomyocytes, and hepatocytes show that the effects of perturbing the cell cycle after establishing the proper transcriptional state occurs in more than one cell lineage. For spinal motor neurons and cardiomyocytes, the differentiation appeared to be more complete, including both histological and molecular features. The hepatocytes were less complete, and resembled hepatoblast-like cells. However, in each case direct programming induced characteristic genes in each lineage.

The ability to directly program cell types suggests an underlying logic of how cell types are normally specified. In normal embryonic development, and in stem cell protocols that seek to mimic this process, proliferation and differentiation are usually simultaneously specified by growth factors. Sequential changes to the composition and concentration of these growth factors specify cell type identity and maintain an expanding embryo. These changes generate numerous intermediate cell types, until cell cycle exit drives cells into terminal differentiation. In contrast, removing growth factors at an early stage can shortcut cells into adopting late, terminal fates. In this sense, proliferative signals may serve as a general "rate-limiting step" in everyday differentiation. For practical applications, the direct programming process described herein provides an alternative to current strategies of embryonic stem cell differentiation, which seek to mimic the natural differentiation pathways.

Materials and Methods

ESC culture and cell lines. ESCs were cultured in standard media (DMEM with LIF+15% fetal bovine serum) on 0.1% gelatin-coated dishes. The Tet-Off Hnf4α line was cultured with 0.2 μg/ml doxycycline.

ESC differentiation. Twenty-four hours before starting, ESCs are trypsinized and spread out as monolayer onto gelatin in standard ES media. At day 0 (ESCs), the media was switched from standard ES media to either N2B27 media (Invitrogen), 20% Knockout Serum Replacement (KOSR)(Invitrogen), 2% horse serum (HS)(Invitrogen)+10 μg/ml insulin, or just 15% FBS without LIF. Doxycycline was also added at day 0 (3 μg/ml) to induce expression or removed entirely for the Hnf4α line. Media was refreshed daily.

For the neurons, the ES cells were seeded onto plates pre-coated with a mix of poly-d-lysine (100 μg/ml) and laminin (50 μg/ml) instead of gelatin for adherence. 1000 U/ml of LIF or 10 ng/ml Bmp4 was added when needed. Dexamethasone (Sigma) was used at 0.1 μM.

RNA isolation and qPCR. RNA was isolated using Qiagen Rnaeasy™ Plus Kit. Purified RNA was then reverse transcribed using Bio-rad's iSCRIPT™ cDNA synthesis kit. Quantitative PCR was performed using Bio-rad's SYBR™ green Supermix.

Immunostaining Antibodies for Tubb3 and AFP were provided respectively by Cell Signaling (D71G9), Sino Biological (clone 27). Cells were fixed in 4% PFA and permeabilized with 0.1% Triton.

REFERENCES

1. Freeman M, and Gurdon J B (2002) Regulatory principles of developmental signaling. Annu. Rev. Cell. Dev. Biol. 18:515-39.
2. Li V C, and Kirschner M W (2014) Molecular ties between the cell cycle and differentiation in embryonic stem cells. P.N.A.S. 111:9503-8.
3. Salani S, Donadoni C, Rizzo F, Bresolin N, Comi G P, Corti S (2012) Generation of skeletal muscle cells from embryonic and induced pluripotent stem cells as an in vitro model and for therapy of muscular dystrophies. J Cell Mol Med. 16:1353-64.
4. Mazzoni E O, et al. (2013) Synergistic binding of transcription factors to cell-specific enhancers programs motor neuron identity. Nat. Neurosci. 16:1219-27.
5. Turbendian H K, et al. (2013) GATA factors efficiently direct cardiac fate from embryonic stem cells. Development 140:1639-44.
6. DeLaForest A, Nagaoka M, Si-Tayeb K, Noto F K, Konopka G, Battle M A, Duncan S A (2011) HNF4A is essential for specification of hepatic progenitors from human pluripotent stem cells. Development 138:4143-53.
7. Nishiyama A, et al. (2009) Uncovering early response of gene regulatory networks in ESCs by systematic induction of transcription factors. Cell Stem Cell 5:420-33.

What is claimed herein is:

1. A method of differentiating a pluripotent stem cell, the method comprising:

i) contacting the pluripotent stem cell with one or more nucleic acids encoding one or more terminal transcription factors; and ii) inhibiting the cell cycle of the pluripotent stem cell, wherein the cell cycle is inhibited by one or more of the following:

reducing serum levels; reducing serum levels below 5%; contacting the cell with a PI3K inhibitor; contacting the cell with a Myc inhibitor; contacting the cell with a MAPK inhibitor; contacting the cell with a MEK1/2 inhibitor; contacting the cell with a CDK inhibitor; contacting the cell with an Id inhibitor; contacting the cell with a Ink family agonist; contacting the cell with a Cip/Kip family agonist; and culturing the cell in a media lacking a factor selected from the group consisting of: Bmp; Fgf; Activin; or TGFβ;

wherein steps i) and ii) occur either:

a) concurrently; or b) within 15 days of each other in either order; and whereby a differentiated cell is generated.

2. The method of claim 1, wherein steps i) and ii) occur within 14 days of each other.

3. The method of claim 1, wherein steps i) and ii) occur within 7 days of each other.

4. The method of claim 1, wherein steps i) and ii) occur within 2 days of each other.

5. The method of claim 1, wherein steps i) and ii) occur within 24 hours of each other.

6. The method of claim 1, wherein steps i) and ii) occur simultaneously.

7. The method of claim 1, wherein the cell cycle is inhibited by reducing or removing growth factors.

8. The method of claim 1, wherein the PI3K inhibitor is LY294002.

9. The method of claim 1, wherein the E2F transcription factor inhibitor is HLM006474.

10. The method of claim 1, wherein the Myc inhibitor is JQ1 or 10058-F4.

11. The method of claim 1, wherein the MAPK inhibitor is PD98059.

12. The method of claim 1, wherein the CDK inhibitor is a CDK4 inhibitor, a CDK2 inhibitor, p16, p15, p18, p19, p21, p27, or p57.

13. The method of claim 1, wherein the pluripotent stem cell is an embryonic stem cell.

* * * * *

UNITED STATES PATENT AND TRADEMARK OFFICE

CERTIFICATE OF CORRECTION

PATENT NO. : 10,767,162 B2
APPLICATION NO. : 16/222184
DATED : September 8, 2020
INVENTOR(S) : Victor Chun Li et al.

It is certified that error appears in the above-identified patent and that said Letters Patent is hereby corrected as shown below:

In the Specification

Column 1, Lines 18-21:
"This invention was made with federal funding under Grant No. GM26875 awarded by the National Institutes of Health. The U.S. government has certain rights in the invention."

Should be replaced with:
— This invention was made with government support under GM026875 and HD073104 awarded by National Institutes of Health (NIH). The government has certain rights in this invention. —

Signed and Sealed this
Fifteenth Day of November, 2022

Katherine Kelly Vidal
*Director of the United States Patent and Trademark Office*